(12) United States Patent
Nagler et al.

(10) Patent No.: US 8,094,894 B2
(45) Date of Patent: Jan. 10, 2012

(54) RADIOACTIVE-EMISSION-MEASUREMENT OPTIMIZATION TO SPECIFIC BODY STRUCTURES

(75) Inventors: Michael Nagler, Tel-Aviv (IL); Eli Dichterman, Haifa (IL); Yoel Zilberstein, Haifa (IL); Ran Ravhon, Kiryat-Motzkin (IL); Omer Ziv, Rechovot (IL); Benny Rousso, Rishon-LeZion (IL); Shlomo Ben-Haim, Caesarea (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 1018 days.

(21) Appl. No.: 11/607,075

(22) Filed: Dec. 1, 2006

(65) Prior Publication Data

US 2007/0156047 A1    Jul. 5, 2007

Related U.S. Application Data

(63) Continuation-in-part of application No. PCT/IL2005/000575, filed on Jun. 1, 2005, and a continuation-in-part of application No. 09/641,973, filed on Aug. 21, 2000, and a continuation-in-part of application No. 10/343,792, filed on Feb. 4, 2003, and a continuation-in-part of application No. 10/616,307, (Continued)

(51) Int. Cl.
  *G06K 9/00* (2006.01)
(52) U.S. Cl. .................. 382/128; 600/407
(58) Field of Classification Search .............. 382/128; 600/407
See application file for complete search history.

(56) References Cited

U.S. PATENT DOCUMENTS 2,776,377 A    1/1957 Anger
(Continued)

FOREIGN PATENT DOCUMENTS

DE    1516429    12/1969
(Continued)

OTHER PUBLICATIONS

International Search Report Dated Jul. 11, 2008 From the International Searching Authority of the Patent Cooperation Treaty Re.: Application No. PCT/IL06/01511.

(Continued)

*Primary Examiner* — Hadi Akhavannik

(57) ABSTRACT

Systems, methods, and probes are provided for functional imaging by radioactive-emission-measurements, specific to body structures, such as the prostate, the esophagus, the cervix, the uterus, the ovaries, the heart, the breast, the brain, and the whole body, and other body structures. The nuclear imaging may be performed alone, or together with structural imaging, for example, by x-rays, ultrasound, or MRI. Preferably, the radioactive-emission-measuring probes include detectors, which are adapted for individual motions with respect to the probe housings, to generate views from different orientations and to change their view orientations. These motions are optimized with respect to functional information gained about the body structure, by identifying preferred sets of views for measurements, based on models of the body structures and information theoretic measures. A second iteration, for identifying preferred sets of views for measurements of a portion of a body structure, based on models of a location of a pathology that has been identified, makes it possible, in effect, to zoom in on a suspected pathology. The systems are preprogrammed to provide these motions automatically.

24 Claims, 100 Drawing Sheets

Related U.S. Application Data filed on Jul. 10, 2003, and a continuation-in-part of application No. 10/533,568, filed on Jan. 5, 2006, now Pat. No. 7,652,259.

(60) Provisional application No. 60/575,369, filed on Jun. 1, 2004, provisional application No. 60/625,971, filed on Nov. 9, 2004, provisional application No. 60/630,561, filed on Nov. 26, 2004, provisional application No. 60/632,236, filed on Dec. 2, 2004, provisional application No. 60/632,515, filed on Dec. 3, 2004, provisional application No. 60/635,630, filed on Dec. 14, 2004, provisional application No. 60/636,088, filed on Dec. 16, 2004, provisional application No. 60/640,215, filed on Jan. 3, 2005, provisional application No. 60/648,385, filed on Feb. 1, 2005, provisional application No. 60/648,690, filed on Feb. 2, 2005.

(56) References Cited

U.S. PATENT DOCUMENTS

| | | | |
|---|---|---|---|
| 3,340,866 A | 9/1967 | Nöller | |
| 3,684,887 A | 8/1972 | Hugonin | |
| 3,690,309 A | 9/1972 | Pluzhnikov et al. | |
| 3,719,183 A | 3/1973 | Schwartz | |
| 3,739,279 A | 6/1973 | Hollis | |
| 3,971,362 A | 7/1976 | Pope et al. | |
| 4,015,592 A | 4/1977 | Bradley-Moore | |
| 4,278,077 A | 7/1981 | Mizumoto | |
| 4,302,675 A | 11/1981 | Wake et al. | |
| 4,364,377 A | 12/1982 | Smith | |
| 4,521,688 A | 6/1985 | Yin | |
| H12 H | 1/1986 | Bennett et al. | |
| H000012 H | 1/1986 | Bennett et al. | |
| 4,595,014 A | 6/1986 | Barrett et al. | |
| 4,674,107 A | 6/1987 | Urban et al. | |
| 4,689,041 A | 8/1987 | Corday et al. | |
| 4,689,621 A | 8/1987 | Kleinberg | |
| 4,731,536 A | 3/1988 | Rische et al. | |
| 4,773,430 A | 9/1988 | Porath | |
| 4,828,841 A | 5/1989 | Porter et al. | |
| 4,844,067 A | 7/1989 | Ikada et al. | |
| 4,844,076 A | 7/1989 | Lesho et al. | |
| 4,893,013 A | 1/1990 | Denen et al. | |
| 4,928,250 A | 5/1990 | Greenberg et al. | |
| 4,929,832 A | 5/1990 | Ledly | |
| 4,951,653 A | 8/1990 | Fry et al. | |
| 4,959,547 A | 9/1990 | Carroll et al. | |
| 4,995,396 A | 2/1991 | Inaba et al. | |
| 5,014,708 A | 5/1991 | Hayashi et al. | |
| 5,032,729 A | 7/1991 | Charpak | |
| 5,033,998 A | 7/1991 | Corday et al. | |
| 5,070,878 A | 12/1991 | Denen | |
| 5,088,492 A | 2/1992 | Takayama et al. | |
| 5,119,818 A | 6/1992 | Carroll et al. | |
| 5,151,598 A | 9/1992 | Denen | |
| 5,170,055 A | 12/1992 | Carroll et al. | |
| 5,170,789 A | 12/1992 | Narayan et al. | |
| 5,243,988 A | 9/1993 | Sieben et al. | |
| 5,246,005 A | 9/1993 | Carroll et al. | |
| 5,249,124 A | 9/1993 | DeVito | |
| 5,279,607 A | 1/1994 | Schentag et al. | |
| 5,299,253 A | 3/1994 | Wessels | |
| 5,307,808 A | 5/1994 | Dumoulin et al. | |
| 5,349,190 A | 9/1994 | Hines et al. | |
| 5,383,456 A | 1/1995 | Arnold et al. | |
| 5,386,446 A | 1/1995 | Fujimoto et al. | |
| 5,395,366 A | 3/1995 | D'Andrea | |
| 5,399,868 A | 3/1995 | Jones et al. | |
| 5,415,181 A | 5/1995 | Hofgrefe et al. | |
| 5,441,050 A | 8/1995 | Thurston et al. | |
| 5,448,073 A | 9/1995 | Jeanguillaume | |
| 5,475,219 A | 12/1995 | Olson | |
| 5,484,384 A | 1/1996 | Fearnot | |
| 5,489,782 A | 2/1996 | Wernikoff | |
| 5,493,595 A | 2/1996 | Schoolman | |
| 5,519,221 A | 5/1996 | Weinberg | |
| 5,572,999 A | 11/1996 | Funda et al. | |
| 5,579,766 A | 12/1996 | Gray | |
| 5,604,531 A | 2/1997 | Iddan et al. | |
| 5,617,858 A | 4/1997 | Taverna et al. | |
| 5,635,717 A | 6/1997 | Popescu | |
| 5,657,759 A | 8/1997 | Essen-Moller | |
| 5,672,877 A | 9/1997 | Liebig et al. | |
| 5,682,888 A | 11/1997 | Olson et al. | |
| 5,690,691 A | 11/1997 | Chen et al. | |
| 5,694,933 A | 12/1997 | Madden et al. | |
| 5,695,500 A | 12/1997 | Taylor et al. | |
| 5,716,595 A | 2/1998 | Goldenberg | |
| 5,727,554 A | 3/1998 | Kalend et al. | |
| 5,729,129 A | 3/1998 | Acker | |
| 5,732,704 A | 3/1998 | Thurston et al. | |
| 5,744,805 A | 4/1998 | Raylman et al. | |
| 5,784,432 A | 7/1998 | Kurtz et al. | |
| 5,803,914 A | 9/1998 | Ryals et al. | |
| 5,811,814 A | 9/1998 | Leone et al. | |
| 5,821,541 A | 10/1998 | Tuemer | |
| 5,833,603 A | 11/1998 | Kovacs et al. | |
| 5,838,009 A | 11/1998 | Plummer et al. | |
| 5,842,977 A | 12/1998 | Lesho et al. | |
| 5,846,513 A | 12/1998 | Carroll et al. | |
| 5,857,463 A | 1/1999 | Thurston et al. | |
| 5,871,013 A | 2/1999 | Wainer et al. | |
| 5,880,475 A | 3/1999 | Oka et al. | |
| 5,891,030 A * | 4/1999 | Johnson et al. | 600/407 |
| 5,900,533 A | 5/1999 | Chou | |
| 5,916,167 A | 6/1999 | Kramer et al. | |
| 5,928,150 A | 7/1999 | Call | |
| 5,932,879 A | 8/1999 | Raylman et al. | |
| 5,939,724 A | 8/1999 | Eisen et al. | |
| 5,961,457 A | 10/1999 | Raylman et al. | |
| 5,984,860 A | 11/1999 | Shan | |
| 5,987,350 A | 11/1999 | Thurston | |
| 5,993,378 A | 11/1999 | Lemelson | |
| 6,002,480 A | 12/1999 | Izatt et al. | |
| 6,072,177 A | 6/2000 | McCroskey et al. | |
| 6,076,009 A | 6/2000 | Raylman et al. | |
| 6,082,366 A | 7/2000 | Andra et al. | |
| 6,107,102 A | 8/2000 | Ferrari | |
| 6,115,635 A | 9/2000 | Bourgeois | |
| 6,129,670 A | 10/2000 | Burdette et al. | |
| 6,132,372 A | 10/2000 | Essen-Moller | |
| 6,135,955 A | 10/2000 | Madden et al. | |
| 6,147,353 A | 11/2000 | Gagnon et al. | |
| 6,173,201 B1 | 1/2001 | Front | |
| 6,205,347 B1 | 3/2001 | Morgan et al. | |
| 6,212,423 B1 | 3/2001 | Krakovitz | |
| 6,226,350 B1 | 5/2001 | Hsieh | |
| 6,233,304 B1 | 5/2001 | Hu et al. | |
| 6,236,878 B1 | 5/2001 | Taylor et al. | |
| 6,236,880 B1 | 5/2001 | Raylman et al. | |
| 6,239,438 B1 | 5/2001 | Schubert | |
| 6,240,312 B1 | 5/2001 | Alfano et al. | |
| 6,242,743 B1 | 6/2001 | DeVito | |
| 6,246,901 B1 | 6/2001 | Benaron | |
| 6,252,924 B1 | 6/2001 | Davantes et al. | |
| 6,261,562 B1 | 7/2001 | Xu et al. | |
| 6,263,229 B1 | 7/2001 | Atalar et al. | |
| 6,271,524 B1 | 8/2001 | Wainer et al. | |
| 6,271,525 B1 | 8/2001 | Majewski et al. | |
| 6,280,704 B1 | 8/2001 | Schutt et al. | |
| 6,310,968 B1 | 10/2001 | Hawkins et al. | |
| 6,324,418 B1 | 11/2001 | Crowley et al. | |
| 6,339,652 B1 | 1/2002 | Hawkins et al. | |
| 6,346,706 B1 | 2/2002 | Rogers et al. | |
| 6,381,349 B1 | 4/2002 | Zeng et al. | |
| 6,392,235 B1 | 5/2002 | Barrett et al. | |
| 6,407,391 B1 | 6/2002 | Mastrippolito et al. | |
| 6,415,046 B1 * | 7/2002 | Kerut, Sr. | 382/128 |
| 6,420,711 B2 | 7/2002 | Tuemer | |
| 6,426,917 B1 | 7/2002 | Tabanou et al. | |
| 6,429,431 B1 | 8/2002 | Wilk | |

| | | |
|---|---|---|
| 6,431,175 B1 | 8/2002 | Penner et al. |
| 6,438,401 B1 | 8/2002 | Cheng et al. |
| 6,368,331 B1 | 9/2002 | Front et al. |
| 6,453,199 B1 | 9/2002 | Kobozev |
| 6,459,925 B1 | 10/2002 | Nields et al. |
| 6,480,732 B1 | 11/2002 | Tanaka et al. |
| 6,484,051 B1 | 11/2002 | Daniel |
| 6,490,476 B1 | 12/2002 | Townsend et al. |
| 6,510,336 B1 | 1/2003 | Daghighian et al. |
| 6,516,213 B1 | 2/2003 | Nevo |
| 6,525,320 B1 | 2/2003 | Juni |
| 6,525,321 B2 | 2/2003 | Juni |
| 6,549,646 B1 | 4/2003 | Yeh et al. |
| 6,560,354 B1 | 5/2003 | Maurer et al. |
| 6,567,687 B2 | 5/2003 | Front et al. |
| 6,584,348 B2 | 6/2003 | Glukhovsky |
| 6,587,710 B1 | 7/2003 | Wainer |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,628,983 B1 | 9/2003 | Gagnon |
| 6,628,984 B2 | 9/2003 | Weinberg |
| 6,662,036 B2 | 9/2003 | Cosman |
| 6,632,216 B2 | 10/2003 | Houzego et al. |
| 6,633,658 B1 * | 10/2003 | Dabney et al. ............... 382/128 |
| 6,638,752 B2 | 10/2003 | Contag et al. |
| 6,643,538 B1 | 11/2003 | Majewski et al. |
| 6,680,750 B1 | 1/2004 | Tournier et al. |
| 6,697,660 B1 * | 2/2004 | Robinson ............... 600/409 |
| 6,728,583 B2 | 4/2004 | Hallett |
| 6,748,259 B1 | 6/2004 | Benaron et al. |
| 6,766,048 B1 | 7/2004 | Launay et al. |
| 6,771,802 B1 | 8/2004 | Patt et al. |
| 6,943,355 B2 | 9/2005 | Shwartz et al. |
| 6,963,770 B2 | 11/2005 | Scarantino et al. |
| 7,043,063 B1 | 5/2006 | Noble et al. |
| 7,142,634 B2 | 11/2006 | Engler et al. |
| 7,176,466 B2 | 2/2007 | Rousso et al. |
| 7,187,790 B2 | 3/2007 | Sabol et al. |
| 7,468,513 B2 | 12/2008 | Charron et al. |
| 7,490,085 B2 | 2/2009 | Walker et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0103431 A1 | 8/2002 | Toker et al. |
| 2002/0148970 A1 | 10/2002 | Wong et al. |
| 2002/0168317 A1 | 11/2002 | Daighighian et al. |
| 2002/0183645 A1 | 12/2002 | Nachaliel |
| 2002/0188197 A1 | 12/2002 | Bishop et al. |
| 2003/0001837 A1 | 1/2003 | Baumberg |
| 2003/0013966 A1 | 1/2003 | Barnes et al. |
| 2003/0063787 A1 | 4/2003 | Natanzon et al. |
| 2003/0081716 A1 | 5/2003 | Tumer |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215124 A1 | 11/2003 | Li |
| 2003/0216631 A1 | 11/2003 | Bloch et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0054248 A1 | 3/2004 | Kimchy et al. |
| 2004/0054278 A1 | 3/2004 | Kimchy et al. |
| 2004/0081623 A1 | 4/2004 | Eriksen et al. |
| 2004/0086437 A1 | 5/2004 | Jackson et al. |
| 2004/0101176 A1 | 5/2004 | Mendonca et al. |
| 2004/0116807 A1 | 6/2004 | Amrami et al. |
| 2004/0153128 A1 | 8/2004 | Suresh et al. |
| 2004/0171924 A1 | 9/2004 | Mire et al. |
| 2004/0184644 A1 | 9/2004 | Leichter et al. |
| 2004/0195512 A1 | 10/2004 | Crosetto |
| 2004/0204646 A1 | 10/2004 | Nagler et al. |
| 2004/0251419 A1 | 12/2004 | Nelson et al. |
| 2005/0020915 A1 | 1/2005 | Bellardinelli et al. |
| 2005/0055174 A1 | 3/2005 | David et al. |
| 2005/0205792 A1 | 9/2005 | Rousso et al. |
| 2005/0211909 A1 | 9/2005 | Smith |
| 2005/0215889 A1 | 9/2005 | Patterson, II |
| 2005/0253073 A1 | 11/2005 | Joram et al. |
| 2005/0266074 A1 | 12/2005 | Zilberstein et al. |
| 2006/0074290 A1 | 4/2006 | Chen et al. |
| 2006/0160157 A1 | 7/2006 | Zuckerman |
| 2006/0237652 A1 | 10/2006 | Kimchy et al. |
| 2006/0257012 A1 | 11/2006 | Kaufman et al. |
| 2007/0166227 A1 | 7/2007 | Liu et al. |
| 2007/0194241 A1 | 8/2007 | Rousso et al. |
| 2008/0033291 A1 | 2/2008 | Rousso et al. |
| 2008/0042067 A1 | 2/2008 | Rousso et al. |
| 2008/0128626 A1 | 6/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260637 A1 | 10/2008 | Dickman |
| 2008/0277591 A1 | 11/2008 | Shahar et al. |
| 2009/0078875 A1 | 3/2009 | Rousso et al. |
| 2009/0152471 A1 | 6/2009 | Rousso et al. |
| 2009/0190807 A1 | 7/2009 | Rousso et al. |
| 2010/0245354 A1 | 9/2010 | Rousso et al. |

FOREIGN PATENT DOCUMENTS

| | | |
|---|---|---|
| DE | 19814199 | 10/1999 |
| DE | 19815362 | 10/1999 |
| EP | 0543626 | 5/1993 |
| EP | 0697193 | 2/1996 |
| EP | 0887661 | 12/1998 |
| GB | 20311423 | 4/1980 |
| JP | 6-109848 | 4/1994 |
| JP | 06-109848 | 4/1994 |
| WO | WO 92/00402 | 1/1992 |
| WO | WO 92/00402 | 9/1992 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/31522 | 2/2000 |
| WO | WO 00/18294 | 4/2000 |
| WO | WO 00/22975 | 4/2000 |
| WO | WO 00/18294 | 6/2000 |
| WO | WO 00/31522 | 6/2000 |
| WO | WO 01/89384 | 11/2001 |
| WO | WO 02/58531 | 1/2002 |
| WO | WO 02/16965 | 2/2002 |
| WO | WO 02/058531 | 8/2002 |
| WO | WO 2004/042546 | 5/2004 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054281 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

International Search Report Dated Jul. 25, 2008 From the International Searching Authority of the Patent Cooperation Treaty Re.: Application No. PCT/IL2007/001588.

Official Action Dated Sep. 4, 2008 From the US Patent and Trademark Office Re.: U.S. Appl. No. 10/533,568.

Official Action Dated Oct. 7, 2008 From the US Patent Office Re.: U.S. Appl. No. 10/616,301.

Official Action Dated Jul. 12, 2007 From the US Patent and Trademark Office Re.: U.S. Appl. No. 10/616,301.

Official Action Dated Dec. 13, 2007 From the US Patent and Trademark Office Re.: U.S. Appl. No. 10/616,301.

Official Action Dated Jul. 15, 2008 From the United States Patent and Trademark Office Re.: U.S. Appl. No. 09/641,973.
Official Action Dated Mar. 21, 2008 From the US Patent and Trademark Office Re.: U.S. Appl. No. 10/533,568.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary Partial European Search Report Dated Nov. 11, 2008 From the European Patent Office Re.: Application No. 01951883.6.
Written Opinion Dated Jul. 25, 2008 From the International Searching Authority of the Patent Cooperation Treaty Re.: Application No. PCT/IL05/001173.
Gugnin et al "Radiocapsule for Recording The Ionizing Radiation In The Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2—p. 585, § 1.
Communication Pursuant to Article 94(3) EPC Dated Apr. 16, 2010 From the European Patent Office Re. Application No. 01951883.6.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Reutter et al. "Direct Least Squares Estimation of Spatiotemporal Distributions From Dynamic SPECT Projections Using A Spatial Segmentation and Temporal B-Splines", IEEE Transactions on Medical Imaging, 19(5): 434-450, 2000.
Huesman et al; "Kinetic Parameter Estimation From SPECT Cone-Beam Projection Measurements", Physics in Medicine and Biology, 43(4): 973-982, 1998.
Reutter et al. "Kinetic Parameter Estimation From Attenuated SPECT Projection Measurements", IEEE Transactions on Nuclear Science, 45(6): 3007-3013, 1998.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002. Not PA in 20355; Not PA in 21303; Suppl. IDS II in 25855; Suppl. IDS in 29684/25571/27030/28541.
Jeanguillaume et al. "From the Whole-Body Counting to Imaging: The Computer Aided Collimation Gamma Camera Project (CACAO)", Radiation Projection Dosimetry 89(3-4): 349-352, 2000.
Quartuccia et al. "Computer Assisted Collimation Gama Camera: A New Approach to Imaging Contaminated Tissues", Radiation Projection Dosimetry, 89(3-4): 343-348, 2000.
Piperno et al. "Breast Cancer Screening by Impedance Measurements", Frontiers Med. Biol. Engng., 2(2): 11-17, 1990.
Rajshekhar "Continuous Impedance Monitoring During CT-Guided Stereotactic Surgery: Relative Value in Cystic and Solid Lesions", British Journal of Neurosurgery, 6: 439-444, 1992.
Jessup "Tumor Markers—Prognostic and Therapeutic Implications for Colorectal Carcinoma", Surgical Oncology, 7: 139-151, 1998.
Corstens et al. "Nuclear Medicine's Role in Infection and Inflammation", The Lancet, 354: 765-770, 1999.
Mori et al. "OvereZpression of Matrix Metalloproteinase-7mRNA in Human Colon Carcinomas"; Cancer, 75: 1516-1519, 1995.
Erbil et al. "Use and Limitations of Serum Total and Lipid-Bound Sialic Acid Concentrations as Markers for Colorectal Cancer", Cancer, 55: 404-409, 1985.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Day et al. "Localization of Radioiodinated Rat Fibrogen in Transplanted Rat Tumors", Journal of the National Cancer Institute, 23(4): 799-812, 1959.
Bromiley et al. "Attenuation Correction in PET Using Consistency Conditions and A Three-Dimensional Template", IEEE Transactions on Nuclear Science, 48(4): 1371-1377, 2001. p. 1376, col. 2, §-2.
Hayakawa et al. "A PET-MRI Registration Technique for PET Studies of the Rat Brain", Nuclear Medicine & Biology, 27: 121-125, 2000. p. 121, col. 1.
Lavallée et al. "Building A Hybrid Patient's Model for Augmented Reality in Surgery: A Registration Problem", Computing in Biological Medicine, 25(2): 149-164, 1995. p. 149-150.
Kojima et al. "Quantitative Planar Imaging Method for Measurement of Renal Activity by Using A Conjugate-Emission Image and Transmission Data", Medical Physics, 27(3): 608-615, 2000. p. 608.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Hassan et al. "A Radiotelemetry Pill for the Measurement of Ionising Radiation Using a Mercuric Iodide Detector", Phys. Med. Biol., 23(2): 302-308, 1978.
Hoffman et al. "Intraoperative Probes and Imaging Probes", European Journal of Nuclear Medicine, 26(8): 913-935, 1999.
Zhang et al. "An Innovative High Efficiency and High Resolution Probe for Prostate Imaging", The Journal of Nuclear Medicine, 68: 18, 2000. Abstract.
Kojima et al. "Quantitative Planar Imaging Method for Measurement of Renal Activity by Using A Conjugate-Emission Image and Transmission Data", Medical Physics, 27(3): 608-615, 2000. p. 608.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Communication Pursuant to Article 94(3) EPC Dated Jul. 22, 2009 From the European Patent Office Re.: Application No. 06809851.6.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.

Invitation to Pay Additional Fees Dated Feb. 15, 2007 From the International Searching Authority Re.: Application No. PCT/IL05/00575.
Notice of Allowance Dated Jul. 16, 2009 From the US Patent and Trademark Office Re.: U.S. Appl. No. 12/084,559.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Jul. 15, 2009 From the US Patent and Trademark Office Re.: U.S. Appl. No. 10/616,301.
Official Action Dated Dec. 16, 2008 From the US Patent and Trademark Office Re.: U.S. Appl. No. 10/343,792.
Official Action Dated Jul. 20, 2009 From the US Patent and Trademark Office Re.: U.S. Appl. No. 11/980,617.
Official Action Dated Dec. 23, 2008 From the US Patent and Trademark Office Re.: U.S. Appl. No. 09/727,464.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Apr. 7, 2009 to Official Action of Oct. 7, 2008 From the US Patent and Trademark Office Re.: U.S. Appl. No. 10/616,301.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Oct. 31, 2007 to Official Action of Jul. 12, 2007 From the US Patent and Trademark Office Re.: U.S. Appl. No. 10/616,301.
Response to the International Search Report and the Written Opinion of Oct. 10, 2006 From the International Searching Authority Re.: Appliction No. PCT/IL06/00059.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Kinahan et al. "Attenuation Correction for a Combined 3D PET/CT Scanner", Medical Physics, 25(10): 2046-2053, Oct. 1998.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.

Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Wu et al. "ECG-Gated Pinhole SPECT in Mice With Millimeter Spatial Resolution", IEEE Transactions on Nuclear Science, 47(3): 1218-1221, Jun. 2000.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Communication Pursuant to Article 93(3) EPC Dated Mar. 8, 2010 From the European Patent Office Re.: Application No. 06832278.3.
Response Dated May 26, 2010 to Official Action of Mar. 19, 2010 From the US Patent and Trademark Office Re.: U.S. Appl. No. 10/240,239.
Response Dated Jul. 1, 2010 to Official Action of Mar. 2, 2010 From the US Patent and Trademark Office Re.: U.S. Appl. No. 11/980,617.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.
Official Action Dated Sep. 2, 2009 From the US Patent and Trademark Office Re.: U.S. Appl. No. 10/343,792.
Official Action Dated Aug. 11, 2009 From the US Patent and Trademark Office Re.: U.S. Appl. No. 09/641,973.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Sep. 16, 2009 From the US Patent and Trademark Office Re.: U.S. Appl. No. 09/727,464.
Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Response Dated Nov. 16, 2009 to Official Action of Jul. 15, 2009 From the US Patent and Trademark Office Re.: U.S. Appl. No. 10/616,301.
Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.

Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 19, 2010 From the US Patent and Trademark Office Re.: U.S. Appl. No. 10/240,239.
Official Action Dated Feb. 23, 2010 From the US Patent and Trademark Office Re.: U.S. Appl. No. 09/641,973.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas el al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for A High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.

Official Action Dated Apr. 9, 2010 From the US Patent and Trademark Office Re.: U.S. Appl. No. 11/798,017.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office Re.: U.S. Appl. No. 09/641,973.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
Response Dated Aug. 25, 2010 to Official Action of Jul. 27, 2010 From the US Patent and Trademark Office Re.: U.S. Appl. No. 10/616,307.
Response Dated Jul. 8, 2010 to Communication Pursuant to Article 94(3) EPC of Mar. 8, 2010 From the European Patent Office Re.: Application No. 06832278.3.
Notice of Allowance Dated Jul. 22, 2010 From the US Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Response dated Sep. 1, 2010 to Official Action of Aug. 3, 2010 From the US Patent and Trademark Office Re.: U.S. Appl. No. 11/980,690.
Response Dated Jun. 1, 2010 to Official Action of Mar. 1, 2010 From the US Patent and Trademark Office Re.: U.S. Appl. No. 11/794,799.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.

Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Response Dated Dec. 15, 2010 to Official Action of Jul. 19, 2010 From the US Patent and Trademark Office Re.: U.S. Appl. No. 11/656,548.
Official Action Dated Jan. 31, 2011 From the US Patent and Trademark Office Re. U.S. Appl. No. 11/667,793.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Communication Pursuant to Article 94(3) EPC Dated Mar. 2, 2011 From the European Patent Office Re.: Application No. 06756259.5.
Communication Pursuant to Rules 70(2) and 70a(2) EPC Dated Apr. 4, 2011 From the European Patent Office Re. Application No. 05803689.8.
International Search Report Dated Feb. 1, 2006 From the International Searching Authority of the Patent Cooperation Treaty Re.: Application No. PCT/IL05/00048.
International Search Report Dated Aug. 3, 2006 From the International Searching Authority of the Patent Cooperation Treaty Re.: Application No. PCT/IL05/001173.
International Search Report Dated Mar. 23, 2006 From the International Searching Authority of the Patent Cooperation Treaty Re.: Application No. PCT/IL05/00572.
Interview Summary Dated Mar. 25, 2011 From the US Patent and Trademark Office Re.: U.S. Appl. No. 10/836,223.
Interview Summary Dated May 31, 2011 From the US Patent and Trademark Office Re. U.S. Appl. No. 10/616,301.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Notice of Allowance Dated Nov. 15, 2010 From the US Patent and Trademark Office Re. U.S. Appl. No. 10/616,301.
Notice of Allowance Dated Feb. 23, 2011 From the US Patent and Trademark Office Re.: U.S. Appl. No. 11/980,690.
Notice of Non-Compliant Amendment Dated Feb. 14, 2011 From the US Patent and Trademark Office Re.: U.S. Appl. No. 10/616,307.
Official Action Dated Mar. 15, 2011 From the US Patent and Trademark Office Re.: U.S. Appl. No. 10/343,792.
Official Action Dated Apr. 20, 2011 From the US Patent and Trademark Office Re.: U.S. Appl. No. 11/798,017.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Official Action Dated Apr. 27, 2011 From the US Patent and Trademark Office Re.: U.S. Appl. No. 10/836,223.
Response Dated Mar. 3, 2011 to Notice of Non-Compliant Amendment of Feb. 14, 2011 From the US Patent and Trademark Office Re.: U.S. Appl. No. 10/616,307.
Response Dated Apr. 5, 2011 to Official Action of Nov. 10, 2010 From the US Patent and Trademark Office Re.: U.S. Appl. No. 10/836,223.
Response Dated Mar. 8, 2011 to Official Action of Dec. 8, 2010 From the US Patent and Trademark Office Re.: U.S. Appl. No. 11/980,690.
Response Dated Feb. 10, 2011 to Notice of Allowance of Nov. 15, 2010 From the US Patent and Trademark Office Re. U.S. Appl. No. 10/616,301.
Response Dated Mar. 24, 2011 to Official Action of Dec. 8, 2010 From the Ijs Patent and Trademark Office Re.: U.S. Appl. No. 09/641,973.
Response Dated Jan. 27, 2011 to Official Action of Nov. 1, 2010 From the US Patent and Trademark Office Re.: U.S. Appl. No. 12/728,383.
Response Dated Mar. 31, 2011 to Official Action of Jan. 31, 2011 From the US Patent and Trademark Office Re. U.S. Appl. No. 11/667,793.
Supplementary European Search Report and the European Search Opinion Dated Mar. 16, 2011 From the European Patent Office Re. Application No. 05803689.8.
Written Opinion Dated Mar. 26, 2007 From the International Searching Authority of the Patent Cooperation Treaty Re.: Application No. PCT/IL05/00394.
Chengazi et al. "Imaging Prostate Cancer With Technetium-99m-7E11-C5.3 (CYT-351)", Journal of Nuclear Medicine, 38: 675-682, 1997.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Lavall?e et al. "Building a Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Mao et al. "Human Prostatic Carcinoma: An Electron Microscope Study", Cancer Research, XP002625777, 26(5): 955-973, May 1966.
McJilton et al. "Protein Kinase C? Interacts With Bax and Promotes Survival of Human Prostate Cancer Cells", Oncogene, 22; 7958-7968, 2003.
Mettler et al. "Legal Requirements and Radiation Safety", Essentials of Nuclear Medicine Imaging, 2nd Ed., Chap.13: 323-331, 1985.
Storey et al. "Tc-99m Sestamibi Uptake in Metastatic Prostate Carcinoma", Clinical Nuclear Medicine, XP009145398, 25(2): 133-134, Feb. 2000.
Xu et al. "Quantitative Expression Profile of Androgen-Regulated Genes in Prostate Cancer Cells and Identification of Prostate-Specific Genes", International Journal of Cancer, 92: 322-328, 2001.
Notice of Allowance Dated Jun. 23, 2011 From the US Patent and Trademark Office Re.: U.S. Appl. No. 10/616,301.
Official Action Dated Jun. 28, 2011 From the US Patent and Trademark Office Re. U.S. Appl. No. 11/628,074.
Examination Report Dated Jun. 22, 2011 From the Government of India, Patent Office, Intellectual Property Building Re. Application No. 2963/CHENP/2006.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Official Action Dated Jul. 12, 2011 From the US Patent and Trademark Office Re.: U.S. Appl. No. 09/641,973.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.

Communication Relating to the Results of the Partial International Search Dated May 21, 2008 From the International Searching Authority of the Patent Cooperation Treaty Re.: Application No. PCT/IL2007/001588.
International Preliminary Report on Patentability Dated Apr. 16, 2009 From the International Bureau of WIPO Re.: Applicaiton No. PCT/IL2007/000918.
International Search Report Dated Oct. 10, 2006 From the International Searching Authority of the Patent Cooperation Treaty Re.: Application No. PCT/IL06/00059.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
international Search Report Dated Aug. 3, 2006 From the international Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Office Action Dated Dec. 2, 2007 From the Israeli Patent Office Re.: Application No. 158442.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Jul. 2, 2004 From the US Patent and Trademark Office Re.: U.S. Appl. No. 09/641,973.
Official Action Dated May 3, 2007 From the US Patent and Trademark Office Re.: U.S. Appl. No. 10/240,239.
Official Action Dated Sep. 5, 2002 From the US Patent and Trademark Office Re.: U.S. Appl. No. 12/084,559.
Official Action Dated Oct. 7, 2008 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.

Official Action Dated Mar. 15, 2004 From the US Patent and Trademark Office Re.: U.S. Appl. No. 09/765,316.
Official Action Dated Jan. 17, 2006 From the United States Patent and Trademark Office Re.: U.S. Appl. No. 11/034,007.
Official Action Dated Apr. 20, 2006 From the United States Patent and Trademark Office Re.: U.S. Appl. No. 10/240,239.
Official Action Dated Jun. 23, 2006 From the United States Patent and Trademark Office Re.: U.S. Appl. No. 09/727,464.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Supplementary European Search Report Dated Dec. 12, 2005 From the European Patent Office Re.: Application No. 03810570.6.
Supplementary Partial European Search Report Dated Sep. 4, 2007 From the European Patent Office Re.: Application No. 0 2716285.8.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Written Opinion Dated Oct/ 10, 2006 From the International Searching Authority of the Patent Cooperation Treaty Re.: Application No. PCT/IL06/00059.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Mar. 26, 2007 From the International Searching Authority of the Patent Cooperation Treaty Re.: Application No. PCT/IL05/00394.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Hassan et al. "A Radiotelemetry Pill for the Measurement of Ionising Radiation Using a Mercuric Iodide Detector", Physics in Medicine and Biology, 23(2): 302-308, 1978.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry 89(3-4): 349-352, 2000.
Jessup "Tumor Markers—Prognostic and Therapeutic Implications for Colorectal Carcinoma", Surgical Oncology, 7: 139-151, 1998.
Lavallée et al. "Building a Hybrid Patient's Model for Augmented Reality in Surgery: A Registration Problem", Computing in Biological Medicine, 25(2): 149-164, 1995.
Mori et al. "Overexpression of Matrix Metalloproteinase-7mRNA in Human Colon Carcinomas", Cancer, 75: 1516-1519, 1995.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.

* cited by examiner

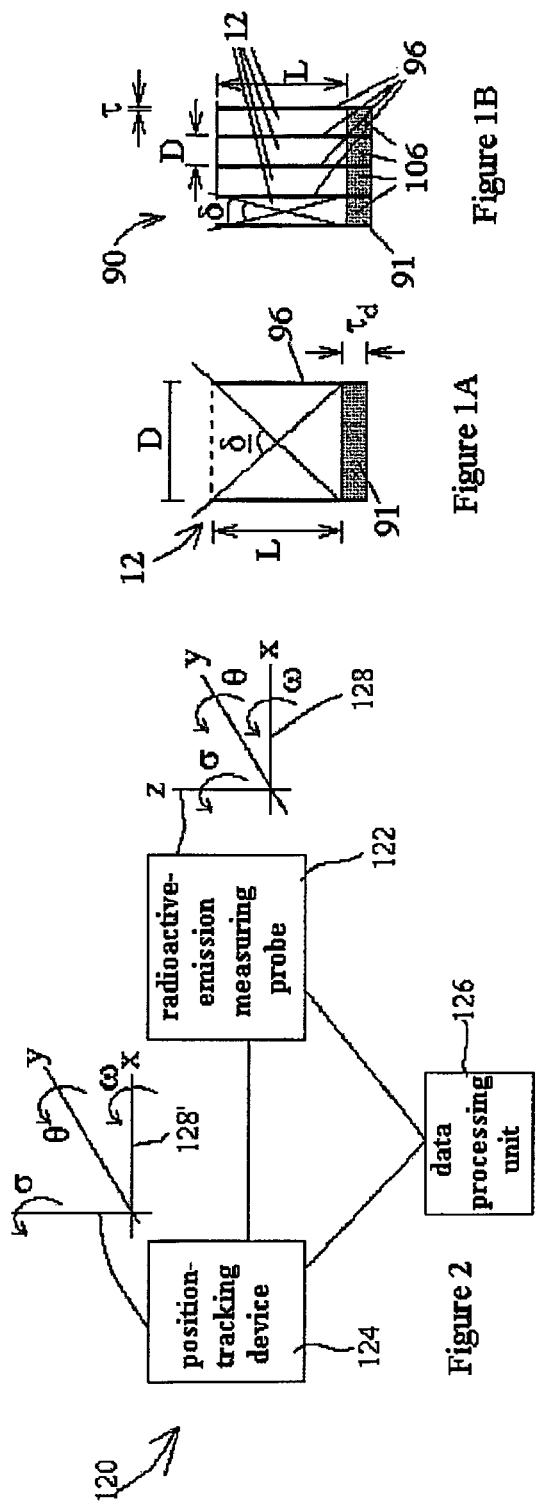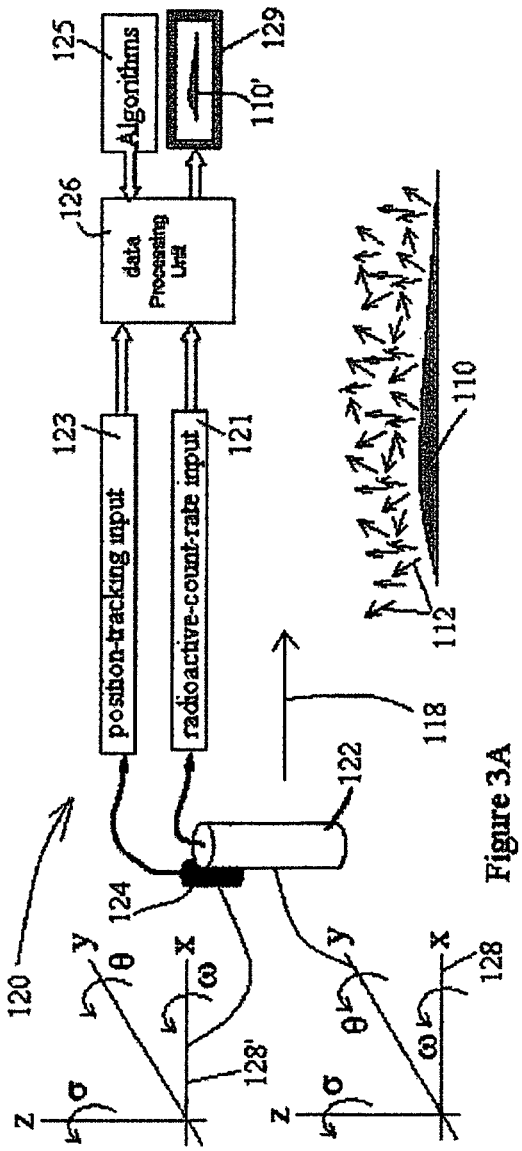

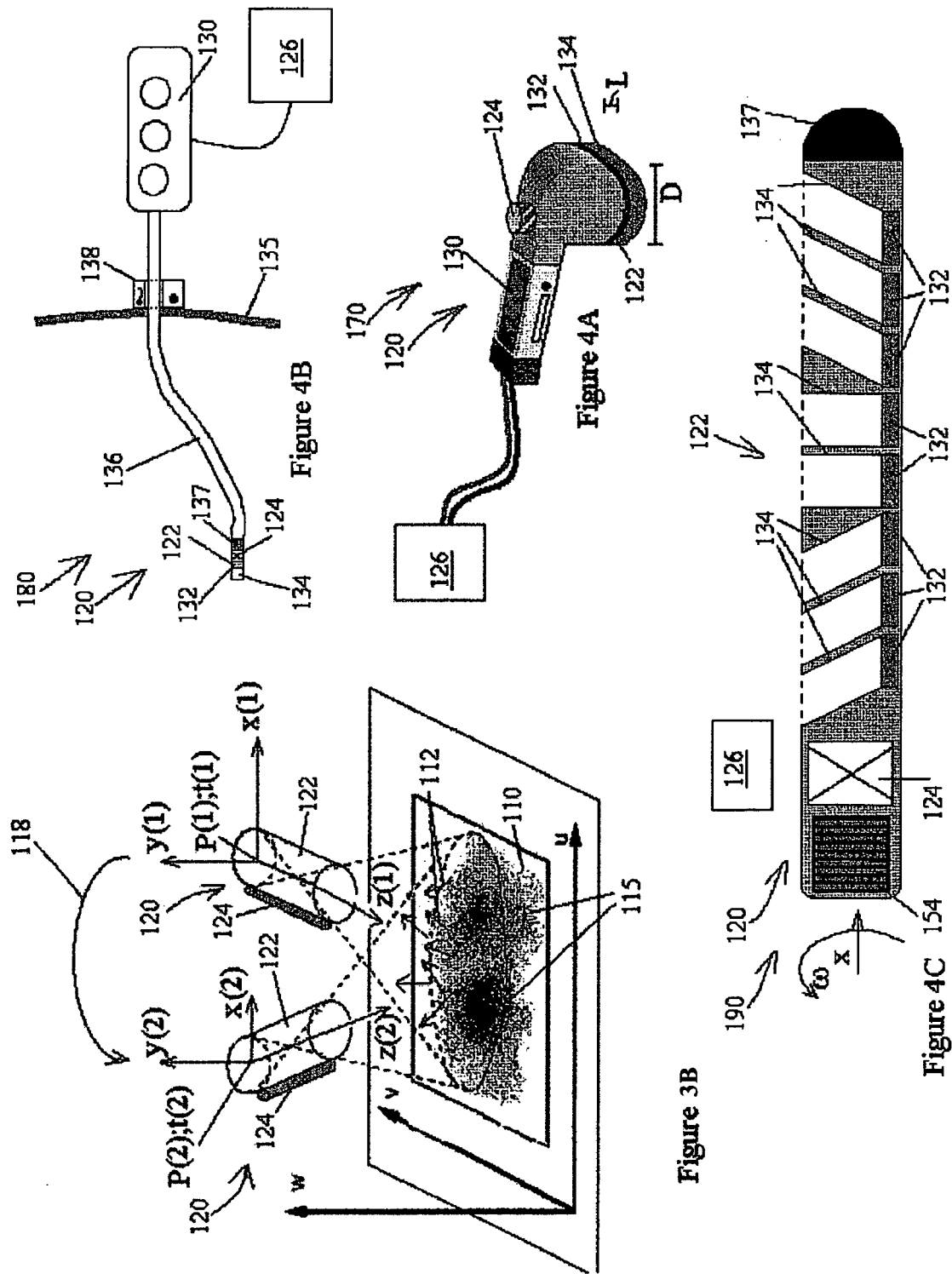

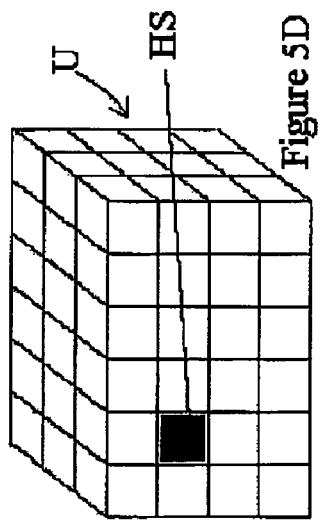
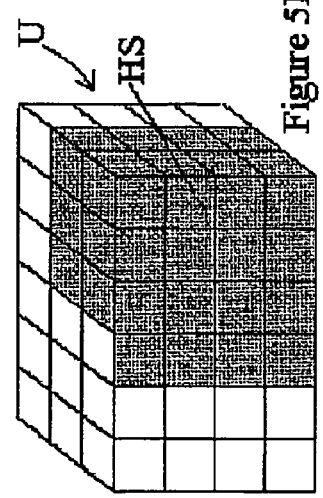
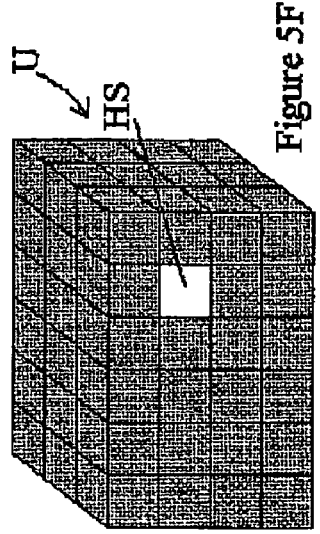
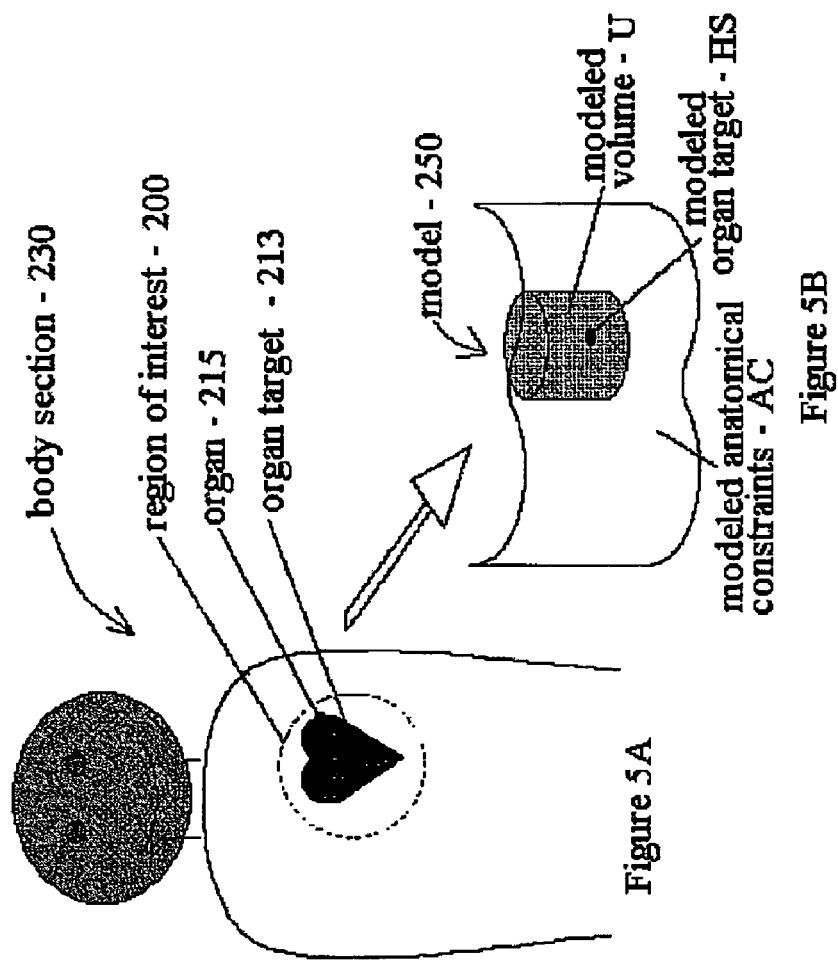

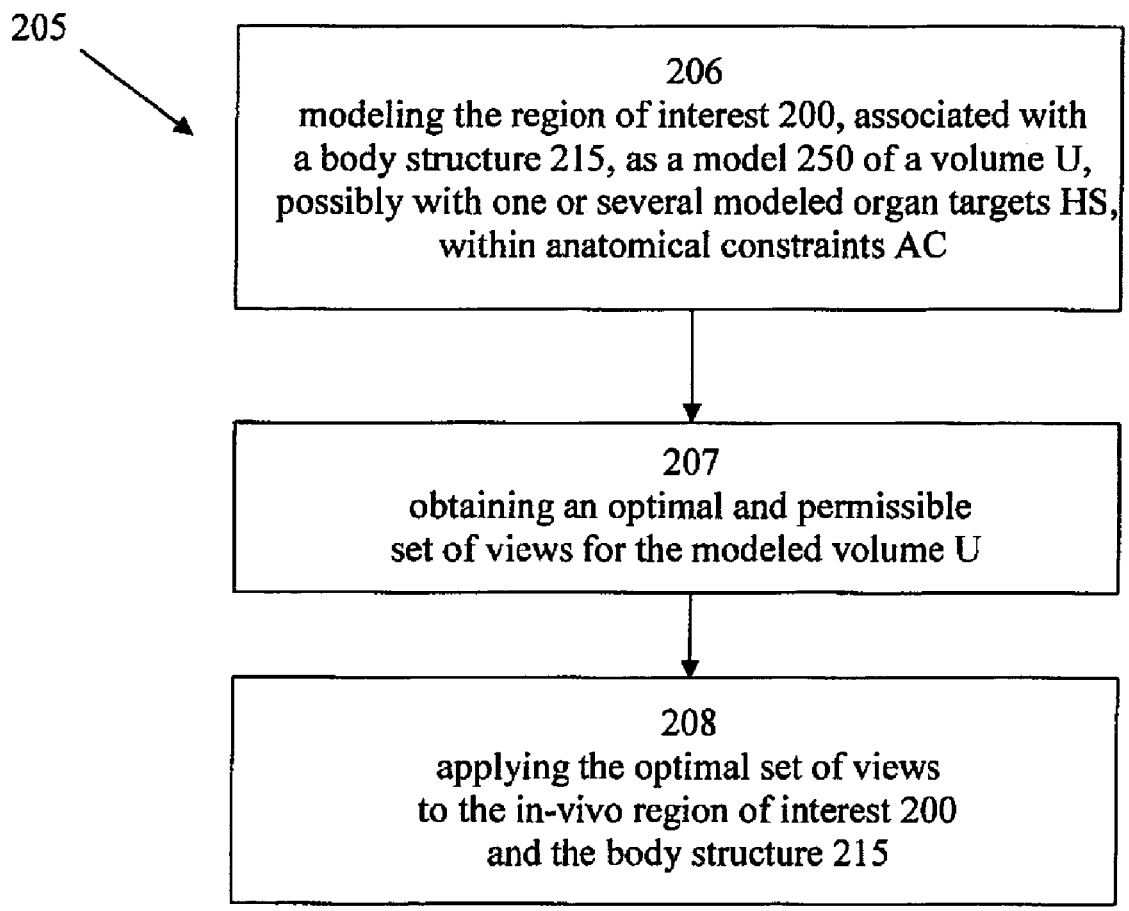

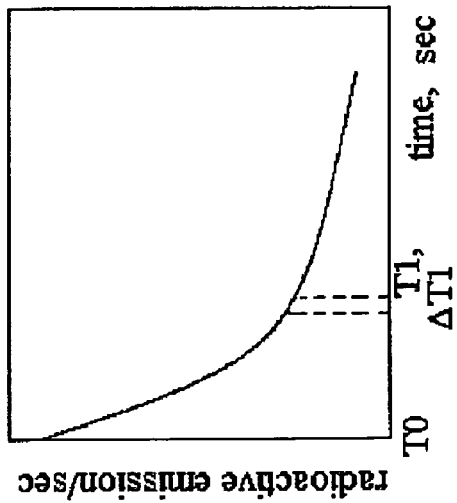
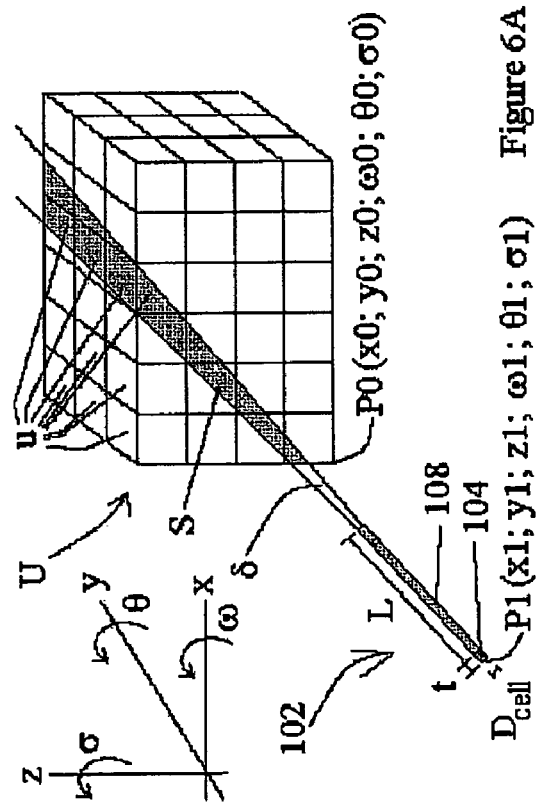
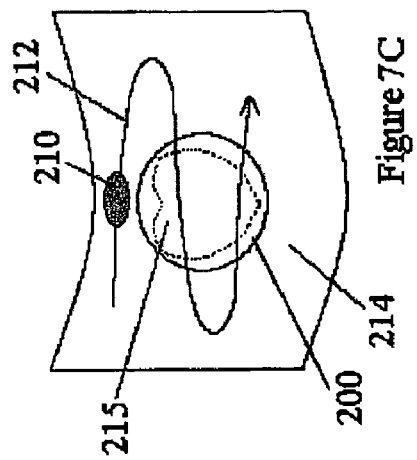
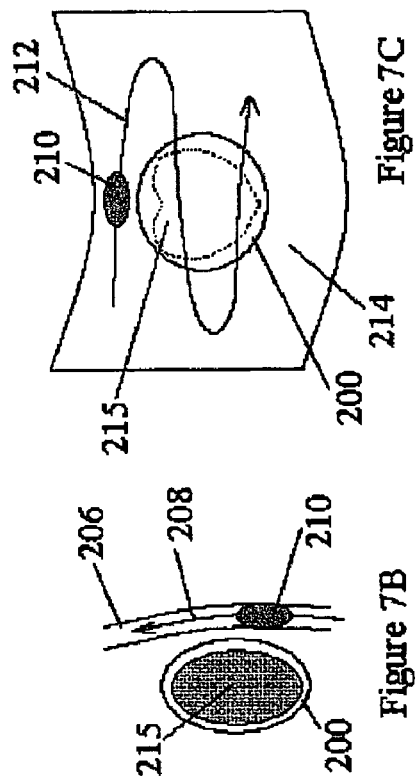
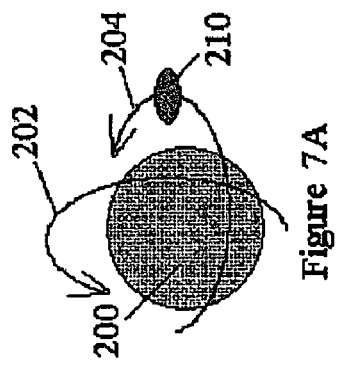

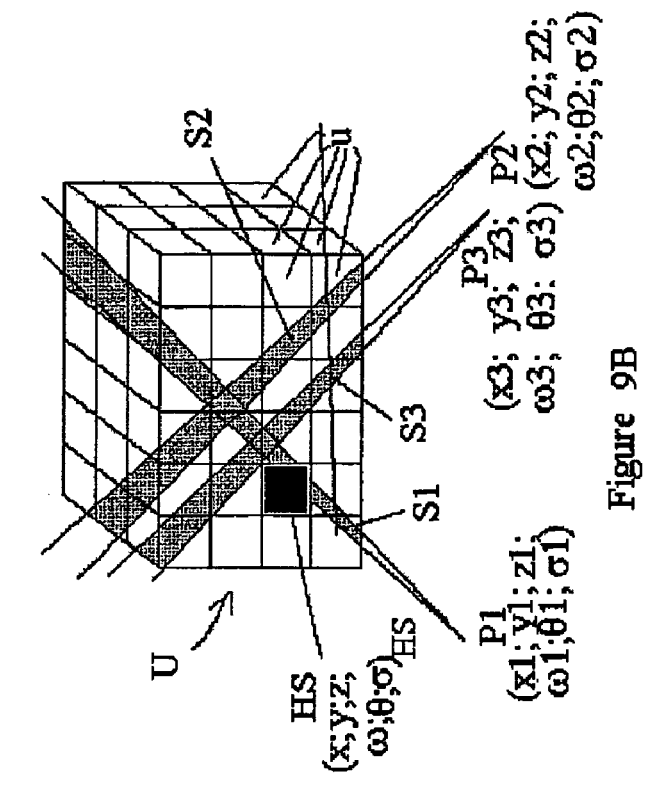
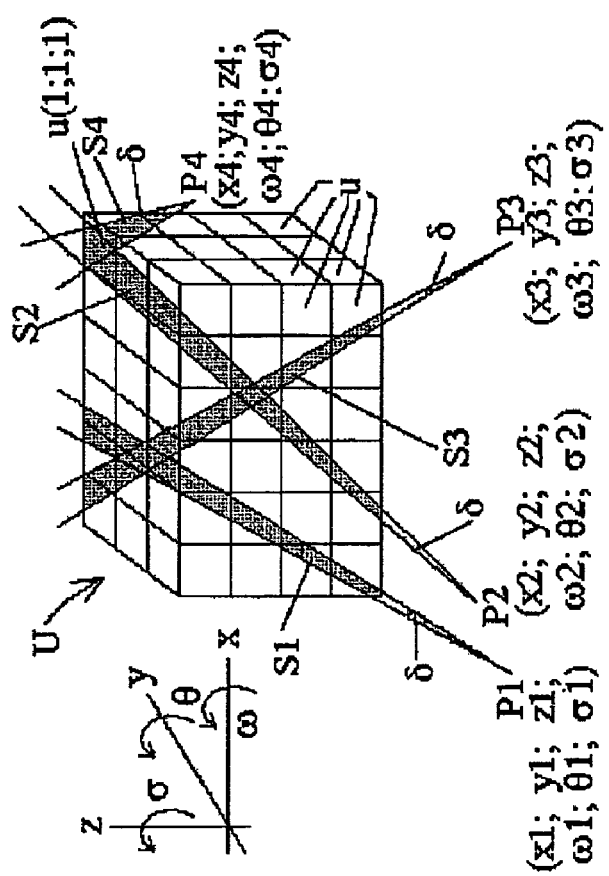
Figure 9B
Figure 9A

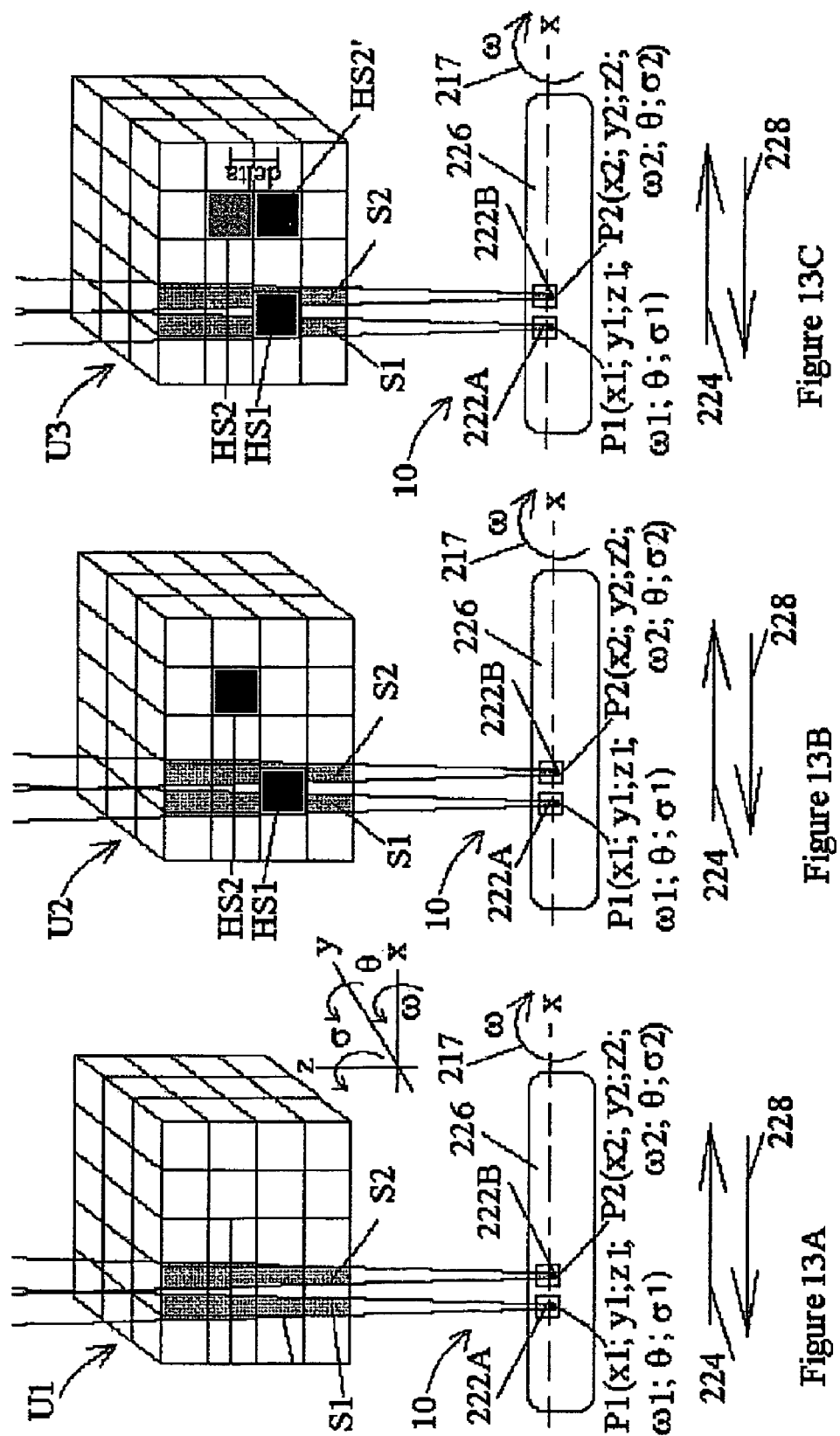

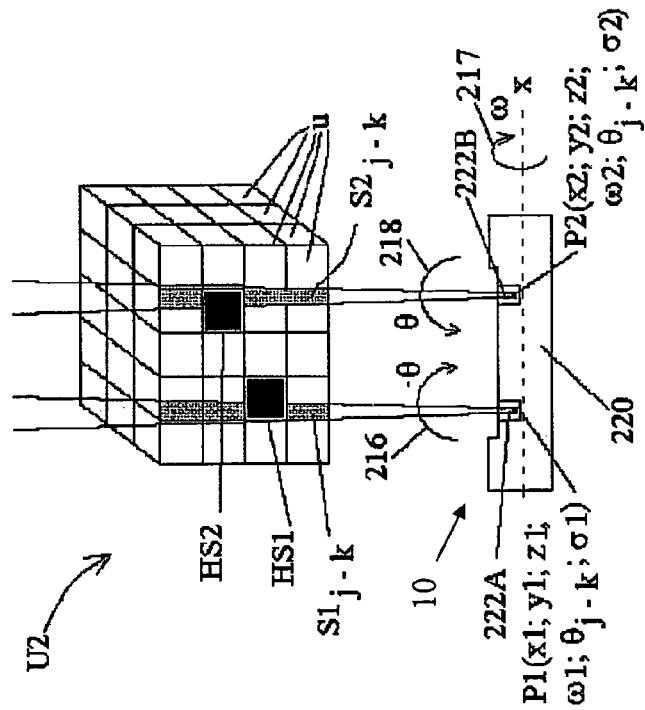
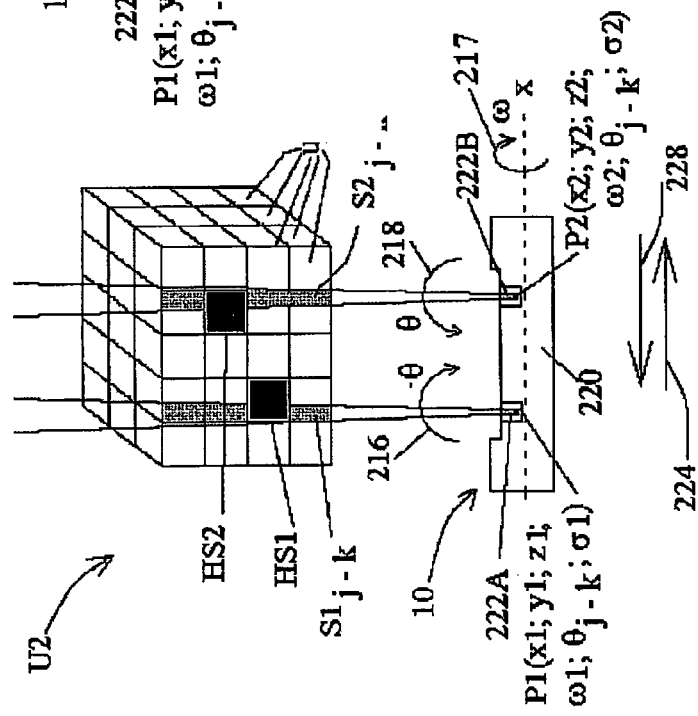

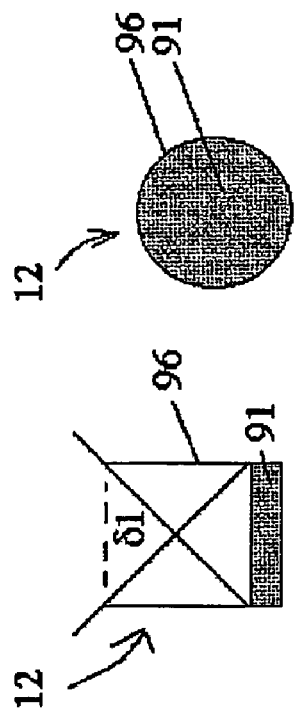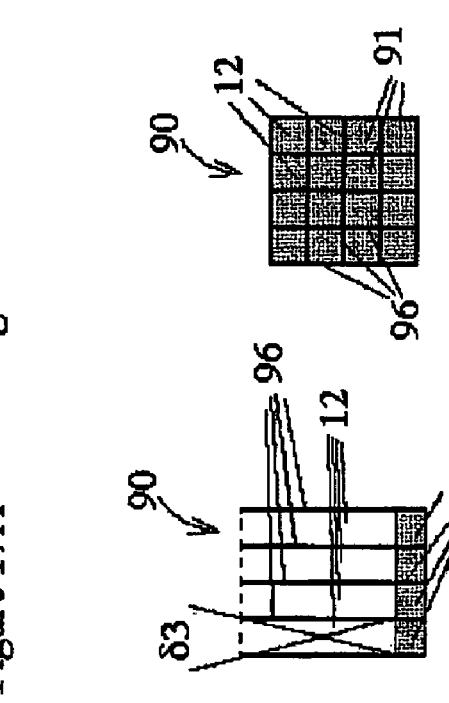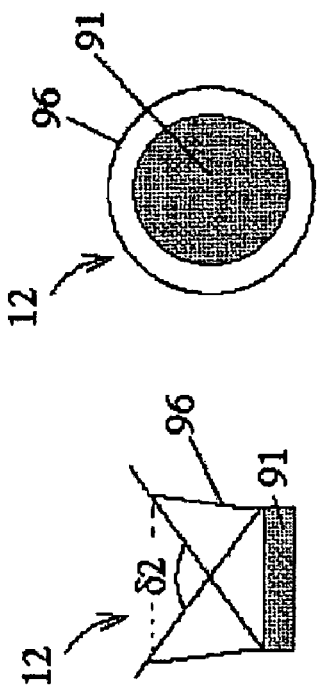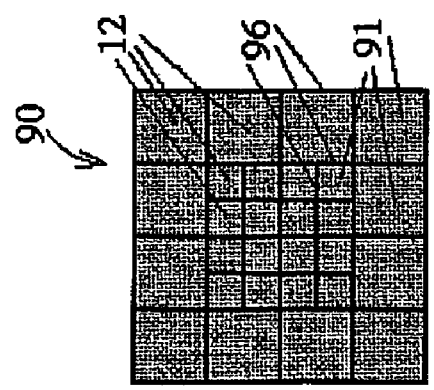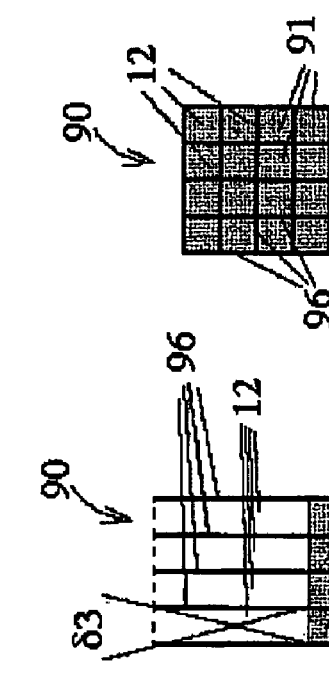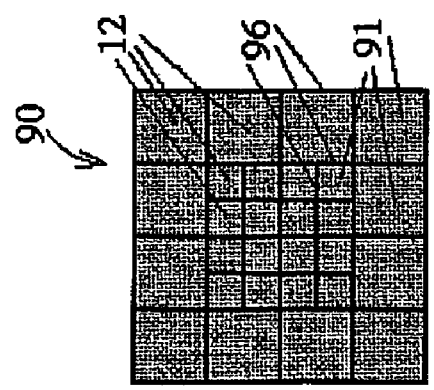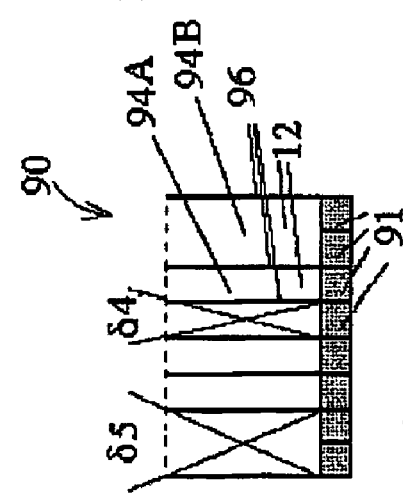

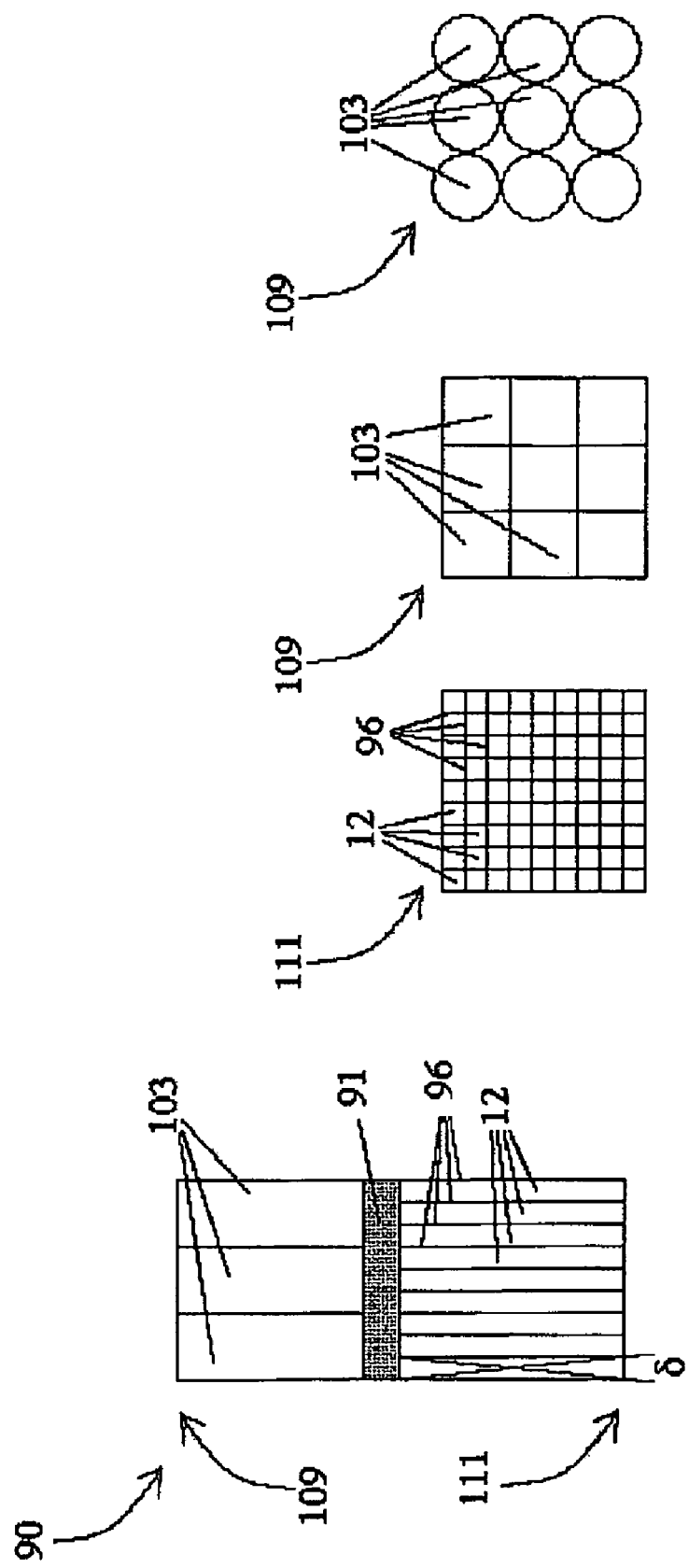

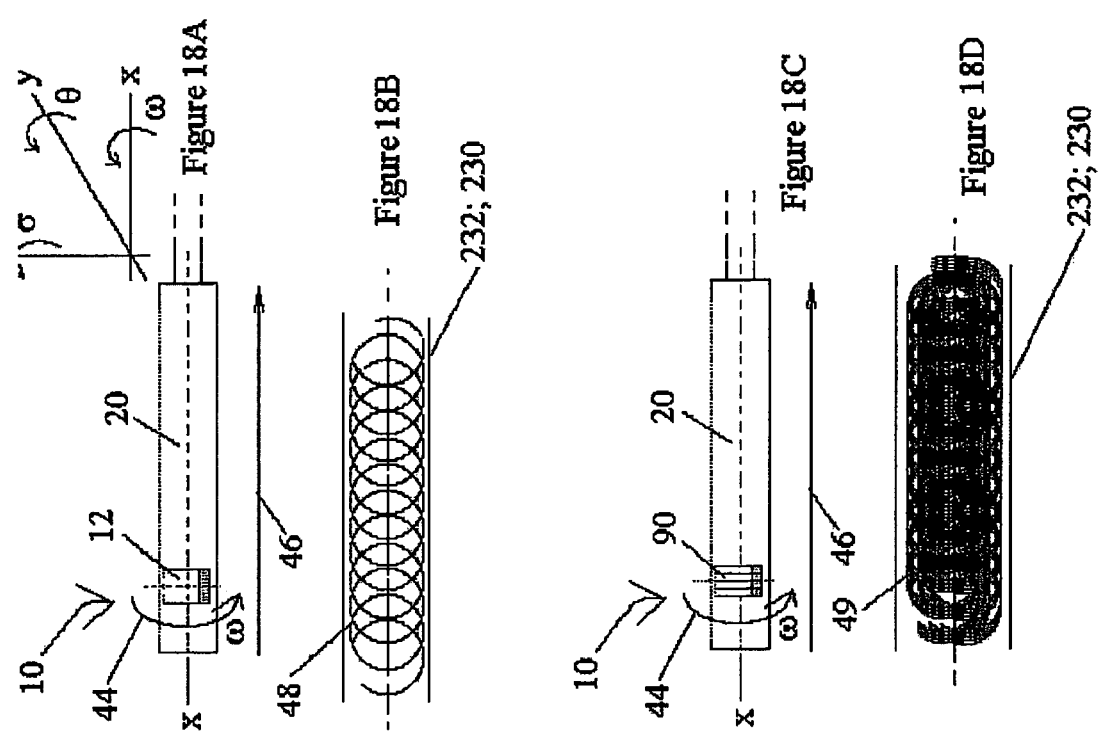

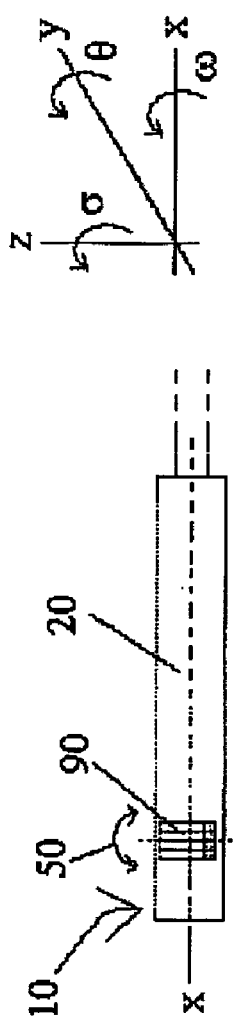
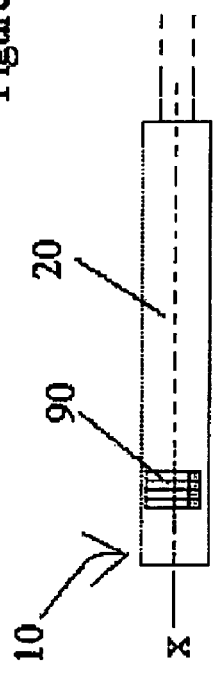
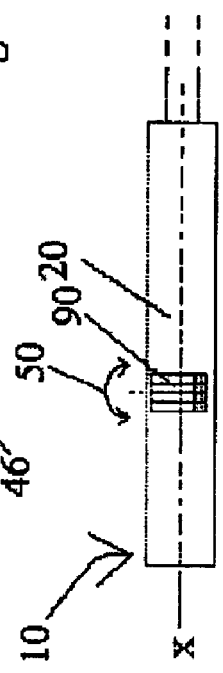
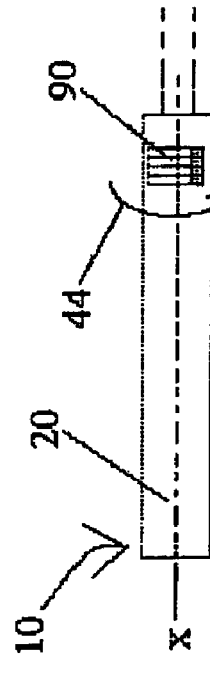
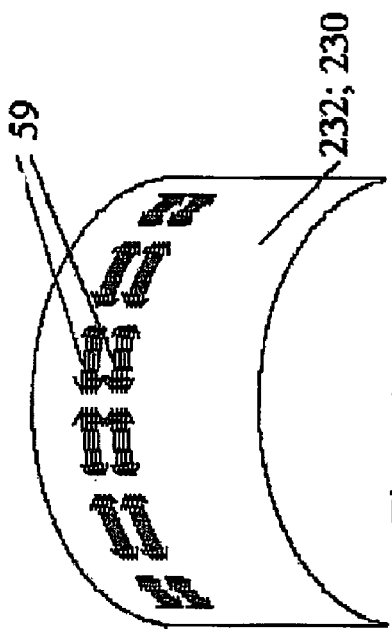

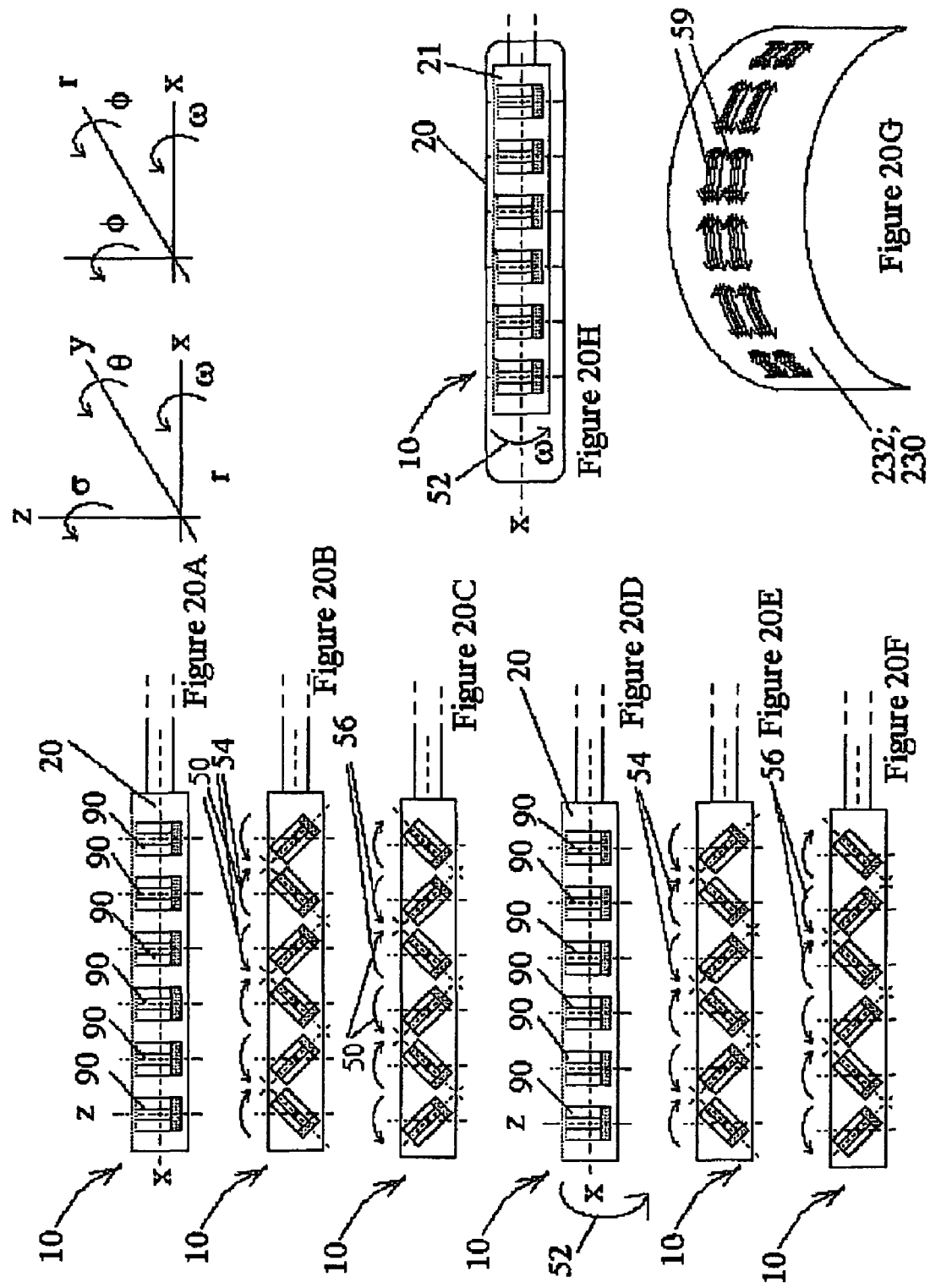

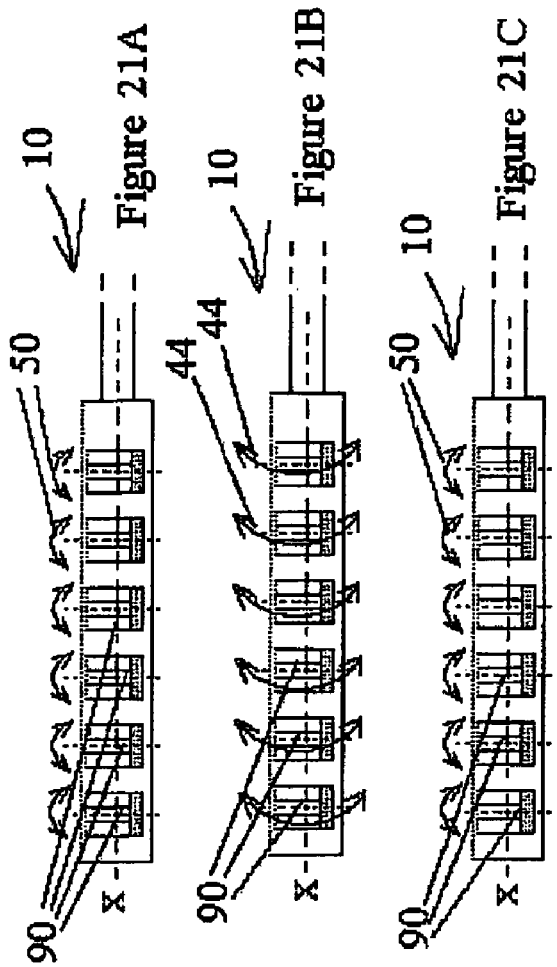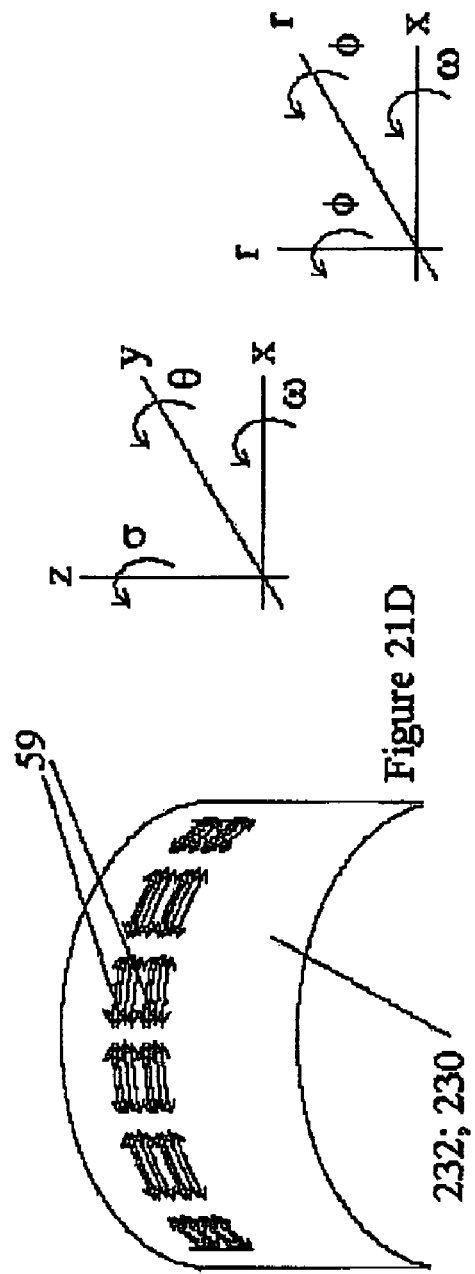

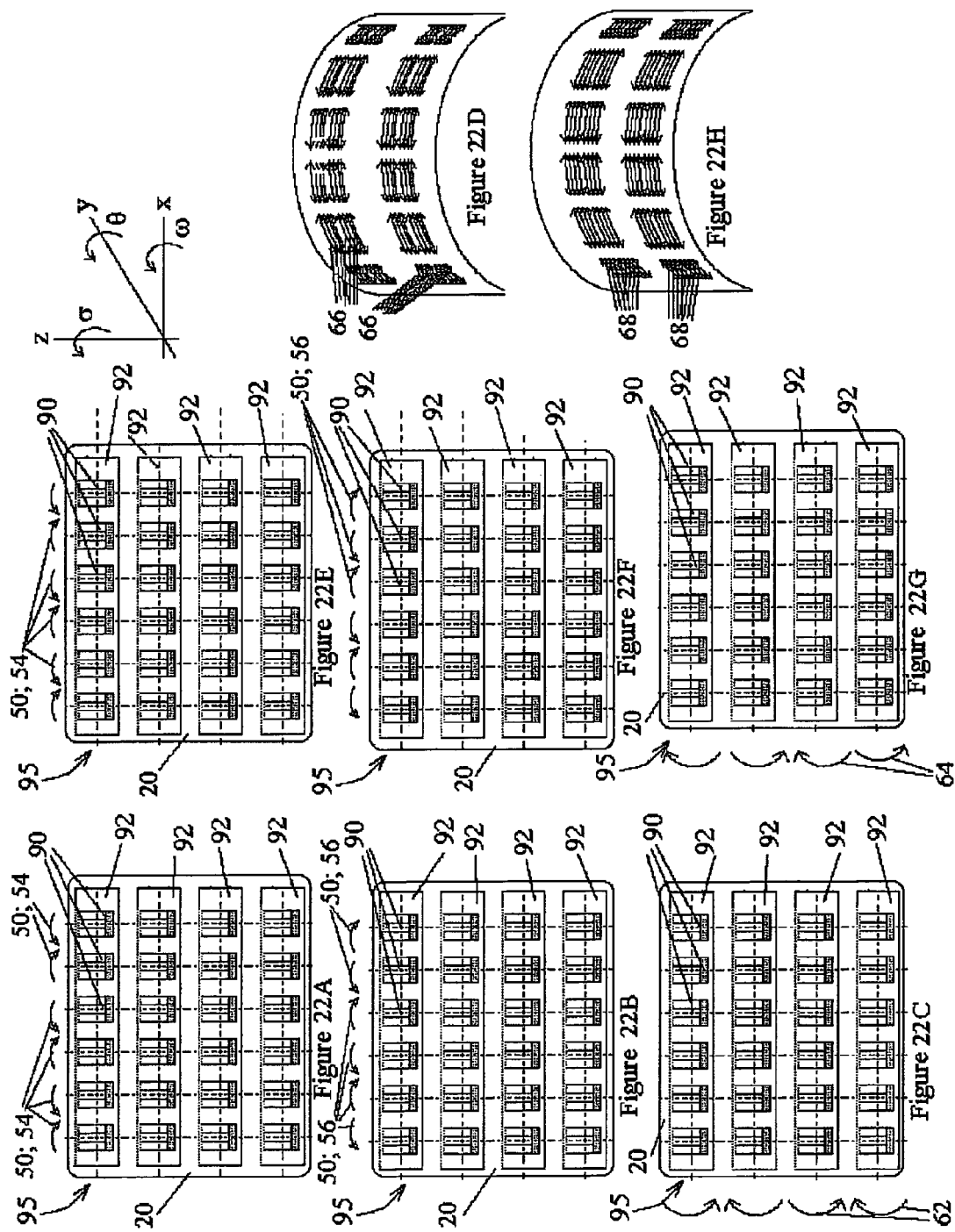

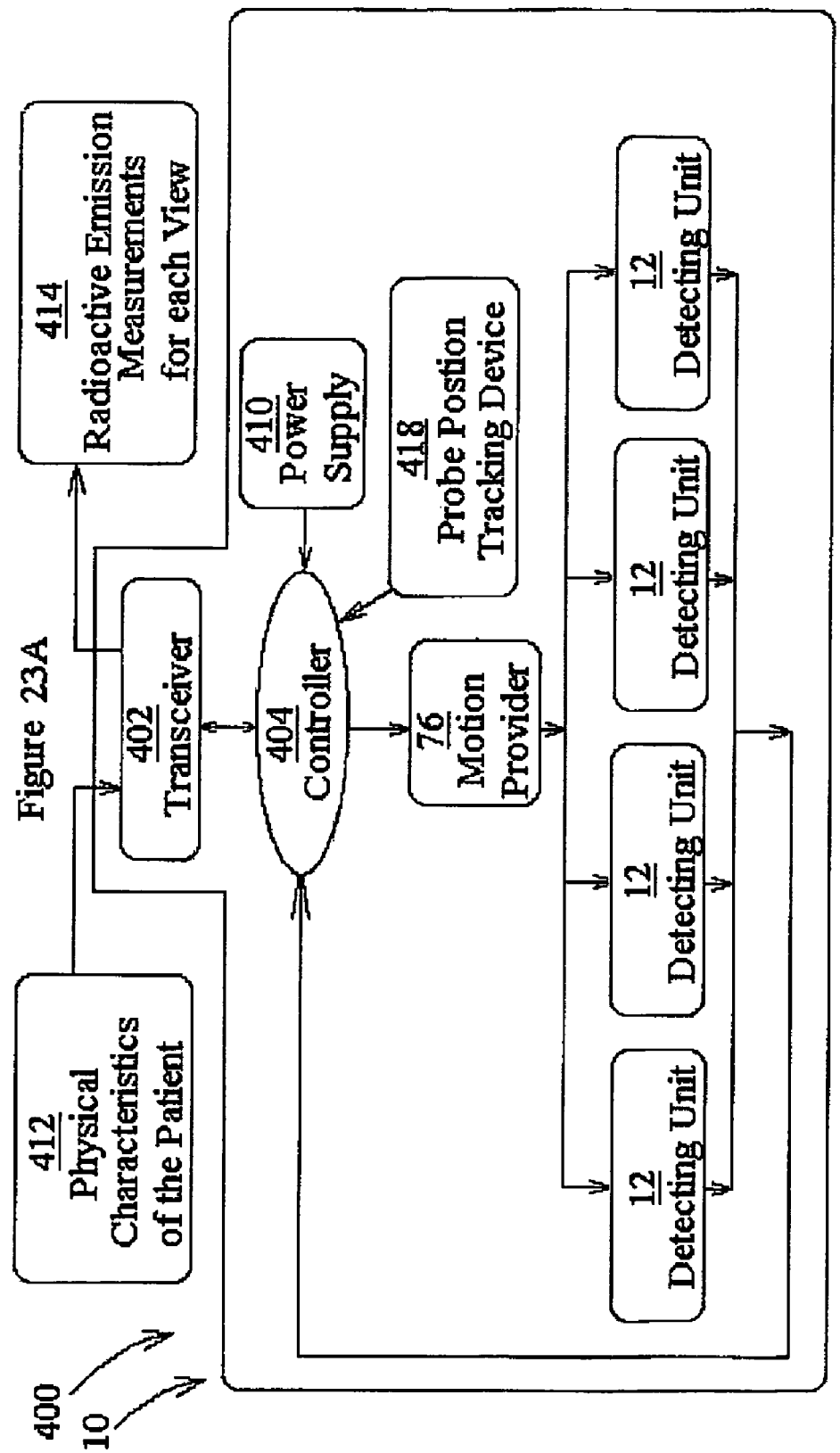

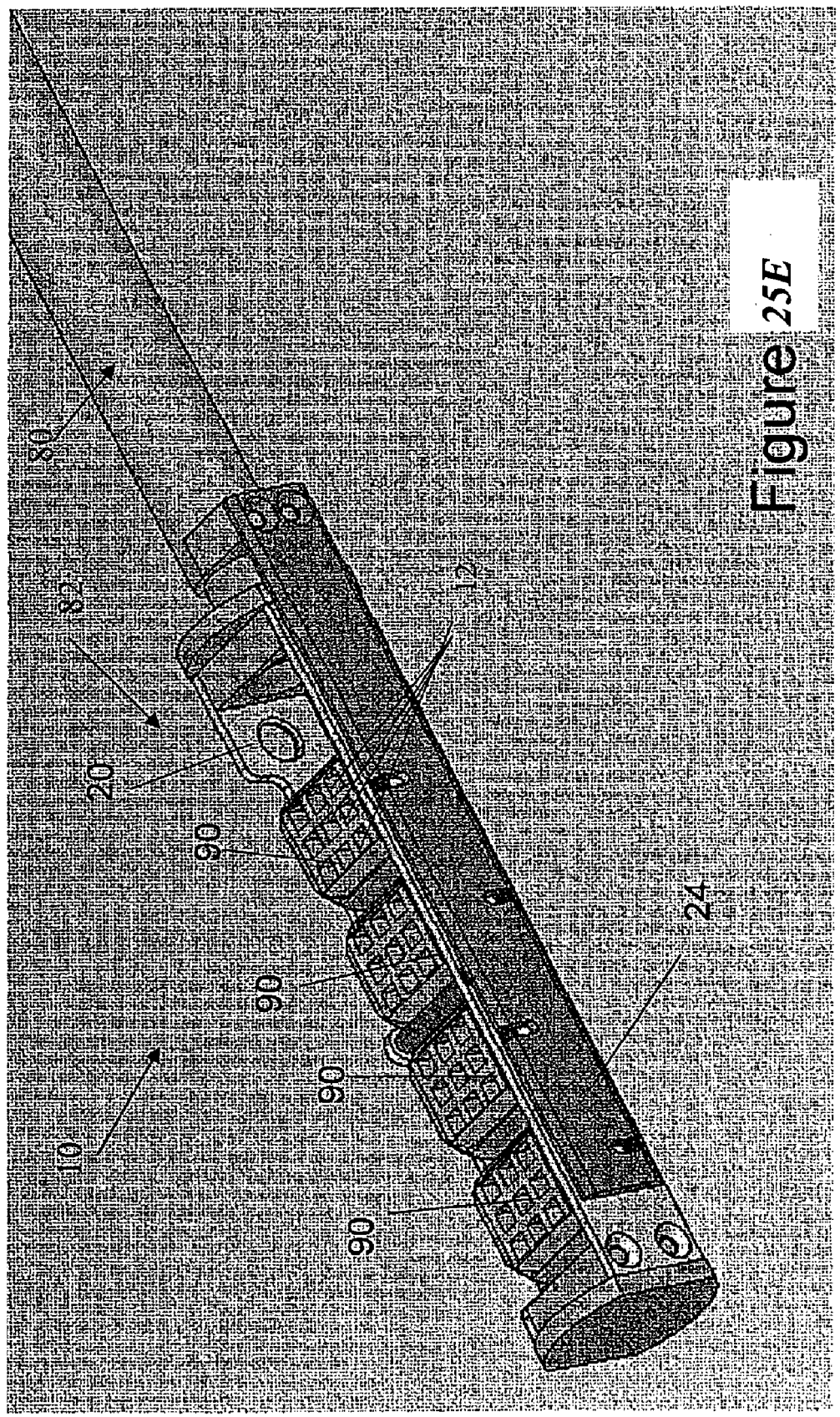

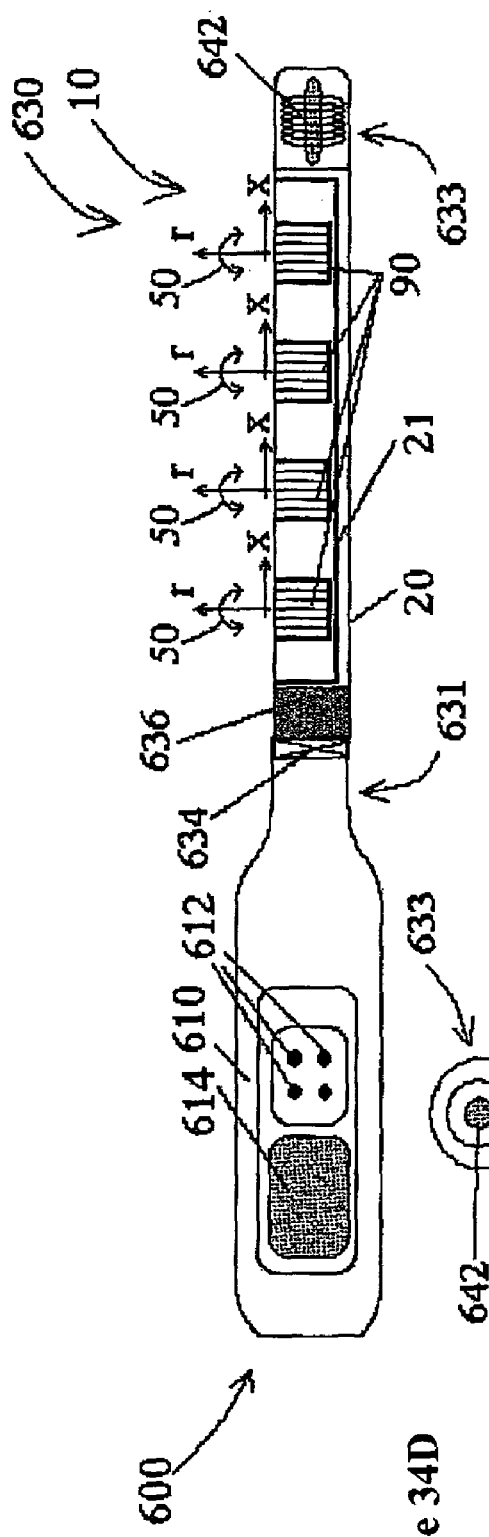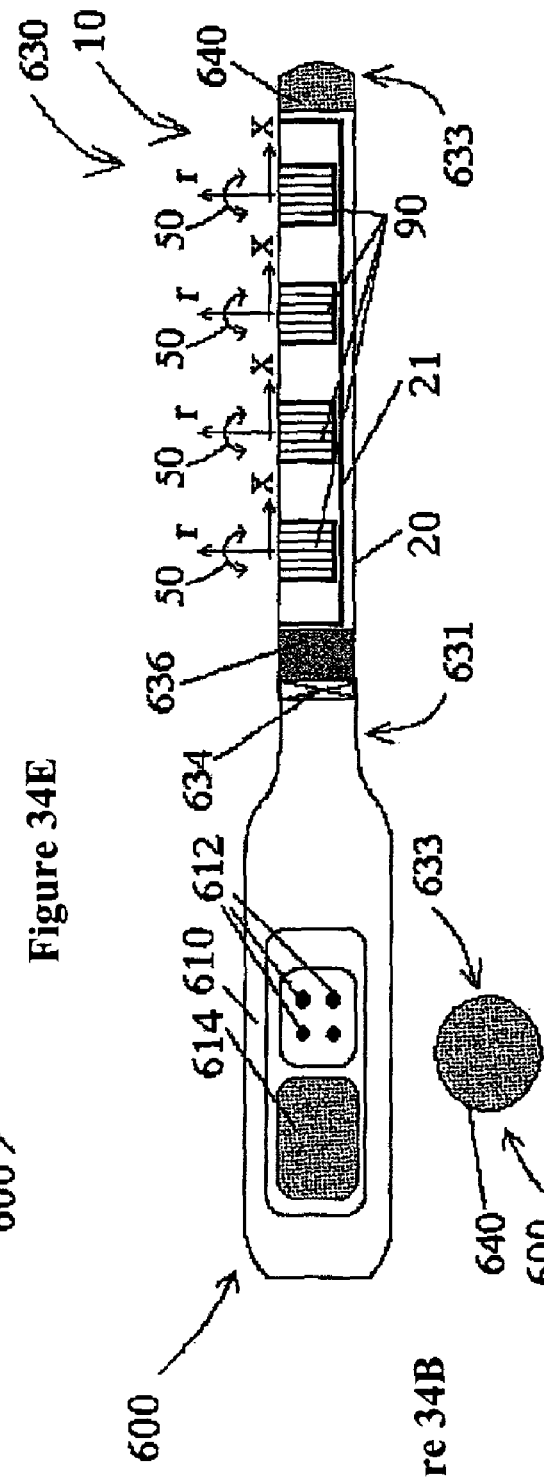
Figure 34D
Figure 34E
Figure 34B
Figure 34C

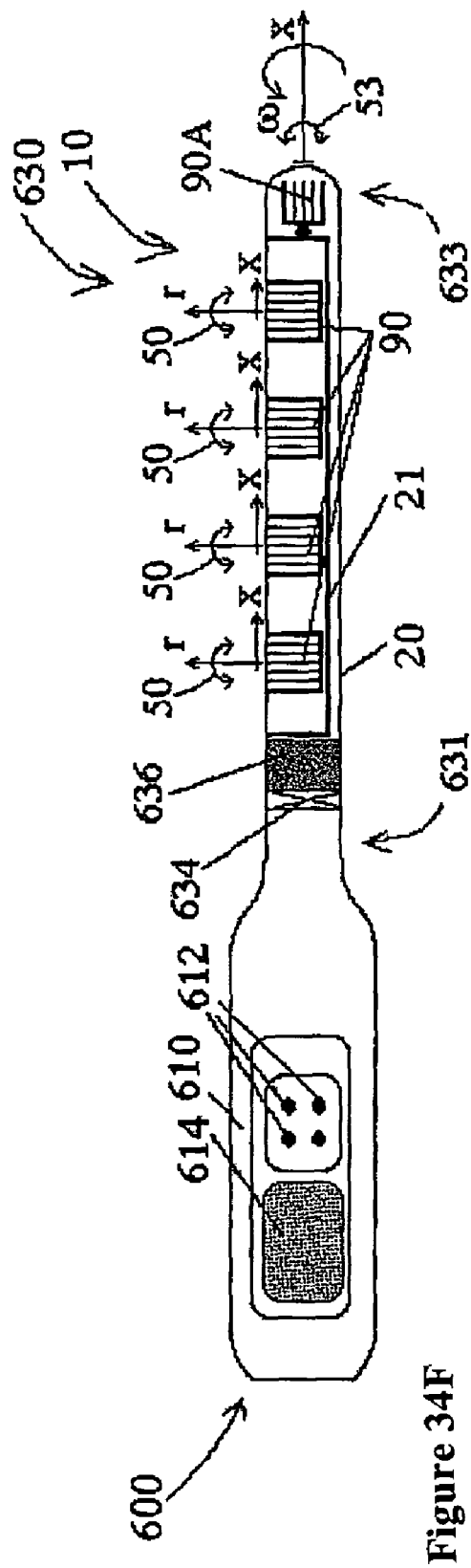
Figure 34F
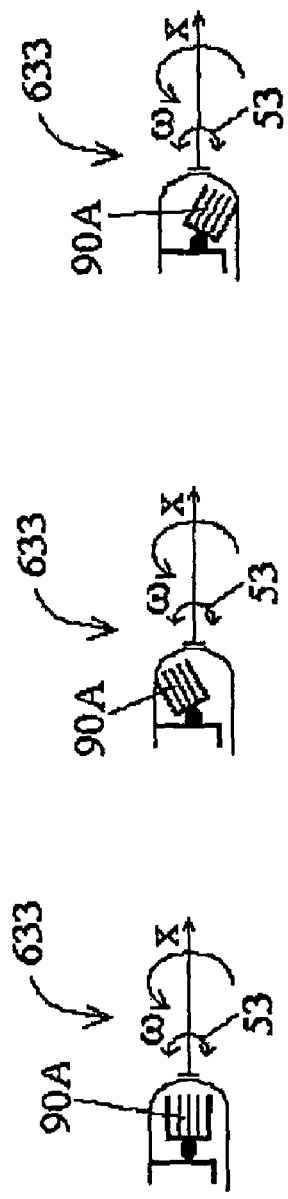
Figure 34G
Figure 34H
Figure 34I

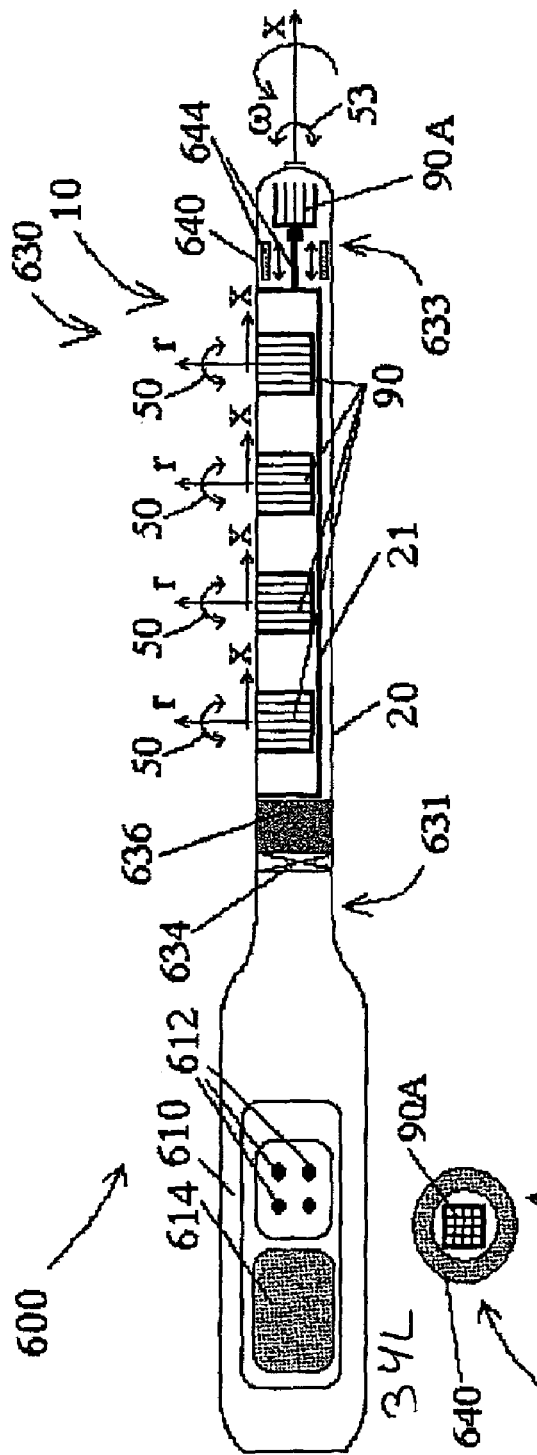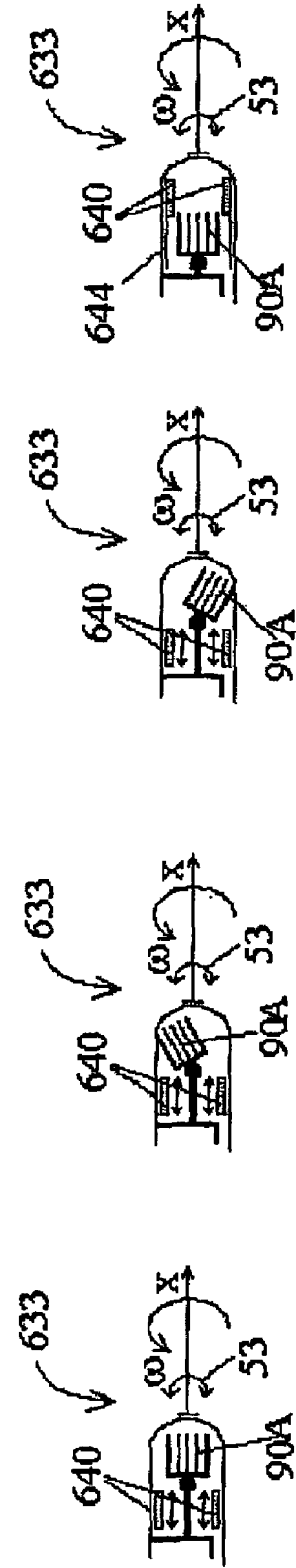
Figure 34L
Figure 34M
Figure 34N
Figure 34O
Figure 34P
Figure 34Q

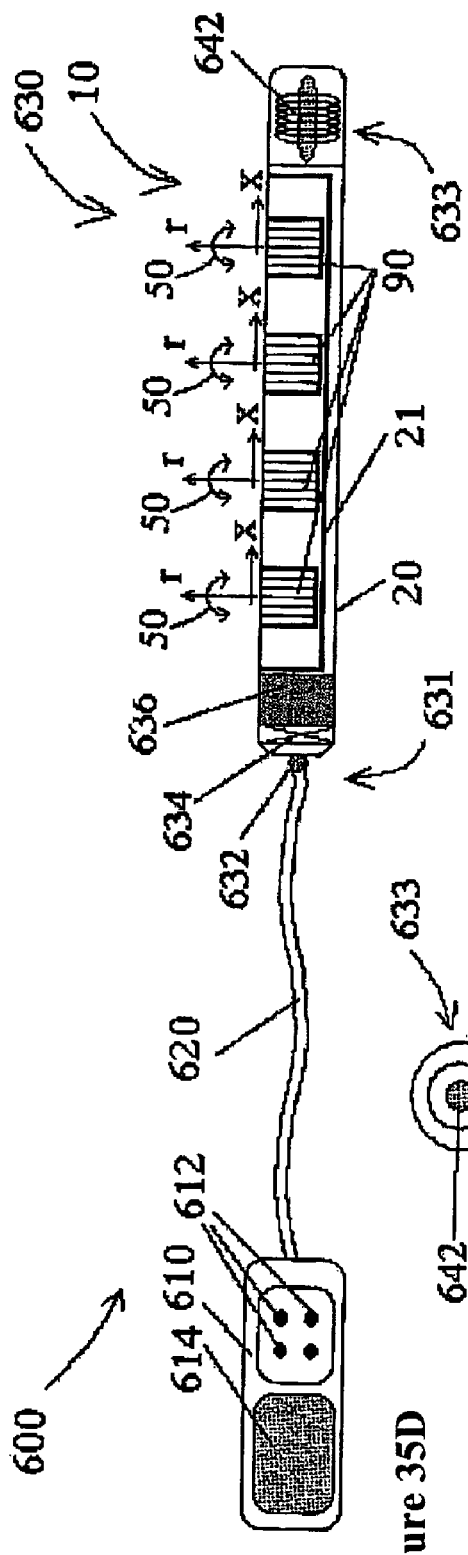
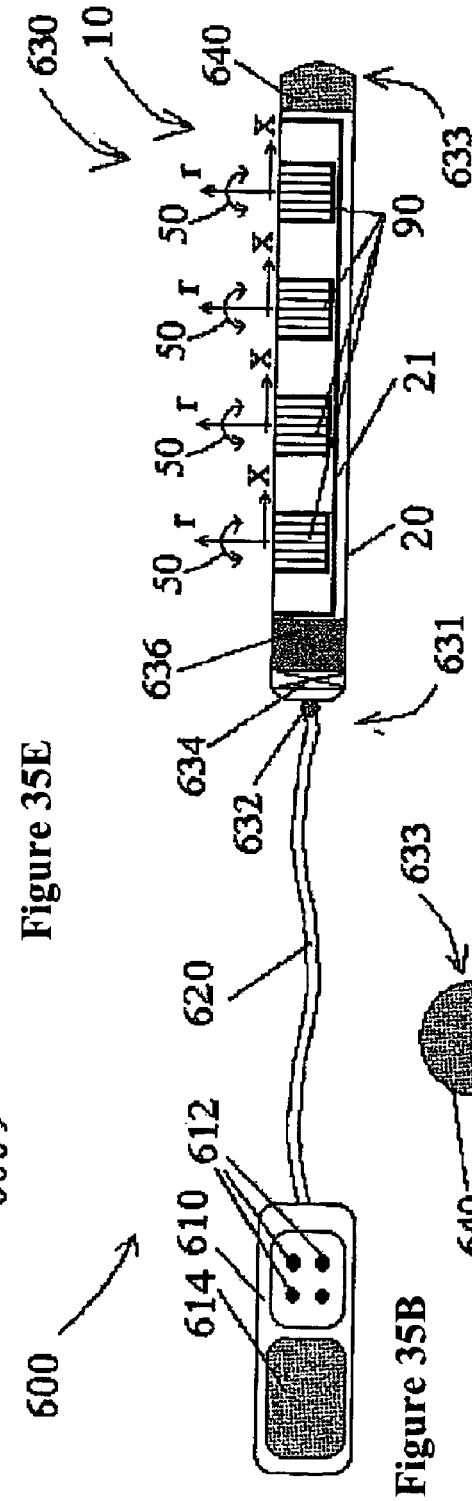
Figure 35D
Figure 35E
Figure 35B
Figure 35C

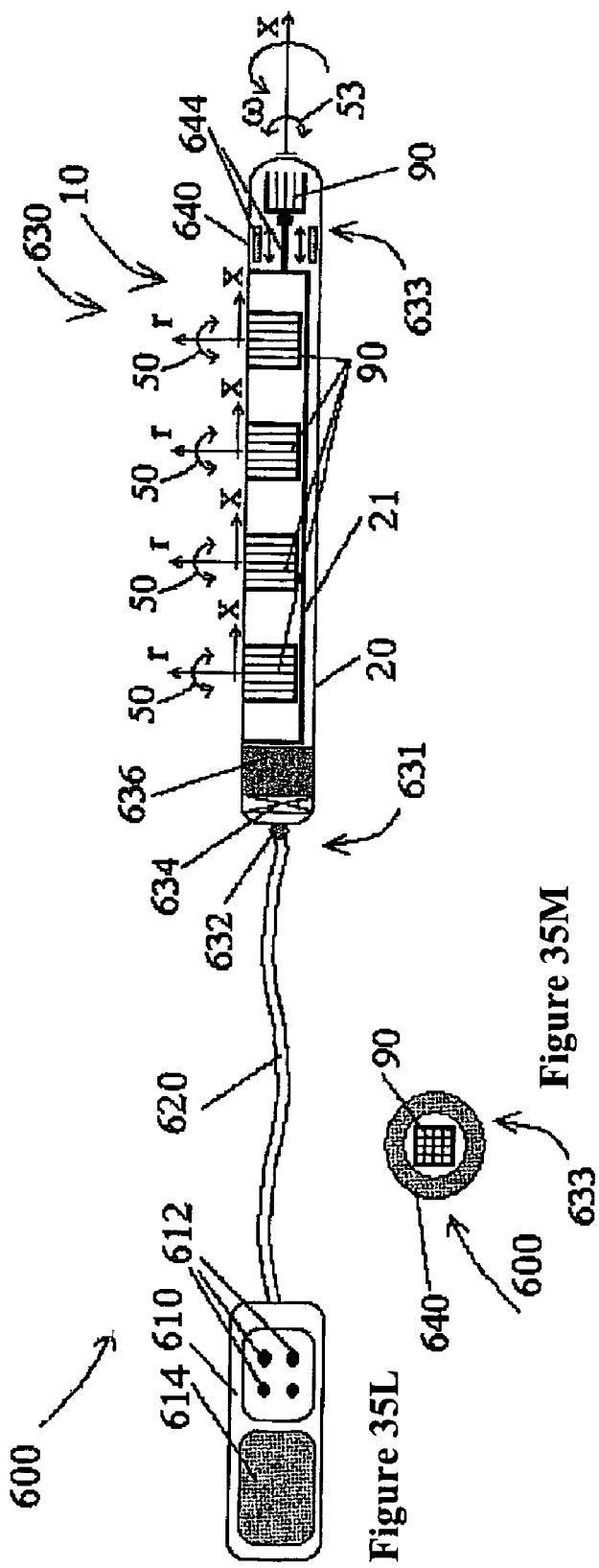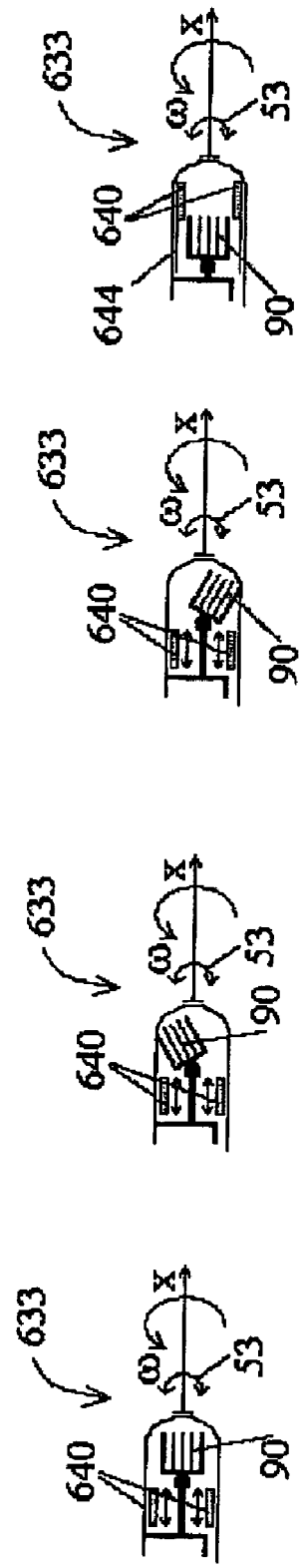
Figure 35L
Figure 35M
Figure 35N
Figure 35O
Figure 35P
Figure 35Q

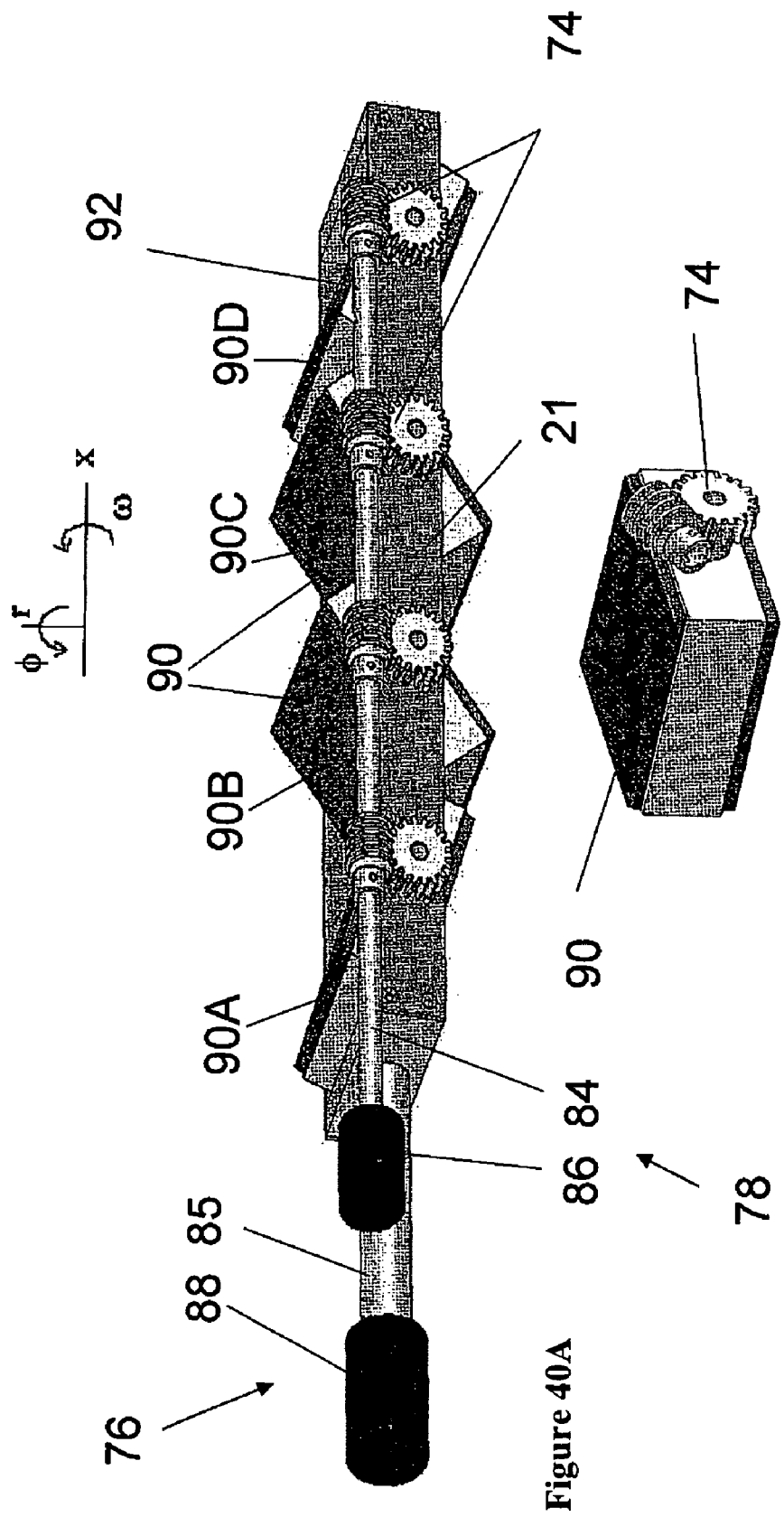

Design Elements
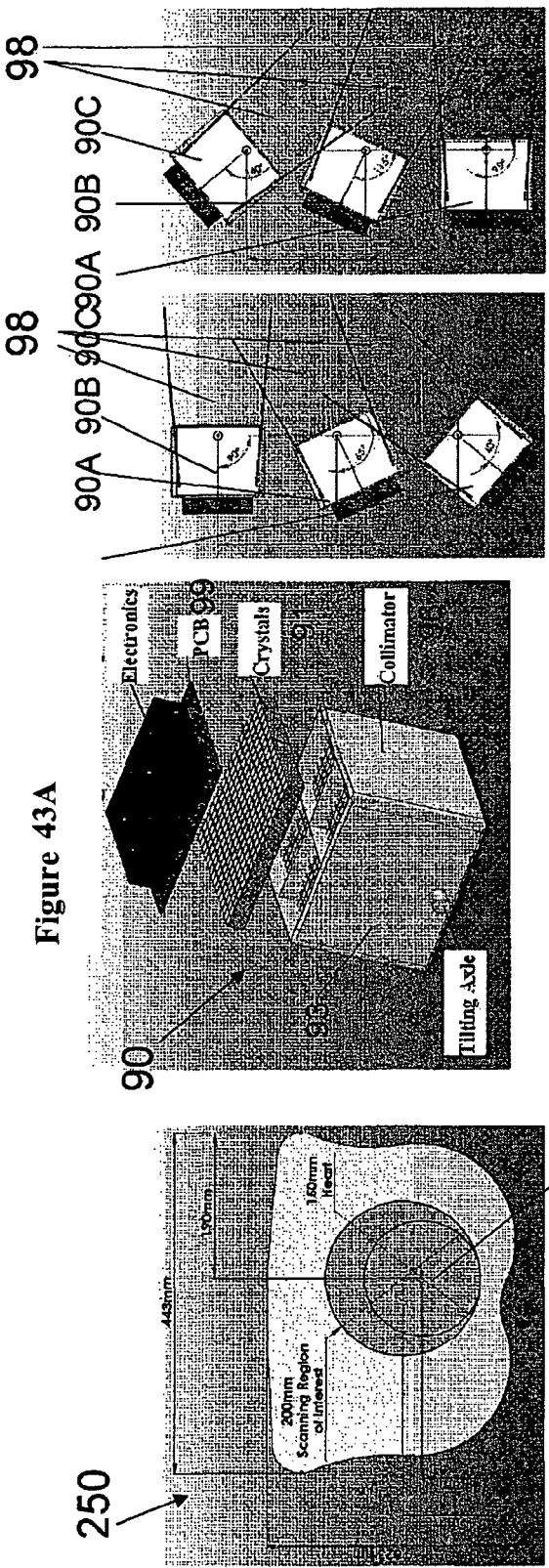
Figure 43A
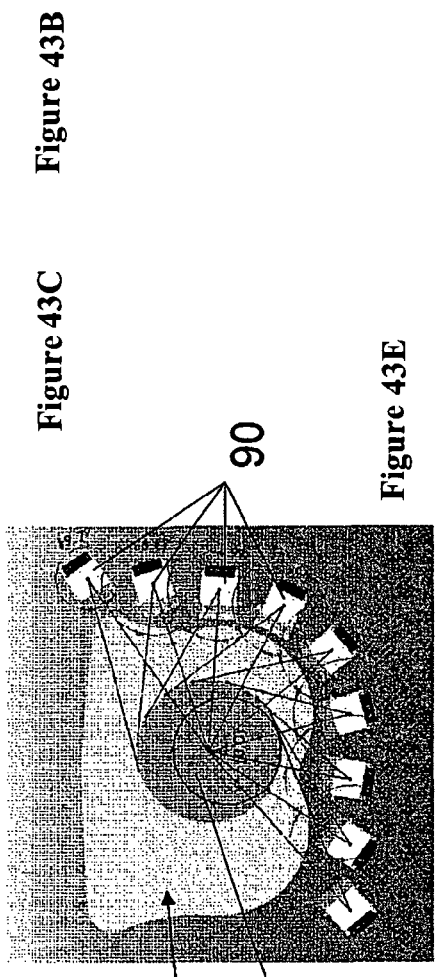
Figure 43B
Figure 43C
Figure 43E
Figure 43D

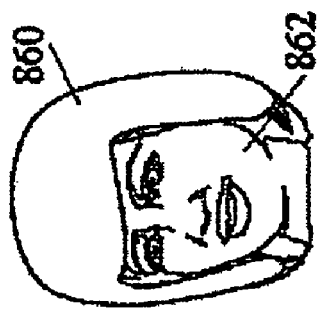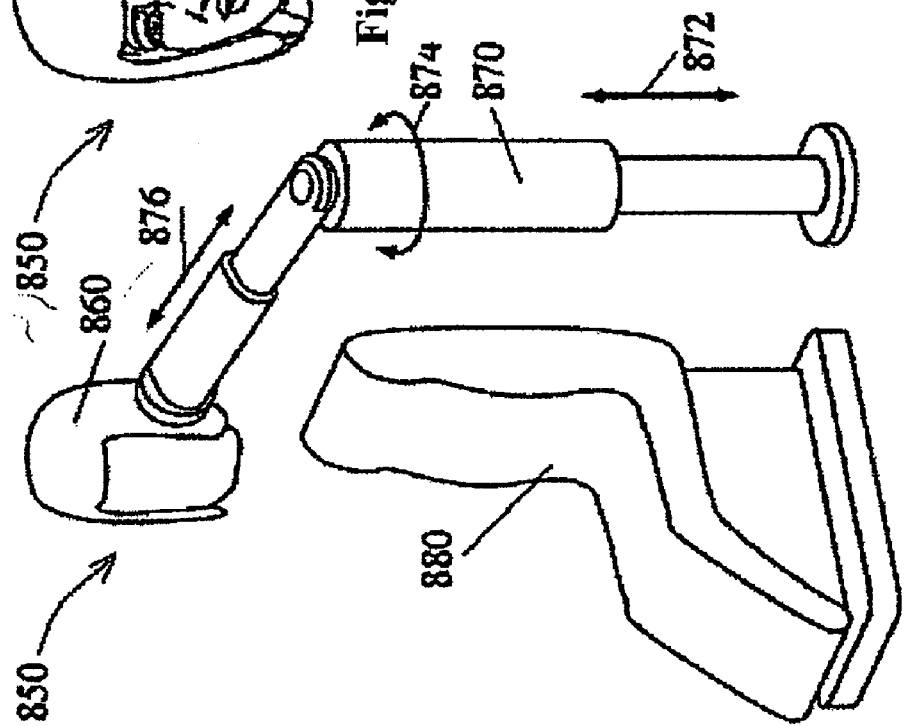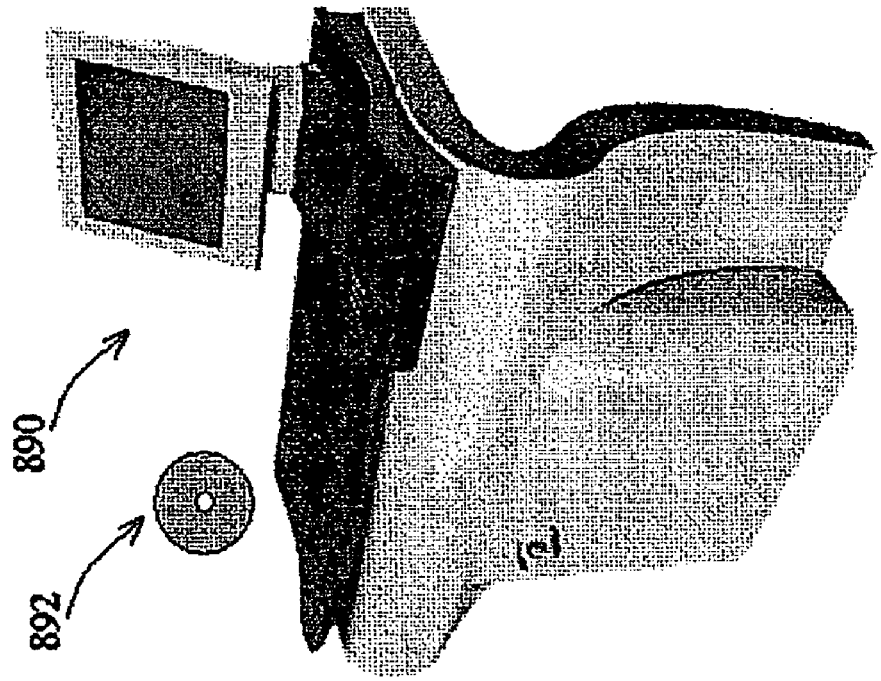

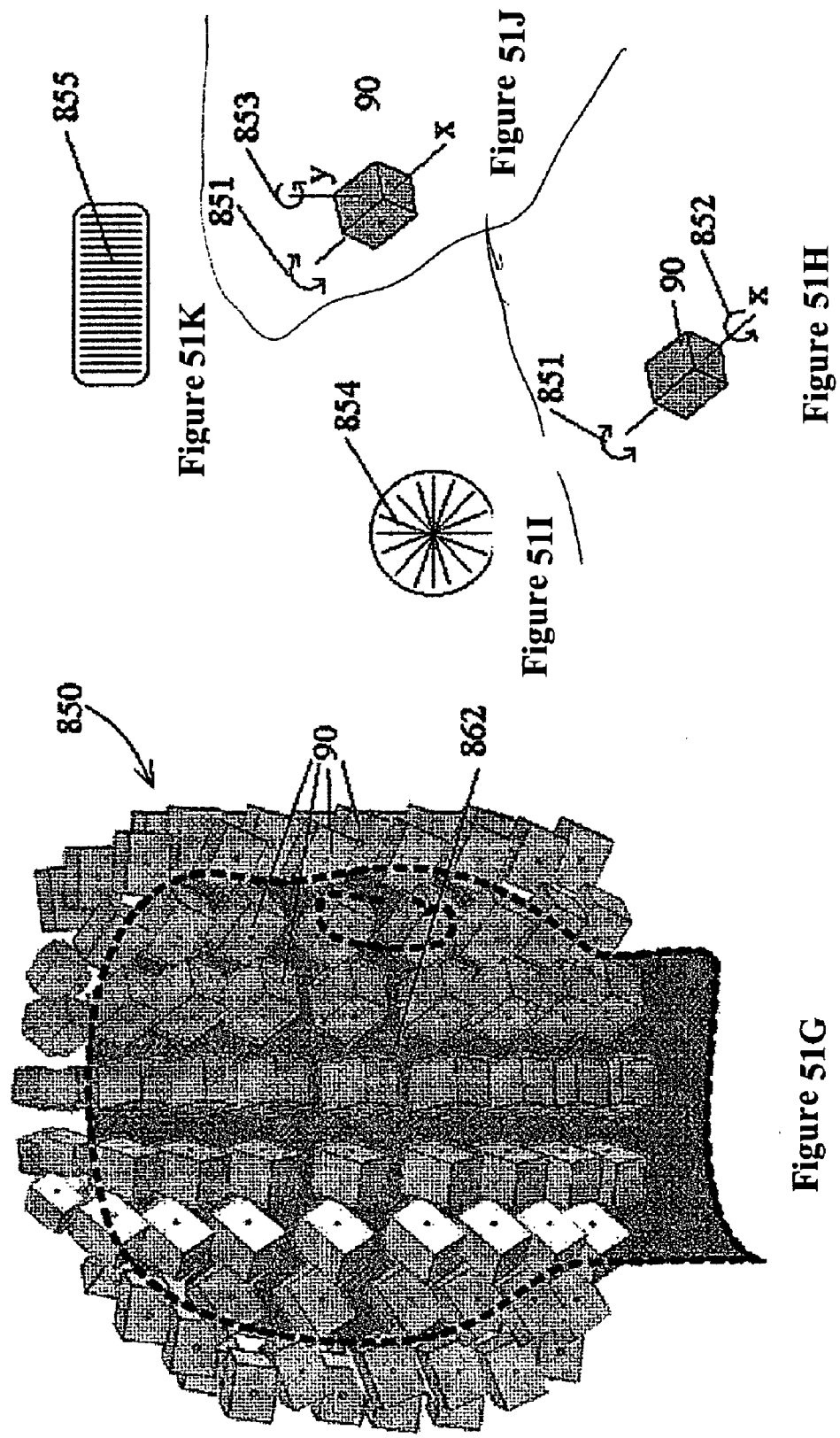

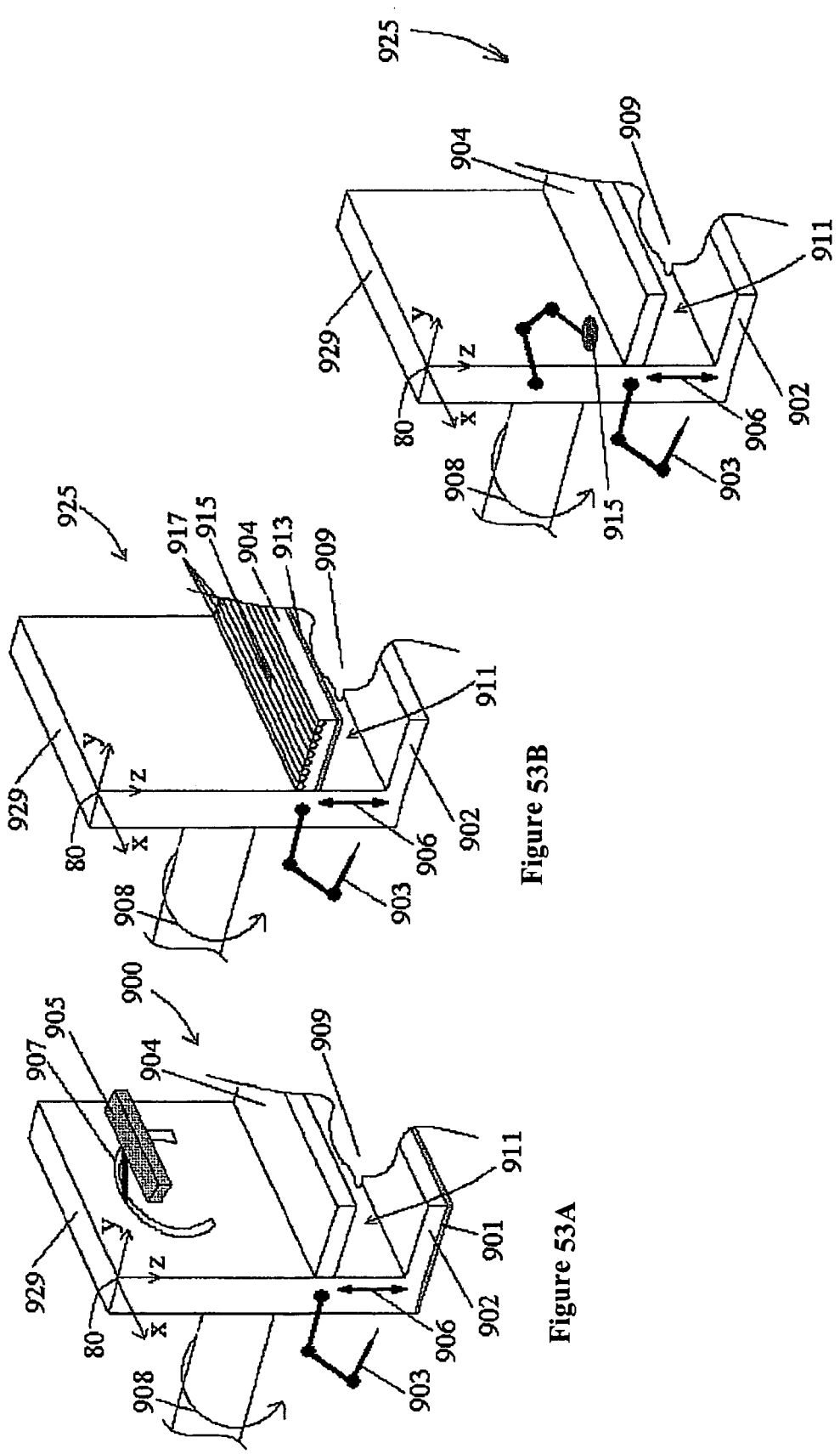

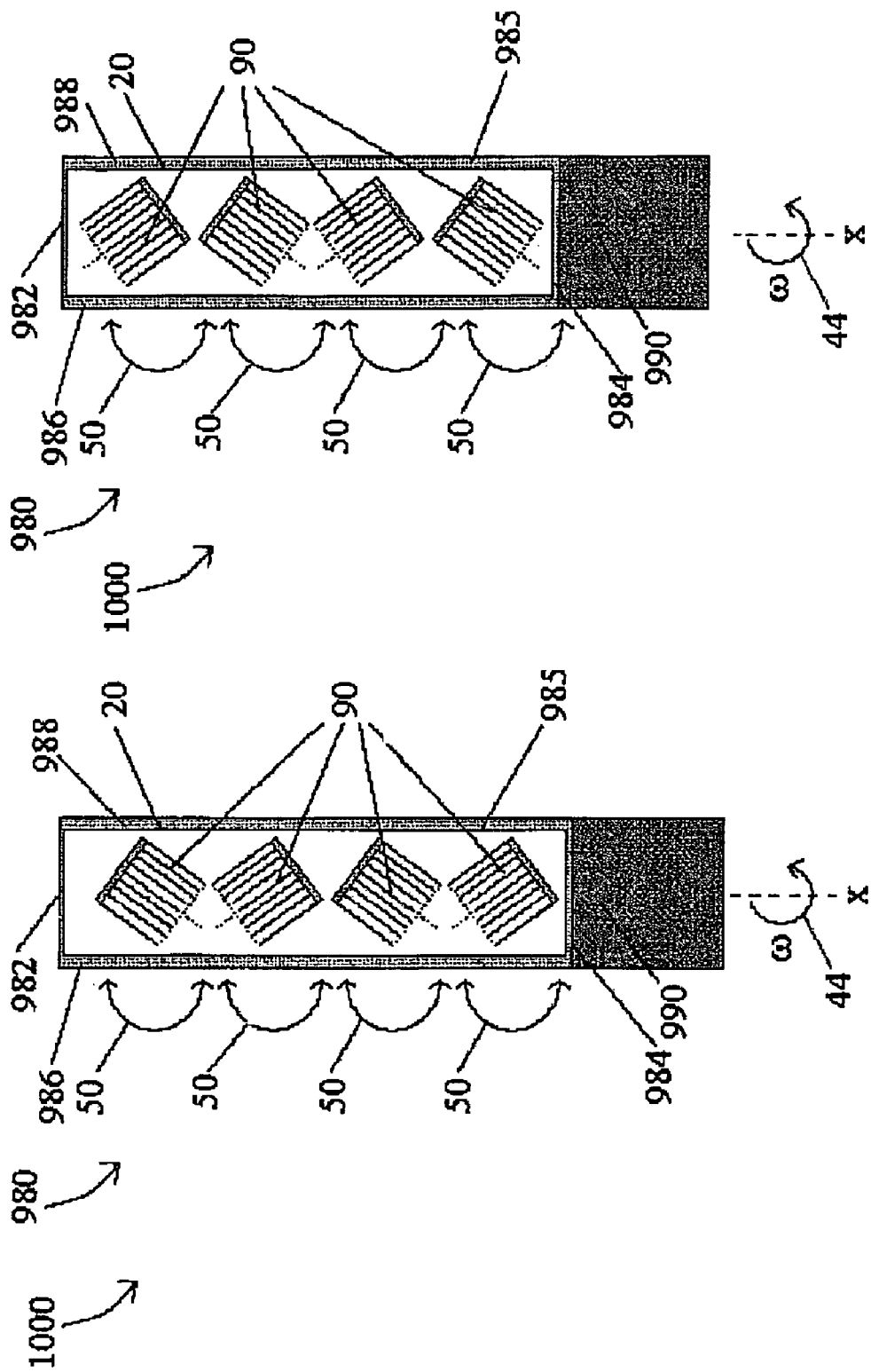

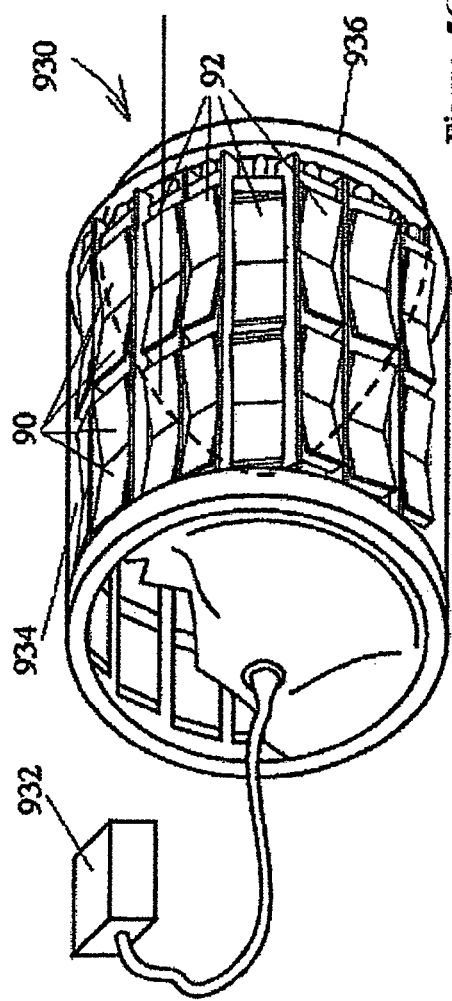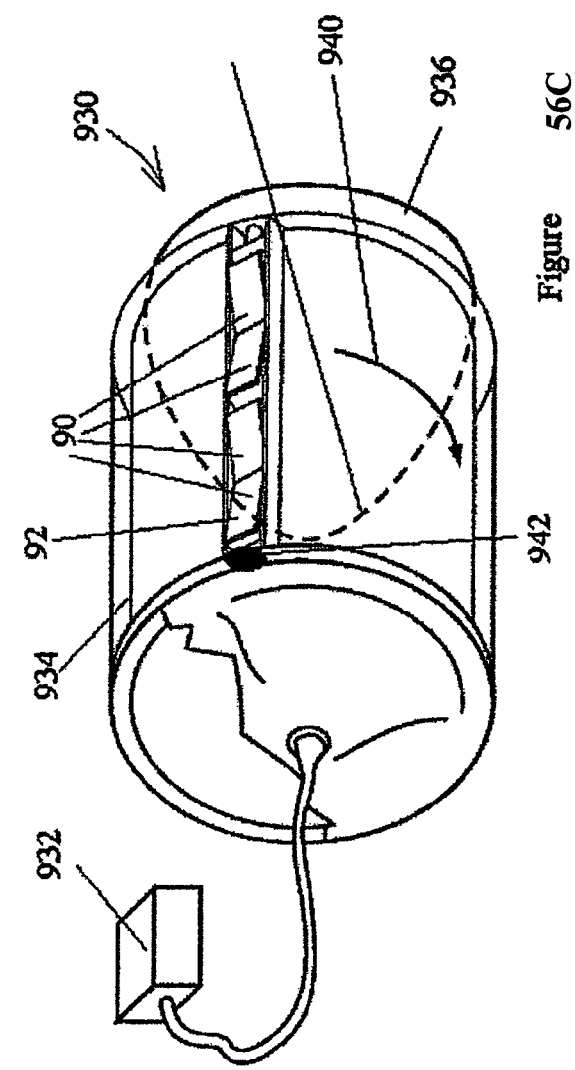
Figure 56B
Figure 56C

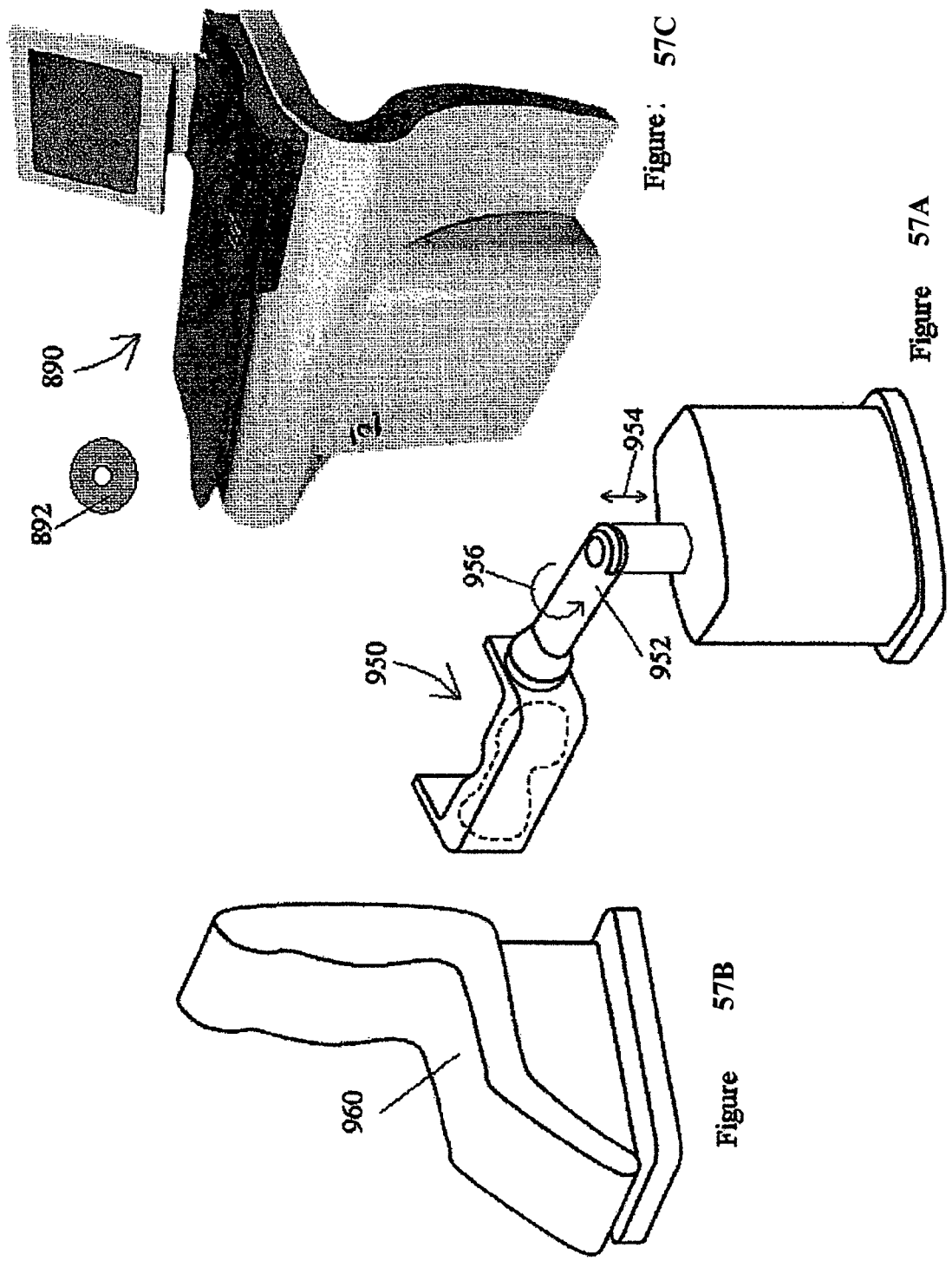

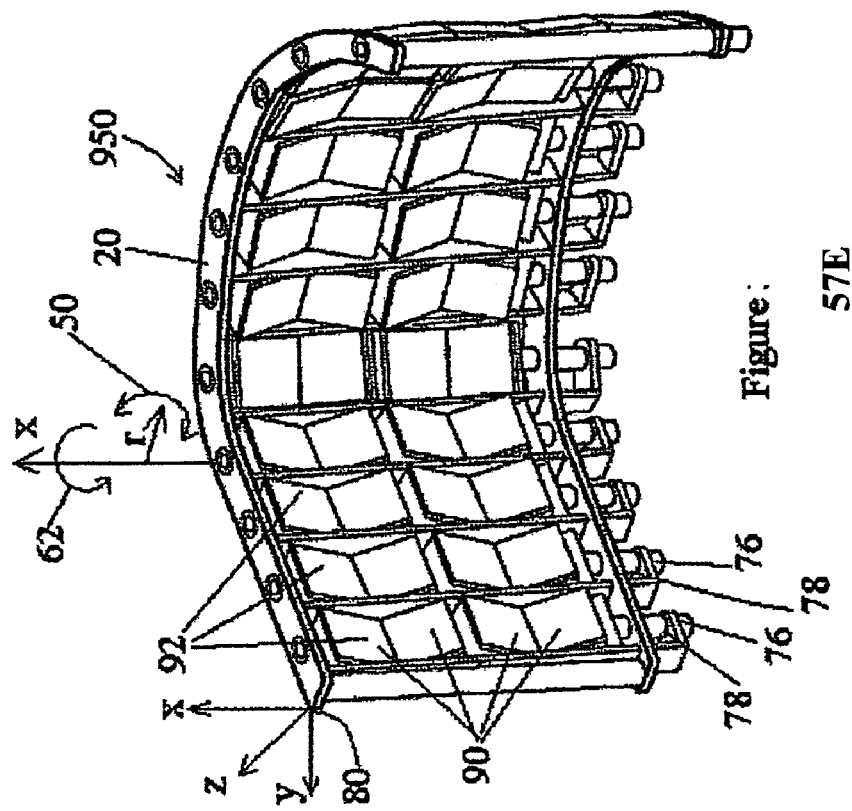
Figure: 57E
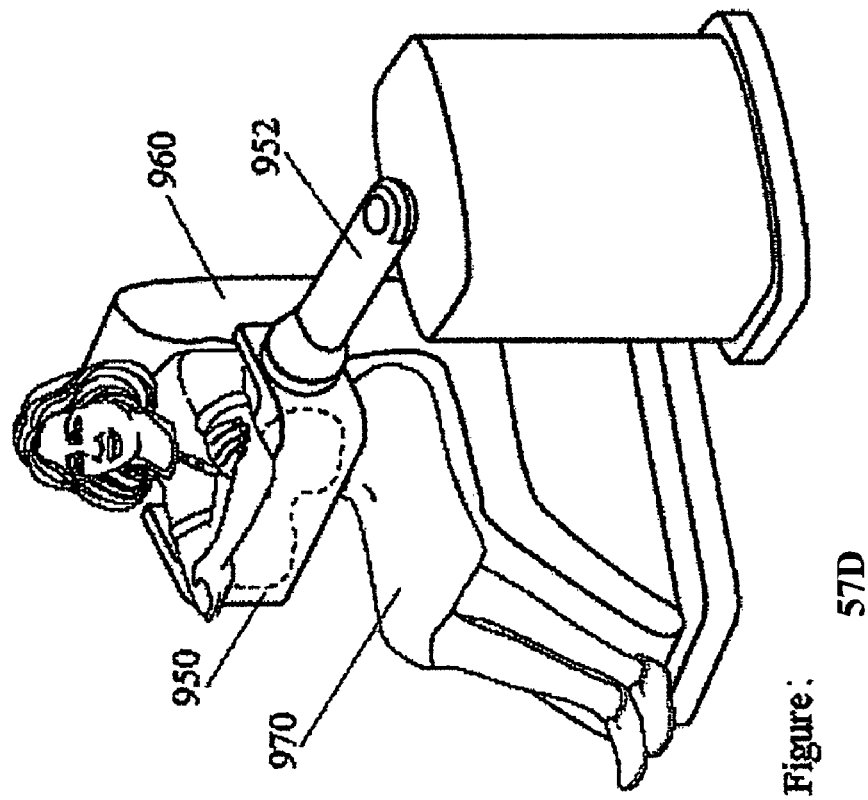
Figure: 57D

RADIOACTIVE-EMISSION-MEASUREMENT OPTIMIZATION TO SPECIFIC BODY STRUCTURES

RELATED APPLICATIONS

This application is a continuation-in-part of PCT Patent Application No. PCT/IL2005/000575 filed on Jun. 1, 2005, which claims the benefit of U.S. Provisional Patent Application Nos. 60/648,690 filed on Feb. 2, 2005, 60/648,385 filed on Feb. 1, 2005, 60/640,215 filed on Jan. 3, 2005, 60/636,088 filed on Dec. 16, 2004, 60/635,630 filed on Dec. 14, 2004, 60/632,515 filed on Dec. 3, 2004, 60/632,236 filed on Dec. 2, 2004, 60/630,561 filed on Nov. 26, 2004, 60/625,971 filed on Nov. 9, 2004 and 60/575,369 filed on Jun. 1, 2004.

This application is also a continuation-in-part of U.S. patent application Ser. No. 09/641,973 filed on Aug. 21, 2000.

This application is also a continuation-in-part of U.S. patent application Ser. No. 10/343,792 filed on Feb. 4, 2003.

This application is also a continuation-in-part of U.S. patent application Ser. No. 10/616,307 filed on Jul. 10, 2003.

This Application is also a continuation-in-part of U.S. patent application Ser. No. 10/533,568 filed on May 3, 2005.

All of the above Applications are incorporated herein by reference

FIELD AND BACKGROUND OF THE INVENTION

The present invention relates to nuclear imaging and more particularly, to systems, methods, and probes for radioactive-emission-measurement optimization to specific body structures, possibly together with structural imaging, for example, by x-rays, ultrasound, or MRI.

Radioactive-emission imaging relies on the fact that in general, pathologies, such as malignant tumors, malfunctioning organs, and inflammations, display a level of activity different from that of healthy tissue. Thus, radiopharmaceutical, which circulate in the blood stream, are picked up by the active pathologies to a different extent than by the surrounding healthy tissue; in consequence, the pathologies are operative as radioactive-emission sources and may be detected by radioactive-emission imaging.

The pathological feature may appear as a concentrated source of high radiation, or a hot region, as may be associated with a tumor, or as a region of low-level radiation, which is nonetheless above the background level, as may be associated with carcinoma. Additionally, a reversed situation is possible. Dead tissue has practically no pick up of radiopharmaceuticals, and is thus operative as a region of little radiation, or a cold region, below the background level.

Thus radiopharmaceuticals may be used for identifying active pathologies as well as dead tissue, and the image that is constructed is generally termed, a functional image.

The mechanism of localization of a radiopharmaceutical in a particular organ of interest depends on various processes in the organ of interest, such as antigen-antibody reactions, physical trapping of particles, receptor site binding, removal of intentionally damaged cells from circulation, and transport of a chemical species across a cell membrane and into the cell by a normally operative metabolic process. A summary of the mechanisms of localization by radiopharmaceuticals is described in http://www.lunis.luc.edu/nucmed/tutorial/radpharm/i.htm. For example:

1. Active transport involves the use of a normally operative metabolic pathway in the body, for moving a radiopharmaceutical across a cell membrane and into the cell. An example of a radiopharmaceutical that may be used for active transport is $I^{131}$ in the form of NaI, for thyroid imaging.

2. Phagocytosis involves physical entrapment of colloidal particles by Kupffer cells in the RE System. An example of a radiopharmaceutical that may be used for phagocytosis is $Tc^{99m}$ in the form of sulfur colloid, for liver and spleen imaging.

3. Capillary blockage involves intentional microembolization of a capillary bed with particles. An example of a radiopharmaceutical that may be used for capillary blockage is $Tc^{99m}$ in the form of MAA, for pulmonary perfusion imaging.

4. Cell sequestration involves injection of damaged RBC's to produce a spleen scan with no visualization of the liver. An example of a radiopharmaceutical that may be used for cell sequestration is heat damaged autologous $Tc^{99m}$ RBC's.

5. Simple or exchange diffusion involves a mechanism whereby a radiotracer diffuses across cell membranes and then binds or attaches itself to a cell component. An example of a radiopharmaceutical that may be used for simple or exchange diffusion is $F^{18}$, in the form of NaF, for bone imaging.

6. Compartmental Localization involves placement of a radiotracer in a fluid space and imaging of that fluid space. Examples of radiopharmaceuticals that may be used for compartmental localization are $Tc^{99m}$ HAS, for MUGA's, $In^{111}$ DTPA, for cistemograms, and $Xe^{133}$ gas for pulmonary perfusion.

7. Chemisorption involves surface binding of radiopharmaceutical to a solid structure. An example of a radiopharmaceutical that may be used for chemisorption is $In^{111}$ platelets bound to a surface of an active thrombus.

8. Antigen or antibody reaction involves uptake at tumor site due to specific binding of radiolabeled antibody to surface antigens on tumors. Examples of radiopharmaceuticals that may be used for antigen or antibody reaction are $In^{111}$ Oncoscint, for the localization of recurrent ovarian or colorectal carcinoma, or $In^{111}$ ProstaScint for the localization or recurrent cancer.

9. Receptor binding involves the binding of a radiopharmaceutical to high-affinity receptor sites. An example of a radiopharmaceutical that may be used for receptor binding is $In^{111}$ octreotide, for localization of neuroendocrine and other tumors based on binding of a somatostatin analog to receptor sites in tumors.

Examples of other radiopharmaceuticals include the following:

1. anti-CEA, a monoclonal antibody fragment, which targets CEA—produced and shed by colorectal carcinoma cells—and may be labeled by $Tc^{99m}$ or by other radioisotopes, for example, iodine isotopes (Jessup J M, 1998, Tumor markers—prognostic and therapeutic implications for colorectal carcinoma, Surgical Oncology; 7: 139-151);

2. $In^{111}$-Satumomab Pendetide (Oncoscint®), designed to target TAG-72, a mucin-like glycoprotein, expressed in human colorectal, gastric, ovarian, breast and lung cancers, but rarely in healthy human adult tissues (Molinolo A; Simpson J F; et al., 1990, Enhanced tumor binding using immunohistochemical analyses by second generation anti-tumor-associated glycoprotein 72 monoclonal antibodies versus monoclonal antibody B72.3 in human tissue, Cancer Res., 50(4): 1291-8);

3. Lipid-Associated Sialic Acid (LASA), a tumor antigen, used for colorectal carcinoma, with a similar sensitivity as anti-CEA monoclonal antibody fragment but a greater specificity for differentiating between benign and malignant lesions (Ebril K M, Jones J D, Klee G G, 1985, Use and limitations of serum total and lipid-bound sialic acid concentrations as markers for colorectal cancer, Cancer; 55:404-409);

4. Matrix Metaloproteinase-7 (MMP-7), a proteins enzyme, believed to be involved in tumor invasion and metastasis (Mori M, Barnard G F et al., 1995, Overexpression of matrix metalloproteinase-7 mRNA in human colon carcinoma, Cancer; 75: 1516-1519);

5. $Ga^{67}$ citrate, used for detection of chronic inflammation (Mettler F A, and Guiberteau M J, Eds., 1998, Inflammation and infection imaging, Essentials of nuclear medicine, Fourth edition, Pgs: 387-403);

6. Nonspecific-polyclonal immunoglobulin G (IgG), which may be labeled with both $In^{111}$ or $Tc^{99m}$, and which has a potential to localize nonbacterial infections (Mettler F A, and Guiberteau M J, ibid);

7. Radio-labeled leukocytes, such as such as $In^{111}$ oxine leukocytes and $Tc^{99m}$ HMPAO leukocytes, which are attracted to sites of inflammation, where they are activated by local chemotactic factors and pass through the endothelium into the soft tissue (Mettler F A, and Guiberteau M J, ibid; Corstens F H; van der Meer J W, 1999, Nuclear medicine's role in infection and inflammation, Lancet; 354 (9180): 765-70); and 8. $Tc^{99m}$ bound to Sodium Pertechnetate, which is picked up by red blood cells, and may be used for identifying blood vessels and vital organs, such as the liver and the kidneys, in order to guide a surgical instrument without their penetration.

The particular choice of a radionuclide for labeling antibodies depends upon the chemistry of the labeling procedure and the isotope nuclear properties, such as, the number of gamma rays emitted, their respective energies, the emission of other particles, such as beta or positrons, the isotope half-life, and the existence of different isotopes of identical chemistry but different half-lives (e.g., $I^{131}$ and $I^{133}$). The usual preferred emission for medical applications is that of gamma rays, with an energy range of approximately 11-511 KeV. However, beta and positron radiation may also be detected.

The detector may be a room temperature, solid-state CdZnTe (CZT) detector, configured as a single-pixel or a multi-pixel detector, obtained, for example, from eV Products, a division of II-VI Corporation, Saxonburg Pa., 16056, or from IMARAD IMAGING SYSTEMS LTD., of Rehovot, ISRAEL, 76124, www.imarad.com, or from another source. Alternatively, another solid-state detector such as CdTe, HgI, Si, Ge, or the like, or a scintillation detector (such as NaI(Tl), LSO, GSO, CsI, CaF, or the like, or a combination of a scintillation detector and a photomultiplier, to form an Anger camera, or another detector as known, may be used.

FIGS. 1A and 1B schematically illustrate a detecting unit 12 and a block 90 of detecting units 12, respectively, as known.

As seen in FIG. 1A, the detecting unit 12 is formed of a single-pixel detector 91, having a diameter D and a thickness $\tau_d$. Both the detector diameter D, or a diameter equivalent, in the case of a non-circular detector, and the detector thickness $\tau_d$ affect the detecting efficiency. The detector diameter D determines the surface area on which radioactive emission impinges; the greater the surface area, the greater the efficiency. The detector thickness $\tau_d$ affects the stopping power of the detector. High energy gamma rays may go through a thin detector; the probability of their detection increases with the detector thickness $\tau_d$.

FIG. 1A illustrates a single-pixel detector 91, which by itself cannot generate an image; rather, all counts are distributed over the surface area of the detector 91.

As seen in FIG. 1B, the block 90 includes a plurality of the detecting unit 12, formed by dividing the detector 91 into a plurality of electrically insulated pixels 106, each associated with a collimator 96. The collimators 96 are of the diameter or diameter equivalent D, a length L, and a septa thickness r. The collimators 96 may be, for example, of lead, tungsten or another material which substantially blocks gamma and beta rays. The collimators 96 may be shaped as tubes, rectangular grids, or grids of another polygon. Wide-angle or narrow-angle collimators are also possible.

The collimator's geometry, and specifically, the ratio of D/L, provides the detecting unit 12 with a collection solid angle δ analogous to a viewing solid angle of an optical camera. The collection solid angle δ limits the radioactive-emission detection to substantially only that radioactive emission, which impinges on the detector 91 after passing through a "corridor" of the collimator 96 (although in practice, some high-energy gamma rays may penetrate the collimator's walls). With no collimator, the collection angle δ, is essentially a solid angle of 4π steradians.

Thus, the collimator's geometry affects both the detection efficiency and the image resolution, which are defined as follows:

i. The detection efficiency is the ratio of measured radiation to emitted radiation; and ii. The image resolution is the capability of making distinguishable closely adjacent manifestations of a pathology, or the capability to accurately determine the size and shape of individual manifestations of a pathology.

Naturally, it is desired to optimize both the detection efficiency and the image resolution. Yet, they are inversely related to each other. The detection efficiency increases with increasing collimator's collection angle, and the image resolution decreases with increasing collimator's collection angle.

In other words, while a wide-aperture, single-pixel detecting unit, such as that of FIG. 1A provides high efficiency, it does not lend itself to the generation of a two-dimensional image, and the wide aperture blurs the information regarding the direction from which the radiation comes. Yet as the resolution is increased, for example, to the detecting unit 12 of FIG. 1B, the detection efficiency is decreased.

Commonly owned US Applications 20040015075 and 20040054248 and commonly owned PCT publication WO2004/042546, all of whose disclosures are incorporated herein by reference, describe systems and methods for scanning a radioactive-emission source with a radioactive-emission-measuring probe of a wide-aperture collimator, and at the same time, monitoring the position of the radioactive-emission-measuring probe, at very fine time intervals, to obtain the equivalence of fine-aperture collimation. In consequence, high-efficiency, high-resolution images of a radioactivity emitting source are obtained.

A system according to US Applications 20040015075 and 20040054248 and PCT publication WO2004/042546 is seen in FIGS. 2-3B.

FIG. 2 schematically illustrates the basic component of a system 120, comprising a radioactive-emission-measuring probe 122 and a position-tracking device 124, both in communication with a data processing unit 126. The radioactive-emission-measuring probe 122 is associated with a first coordinate system 128, and the position-tracking device 124 is associated with a second coordinate system 128', wherein the position-tracking device 124 monitors the position of the radioactive-emission-measuring probe 122 as a function of time. The data processing unit 126 processes the measurements of both the radioactive-emission-measuring probe 122 and the position-tracking device 124 and combines them, to form the image.

FIG. 3A schematically illustrates the manner of operating the radioactive-emission-measuring probe 122 with the position-tracking device 124 of the system 120. The radioactive-emission-measuring probe 122 moves about an area of radioactive emission 110, for example, in the direction of an arrow 118, so as to measure a radioactive emission distribution 112, as a function of time, while the position-tracking device 124 monitors the position of probe 122. The radioactive-emission-measuring probe 122 may be a single-pixel detector of high efficiency, which is incapable, by itself, of producing images. Nonetheless, a data processing unit 126, processes a radioactive-count-rate input 121 together with a position-tracking input 123, using algorithms 125, to reconstruct an image 110' of the area of radioactive emission 110, for example, on a display unit 129.

Images according to this concept are illustrated in FIGS. 3B-3B. The area of radioactive emission 110 is located in a two-dimensional coordinates u;v, and includes two hot points 115 (FIG. 3B). The system 120 moves from a position P(1) at a time t(1), to a position P(2) at a time t(2), while measuring the radioactive emission distribution 112 of the area of radioactive emission 110, including the hot points 115.

An example of a suitable position-tracking device 124 is miniBird™, which is a magnetic tracking and location system commercially available from Ascension Technology Corporation, P.O. Box 527, Burlington, Vt. 05402 USA (http://www.ascension-tech.com/graphic.htm). The miniBird™ measures the real-time position and orientation (in six degrees of freedom) of one or more miniaturized sensors, so as to accurately track the spatial location of probes, instruments, and other devices. The dimensions of miniBird™ 124 are 18 mm×8 mm×8 mm for the Model 800 and 10 mm×5 mm×5 mm the Model 500. Alternatively, an optical tracking device, of Northern Digital Inc., Ontario, Canada NDI-POLARIS, which provides passive or active systems, a magnetic tracking device of NDI-AURORA, an infrared tracking device of E-PEN system, http://www.e-pen.com, or an ultrasonic tracking device of E-PEN system may be used. Additionally or alternatively, the position-tracking device may be an articulated-arm position-tracking device, an accelerometer-based position-tracking device, a potentiometer-based position-tracking device, or a radio-frequency-based position-tracking device.

Commonly owned US application 20040054248 and commonly owned PCT publication WO2004/042546 further disclose various extracorporeal and intracorporeal systems 120, of radioactive-emission-measuring probes 122, of relatively wide apertures, associated with position-tracking devices 124. Examples of extracorporeal and intracorporeal radioactive-emission-measuring probes of this type, operative with position-tracking devices, are seen in FIGS. 4A-4C.

FIG. 4A schematically illustrates a hand-held, extracorporeal probe 170, formed as the system 120, and having the radioactive-emission-measuring probe 122 of a detector 132, a collimator 134 and a controller 130, and further including the position-tracking device 124, wherein the radioactive-emission-measuring probe 122 and the position-tracking device 124 are associated with the data processing unit 126, as taught in conjunction with FIGS. 2-3B.

FIG. 4B schematically illustrates an intracorporeal probe 180, formed as the system 120, mounted on a catheter 136, and having the radioactive-emission-measuring probe 122, of the detector 132 and the collimator 134, and the position-tracking device 124, wherein the probe 122 and the position tracking device 124 are associated with the data processing unit 126, as taught in conjunction with FIGS. 2-3B. The intracorporeal probe 180 is configured to penetrate a tissue 135, via a trucar valve 138. A structural imager, such as an ultrasound imager 137 or an MRI probe 137 may further be included.

FIG. 4C schematically illustrates an intracorporeal probe 190, formed as the system 120, adapted for rectal insertion and having the radioactive-emission-measuring probe 122, formed as a plurality of detectors 132 and collimators 134, and associated with the position-tracking device 124. The intracorporeal probe 190 may be further adapted for motion along the x and ω directions. For example, the intracorporeal probe 190 may include a motor 154 for self-motion in the x and ω directions, so as to crawl into the rectum. The motor 154 may be obtained, for example, from B-K Medical A/S, of Gentofte, DK, and may be adapted to report to the data processing unit 126 the exact position and orientation of the intracorporeal probe 190, based on the number of rotations. In some embodiments, the motor 154 is used in place of the position-tracking device 124. Alternatively, it is used in addition to it. The intracorporeal probe 190 may further include the structural imager 137, such as an ultrasound imager or an MRI probe.

The acquisition of both a functional image of the body, such as a radioactive-emission image, and a structural image, such as an ultrasound, an x-ray, or an MRI image, and their co-registration on a single frame of reference, is disclosed by commonly owned U.S. Pat. No. 6,173,201 to Front, whose disclosure is incorporated herein by reference, as well as by M. W. Vannier and D. E. Gayou, "Automated registration of multimodality images", Radiology, vol. 169 pp. 860-861 (1988); J. A. Correia, "Registration of nuclear medicine images, J. Nucl. Med., vol. 31 pp. 1227-1229 (1990); J-C Liehn, A. Loboguerrero, C. Perault and L. Demange, "superposition of computed tomography and single photon emission tomography immunoscinigraphic images in the pelvis: validation in patients with colorectal or ovarian carcinoma recurrence", Eur. J. Nucl. Med., vol. 19 pp. 186-194 (1992); F. Thomas et al., "Description of a prototype emission transmission computed tomography imaging system", J. Nucl. Med., vol. 33 pp. 1881-1887 (1992); D. A. Weber and M. Ivanovic, "Correlative image registration", Sem. Nucl. Med., vol. 24 pp. 311-323 (1994); and Hasegawa et al., U.S. Pat. No. 5,376, 795.

In essence, several images may be acquired and co-registered to the same frame of reference, as follows:

i. a first functional image scan, based for example, on anti-CEA monoclonal antibody fragment, labeled by iodine isotopes, may be acquired for targeting CEA—produced and shed by colorectal carcinoma cells for detecting a pathological feature, such as colorectal carcinoma;

ii. a second functional image, based for example, on nonspecific-polyclonal immunoglobulin G (IgG), which may be labeled with $Tc^{99m}$, may be acquired for locating blood vessels and vital structures, such as the heart, or the stomach, co-registered with the first functional image and the pathological feature detected on it, in order to locate the pathological feature in reference to blood vessels and vital organs; and iii. a structural image, such as an ultrasound image, may be used for general structural anatomy, co-registered with the first and second functional images, in order to locate the pathological feature in reference to bones and the general anatomic structure.

In this manner, a physician may locate the pathological feature in reference to the blood vessels, vital organs, and the bones.

Additionally, correlation may be used to guide a minimally invasive surgical instrument to the pathological feature, while avoiding the blood vessels, vital organs, and bones. The minimally invasive surgical instrument may be a biopsy needle, a wire, for hot resection, a knife for cold resection, an instrument of focused energy, to produce ablation, for example, by ultrasound, or by laser, an instrument for cryosurgery, an instrument for croyetherapy, or an instrument for bractherapy, wherein seeds of a radioactive metal are planted close to a tumor, for operating as a radioactive source near the tumor.

Commonly owned PCT publication WO2004/042546 further discloses that the surgical instrument may be visible on at least one of the images, for example, on the structural image, to enable the physician to see the instrument, the pathological feature, and the surrounding anatomy on the display 129 (FIG. 3A). Additionally, the surgical instrument may be radioactively labeled, to be visible also on the functional image.

Commonly owned U.S. Pat. No. 6,173,201 discloses a method of stereotactic therapy, wherein a frame, which includes at least three markers, visible on a structural image, is rigidly secured to a patient. The structural image of a region inside the patient's body, which includes a pathological feature and the markers, is acquired. A functional image of the pathological feature is then acquired and co-registered with the structural image, to correlate the images to the same frame of reference. A stereotactic guide is rigidly attached to the frame and is used to guide a surgical instrument, such as a biopsy needle or a brachytherapy needle, to the pathological feature, with reference to the co-registered images.

Commonly owned PCT publication WO2004/042546 further discloses the use of a structural image, such as of ultrasound or MRI, for information about tissue attenuation. The information may then be used to correct the radioactive-emission measurements.

Nuclear imaging for coronary artery disease is also known. For example, U.S. Pat. No. 6,597,940, to Bishop, et al, relates to screening patients for an early stage of coronary artery disease. According to this method, a patient is screened based on the time-activity curve for a radioactive tracer passing through a left ventricle region of the patient's body. According to another aspect of the invention, an array of gamma particle detectors is employed to obtain data for a region of interest that is larger than and encompasses a left ventricle region of the patient's body. An analysis of the data identifies the subset of the region of interest that corresponds to the left ventricle region. According to a further aspect of the present invention, a second technique is employed to locate the left ventricle region. A still further aspect of the present invention relates to obtaining images of a patient's heart using a high temporal resolution gamma camera.

Additionally, U.S. Pat. No. 6,671,541, to Bishop et al. relates to a cardiovascular imaging and functional analysis system and method, wherein a dedicated fast, sensitive, compact and economical imaging gamma camera system that is especially suited for heart imaging and functional analysis is employed. The cardiovascular imaging and functional analysis system of the present invention can be used as a dedicated nuclear cardiology small field of view imaging camera. The disclosed cardiovascular imaging system and method has the advantages of being able to image physiology, while offering an inexpensive and portable hardware, unlike MRI, CT, and echocardiography systems. The cardiovascular imaging system of the invention employs a basic modular design suitable for cardiac imaging with one of several radionuclide tracers. The detector can be positioned in close proximity to the chest and heart from several different projections, making it possible rapidly to accumulate data for first-pass analysis, positron imaging, quantitative stress perfusion, and multigated equilibrium pooled blood (MUGA) tests. In a preferred embodiment, the Cardiovascular Non-Invasive Screening Probe system can perform a novel diagnostic screening test for potential victims of coronary artery disease. The system provides a rapid, inexpensive preliminary indication of coronary occlusive disease by measuring the activity of emitted particles from an injected bolus of radioactive tracer. Ratios of this activity with the time progression of the injected bolus of radioactive tracer are used to perform diagnosis of the coronary patency (artery disease).

SUMMARY OF THE INVENTION

The present invention successfully addresses the shortcomings of the presently known configurations by providing systems, methods, and probes for functional imaging by radioactive-emission-measurements, specific to body structures, such as the prostate, the esophagus, the cervix, the uterus, the ovaries, the heart, the breast, the brain, and the whole body, and other body structures. The nuclear imaging may be performed alone, or together with structural imaging, for example, by x-rays, ultrasound, or MRI. Preferably, the radioactive-emission-measuring probes include detectors, which are adapted for individual motions with respect to the probe housings, to generate views from different orientations and to change their view orientations. These motions are optimized with respect to functional information gained about the body structure, by identifying preferred sets of views for measurements, based on models of the body structures and information theoretic measures. A second iteration, for identifying preferred sets of views for measurements of a portion of a body structure, based on models of a location of a pathology that has been identified, makes it possible, in effect, to zoom in on a suspected pathology. The systems are preprogrammed to provide these motions automatically.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1B schematically illustrate detecting units and blocks for radioactive emission detection as known;

FIG. 2 schematically illustrates the basic component of a system, comprising a radioactive-emission-measuring probe and a position-tracking device, both in communication with a data processing unit;

FIGS. 3A-3B schematically illustrate the manner of operating the radioactive-emission-measuring probe with the position-tracking device;

FIGS. 4A-4C schematically illustrate extracorporeal and intracorporeal radioactive-emission-measuring probes operative with position-tracking devices;

FIGS. 5A-5F present the principles of modeling, for obtaining an optimal set of views, in accordance with embodiments of the present invention;

FIGS. 6A and 6B pictorially illustrate a view and viewing parameters associated with it, in accordance with definitions of the present invention;

FIGS. 7A-7C schematically illustrate anatomical constraints, which are to be modeled, in accordance with embodiments of the present invention;

FIGS. 9A-9F schematically illustrate possible models and collections of views, for a body structure, in accordance with embodiments of the present invention;

FIGS. 13A-13E schematically illustrate possible probe designs, and the process of obtaining views based on a model and a probe design, in accordance with embodiments of the present invention;

FIGS. 17A-17L schematically illustrate various detecting units and blocks, which may be incorporated in probe designs;

FIGS. 18A-18D schematically illustrate possible motions of a radioactive-emission-measuring probe, for a single detecting unit and a single block, in accordance with embodiments of the present invention;

FIGS. 19A-19E schematically illustrate other possible motions of a radioactive-emission-measuring probe, for a single block, in accordance with embodiments of the present invention;

FIGS. 20A-20H schematically illustrate possible motions of a radioactive-emission-measuring probe, having a plurality of pairs of radioactive-emission blocks;

FIGS. 21A-21D schematically illustrate other possible motions of a radioactive-emission-measuring probe, having a plurality of pairs of radioactive-emission blocks;

FIGS. 22A-22H schematically illustrate a radioactive-emission-measuring probe system, comprising a plurality of assemblies, each formed as the probe system of FIGS. 20A-20H, in accordance with embodiments of the present invention;

FIGS. 23A-23D schematically illustrate a radioactive-emission-measuring-probe system, in accordance with embodiments of the present invention;

FIGS. 25A-25E schematically illustrate the external appearance and the internal structure of the radioactive-emission-measuring probe for the prostate, in accordance with an embodiment of the present invention;

FIGS. 40A and 40B schematically illustrate an assembly and a block, in accordance with an embodiment of the present invention FIG. 41 further illustrates a block, in accordance with a preferred embodiment of the present invention;

FIGS. 43A-43E schematically illustrate blocks, arranged for viewing the cardiac model, in accordance with a preferred embodiment of the present invention;

FIGS. 50A-50C schematically illustrate the radioactive-emission-measuring probe for the brain, in accordance with embodiments of the present invention;

FIG. 51A-51K schematically illustrate inner structures of the probe for the brain, in accordance with several embodiments of the present invention;

FIG. 53A schematically illustrates a basic mammograph;

FIGS. 53B and 53C schematically illustrate a mammograph configured for ultrasound imaging, and a mammograph configured for ultrasound imaging with a surgical instrument, respectively, in accordance with embodiments of the present invention;

FIGS. 54A-54E schematically illustrate an assembly, configured for operation with a mammograph-like radioactive-emission-measuring probe for the breast, in accordance with embodiments of the present invention;

FIGS. 56A-56C schematically illustrate a radioactive-emission-measuring probe 930, for imaging a breast under vacuum, in accordance with another preferred embodiment of the present invention; and FIGS. 57A-57F schematically illustrate a radioactive-emission-measuring probe 950, for imaging the breasts in the natural state, in accordance with another preferred embodiment of the present invention.

DESCRIPTION OF THE PREFERRED EMBODIMENTS

Figure 8:
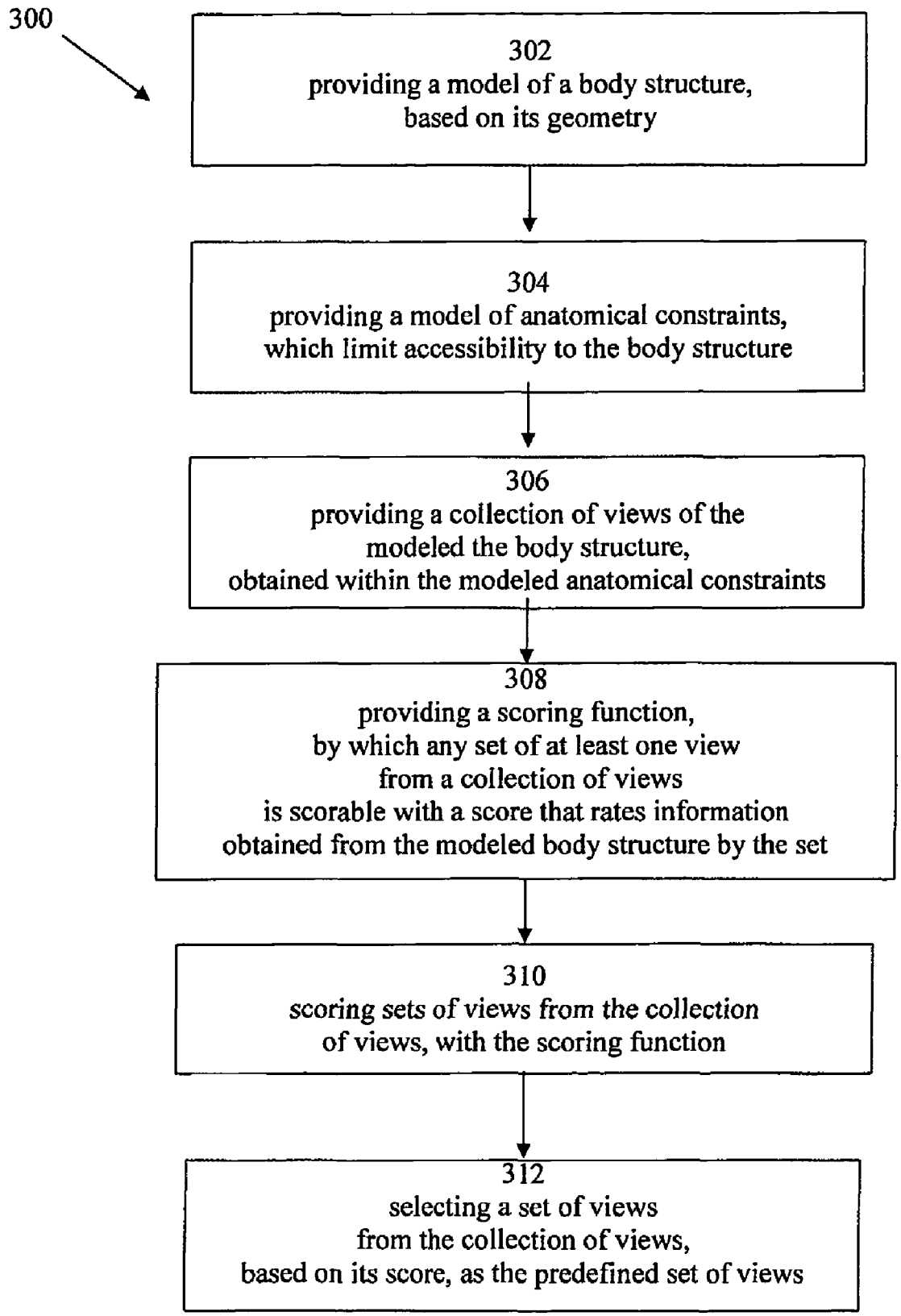
FIG. 8 illustrates, in flowchart form, a method of predefining a set of views for functional imaging, tailored for imaging from esophagus, and optimized with respect to the functional information gained about the body structure, in accordance with embodiments of the present invention.

The present invention relates to of systems, methods, and probes for functional imaging by radioactive-emission-measurements, specific to body structures, such as the prostate, the esophagus, the cervix, the uterus, the ovaries, the heart, the breast, the brain, and the whole body, and other body structures. The nuclear imaging may be performed alone, or together with structural imaging, for example, by x-rays, ultrasound, or MRI. Preferably, the radioactive-emission-measuring probes include detectors, which are adapted for individual motions with respect to the probe housings, to generate views from different orientations and to change their view orientations. These motions are optimized with respect to functional information gained about the body structure, by identifying preferred sets of views for measurements, based on models of the body structures and information theoretic measures. A second iteration, for identifying preferred sets of views for measurements of a portion of a body structure, based on models of a location of a pathology that has been identified, makes it possible, in effect, to zoom in on a suspected pathology. The systems are preprogrammed to provide these motions automatically.

The principles and operation of the radioactive-emission-measuring systems, probes and methods, according to embodiments of the present invention, may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 5A-5F present the principles of modeling, for obtaining an optimal set of views, in accordance with embodiments of the present invention.

FIG. 5A schematically illustrates a body section 230, having a region of interest (ROI) 200. The region of interest 200 may be associated with a body structure 215, with a specific radioactive-emission-density distribution, possibly suggestive of a pathological feature 213, termed herein an organ target 213. Additionally, there may be certain physical viewing constraints, associated with the region of interest 200.

We thus consider the following problem: how can we best identify an optimal and permissible set of views for radioactive-emission measurements of the region of interest 200, for reconstructing a three-dimensional image of it?

In accordance with embodiments of the present invention, our approach is delineated in FIG. 5C, by a method 205, as follows:

in a box 206: modeling the region of interest 200, as a model 250 of a volume U, possibly with one or several modeled organ targets HS, within anatomical constraints AC, as seen in FIG. 5B;

in a box 207: obtaining an optimal and permissible set of views for the modeled volume U FIG. 5B; and in a box 208: applying the optimal set of views to the in-vivo region of interest 200 and the body structure 215 of FIG. 5A.

It will be appreciated that the model 250 of the region of interest 200 may be based on general medical information of the body structure 215 and common pathological features associated with it. Additionally, the model may be based on information related to a specific patient, such as age, sex, weight, and body type. Furthermore, a structural image, such as by ultrasound or MRI, may be used for providing information about the size and location of the body structure 215 in relation to the body section 230, for generating the model 250.

FIGS. 5D-5F schematically illustrate three types of the modeled organ targets HS, as follows:

i. a region of concentrated radiation, or a hot region, for example, as may be associated with a malignant tumor and as seen in FIG. 5D;

ii. a region of low-level radiation, which is nonetheless above background level, for example, as may be associated with carcinoma and as seen in FIG. 5E, and iii. a region of little radiation, or a cold region, below the background level, for example, as may be associated with dead tissue and as seen in FIG. 5F.

Referring further to the drawings, FIGS. 6A and 6B pictorially illustrate a view and viewing parameters associated with it, in accordance with definitions of the present invention.

Seen in FIG. 6A is the volume U, subdivided into voxels u. The volume U is defined in a six-degree coordinate system x;y;z;ω;θ;σ and has a point of origin $P0(x0; y0; z0; \omega 0; \theta 0; \sigma 0)$. A detecting unit 12 is positioned at a location and orientation $P1(x1; y1; z1; \omega 1; \theta 1; \sigma 1)$. The detecting unit 12 has a detector 91 of a specific detector material of a thickness t, and a collimator 96 of a diameter D and a length L, so as to define a collection angle δ.

FIG. 6B schematically illustrates the emission rate of the volume U, as a function of time, given that a radioactive material of a specific half-life has been administered at a time T0.

A view may thus be defined as a group of nonzero probabilities of detecting a radioactive emission associated with all the voxels that form a sector S (FIG. 6A).

A view is sometimes referred to as a projection, and the two terms are synonymous. Furthermore, a view defined over a sector S can be naturally extended to be defined over the set of all voxels, by simply associating a zero probability with every voxel outside the S. This makes possible the application of mathematical operations over the entire volume U.

A view is dependent on the following viewing parameters:

Location and Orientation Parameters:

A location and an orientation in a six-dimensional space, $P1(x1; y1; z1; \omega 1; \theta 1; \sigma 1)$, with respect to the origin $P0(x0; y0; z0; \omega 0; \theta 0; \sigma 0)$ of the volume U, in which the detecting unit 12 is positioned;

Detecting-unit Parameters:

The collection angle δ, which together with the location and orientation parameters, $P1(x1; y1; z1; \omega 1; \theta 1; \sigma 1)$ with respect to the origin $P0(x0; y0; z0; \omega 0; \theta 0; \sigma 0)$ define the sector S;

The detector material, which affects the detector efficiency;

The detector thickness t, which affects the detector's stopping power, hence, its efficiency; and The diameter of the detecting unit, or the effective diameter, calculated so as to produce a circle of the same area, when the geometry is not a circle;

Attenuation Parameters:

Attenuation properties of all the voxels within the sector S, as they affect the probabilities that radioactive emissions from a specific voxel within the sector S will reach the detector, wherein different voxels within the sector S may have different attenuation properties, since several types of tissue may be involved;

Radiopharmaceutical Parameters:

The half life $t_{1/2}$, of the radiopharmaceutical, the types of radioactive emission, whether gamma or beta, and the energies of the radioactive emission affect the probability of detection; and Time Parameters:

Given that T0 is the time of administrating the radiopharmaceutical, the time T1 since administration, and the duration of the measurement ΔT1, affect the number of emissions that occur during the radioactive-emission measurement.

Some of these viewing parameters are fixed for a particular situation. Specifically, the tissue attenuation parameters are given. Additionally, the time T1 since administration of the radiopharmaceutical is generally governed by the blood pool radioactivity, since it is generally necessary to wait until the blood pool radioactivity dies out for low-level detection to be possible. For the remaining viewing parameters, optimization may be carried out.

The remaining viewing parameters may be divided into two categories:

i. viewing parameters in the design of a radioactive-emission-measuring probe;

ii. viewing parameters for an optimal set of views, for a given probe.

Viewing Parameters for an Optimal Set of Views, for a Given Probe

Referring further to the drawings, FIGS. 7A-7C schematically illustrate anatomical constraints, which may hinder measurements.

FIG. 7A schematically illustrates the region of interest 200, for which a three-dimensional radioactive-emission image is desired. The region of interest 200 is in free space, with no constraints to limit accessibility to it. Thus, a radioactive-emission-measuring probe 210 may travel, for example, along tracks 202 and 204, and any other track, unhindered.

In FIG. 7B, the region of interest 200 is associated with the body structure 215, such as a prostrate, in vivo. For obtaining a radioactive-emission image, the radioactive-emission-measuring probe 210 may be inserted transrectally, so as to travel in a rectum 206, for example, in the direction of an arrow 208. Its ability to image the prostrate is limited by anatomical constraints.

In FIG. 7C, the region of interest 200 is associated with the body structure 215, such as a body structure, in vivo, and the radioactive-emission-measuring probe 210 may be an extracorporeal probe, which may perform radioactive-emission measurements from outside the body, on an extracorporeal surface 214, for example when moving along a track 212.

In each of these cases, it is desired that a reconstructed three-dimensional radioactive-emission image of the region of interest 200 be obtained, at a predetermined quality. This is achieved by predefining an optimal set of radioactive-emission measurement views, tailored to the specific organ 215 and optimized with respect to the information gained, regarding the body structure 215.

Referring further to the drawings, FIG. 8 illustrates, in flowchart form, a method 300 for predefining a set of radioactive-emission measurement views, for functional imaging, tailored for imaging from esophagus and optimized with respect to the functional information gained, regarding the body structure 215, in accordance with embodiments of the present invention. The method 300 comprises:

in a box 302: providing a model of the body structure 215, based on its geometry;

in a box 304: providing a model of anatomical constraints, which limit accessibility to the body structure;

in a box 306: providing a collection of views of the modeled body structure, obtained within the modeled anatomical constraints;

in a box 308: providing a scoring function, by which any set of at least one view, from a collection of views is scorable with a score that rates information, obtained from the modeled body structure by the set;

in a box 310: forming sets of views from the collection of views and scoring them, with the scoring function; and in a box 312: selecting a set of views, from the collection of views, based on its score, as the predefined set of views.

The model of the body structure is based on anatomical knowledge regarding its size, shape, and weight. In fact different models may be provided, for example, for different ages, sexes, weights, and body types, such as heavy-built, medium-built, or small-built. In accordance with a first embodiment, the body structure is modeled assuming no radioactive emission throughout its volume. In accordance with other embodiments, the body structure may be modeled with one or more modeled organ targets, simulating different pathological features. Specifically, the modeled organ targets may be hot regions, of a radioactive-emission intensity, higher than the background level, regions of low-level radioactive-emission intensity, which is nonetheless above the background level, and cold regions, of a radioactive-emission intensity, lower than the background level. These may be distributed in accordance with medical records, which teach of sites within the body structure that may be more susceptible to certain pathologies.

Similarly, the model of anatomical constraints, which limit accessibility to the body structure, is based on anatomical knowledge, and different models may be provided, for example, for different ages, sexes, weights, and body types.

The collection of views may be obtained by several methods. It may be calculated analytically, for the modeled body, based on the view parameters. Additionally or alternatively, computer simulations of the modeled body and the view parameters may provide the collection of views. Additionally or alternatively, measurements may be performed, using a point source and a detecting unit of appropriate parameters, at different locations and orientations of the detecting unit, so as to simulate the desired geometries.

It will be appreciated that a combination of these may be used. For example, the measurements may be performed in air, but corrected analytically or by computer simulations, for tissue attenuation.

Referring further to the drawings, FIGS. 9A-9F schematically illustrate possible models and collections of views, for an organ, in accordance with embodiments of the present invention, as follows:

FIG. 9A schematically illustrates four views, formed by sectors S1, S2, S3, and S4, through the volume U, which has an even distribution of radioactive emission.

FIG. 9B schematically illustrates three views, formed by sectors S1, S2, and S3, through the volume U, which includes a modeled pathological feature, as the modeled organ target, HS.

Figure 9C:
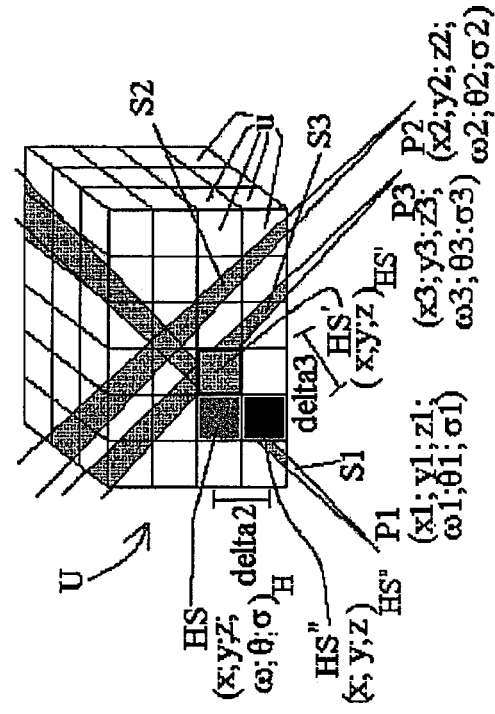

FIG. 9C schematically illustrates three views, formed by sectors S1, S2, and S3, through the volume U, which includes a modeled organ target, HS', of the same type as the modeled organ target HS, (that is, either a hot region or a cold region) but somewhat displaced along the x;y;z coordinate system. Additionally, the modeled organ target HS of FIG. 9B is superimposed in FIG. 9C, for illustrative purposes, in order to show the displacement delta1 between the modeled organ target HS of FIG. 9B and the modeled organ target HS' of FIG. 9C.

Figure 9D:
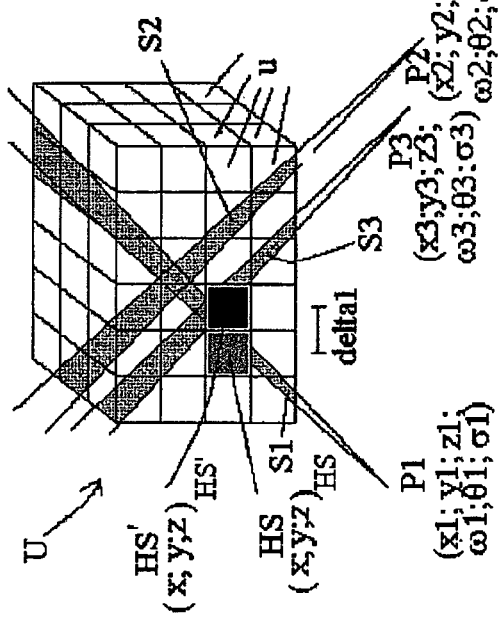

FIG. 9D schematically illustrates three views, formed by sectors S1, S2, and S3, through the volume U, which includes a modeled organ target, HS", of the same type as the modeled organ targets HS and HS', but somewhat displaced along the x; y; z coordinate system from them. Additionally, the modeled organ targets HS of FIG. 9B and HS' of FIG. 9C are superimposed in FIG. 9D, for illustrative purposes, in order to show the displacements delta2 and delta3, vis a vis HS" of FIG. 9D.

Figure 9E:
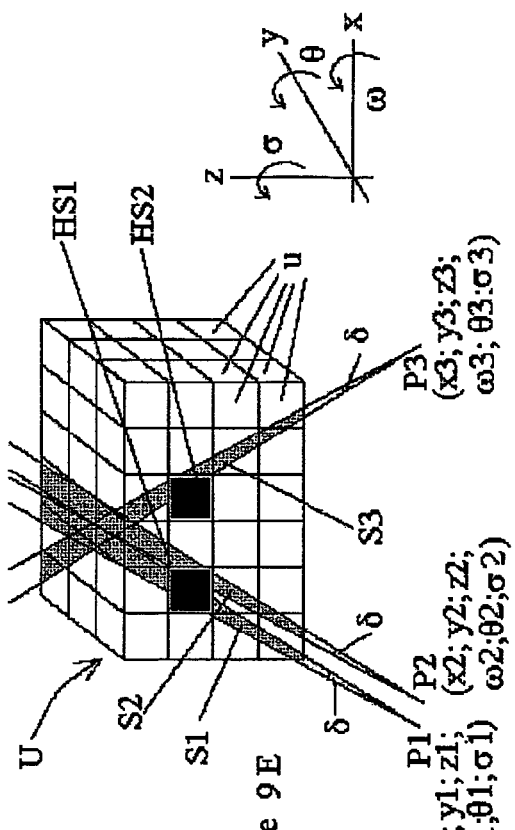
Figure 9F:
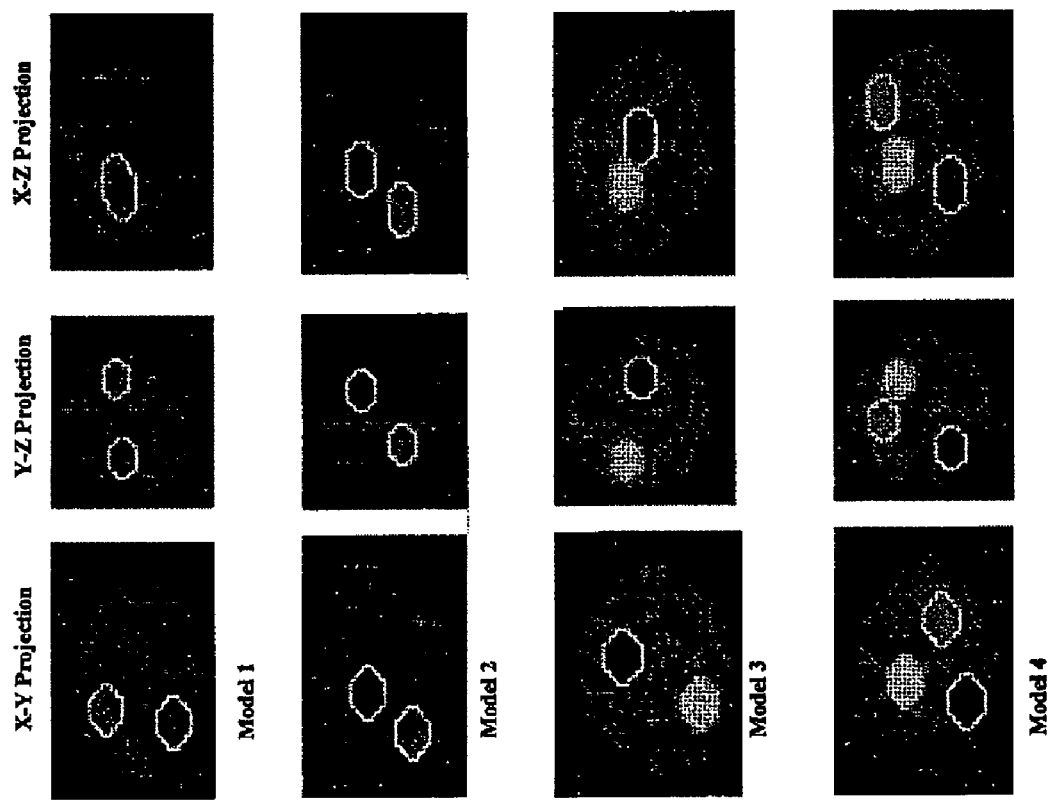

FIG. 9E schematically illustrates three views, formed by sectors S1, S2, and S3, through the volume U, which includes two modeled organ targets, HS1 and HS2;

FIG. 9F schematically illustrates four possible models of organs, as elliptical volumes, each with a slightly different distribution of modeled organ targets.

The modeled organ targets may be termed emittance models. In general, an emittance model is based on a particular radiopharmaceutical, which fixes both the rate of emission and the change in the rate of emission with time, determining the difference between the modeled organ target and the background level, as a function of time. To study the effect of different radiopharmaceuticals on the views, one may provide different emittance models, based on different radiopharmaceuticals and different elapsed times from their administration.

The choice of an optimal set of views from among a collection of views, such as any of those illustrated in FIGS. 9A-9E, is based on a scoring function, which rates different sets of views in terms of their information regarding the volume U, as provided by each set of views. The scoring function is based on information theoretic measures that rate the quality of the data which each set of views provides.

A brief description of the information theoretic measures, upon which the scoring function may be based, is as follows:
Uniformity:

The information theoretic measure of uniformity requires that the probability of detecting a radioactive emission from each voxel, by one of the views, be substantially equal for all the voxels, that is, substantially uniform for all the voxels.

This is illustrated in conjunction with FIG. 9A. Basically, in one view, a voxel may have high influence on the counts that are measured, while in another, the same voxel may have low influence on the counts that are measured. For example, consider a voxel u(1;1;1), in relation to the views associated with the sectors S2 and S4. The voxel u(1;1;1) has high influence on the counts that are measured by the view associated with the sector S4, but low influence on the counts that are measured by the view associated with the sector S2. The aim under uniformity is to identify a set of views that will balance the influence of each voxel for the entire set of views.

Separability:

The information theoretic measure of separability rates resolution, or the ability of a set of views to distinguish between a pair of close models of the body structure, each having substantially identical dimensions, so as to define substantially identical volumes U, but with a slightly different distribution of modeled organ targets.

Consider for example, a pair of models of substantially identical volumes, as follows: The model of FIG. 9B, which schematically illustrates the volume U, having the modeled organ target HS, whose center is at a location $(x;y;z)_{HS}$, and the model of FIG. 9C, which schematically illustrates the volume U, having the modeled organ target HS', whose center is at a location $(x;y;z)_{HS'}$. In FIG. 9C, the modeled organ target HS of FIG. 9B is superimposed, for illustrative purposes, in order to show the displacement between the two models. The displacement between the modeled organ targets is denoted as delta and may be measured, for example, in mm. In the present example, the displacement between the models of FIGS. 9B and 9C is delta1, along the x-axis.

An optimal set of views, from the standpoint of separability, is that which will best distinguish between HS of FIG. 9B and HS' FIG. 9C. Thus, a score, in terms of separability is given for the pair of models, and relates to a resolution as defined by the difference between the models of the pair. In the present example, the difference is delta1 along the x-axis, around the locations of HS and HS', so the score given by the information theoretic measure of separability, will relate specifically to a resolution as defined by delta1 along the x-axis, around the locations of HS and HS'. Other portions of the volume U and other directions may have different resolutions.

Additionally, consider the model of FIG. 9D, which schematically illustrates the volume U, having the modeled organ target HS", whose center is at a location $(x;y;z)_{HS''}$, wherein HS" is displaced from HS of FIG. 9B, along the z-axis, a displacement delta2. Additionally, HS" is displaced from HS' of FIG. 9C, along the x- and z-axes, a displacement delta3. FIG. 9D further includes the modeled organ targets HS of FIG. 9B and HS' of FIG. 9C, superimposed on it, for illustrative purposes, in order to show the displacements delta2 and delta3, vis a vis HS" of FIG. 9D.

Scores, in terms of separability, may be given to all the paring combinations, that is the models of FIGS. 9B-9C, relating to delta1; the models of FIGS. 9B-9D, relating to delta2, and the models of FIGS. 9C-9D, relating to delta3. An optimal set of views may be selected based on its average scores for all the pairing combinations; for example, the optimal set may be that whose average score for all the pairing combinations is the highest. Alternatively, a weighted average may be applied.

It will be appreciated that where more than one modeled organ target may be included in the volume U.

It will be further appreciated that a set of views may be selected so as to provide high resolution for portions of the volume U, known to be susceptible to pathologies, and low resolution for portions of the volume U, known to be generally free of pathological features.

FIG. 9F schematically illustrates a pair of models of organs, as elliptical volumes, each with a slightly different distribution of modeled organ targets, for identifying an optimal set of views in terms of separability.

Reliability:

The information theoretic measure of reliability rates repeatability in measurement, so that repeated reconstructions are not substantially different. Reliability may be scored with respect to a single model of a body structure, having a specific distribution of modeled organ targets, for example, any one of the models of FIGS. 9B-9E. Yet, preferably, several models of substantially identical volumes are provided, for example, the four models of FIGS. 9B-9E. Substantially identical sets of views may be applied to all the models and be scored with respect to reliability. The optimal set is selected based on its average score for the plurality of the models, for example, the optimal set may be that whose average score for the plurality of the models is the highest.

FIG. 9F schematically illustrates four models of organs, as elliptical volumes, each with a slightly different distribution of modeled organ targets, for identifying an optimal set of views in terms of reliability.

A Weighted Combination:

A weighted combination of several information theoretic measures may also be used. For example, a plurality of models may be provided, all having substantially identical dimensions and volumes, as follows:

i. a first model of the volume U, free of modeled organ targets, as seen in FIG. 9A, for scoring sets of views in terms of uniformity;
ii. at least one pair of models of the volume U, with slightly different distributions of modeled organ targets, as seen in any one of FIGS. 9B-9C, 9B-9D, and (or) 9C-9D, for scoring sets of views in terms of separability;
iii. at least one model of the volume U, with a given distribution of modeled organ targets, as seen in any one of FIGS. 9B, 9C, 9D, and (or) 9E, for scoring sets of views in terms of reliability.

Identical sets of views may be applied to all the models of the volume U, and each view may be scored in terms of uniformity, separability, and reliability. An optimal set of views may be selected based on a summation of the three scores, or based on a weighted average of the three scores.

The Greedy Construction

Some approaches for selecting an optimal set are based on determining a required quality of reconstruction, and finding a set of views that meets that requirement. Others are based on fixing the size for the set (i.e., the number of views in the set) and maximize the quality of the reconstruction for the given set size. Still other approaches define both a desired size for the set and a desired quality of reconstruction and search for a set of the desired size, which meets the desired quality of reconstruction.

However, given a desired size for a set of views and a desired quality of reconstruction, while it may be possible to search through all possible sets of the desired size, scoring each, in order to identify the set that meets the desired quality, such a task may be monumental. For example, where the collection of views includes several thousand views, and a set size of 100 is desired, rating each combination of 100 views would be computationally impractical.

An alternative approach is the Greedy Construction. When applying the Greedy construction, an information theoretic measure is chosen, for example, separability, and an initial set of a minimal number of views is defined. The set is gradually built up, so that with every addition, a view is picked so as to maximize the chosen information theoretic measure of the set.

This may be illustrated in conjunction with FIG. 9E. Given that separability is the chosen information theoretic measure, and an initial set of view S1 is defined, the additions of views S2 and S3 may then be compared in order to determine with which of them is separability maximized. Intuitively, for the present example, the addition of S3 will maximize the chosen information theoretic measure of the set.

It will be appreciated that other scoring functions, as known, may similarly be used.

Performing Measurements

The power of the method of the present invention, of predefining a set of views based on a model of a body structure, using an information theoretic measure, so as to optimize the functional information from the views of the corresponding body structure, in vivo, becomes apparent when compared with the prior art alternatives. The prior art relies on obtaining random views, in vivo, or views dictated by anatomical constraints, with no rigorous approach to the manner by which they are chosen.

The method of the present invention, of predefining a set of views, based on a model of a body structure, using an information theoretic measure, so as to optimize the functional information from the views of the corresponding body structure, in vivo, is further illustrated hereinbelow, in conjunction with FIG. 10.

Figure 10:
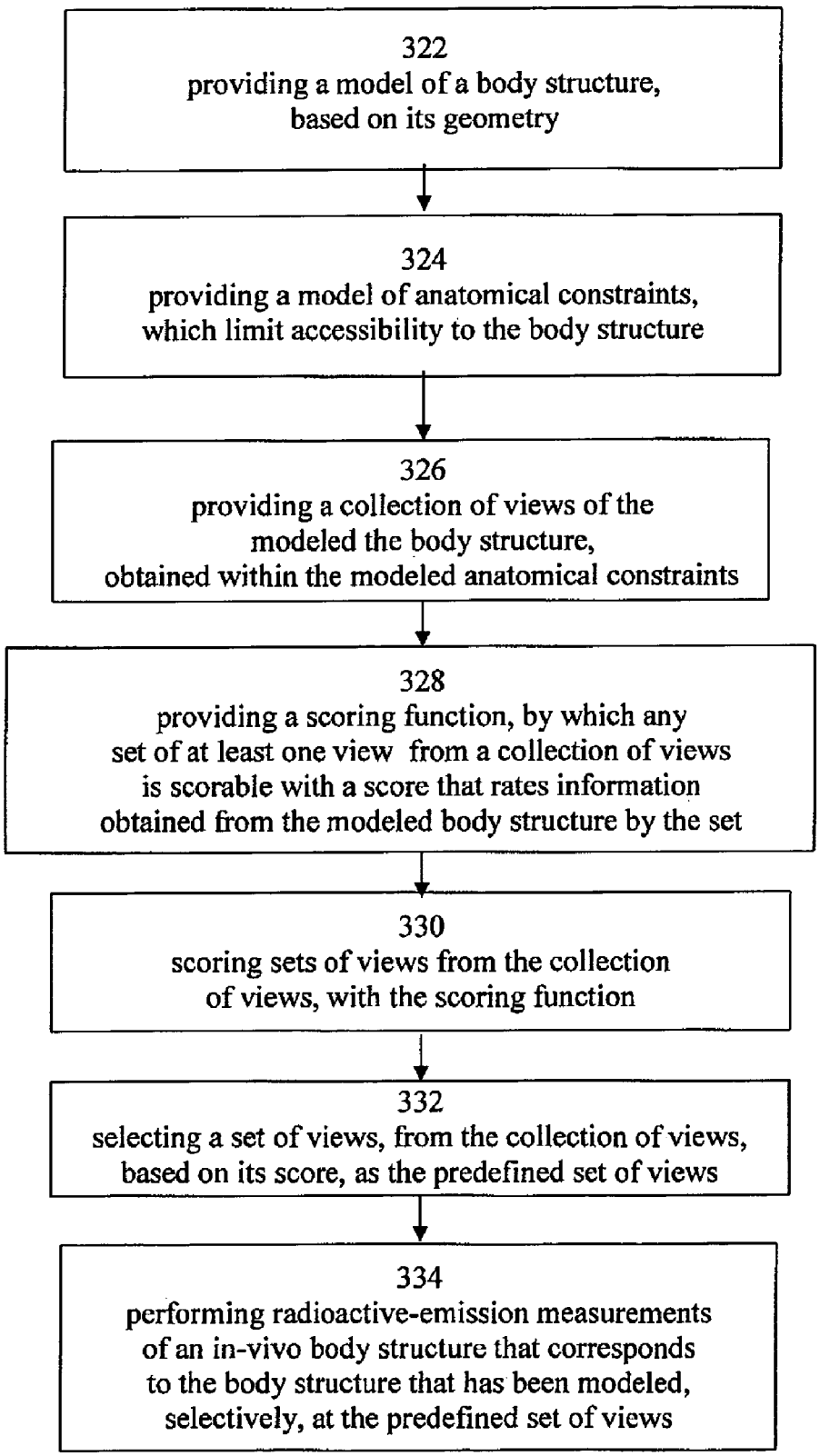
FIG. 10 illustrates, in flowchart form, a method of functional imaging, tailored for imaging from esophagus, and optimized with respect to the functional information gained about the body structure, in accordance with embodiments of the present invention.

Referring further to the drawings, FIG. 10 illustrates, in flowchart form, a method 320 of functional imaging, tailored for imaging from esophagus, and optimized with respect to the functional information gained about the body structure, by using the predefined optimal set of views, in accordance with embodiments of the present invention. The method 320 comprises:

in a box 322: providing a model of a body structure, based on its geometry;
in a box 324: providing a model of anatomical constraints, which limit accessibility to the body structure;
in a box 326: providing a collection of views of the modeled body structure, obtained within the modeled anatomical constraints;
in a box 328: providing a scoring function, by which any set of at least one view, from a collection of views is scorable with a score that rates information, obtained from the modeled body structure by the set;
in a box 330: forming sets of views from the collection of views and scoring them, with the scoring function;
in a box 332: selecting a set of views from the collection of views of the modeled body structure, based on its score, as the predefined set of views; and
in a box 334: performing radioactive-emission measurements of an in-vivo body structure that corresponds to the body structure that has been modeled, selectively at the predefined set of views.

It will be appreciated that the region of interest 200 may include an organ, such as a heart or a pancreas, a gland, such as a thyroid gland or a lymph gland, blood vessels, for example, the coronary artery or the pulmonary artery, a portion of an organ, such as an aorta or a left atrium of a heart, a bone, a ligament, a joint, a section of the body, such as a chest or an abdomen, or a whole body.

A still more powerful approach may be achieved by taking the method of the present invention through second and third iterations, so as to zoom in on suspected pathological features that are identified. Specifically, when a suspected pathological feature is identified, a second, inner region of interest, limited to the region of the pathological feature and its surrounding anatomical structure, can be identified and modeled. An optimal pathology set of views, specifically for the second, inner region of interest, may be predefined, based on information theoretic measures, as before. This is illustrated hereinbelow, in conjunction with FIGS. 11 and 12.

Figure 11:
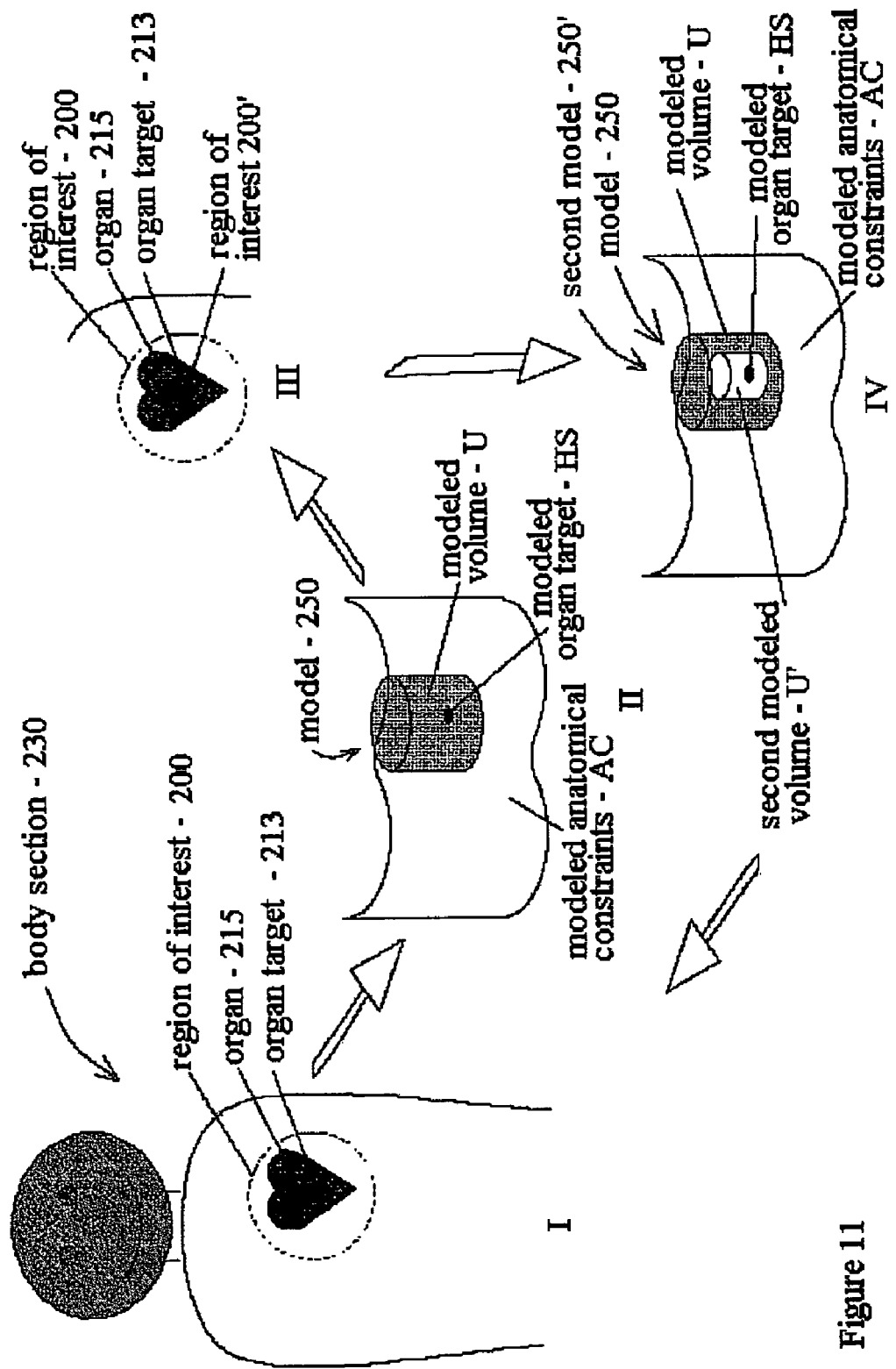
FIG. 11 schematically illustrates the process of modeling in two iterations, for zooming in on a pathological feature, in accordance with embodiments of the present invention.

Referring further to the drawings, FIG. 11 pictorially illustrates a method 340 for zooming in on a suspected pathological feature, as a process of two or more iterations, in accordance with embodiments of the present invention, as follows:

In I: The region of interest 200, associated with the body structure 215, is defined for the body section 230.

In II: The model 250 of the volume U is provided for the region of interest 200, possibly with one or several of the modeled organ targets HS, and within the anatomical constraints AC, for obtaining the optimal set of views for the region of interest 200. The optimal set of views is then applied to the body section 230.

In III: When a suspected organ target 213 is identified, in vivo, by radioactive-emission measurements at the optimal set of views, a second, inner region of interest 200' is defined, encircling the suspected pathological feature.

In IV: A model 250' of a volume U' is provided for the second, inner region of interest 200', preferably, with at least one modeled organ target HS, simulating the suspected organ target 213, for obtaining an optimal pathology set of views for the region of interest 200'. The second, pathology set of views is then applied to the body section 230.

Figure 12:
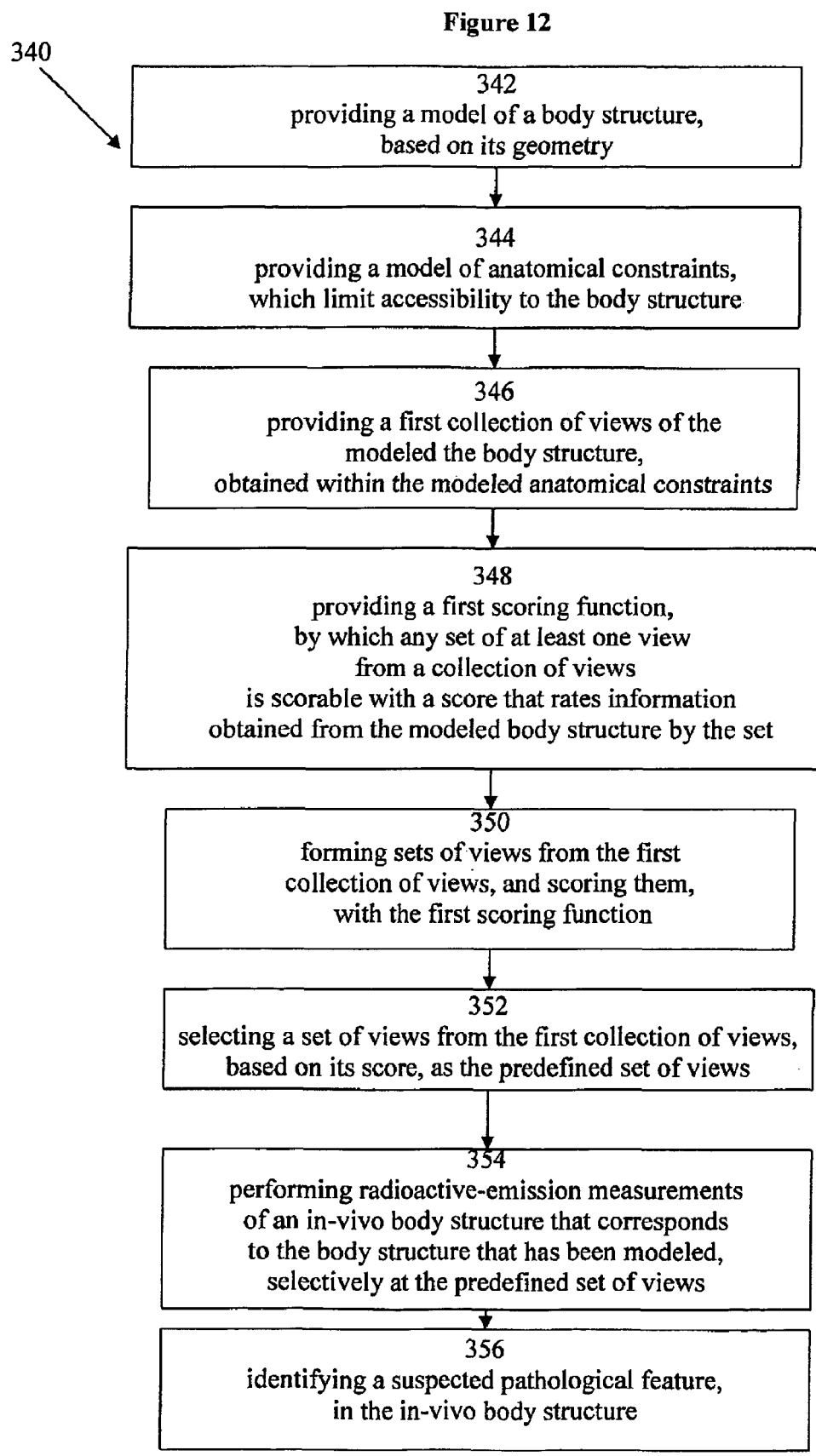
FIG. 12 illustrates, in flowchart form, a method of several iterations for zooming in on a pathological feature, when performing in vivo measurements, in accordance with embodiments of the present invention.
Figure 12:
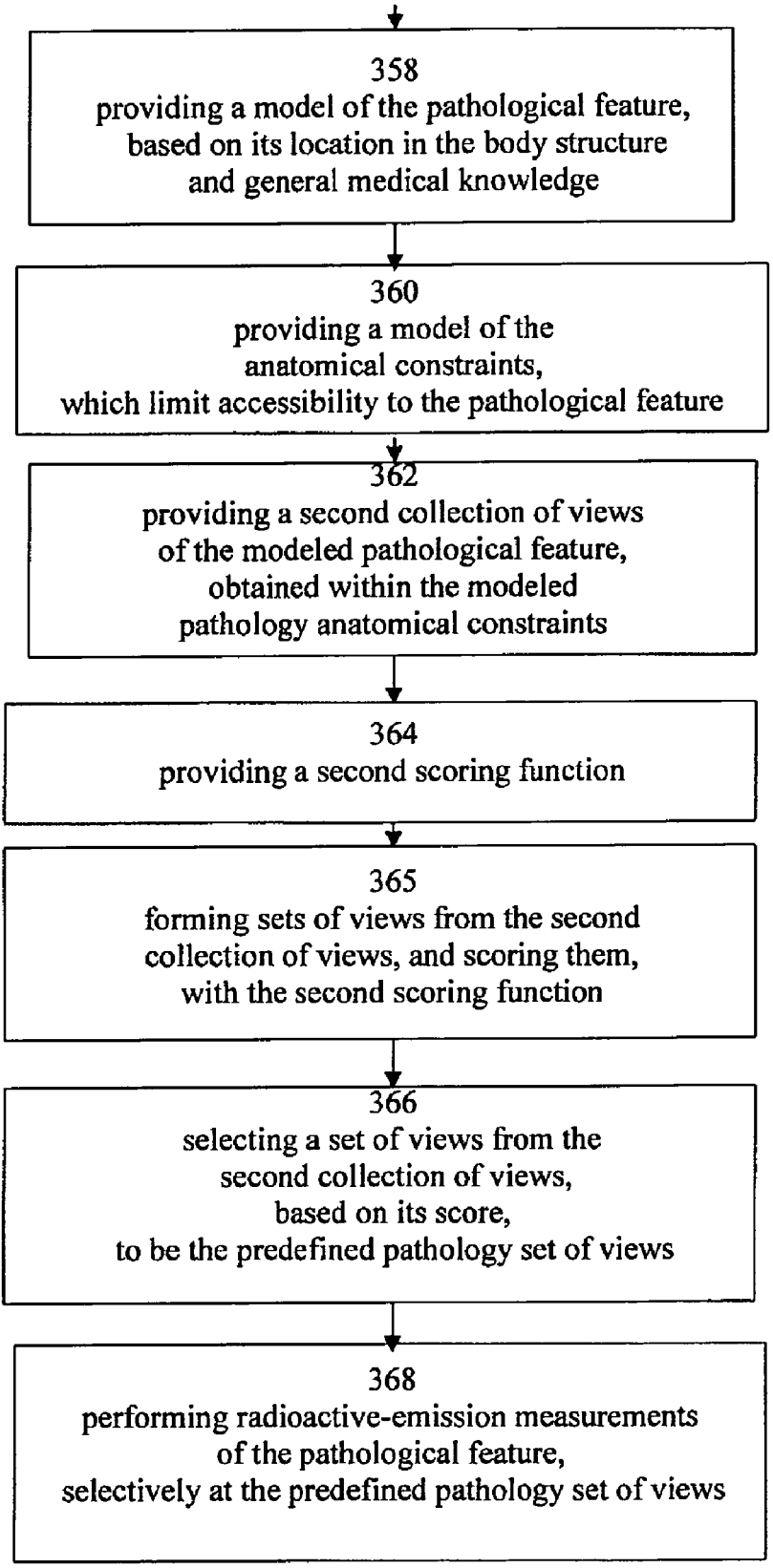

Referring further to the drawings, FIG. 12 illustrates, in flowchart form, the method 340, for zooming in on a suspected pathological feature of the body structure, as a process of two iterations, in accordance with embodiments of the present invention. The method 340 comprises:

in a box 342: providing a model of a body structure, based on its geometry;
in a box 344: providing a model of anatomical constraints, which limit accessibility to the body structure;
in a box 346: providing a first collection of views of the modeled body structure, obtained within the modeled anatomical constraints;
in a box 348: providing a first scoring function, by which any set of at least one view, from a collection of views, is scorable with a score that rates information, obtained from the modeled body structure by the set;
in a box 350: forming sets of views from the first collection of views, and scoring them, with the first scoring function;
in a box 352: selecting a set of views from the first collection of views of the modeled body structure, based on its score, as the predefined set of views;
in a box 354: performing radioactive-emission measurements of an in-vivo body structure that corresponds to the body structure that has been modeled, selectively at the predefined set of views;
in a box 356: identifying a suspected pathological feature, in the in-vivo body structure;
in a box 358: providing a model of the suspected pathological feature, based on its location in the body structure and general medical knowledge;
in a box 360: providing a model of the anatomical constraints, which limit accessibility to the suspected pathological feature;
in a box 362: providing a second collection of views of the modeled suspected pathological feature, obtained within the modeled pathology's anatomical constraints;
in a box 364: providing a second scoring function;
in a box 365: forming sets of views from the second collection of views, and scoring them, with the second scoring function;
in a box 366: selecting a set of pathology views from the second collection of views, based on its score, as the predefined pathology set of views; and in a box 368: performing radioactive-emission measurements of the suspected pathological feature, selectively at the predefined pathology set of views.

It will be appreciated that the model of the suspected pathological feature may be provided responsive to a patient's complaint, a physician's examination, or based on input from another imaging system, for example, x-rays, CT, MRI, ultrasound, and gamma scanning, for example, with a hand-held gamma camera, rather then based on the findings of the first set of measurements, of the step 356, hereinabove.

Design of a Radioactive-Emission-Measuring Probe

While the embodiments described in conjunction with FIGS. 5A-12 relate to predefining a set of optimal views for a given radioactive-emission-measuring probe and a body structure, another side of the same coin relates to an optimal design of the radioactive-emission-measuring probe and probe system for the body structure, optimized with respect to functional information gained.

Thus, the embodiments described hereinbelow, in conjunction with FIGS. 13A-15 illustrate methods of designing probes and probe systems, optimized with respect to information gained about a body structure.

Referring further to the drawings, FIGS. 13A-13E schematically illustrate possible designs of the radioactive-emission-measuring probe 10, and the process of obtaining views for a given probe design, in accordance with embodiments of the present invention.

FIGS. 13A-13C schematically illustrate the radioactive-emission-measuring probe 10 as a radioactive-emission-measuring probe 226 arranged for measuring the radioactive-emission-density distribution of three bodies, U1, U2 and U3. The volume U1 of FIG. 13A has been modeled with no modeled organ targets, in order to score the radioactive-emission-measuring probe 226 in terms of uniformity. The volume U2 of FIG. 13B includes two modeled organ targets, HS1 and HS2, and may be used for scoring the radioactive-emission-measuring probe 226 in terms of reliability. The volume U3 of FIG. 13C includes two modeled organ targets, HS1 and HS2', so as to form a pair with the volume U2 of FIG. 13B, and the pair may be used for scoring the radioactive-emission-measuring probe 226 in terms of separability. Additionally, the volume U3 may be used to obtain a second score in terms of reliability, and the two reliability scores may be averaged. It will be appreciated that additional bodies, of different radioactive emission density distributions may be used, for obtaining additional scores in terms of reliability, and for forming additional pairs, for additional scores in terms of separability, wherein the scores in terms of each scoring function may be averaged. Additionally, the scores of the three functions may be combined, for example, as a sum, or as a weighted average. It will be appreciated that only one of the scoring functions, or only two of the scoring functions may be used. Additionally or alternatively, another scoring function or other scoring functions may be used.

According to the present example, the probe 226 has two detecting units 222A and 222B whose collimators are arranged in parallel. The two detecting units 222A and 222B are adapted for motion in the directions of ±x, within the probe 226, as shown by arrows 224 and 228, so as to provide coverage of a plane within the bodies U1 U2 and U3, in parallel sectors. Upon reaching the end of the travel in the +x direction, as shown by the arrow 224, the two detecting units 222A and 222B may be rotated in the direction of ω, as shown by an arrow 217, and return in the −x direction of the arrow 228. In this manner, complete coverage of the whole body is provided. A representative collection of views of the probe 226 may be defined as a set of views of the bodies U1, U2, and U3, taken at predetermined increments of Δx and Δω.

Intuitively, a set formed of parallel sectors may score poorly in terms of uniformity since radioactive emissions from voxels closer to the detecting unit have higher probabilities of being detected than radioactive emissions from voxels far from the detecting unit. Additionally, a set formed of parallel sectors may score poorly in terms of separability, since it cannot distinguish between two models, which only differ in the depth of a pathological feature, along the z-axis.

FIG. 13D schematically illustrate the radioactive-emission-measuring probe 10 as a radioactive-emission-measuring probe 220, arranged for measuring the radioactive-emission-density distribution of the volume U2, which may be used for scoring the radioactive-emission-measuring probe 220 in terms of reliability.

The probe 220 has the two detecting units 222A and 222B, arranged to sweep a plane within the volume U2, in a windshield-wiper-like manner, along ±θ, as illustrated by arrows 216 and 218. When sweeping along ±θ is completed, the detecting units 222A and 222B rotate a few degrees along ω, as illustrated by the arrow 217, and sweeping along ±θ is repeated in the new orientation. In this manner, coverage of the whole volume U2 is performed, from two locations and a large plurality of orientations. A representative collection of views of the probe 220 may be defined as a set of views of the volume U2, taken at predetermined increments of Δθ and Δω.

The significance of the present embodiment, is as follows:
i. The different detecting units 222A and 222B provide views from different orientations; and
ii. The different detecting units 222A and 222B may change their view orientations.

A score may be applied to this set, based on the information theoretic measure of reliability.

It will be appreciated that similarly, the probe 220 may be arranged for measuring the radioactive-emission-density distribution of the volume U1 (FIG. 13A) and of the volume U3 (FIG. 13C), and possibly also of other bodies, in order to score the radioactive-emission-measuring probe 220 also in terms of uniformity and separability. The scores of the three functions may be combined, for example, as a sum, or as a weighted average. It will be appreciated that only one of the scoring functions, or only two of the scoring functions may be used. Additionally or alternatively, another scoring function or other scoring functions may be used.

Intuitively, the set of representative collection of views of the present example is likely to score more highly in terms of separability than that of the probe 226 of FIG. 13A, as it provides views from different locations and orientations.

In FIG. 13E the detecting units 222A and 222B of the probe 220 are further adapted for motion in the directions of ±x, within the probe 220, as shown by the arrows 224 and 228.

Intuitively, the set of representative collection of views of the present example is likely to score more highly in terms of all three information theoretic measures, than those of the probe of FIGS. 13A-13C and of the probe of FIG. 13D, as the present example provides views from a large plurality of locations and orientations.

In this manner, the information theoretic measures may be used for scoring representative collections of views of suggested probe designs, and an optimal probe design may be chosen based on this score, as described hereinbelow, in conjunction with FIG. 14, hereinbelow.

Figure 14:
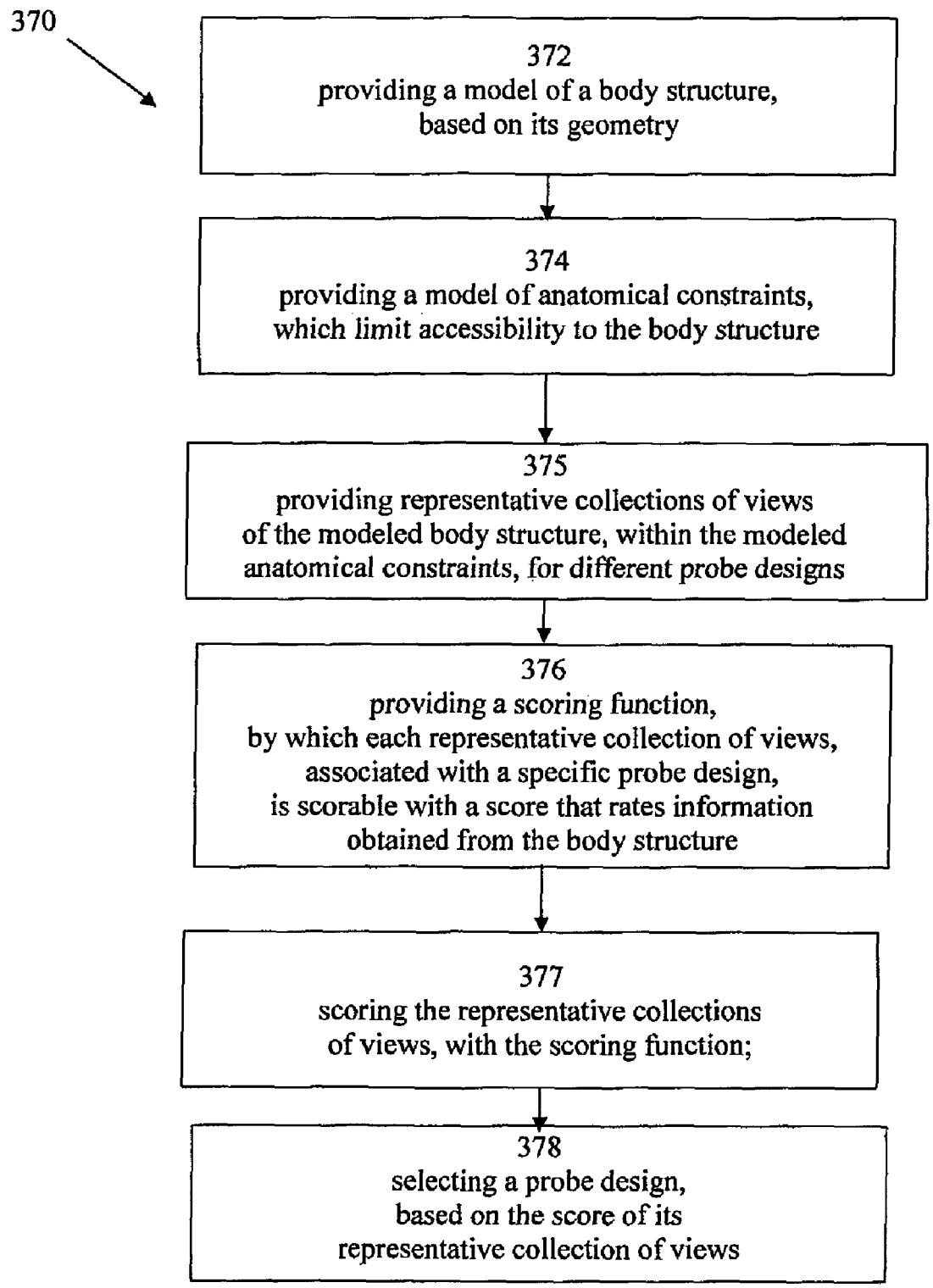
FIG. 14 illustrates, in flowchart form, a method of selecting a probe design optimized with respect to information gained about a body structure, in accordance with embodiments of the present invention.

Referring further to the drawings, FIG. 14 illustrates, in flowchart form, a method 370 for identifying a probe optimized with respect to information gained about the body structure. The method 370 comprises:

in a box 372: providing a model of a body structure, based on its geometry;

in a box 374: providing a model of anatomical constraints, which limit accessibility to the body structure;

in a box 375: providing representative collections of views of the modeled body structure, within the modeled anatomical constraints, for different probe designs;

in a box 376: providing a scoring function, by which each representative collection of views, associated with a specific probe design, is scorable with a score that rates information, obtained from the body structure;

in a box 377: scoring the representative collections of views, with the scoring function; and in a box 378: selecting a probe design, based on the score of its representative collection of views.

In this manner, a comparison of the quality of the data that may be produced by each probe design can be made. This analysis is important at the probe-design stage, in order to eliminate situations where views which are anatomically possible and which are desired from the standpoint of information theoretic measures, are unattainable because of probe design limitations. For example, the probe 190 of FIG. 4C, hereinabove, cannot be used for the windshield-wiper-like motion, shown in FIG. 13D, by the arrows 216 and 218; however, this type of coverage has proved very valuable. Enforcing the method 370 for probe design will favor another design.

Additionally, when selecting a probe design, it is generally desired to consider secondary issues, such as the rate of data collection, the cost of the probe, the complexity of the design, for example, in terms of the number of motors and motion-transfer systems, and the like.

The rate of data collection is important both because it may be associated with patient discomfort and because it affects the number of patients that may be examined in a period of time. Where data collection with one probe design may take an hour and with another probe design it may take 10 minutes, the design of the faster probe is highly advantageous. Complexity and cost are important because they affect the accessibility of the general public to the probe.

Thus, a design scoring function may be provided, for rating each probe design with a design score, based on any one or a combination of the secondary issues. The design scoring function may be used for selecting a probe design from several that have been found acceptable in terms of the quality of the data, by the method 370 of FIG. 14.

Figure 15:
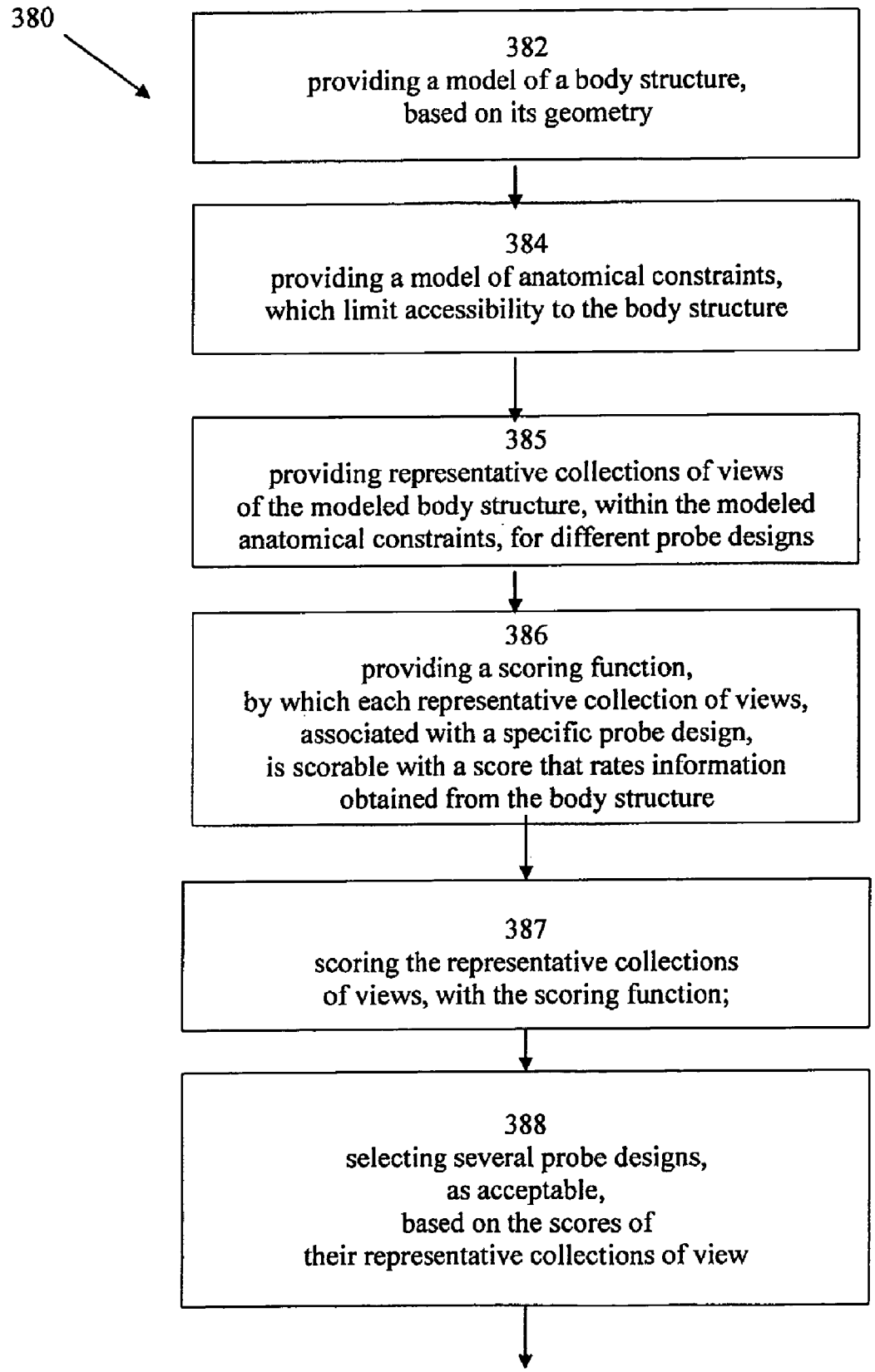
FIG. 15 illustrates, in flowchart form, a method of selecting a probe design, based on the rate of data collection and other design considerations, in accordance with embodiments of the present invention.
Figure 15:
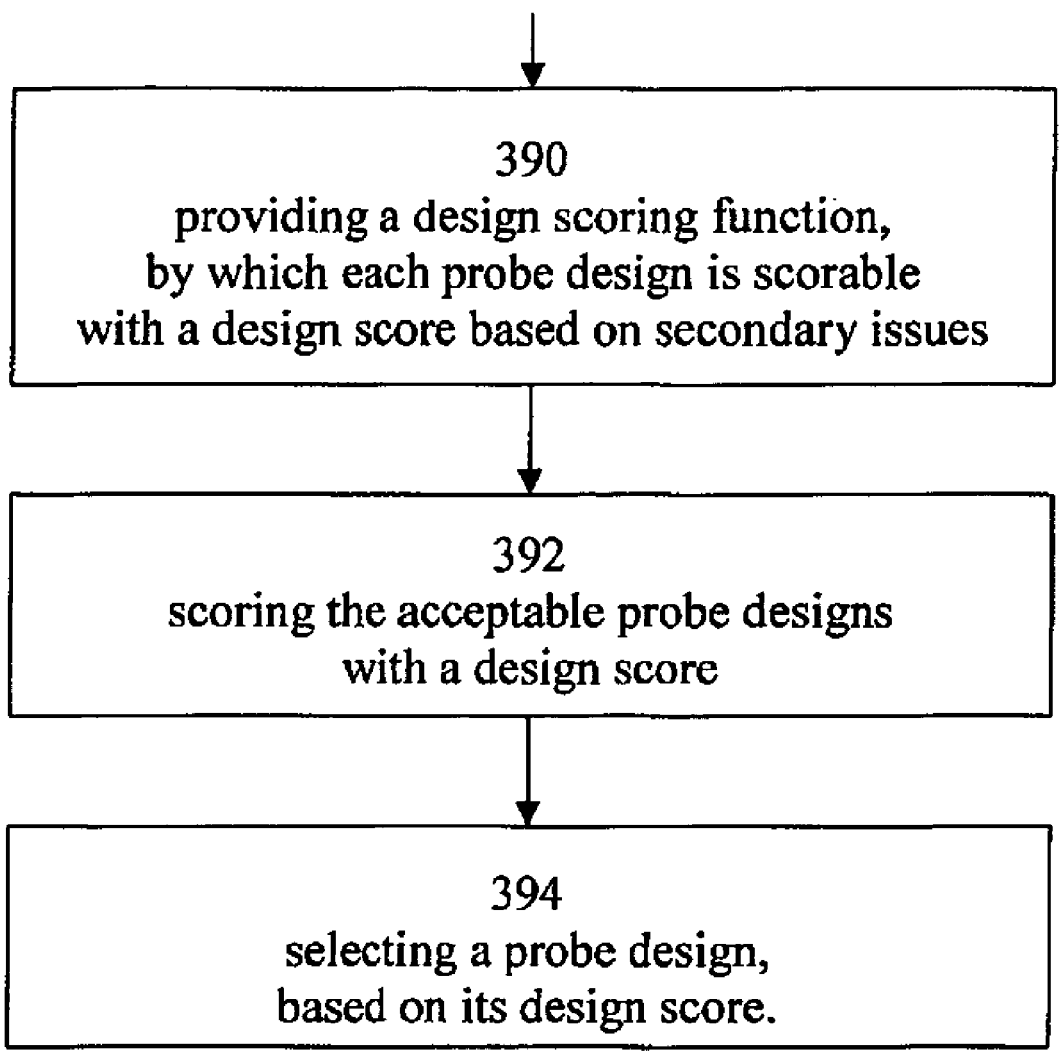

Referring further to the drawings, FIG. 15 illustrates, in flowchart form, a method 380 of selecting a probe design, optimized with respect to information gained about a body structure and secondary issues, in accordance with embodiments of the present invention. The method 380 comprises:

in a box 382: providing a model of a body structure, based on its geometry;

in a box 384: providing a model of anatomical constraints, which limit accessibility to the body structure;

in a box 385: providing representative collections of views of the modeled body structure, within the modeled anatomical constraints, for different probe designs;

in a box 386: providing a scoring function, by which each representative collection of views, associated with a specific probe design, is scorable with a score that rates information, obtained from the body structure;

in a box 387: scoring the representative collections of views, with the scoring function;

in a box 388: identifying several probe designs as acceptable, based on the scores of their representative collections of view;

in a box 390: providing a design scoring function, by which each probe design is scorable, based on the secondary issues;

in a box 392: scoring the acceptable probe designs with a design score;

in a box 394: selecting a probe design, based on its design score.

It will be appreciated other manners of combining the scoring function, which rates information, and the design scoring function, which rates secondary issues, are possible. For example, a combined scoring function, which takes both into account, may be used.

As will be shown, hereinbelow, in conjunction with FIGS. 19A-22H, many different probe designs may provide substantially the same information, but are different in terms of their secondary considerations, that is, at different rates of data collection, different costs and different complexity of their designs, for example, in terms of the number of motors and motion-transfer systems. Thus these may score similarly in terms of functional information, and a design scoring function may be used to choose from amongst them.

Referring further to the drawings, FIGS. 16A-16L schematically illustrate the process of obtaining views with the radioactive-emission-measuring probe 10, based on the model 250 of the volume U, in accordance with embodiments of the present invention.

The views that are obtained by the present example may be used both as:

i. a collection of views for the volume U, from which an optimal set of views may be chosen, in accordance with the teachings of FIGS. 8, 10, and 12, hereinabove; and ii. a representative collection of views of the probe 10, in accordance with the teachings of FIGS. 14 and 15, hereinabove.

Referring further to the drawings, FIGS. 16M-16U schematically illustrate experimental results obtained with the radioactive-emission-measuring probe 10, in accordance with embodiments of the present invention.

Figure 16A:
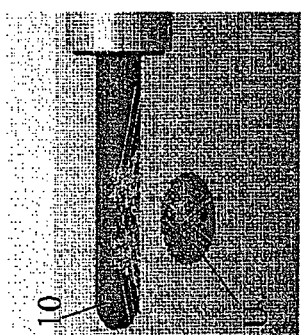
FIGS. 16A-16L schematically illustrate the process of obtaining views with the radioactive-emission-measuring probe, based on a modeled volume, in accordance with embodiments of the present invention.
Figure 16B:
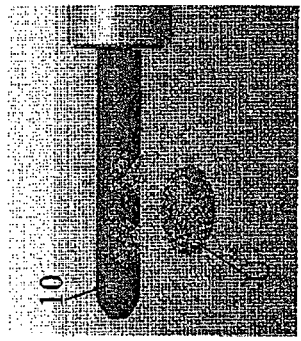
Figure 16C:
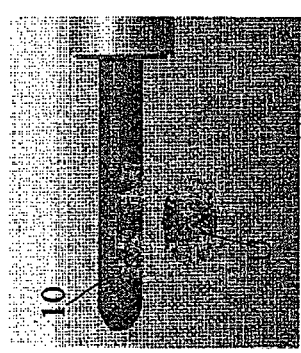
Figure 16D:
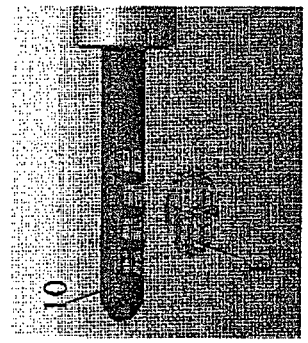
Figure 16E:
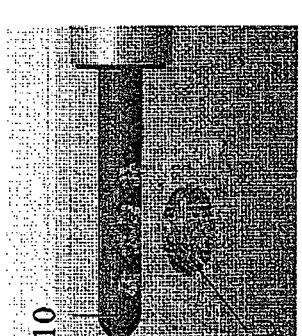
Figure 16F:
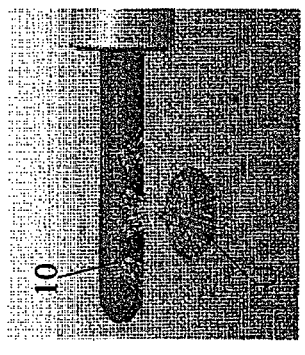
Figure 16G:
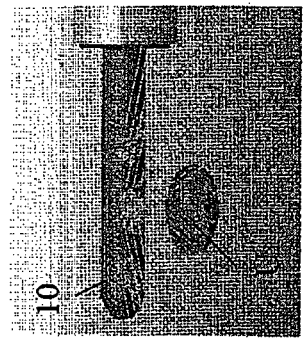
Figure 16H:
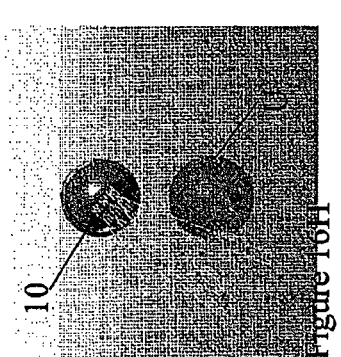
Figure 16I:
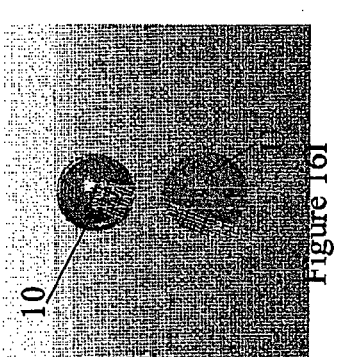
Figure 16J:
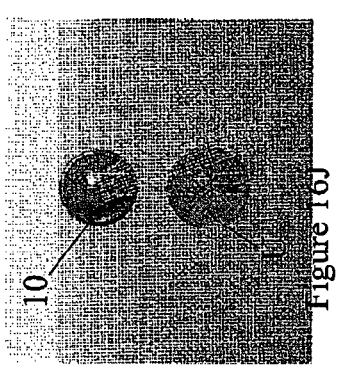
Figure 16K:
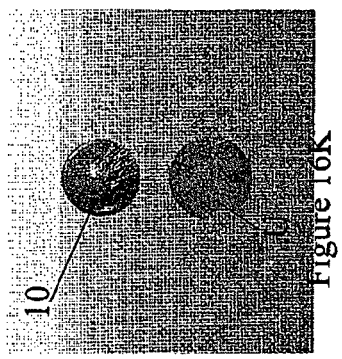
Figure 16L:
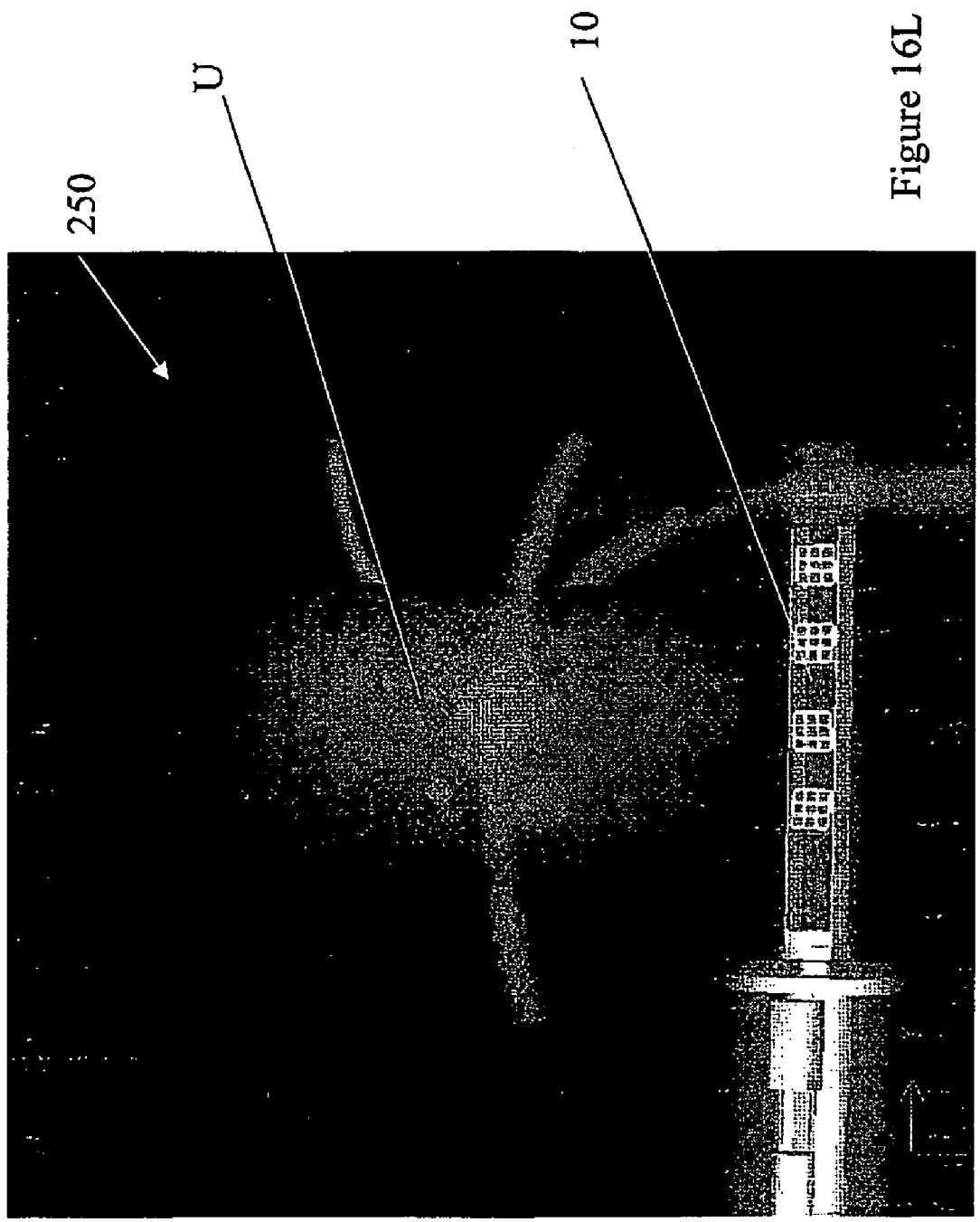
Figure 16O:
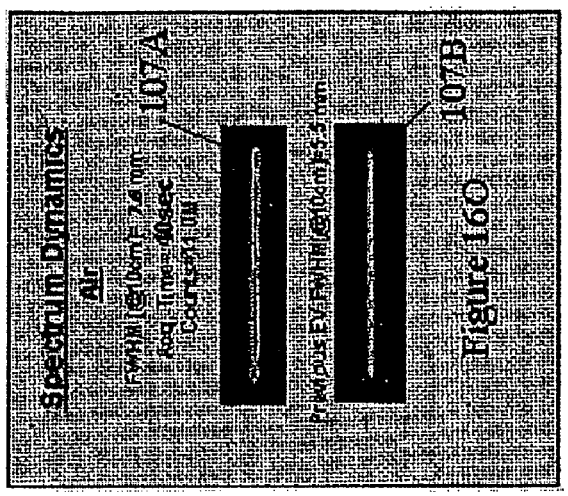
FIGS. 16M-16U schematically illustrate experimental results, obtained with the radioactive-emission-measuring probe, for a modeled volume having organ targets, in accordance with embodiments of the present invention.
Figure 16R:
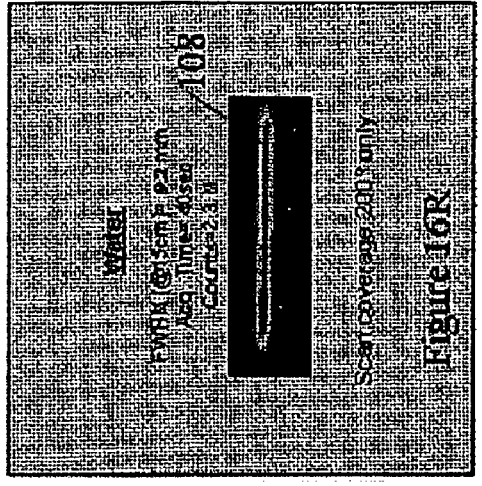
Figure 16N:
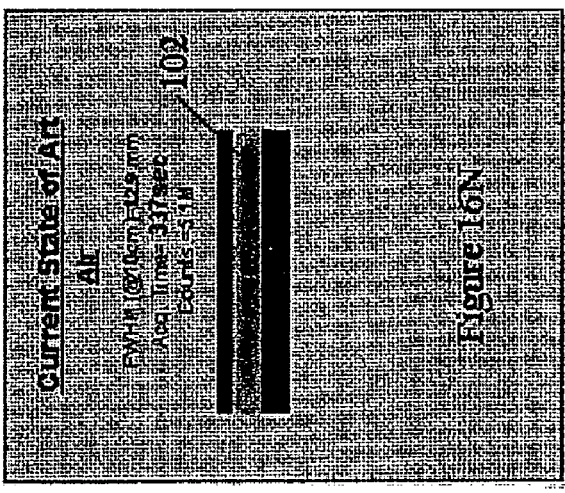
Figure 16Q:
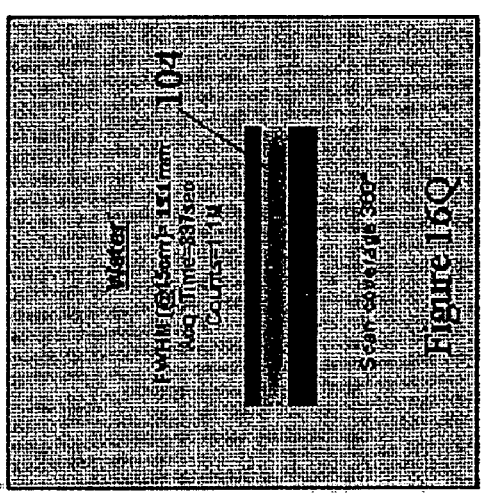
Figure 16M:
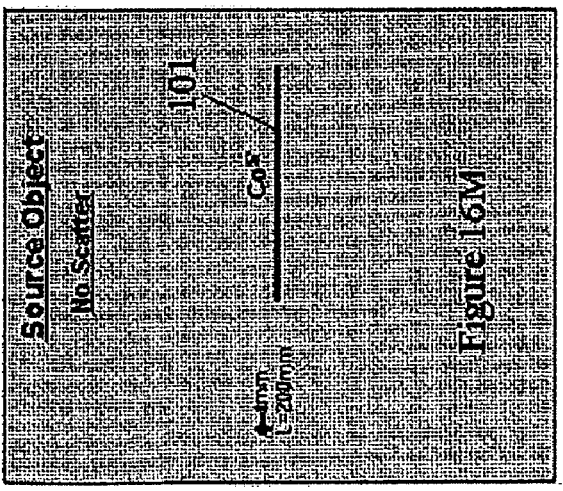

FIGS. 16M-16O schematically illustrate line-source measurements of a wire source 101 in air, with a state of the art gamma camera and with the probes of the present invention.

As seen in FIG. 16M, the wire source 101 is Cobolt-57, of 1 mm in diameter and 200 mm in length.

FIG. 16N illustrates an image 102 of a current state of the art gamma camera (not shown), for which a value of FWHM was 12.9 mm at a measuring distance of 10 cm from the source 101. About 5.1M counts were obtained after 337 seconds of counting. A 360-degree scan had been made.

FIG. 16O illustrates images 107A and 107B of the probe 10 of the present invention, for which values of FWHM were 7.6 mm for the image 107A and 5.5 mm for the image 107B, at a measuring distance of 10 cm from the source 101. About 11M counts were obtained after 40 seconds of counting. In other words, for a counting time of about ⅒ that of the state of the art camera, the number of counts was more than twice that of the state of the art camera and the FWHM value was between 0.6 and 0.4 that of the state of the art camera, yielding a much sharper peak.

Figure 16P:
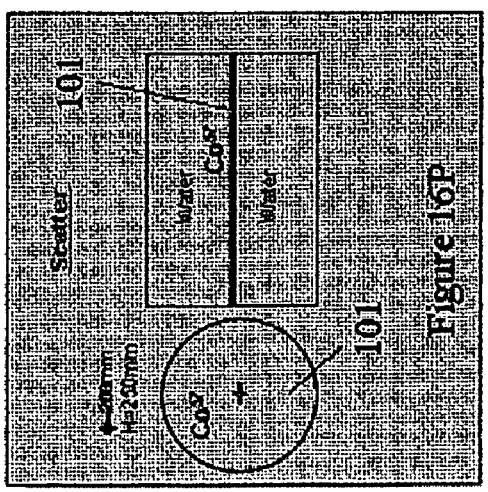

FIGS. 16P-16R schematically illustrate line-source measurements of a wire source 101, in water, with a state of the art gamma camera and with the probes of the present invention.

As seen in FIG. 16Q, of an image 104, results of a current state of the art gamma camera (not shown) were FWHM of 15.1 mm at a measuring distance of 15 cm from the source 101, and 1.1M counts after 337 seconds of counting.

As seen in FIG. 16O, of an image 108, results of the probe 10 of the present invention were FWHM of 9.2 mm, at a measuring distance of 15 cm from the source 101, and 2.3M counts after 40 seconds of counting. Again, for a counting time of about 1/10 that of the state of the art camera, the number of counts were more than twice and the FWHM value was between 0.6 of the state of the art camera, yielding a much sharper peak.

Figure 16S:
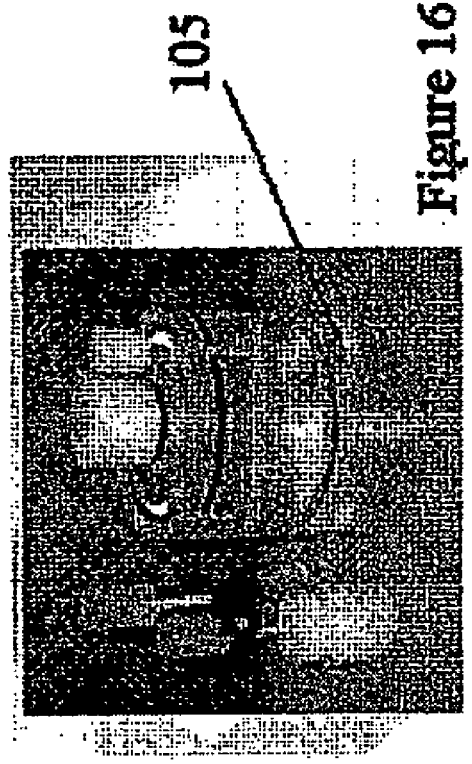
Figure 16T:
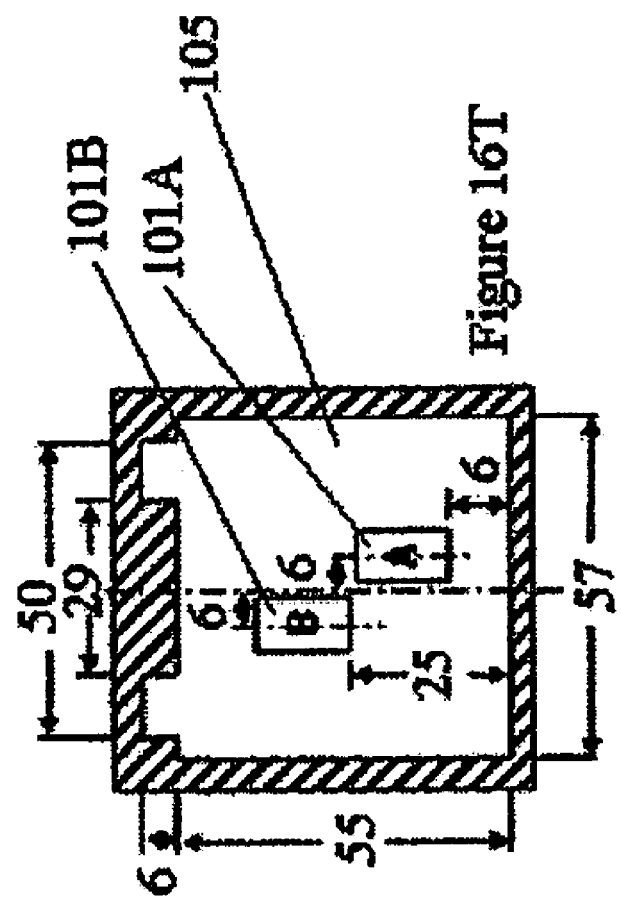

FIGS. 16S and 16T schematically illustrate a Three-dimensional source, formed of two pellets 101A and 101B, in a Perspex phantom cylinder 105. The pellet 101A had a source to background ratio of 3:1 and the pellet 101B had a source to background ratio of 2:1. They were arranged as shown in FIG. 16T, the distances being given in mm.

A series of coronal, sagittal, and transverse images were taken, by a state of the art gamma camera and by the probe of the present invention. A total of 2,500 counts were obtained, for which the state of the art camera required 9 minutes, and the probe of the present invention required 1 minute.

Figure 16U:
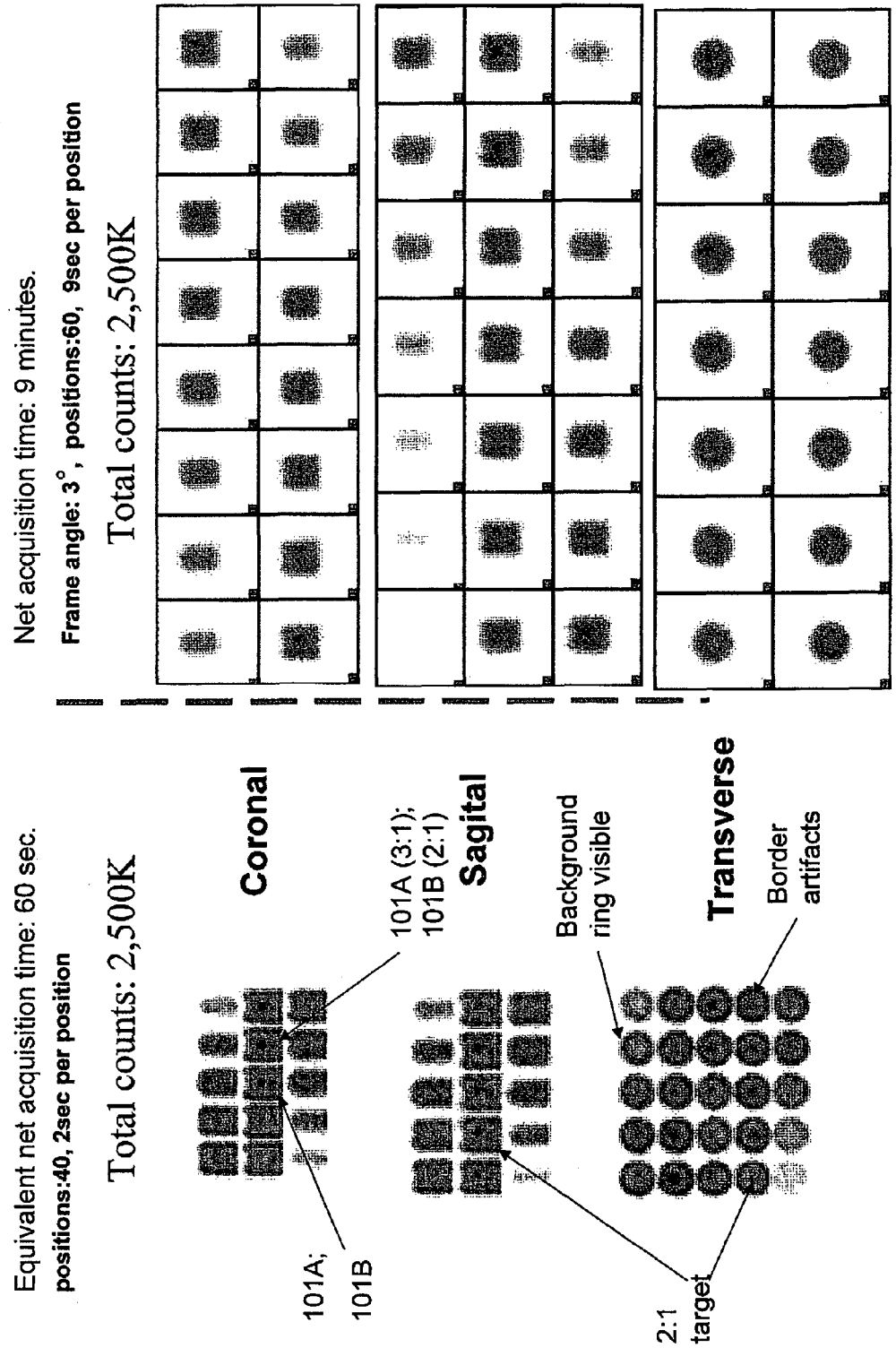

As seen on FIG. 16U, the state of the art camera provided little resolution, while the probe of the present invention resolved both the 3:1 source 101A and the 2:1 source 101B, as well as border artifacts and background rings.

EXAMPLES OF PROBE SYSTEMS

Reference is now made to the following examples of radioactive-emission-measuring probes and probe systems, for the comparative study taught in conjunction with FIGS. 14 and 15.

Example 1

Referring further to the drawings, FIGS. 17A-17H schematically illustrate detecting units 12 and blocks 90 that may be considered for possible probe designs.

FIGS. 17A and 17B schematically illustrate side and top views, respectively, of the basic detecting unit 12 (see also FIG. 1A), having a detector 91 and a wide-bore collimator 96, formed as a tube, of a collection angle $\delta 1$.

FIGS. 17C and 17D schematically illustrate side and top views, respectively, of the detecting unit 12, with the collimator 96 formed as a wide angle collimator, of a collection angle $\delta 2$.

FIGS. 17E and 17F schematically illustrate side and top views, respectively, of the block 90 (see also FIG. 1B) of the detecting units 12, with the collimator 96 formed as a grid, and each of the detecting unit 12 having a collection angle $\delta 3$. As few as two or four, and as many as a hundred or several hundred of the detecting units 12 may be included in the block 90.

FIGS. 17G and 17H schematically illustrate side and top views, respectively, of the block 90 of the detecting units 12, with the collimator 96 formed as a grid, with two sizes of the detecting units 12, as follows: small detecting units 94A, of collection angles $\delta 4$, at the center of the grid, and large detecting units 94B, of collection angles $\delta 5$, at the periphery. It will be appreciated that other arrangements of detecting units of different sizes may be used.

It will be appreciated that a combination of these may be used. For example, the block 90 may include wide-angle collimators at the periphery and normal collimators of 90-degrees at the center.

FIGS. 17I-17L schematically illustrate the block 90, wherein the detector 91 is a single-pixel scintillation detector, such as NaI(Tl), LSO, GSO, CsI, CaF, or the like, operative with photomultipliers 103.

As seen in FIG. 17I, the block 90, having proximal and distal ends 109 and 111, respectively, vis a vis an operator (not shown), is formed of the scintillation detector 91, of a single pixel, and the collimators 96, to create the detecting units 12. A plurality of photomultipliers 103 is associated with the single pixel scintillation detector 91, and with proper algorithms, as known, their output can provide a two dimensional image of the scintillations in the single pixel scintillation detector 91. In essence, this is an Anger camera, as known.

The distal view 111 of the collimator grid is seen in FIG. 17J.

Two optional proximal views 109 of the photomultipliers 103 are seen in FIGS. 17K and 17L, as a square grid arrangement, and as an arrangement of tubes.

Example 2

Referring further to the drawings, FIGS. 18A and 18B schematically illustrate the radioactive-emission-measuring probe 10, of the single detecting unit 12 (see FIGS. 1A and 17A). The single detecting unit 12 has a motion with respect to the housing 20, which is a combination of a rotational motion around the x-axis, in the direction of $\omega$, denoted by an arrow 44, and a translational motion along the x-axis, denoted by an arrow 46.

As a consequence, a spiral trace 48 is formed, for example, on an inner surface of a body lumen 232, as seen in FIG. 18B.

Preferably, the motions of the detecting unit 12 are contained within the housing 20, so that the external surface of the probe 10 remains stationary. The external surface of the probe may be formed of a carbon fiber, a plastic, or another material, which is substantially transparent to nuclear radiation.

Example 3

Referring further to the drawings, FIGS. 18C and 18D schematically illustrate the radioactive-emission-measuring probe 10, of the single block 90 (FIGS. 1B and 17E). Note that all the detecting units 12 of the single block 90 move as a single body. The single block 90 has a motion with respect to the housing 20, which is a combination of the rotational motion around the x-axis, in the direction of $\omega$, denoted by the arrow 44, and the translational motion along the x-axis, denoted by the arrow 46.

As a consequence, a plurality of spiral traces 49 is formed, for example, on an inner surface of a body lumen, as seen in FIG. 18D.

Preferably, the motions of the block 90 are contained within the housing 20, so that the external surface of the probe 10 remains stationary, wherein the external surface of the probe is substantially transparent to nuclear radiation.

Example 4

Referring further to the drawings, FIGS. 19A-19E schematically illustrate the radioactive-emission-measuring probe 10, of the single block 90 of a plurality of the detecting units 12.

For understanding the motion of the probe 10 of the present example, it is desirable to define a cylindrical coordinate system of a longitudinal axis, x, and a radius r, wherein the motion around the longitudinal axis, x, is denoted by $\omega$, while the motion around the radius r is denoted by $\phi$.

The single block 90 has a motion with respect to the housing 20, which is performed in steps, as follows:
i. the windshield-wiper like oscillatory motion, around the radius r, in the direction of $\pm\phi$, as denoted by the arrow 50;

ii. the translational motion along the x-axis, by an amount Δx, to a new measuring position, as denoted by the arrow 46;

iii. after traversing the length of the probe, a rotational motion around the x-axis, in the direction of ω, by an amount Δω, as denoted by the arrow 44, in order to perform the same measurements at a new measuring position of ω.

As a consequence, a plurality of broken line traces 59 are formed, as seen in FIG. 19E.

Preferably, the motions of the block 90 are contained within the housing 20, so that the external surface of the probe 10 remains stationary, wherein the external surface of the probe is substantially transparent to nuclear radiation.

Example 5

Referring further to the drawings, FIGS. 20A-20H schematically illustrate the radioactive-emission-measuring probe 10, having at least one pair, or a plurality of pairs of blocks 90, adapted for the windshield-wiper like oscillatory motion, around the radius r, as denoted by the arrows 50. The oscillatory motions may be synchronized in an antipodal manner, so as to be diametrically opposed to each other, as shown in FIGS. 20B and 20E, by the arrows 54, and as shown in FIGS. 20C and 21F by the arrows 56. It will be appreciated that the oscillatory motions need not be synchronized in an antipodal manner. Rather, all the blocks 90 may move together, or each block 90 may move independently. It will be appreciated that an odd number of blocks 90 is also possible.

Additionally, a rotational motion of the housing 20, around the x-axis in the direction of ω, an amount Δω, to a new measuring position along ω, is provided, after each step of the oscillatory motion, as shown in FIG. 20D, by an arrow 52.

The resultant traces are the plurality of broken line traces 59, as seen in FIG. 20G.

In essence, the probe 10 of FIGS. 20A-20H provides views which are essentially the same as those of FIGS. 19A-19E, but in a more efficient way, since a plurality of blocks is involved.

In accordance with the present example, i. The different blocks 90 provide views from different orientations; and ii. The different blocks 90 may change their view orientations.

Preferably, the motions of the blocks 90 are contained within the housing 20, so that the external surface of the probe 10 remains stationary, wherein the external surface of the probe is substantially transparent to nuclear radiation.

In particular, as seen in FIG. 20H, an internal housing 21 may contain all the blocks 90, so that they may be moved together by the motion provider 76, as a single structure, while housing 20 and the external surface of the probe 10 remain stationary.

The operational manner of the probe 10 of FIGS. 20A-20H is described in conjunction with FIG. 23C, hereinabove.

It will be appreciated that the single detecting units 12 may be used in place of the single blocks 90.

Example 6

Referring further to the drawings, FIGS. 21A-21D schematically illustrate the radioactive-emission-measuring probe 10, having at least one pair, or a plurality of pairs of blocks 90, adapted for the windshield-wiper like oscillatory motion, around the radius r, as denoted by the arrow 50. The oscillatory motions are preferably synchronized in an antipodal manner, so as to be diametrically opposed to each other, as in FIGS. 20A-20H. It will be appreciated that the oscillatory motions need not be synchronized in an antipodal manner.

Rather, all the blocks 90 may move together, or each block 90 may move independently. It will be appreciated that an odd number of blocks 90 is also possible.

Additionally, a rotational motion of each of the blocks 90 around the x-axis, in the direction of ω, an amount Δω, to a new measuring position along ω, is provided, after each step of the oscillatory motion, as shown in FIG. 21B, by the arrows 44. This is unlike FIG. 20D, wherein the internal housing 21 moved as a single unit, as shown in FIGS. 20D and 20H.

The resultant traces are the plurality of broken line traces 59, as seen in FIG. 21D. In essence, the probe 10 of FIGS. 21A-21D provides views which are essentially the same as those of FIGS. 19A-19E, and of FIGS. 20A-20H, but in a different manner.

In accordance with the present example, i. The different blocks 90 provide views from different orientations; and ii. The different blocks 90 may change their view orientations.

Preferably, the motions of the blocks 90 are contained within the housing 20, so that the external surface of the probe 10 remains stationary, wherein the external surface of the probe is substantially transparent to nuclear radiation.

It will be appreciated that the detecting units 12 may be used in place of the blocks 90.

Example 7

Referring further to the drawings, FIGS. 22A-22H schematically illustrate a radioactive-emission-measuring probe 95, comprising a plurality of assemblies 92, each assembly 92 being similar in construction to the probe 10 of FIG. 20H, in accordance with embodiments of the present invention.

The plurality of assemblies 92 are preferably arranged in parallel, and their rotational motions, around the x-axis, may be synchronized in an antipodal manner, so as to be diametrically opposed to each other, as shown in FIG. 22C, by arrows 62, and in FIG. 22G, by arrows 64. It will be appreciated that the rotational motion around the x-axis need not be synchronized in an antipodal manner, and may be performed in parallel, or independently.

Thus, the resultant traces are a large plurality of the broken line traces 66 and 68, as seen in FIGS. 22D and 22H.

In essence, the probe 95 of FIGS. 22A-22H provides views which are essentially the same as those of FIGS. 19A-19E, 20A-20H, and 21A-21D, but far more efficiently, since a plurality of assemblies are involved.

In accordance with the present example, i. The different blocks 90 provide views from different orientations;

ii. The different blocks 90 may change their view orientations;

iii. The different assemblies 92 provide views from different orientations; and iv. The different assemblies 92 may change their view orientations.

The operational manner of the probe 95 is described in conjunction with FIG. 23D, hereinbelow, for the at least two assemblies 92A and 92B.

Preferably, the motions of the blocks 90 and of the assemblies 92 are contained within the housing 20, so that the external surface of the probe 95 remains stationary, wherein the external surface of the probe 95 is substantially transparent to nuclear radiation.

It will be appreciated that probe 95 may include a plurality of assemblies 92, which are not parallel to each other. For example, the assemblies 92 may be at right angles to each other, or at some other angle.

It will be appreciated that the assemblies 92 may include the detecting units 12 rather then the blocks 90.

Example 8

Having designed a radioactive-emission-measuring probe capable of obtaining a collection of views, and having predefined a set of views, which is optimal for a body structure, based on its model, the task of performing measurements, selectively at the redefined set of views, would be quite impossible if it were to be performed manually. Generally, between several hundreds and several thousands of views are taken, and manually tuning each to a predetermined location, orientation, and possibly also duration would be impractical. Therefore, the probe and method of the present invention are operative with an overall system, in which computer controlled motion providers govern the motions of the detecting units or of the overall probe. The computer may be any one of a personal computer, a laptop, a palmtop, or another computer, adapted for communication with the probe, or a microcomputer, built into the probe. Additionally, a combination of a microcomputer, built into the probe, and an external computer such as a personal computer, a laptop, a palmtop, or the like, may be used.

Preferably, before measurements are performed, personal details are fed into the computer, and the models of the body structure and anatomical constraints are adapted to these details. The personal details may include age, sex, weight, body type, and the like.

Referring further to the drawings, FIGS. 23A-23D schematically illustrate radioactive-emission-measuring-probe systems 400 in accordance with embodiments of the present invention.

As seen in FIG. 23A, the probe system 400 includes the probe 10, having a controller 404, in communication with one or several motion providers 76, for sending signals of views' locations and orientations to the one or several motion providers 76. The one or several motion providers 76, in turn, govern the motions of one or several of the detecting units 12. The one or several of the detecting units 12 collect the measurements at the predefined locations and orientations and communicate the data to the controller 404. Signals of new locations and orientations are then communicated by the controller 404 to the one or several motion providers 76. Each of the motion providers 76 may control the motion of one of the detecting units 12 or of a plurality of the detecting units 12.

Preferably, the controller 404 registers the location and orientation of each of the detecting unit 12 as it moves. Additionally or alternatively, a position-tracking device may be associated with each of the detecting units 12.

Preferably, a position-tracking device 418 is associated with the probe 10 as a whole, for registering its position with respect to the body, for example, with respect to the body structure 215 (FIG. 5A).

A power supply 410 powers the probe 10. Alternatively, power may be supplied from the grid.

Preferably, a transceiver 402, or a transmitter 402, reports the measurements to an external computer. Alternatively, a cable may be used. Alternatively, the controller 404 includes a microcomputer, or the like, and performs the data analysis.

Additionally, the transceiver 402 may be adapted to receive input data relating to the personal details of the patient, such as the age, sex, weight, body type, and the like, in order to adjust the model of the body structure, hence the locations and orientations of the predefined, optimal set of views, to the particular patient.

Furthermore, the transceiver 402 may be adapted to receive input data from an ultrasound imager, for providing information such as location, size of the body structure and the like, by ultrasound imaging, in order to adjust the model of the body structure, hence the locations and orientations of the predefined, optimal set of views, to the particular patient.

Preferably, the motion of the one or several motion providers 76 relates to motion of the detecting units 12 with respect to the probe housing 20, for example, as taught in conjunction with FIG. 13E, by the motion of detecting units 222A and 222B, with respect to the housing 220, as shown by the arrows 216 and 218.

Alternatively or additionally, the motion of the one or several motion providers 76 may relate to motion of the probe housing as a whole, with respect to the body structure 215 (FIG. 5A), for example, as taught in conjunction with FIG. 13E, by the motion the probe 220, as shown by the arrows 217 and 228.

It will be appreciated that the controller 404, while being part of the system 400, need not part of the actual probe 10. Rather it may be an external computer, communicating with the probe 10 either by cables or via a transceiver.

Figure 23B:
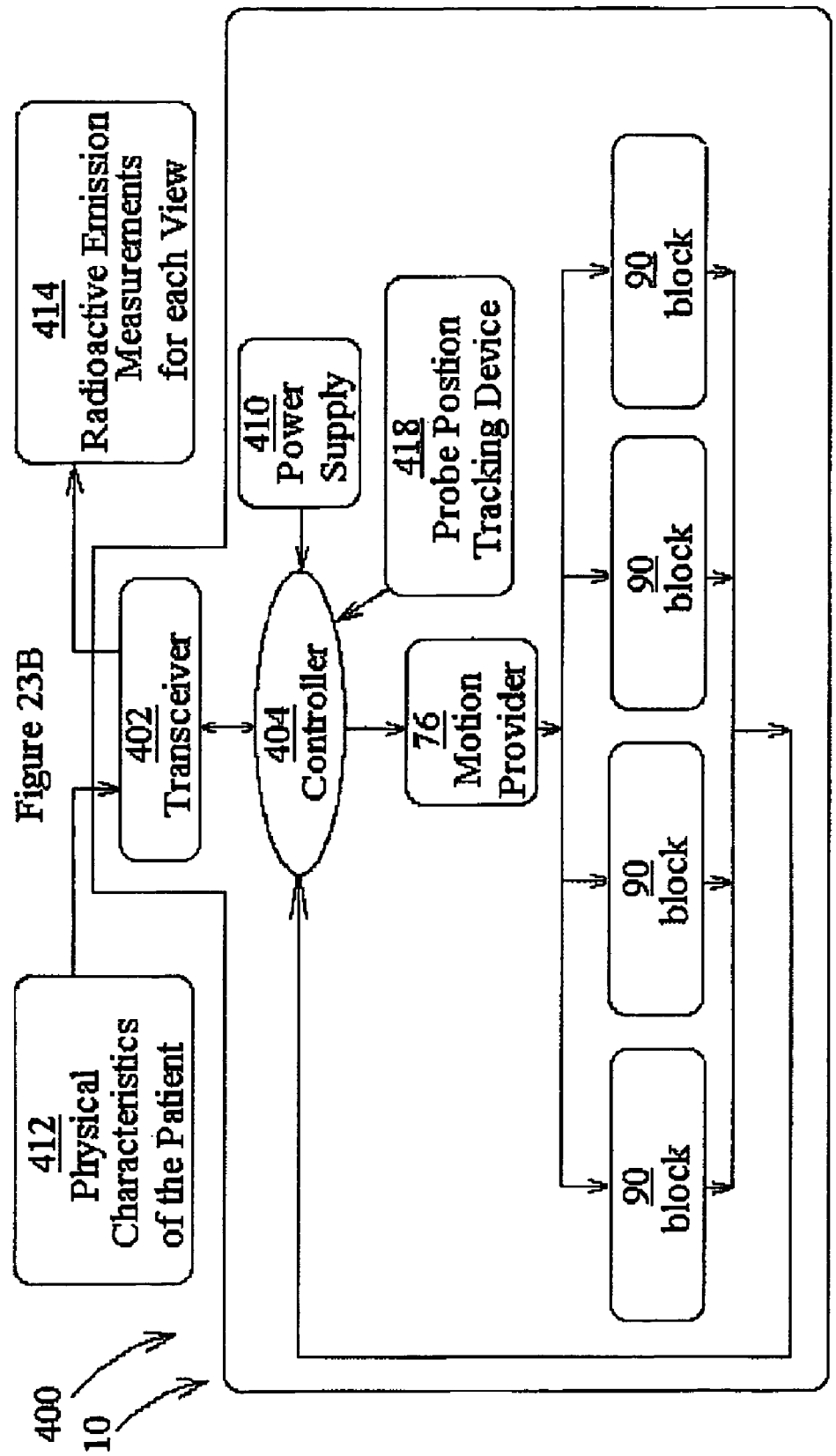

As seen in FIG. 23B, the probe 10 includes the blocks 90, each comprising a plurality of the detecting units 12, each block 90 moving as a single body.

Figure 23C:
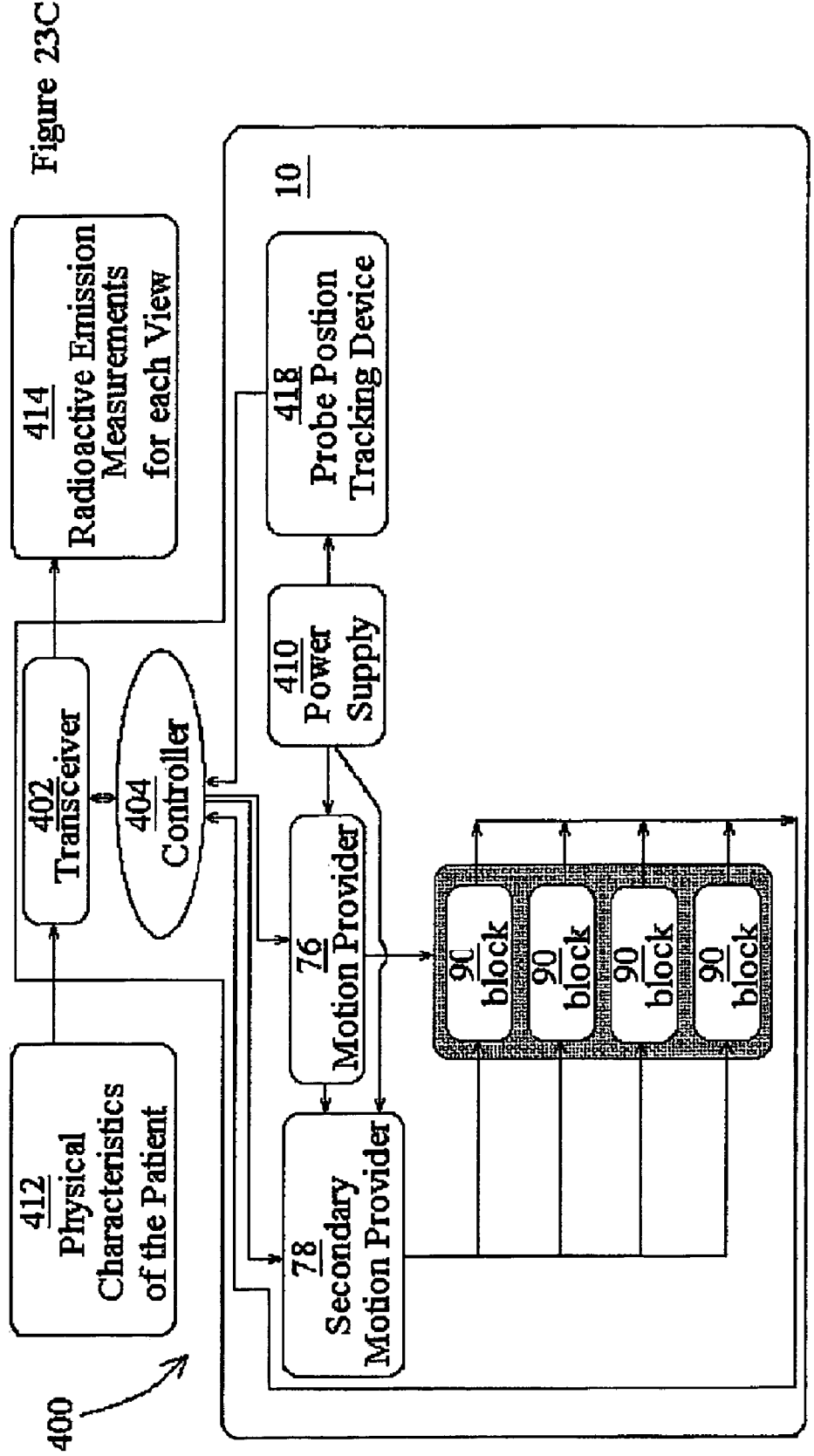

As seen in FIG. 23C, the individual motion of the blocks 90 is governed by a secondary motion provider 78. Additionally, all of the blocks 90 form an assembly 92, which moves by the motion provider 76, for example, within an internal housing 21, as illustrated hereinbelow in conjunction with FIG. 20H. For example, the secondary motion provider 78 may provide the motion described by the arrows 50 of FIGS. 20B and 20C or 20F and 20F, hereinbelow while the motion provider 76 may provide the motion described by the arrow 52 of FIG. 20H, hereinbelow.

It will be appreciated that the multiple motions may be provided to the detecting units 12, rather then to the blocks 90.

It will be appreciated that a tertiary motion provider may also be used and that many arrangements for providing the motions are possible, and known.

Figure 23D:
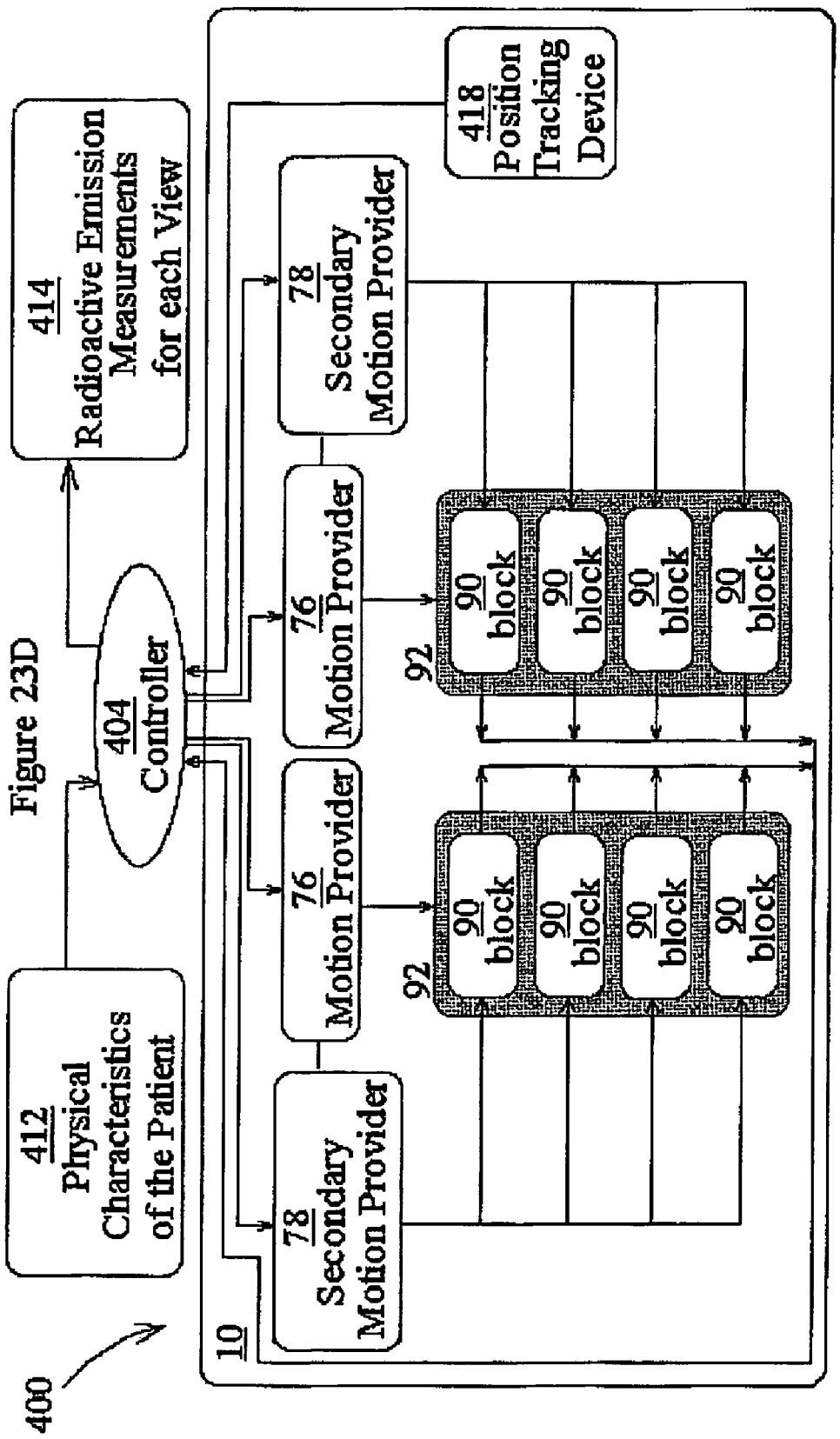

As seen in FIG. 23D, at least two assemblies 92 may be provided, each with a dedicated motion provider 76 and a dedicated secondary motion provider 78. It will be appreciated that the multiple motions may be provided to the detecting units 12, rather then to the blocks 90. It will be appreciated that tertiary motion providers may also be used and that many arrangements for providing the motions are possible, and known.

In the example of FIG. 23D, the controller 404, while being part of the system 400, is not part of the actual probe 10. For example, it may be an external computer, communicating with the probe 10 either by cables or via a transceiver.

EXAMPLES OF PROBE SYSTEMS FOR SPECIFIC APPLICATIONS

Reference is now made to the following examples of radioactive-emission-measuring probes and probe systems, for specific applications.

Example 9

Referring further to the drawings, FIGS. 24A-32 schematically illustrate the radioactive-emission-measuring probe 10, for the prostate, in accordance with an embodiment of the present invention.

Figure 24B:
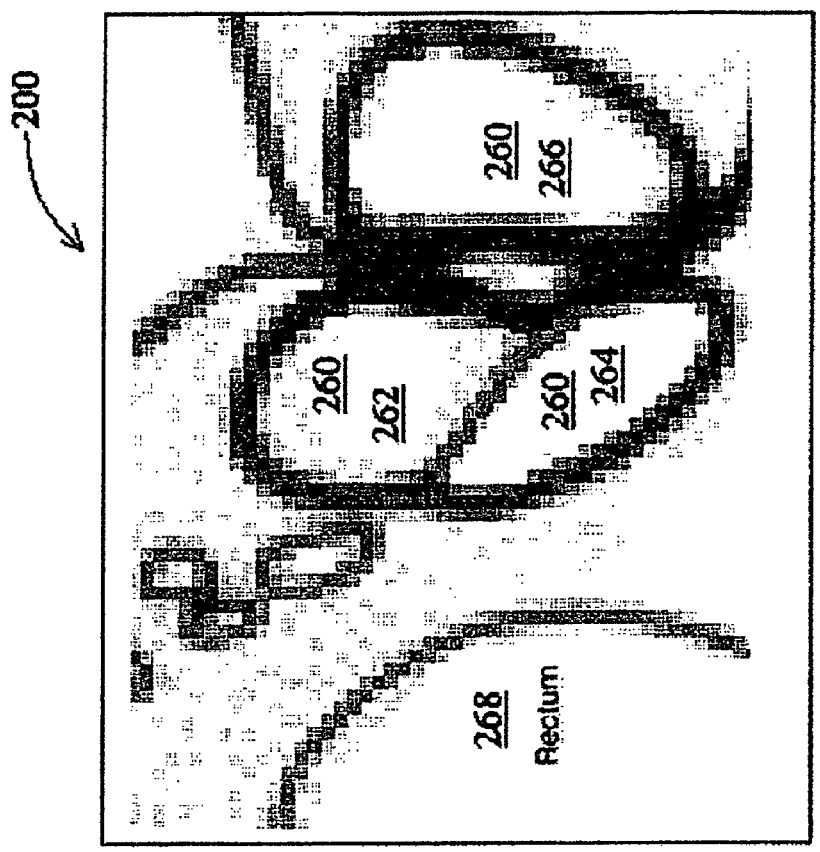
FIGS. 24A-24C schematically illustrate the modeling of a prostate as a process of two iterations, for zooming in on a pathology, in accordance with embodiments of the present invention.
Figure 24A:
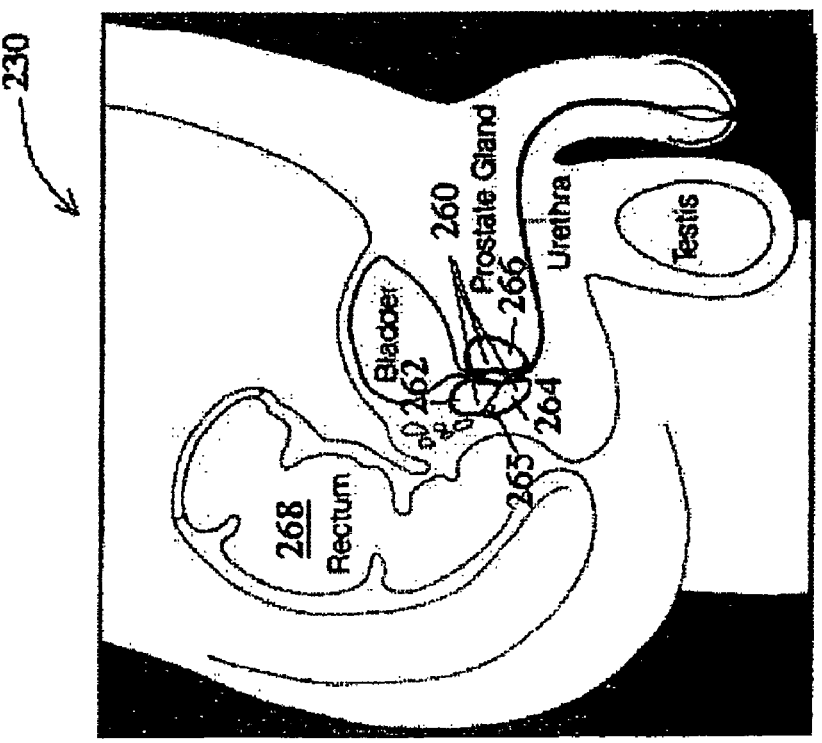
Figure 24C:
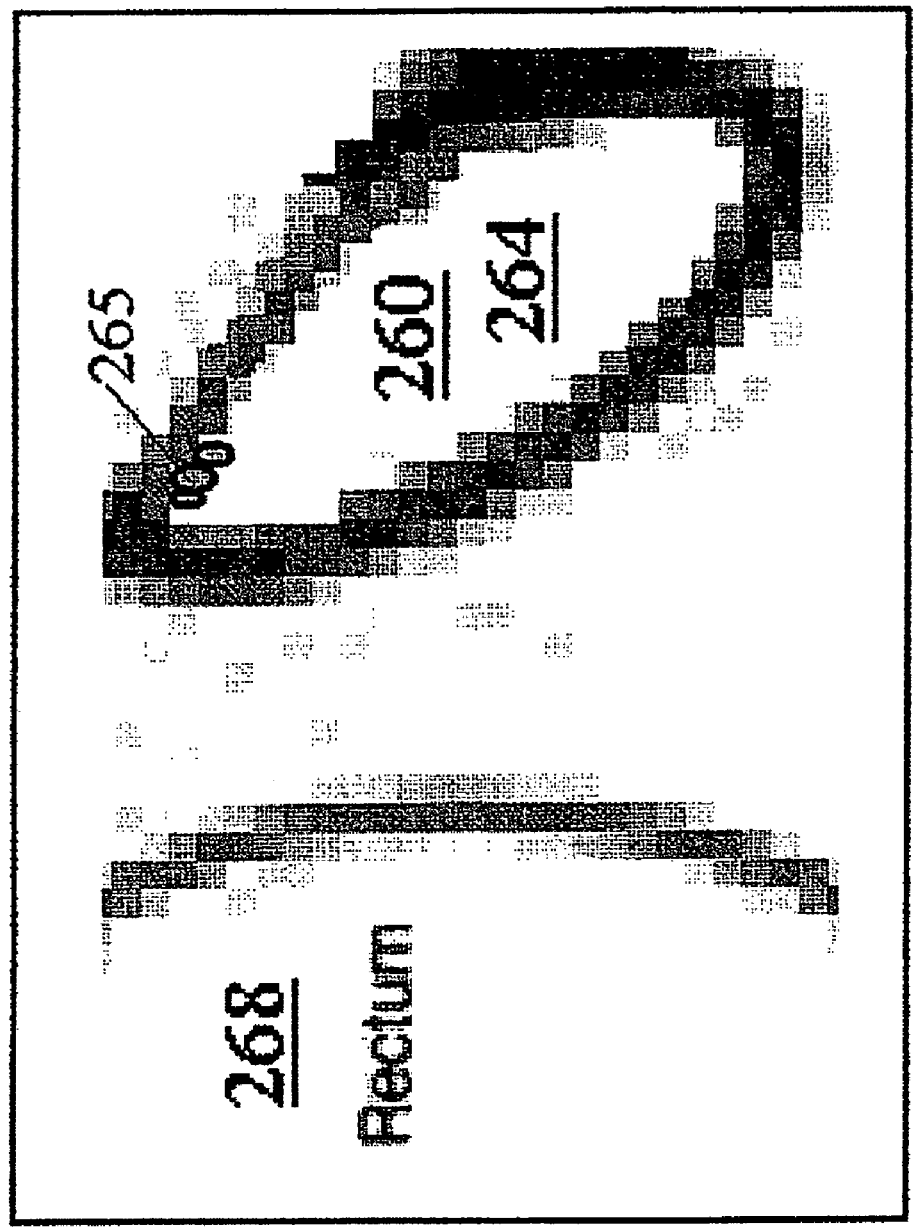
Figure 25A:
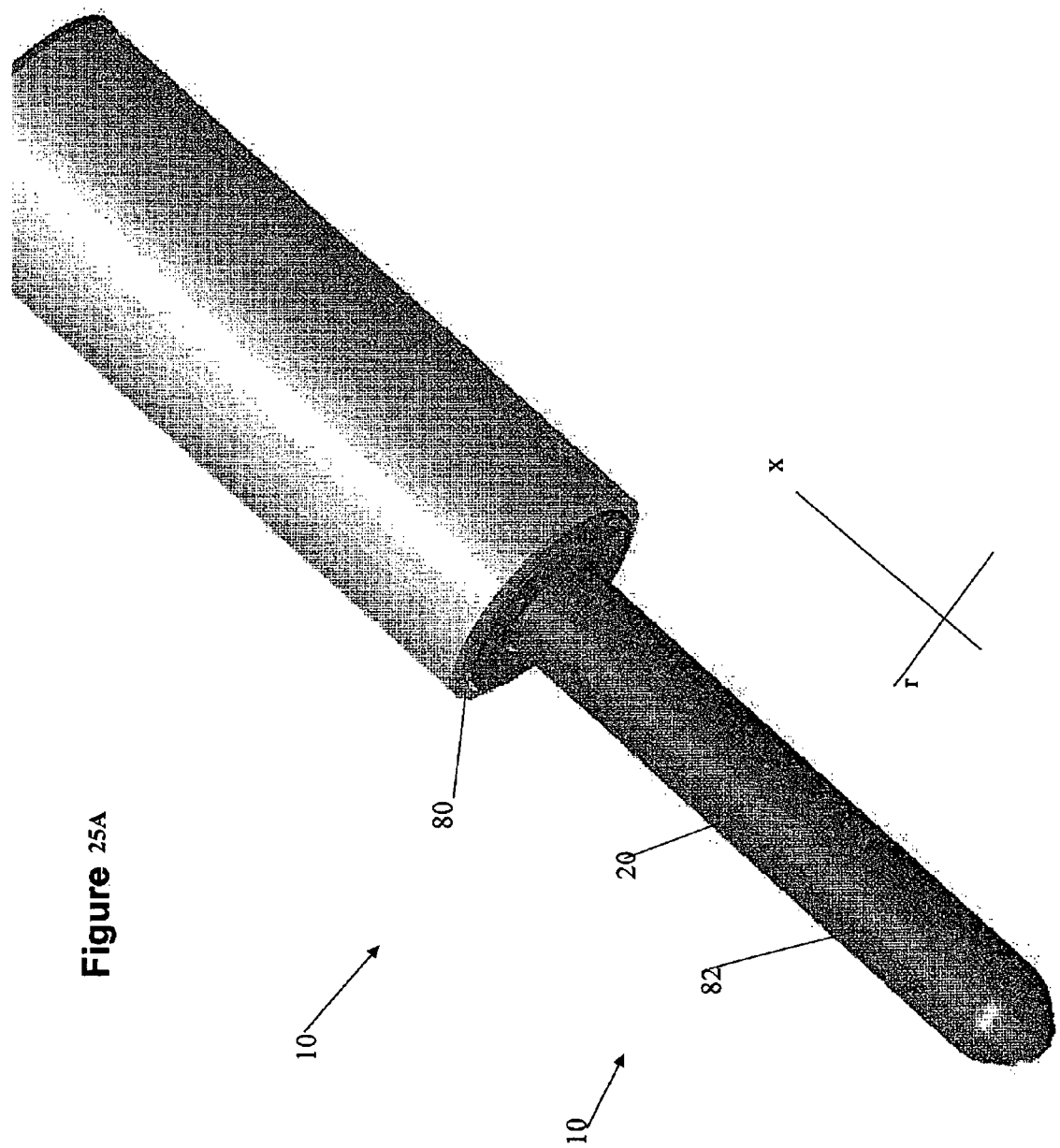
Figure 25B:
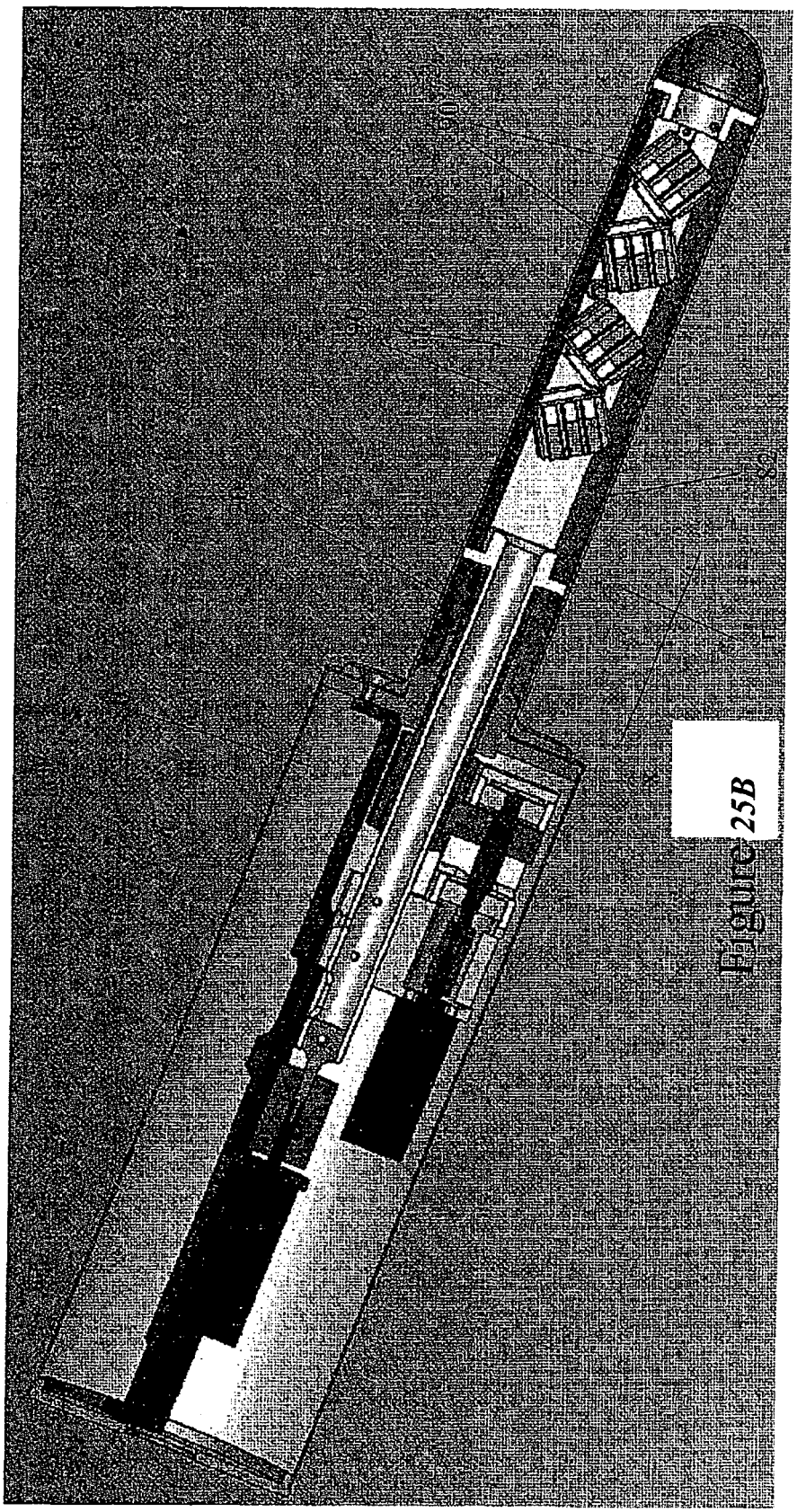
Figure 25C:
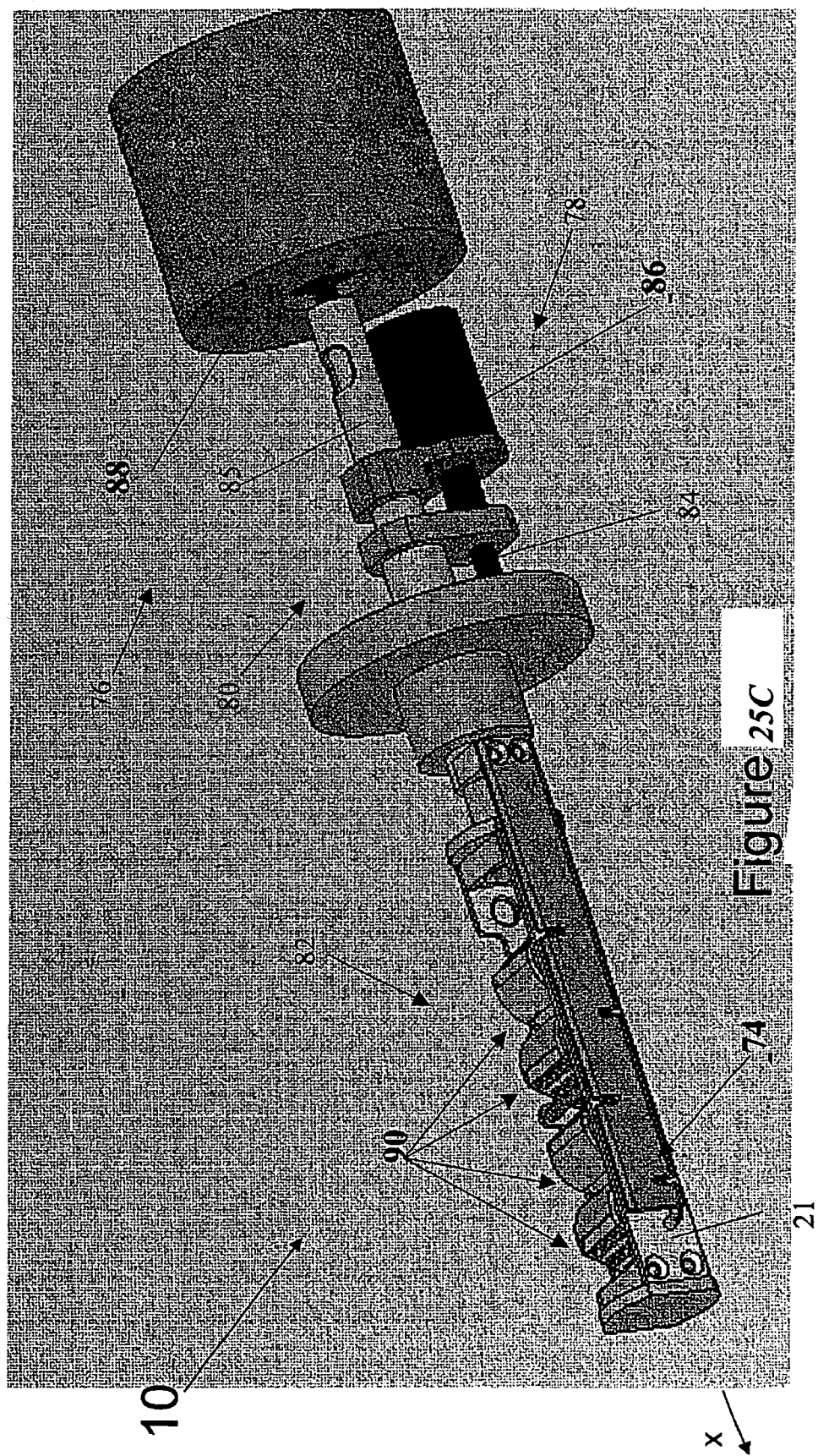
Figure 25D:
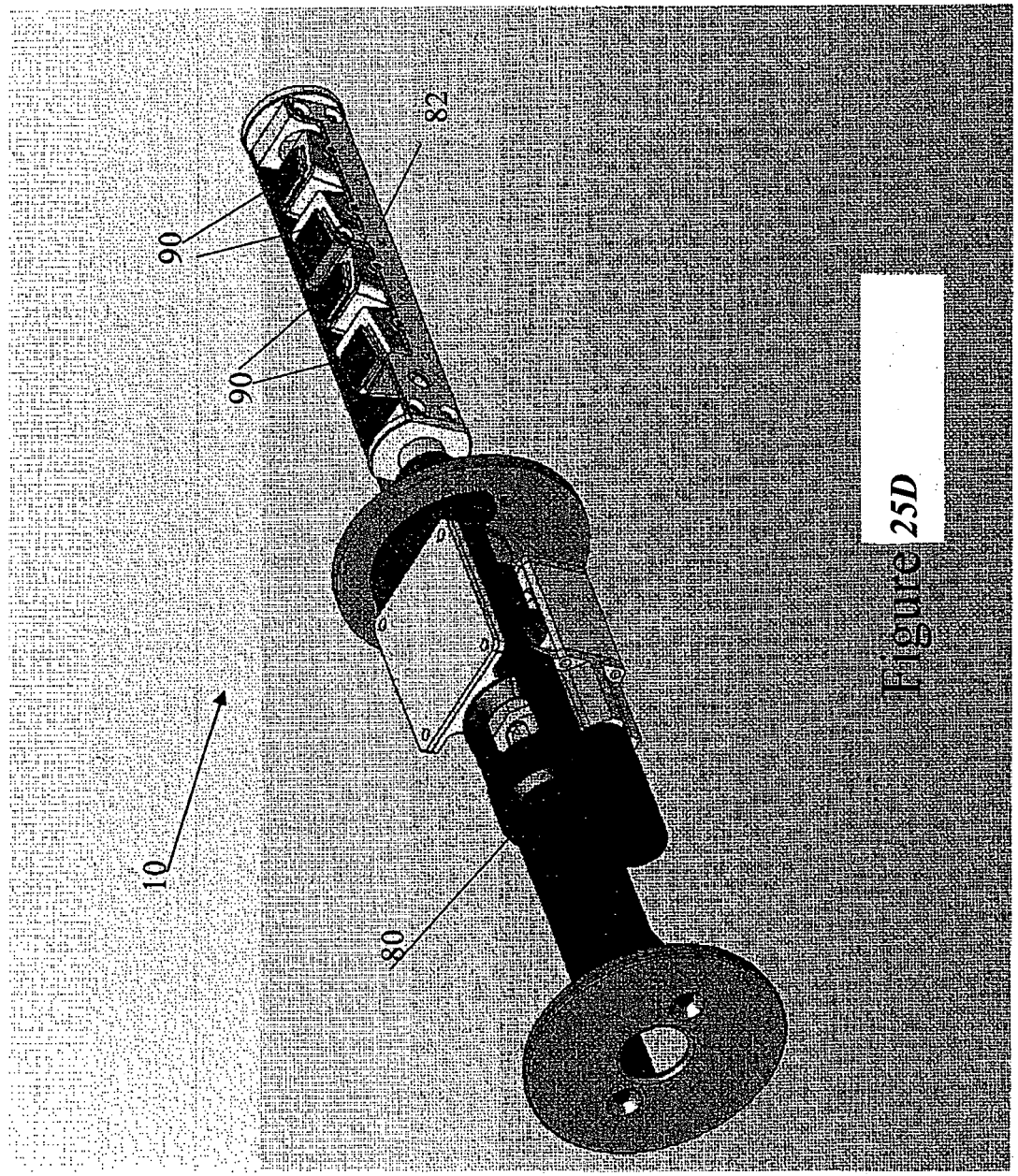

FIGS. 24A-24C schematically illustrate the modeling of a prostate and a location of a pathology, as a process of two iterations, for zooming in on the pathology, in accordance with embodiments of the present invention.

FIG. 24A schematically illustrates a body section 230, which includes a prostate 260, which has sections 262, 264 and 266, and a pathology 265 in section 264. Additionally, the body section 230 includes a rectum 268, from which the prostate 260 may be viewed.

FIG. 24B schematically illustrates the model 200 of the body section 230, including the prostate 260, of sections 262, 264 and 266, and the rectum 268. An optimal set of views is predefined based on the model 200 and a first scoring function. The first scoring function may be based on regions of interest similar to the pathology 265, as known, from medical records of common pathologies. Measurements of radioactive emission are then taken at the predefined views, in vivo, for the prostate 260.

As seen in FIG. 24C, upon discovering the pathology 265, by the in-vivo measurements, a second model 250 of the section 264 is made, for zooming in on the pathology 265, and a second optimal set of views is predefined, based on the second model 250 of the section 264 and a second scoring function, for zooming in on the pathology 265. Measurements of radioactive emission are then taken at the predefined second set of views, in vivo, for the section 264 and the pathology 265.

It will be appreciated that the first and second scoring functions may be based on any one of or a combination of the information theoretic measures of uniformity, separability, and reliability. It will be further appreciated that the first and second scoring functions need not be the same.

FIGS. 25A-25E illustrate an external appearance and an internal structure, of the probe 10. The radioactive-emission-measuring probe 10 for the prostate has an extracorporeal portion 80 and an intracorporeal portion 82, which is adapted for insertion to a rectum. The housing 20 of the intracorporeal potion 82 is preferably shaped generally as a cylinder and defines a longitudinal axis along the x axis, and a radius, perpendicular to the longitudinal axis. The intracorporeal portion 82 preferably includes two pairs of assemblies 90, arranged in the housing 20. It will be appreciated that another number of assemblies, for example, a single pair, or three pairs, is similarly possible. An odd number of assemblies is similarly possible. In essence, the probe 10 of the present example is analogous to the probe 10 of FIG. 23C and FIGS. 20A-20H, and particularly, to FIG. 20H. The rotational motion, in the direction of the arrow 52 of FIG. 20H, is provided by a motor 88 (FIG. 25C) and a main shaft 85. The motor 88 may be an electric motor, for example, a servo motor. The motor 88 and main shaft 85, together, form a motion provider 76 for the rotational motion in the direction of the arrow 52 of FIG. 20H. The oscillatory motion, in the direction of the arrows 50 of FIGS. 20B-20C and 20E-20F, is provided by a secondary motor 86, a secondary shaft 84 and a motion transfer link 74. The secondary motor 86 may also be an electric motor, for example, a servo motor. The secondary motor 86, secondary shaft 84 and the motion transfer link 74, together, form the secondary motion provider 78, in the direction of the arrows 50 of FIGS. 20A-20H.

The significance of the present embodiment, is as follows:
i. The different assemblies 90 provide views from different orientations; and
ii. The different assemblies 90 may change their view orientations independent of each other.

It is important to point out that during the operation of the probe 10, the external surface of the intracorporeal portion 82 (FIG. 25D-25E) remains stationary, while the inner housing 21 (FIG. 25C) rotates around the x axis. The external surface of the intracorporeal portion 82 may be formed of a carbon fiber, a plastic, or another material, which is substantially transparent to nuclear radiation.

FIG. 25E illustrates further the internal structure of the radioactive-emission-measuring probe for the prostate, in accordance with an embodiment of the present invention, showing the assemblies 90 within the housing 20. Each assembly may be a single detecting unit 12, or a plurality of the detecting units 12, for example, 36 of the detecting units 12, for example, as an array of 6×6, or 99 of the detecting units 12, for example, as an array of 11×9, or another number of the detecting units 12, arranged as an array or arranged in another geometry.

Figure 26:
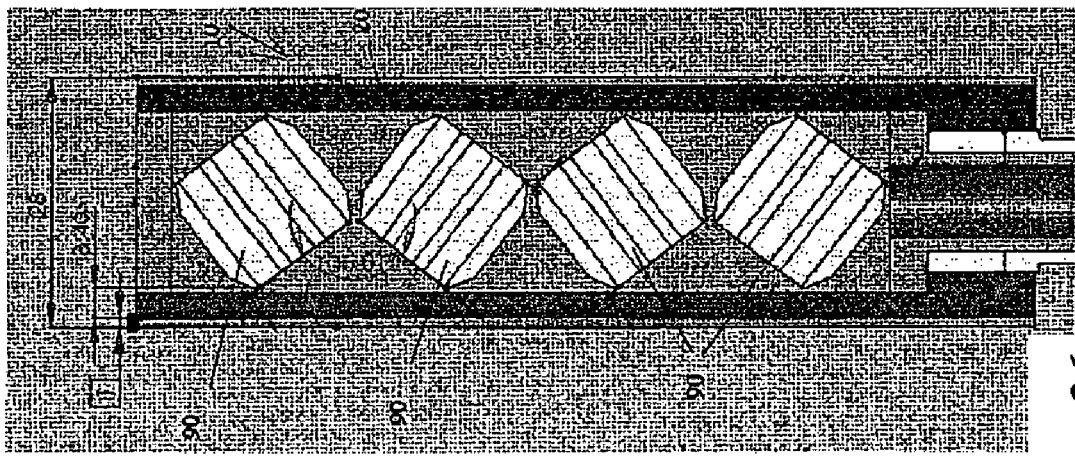
FIG. 26 illustrates further the internal structure of the radioactive-emission-measuring probe for the prostate, in accordance with an embodiment of the present invention.

Referring further to the drawings, FIG. 26 illustrates further the internal structure of the radioactive-emission-measuring probe for the prostate, in accordance with an embodiment of the present invention, showing the oscillatory motion (in the direction of the arrows 50 of FIGS. 20A, and 20C) of the assemblies 90 within the housing 20.

FIGS. 27-30C schematically illustrate the radioactive-emission-measuring probe 10, for the prostate, in accordance with another embodiment of the present invention. In accordance with the present embodiment, the probe 10 further includes an ultrasound transducer 85, arranged, for example, at the tip of the intracorporeal portion 82.

Figure 27:
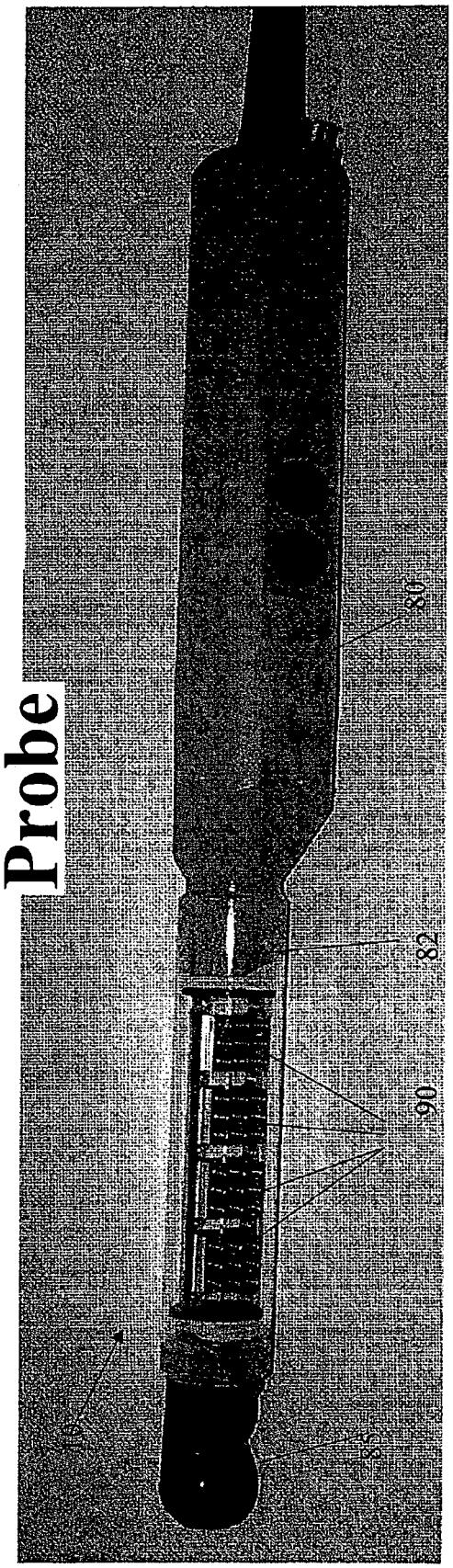
FIG. 27 schematically illustrates the radioactive-emission-measuring probe for the prostate, integrated with an ultrasound probe, in accordance with another embodiment of the present invention.

FIG. 27 illustrates the external appearance of the probe 10 with the ultrasound transducer 85 at its tip.

Figure 28:
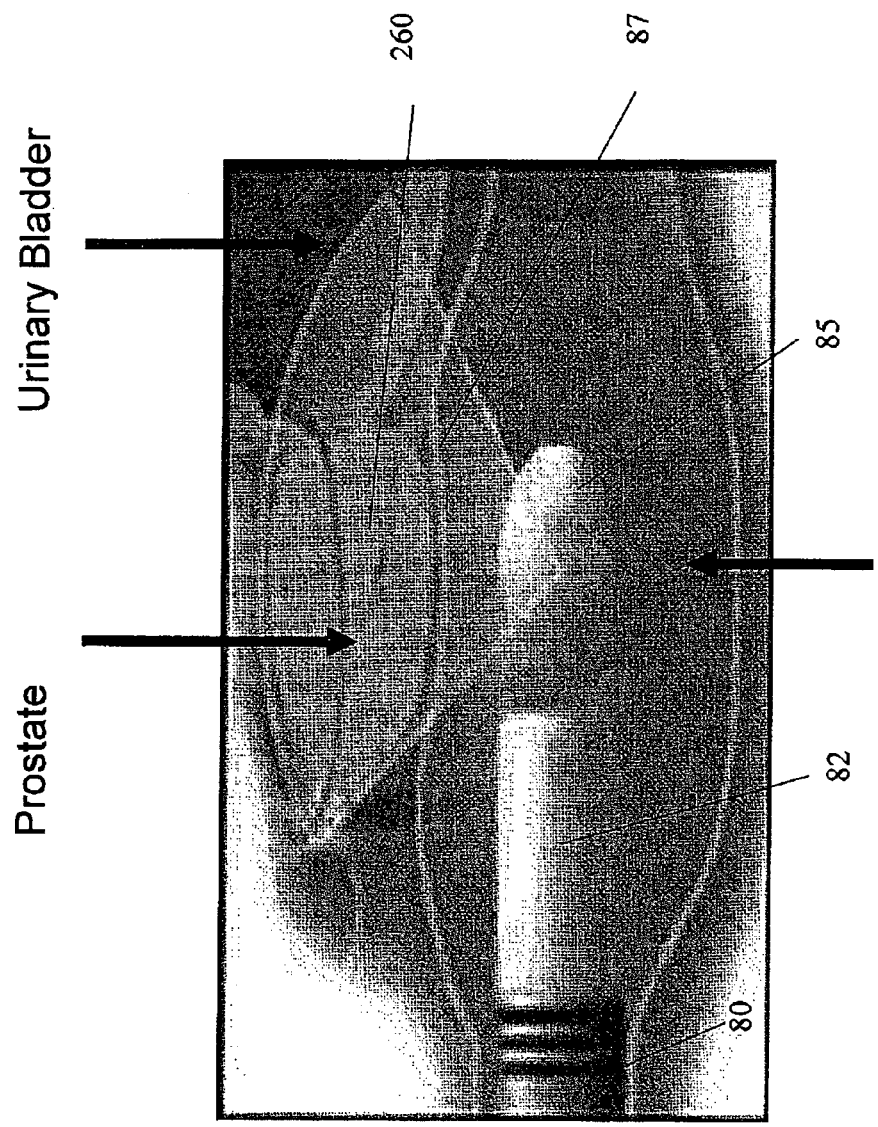
FIG. 28 schematically illustrates an ultrasound wave impinging on a prostate, in accordance with embodiments of the present invention.

FIG. 28 illustrates the ultrasound wave 87, impinging on the prostate 260.

Figures 29A, 29B, 29C:
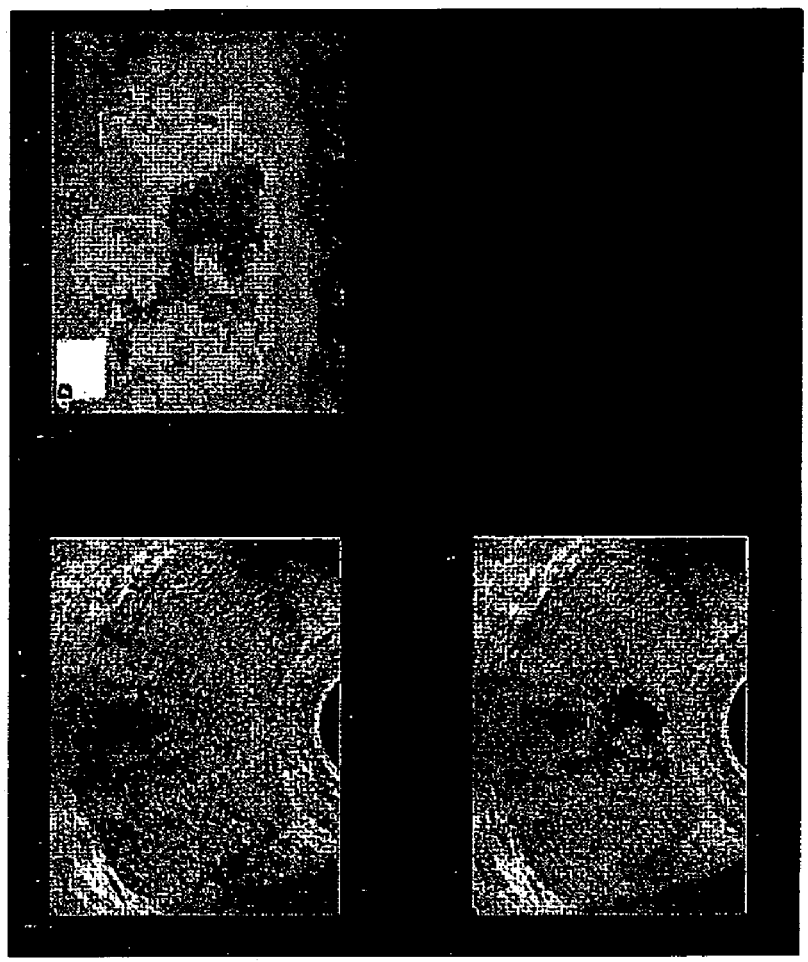
FIGS. 29A-29C illustrate the fusing of a radioactive-emission image and an ultrasound image, in accordance with embodiments of the present invention.

FIGS. 29A-29C illustrate the fusing of a radioactive-emission image and an ultrasound image, to illustrate the functional information of the radioactive-emission image with the structural information of the ultrasound image. The ultrasound image is seen in FIG. 29A, the radioactive-emission image is seen in FIG. 29B, and the fusing of the two is seen in FIG. 29C.

Figure 30:
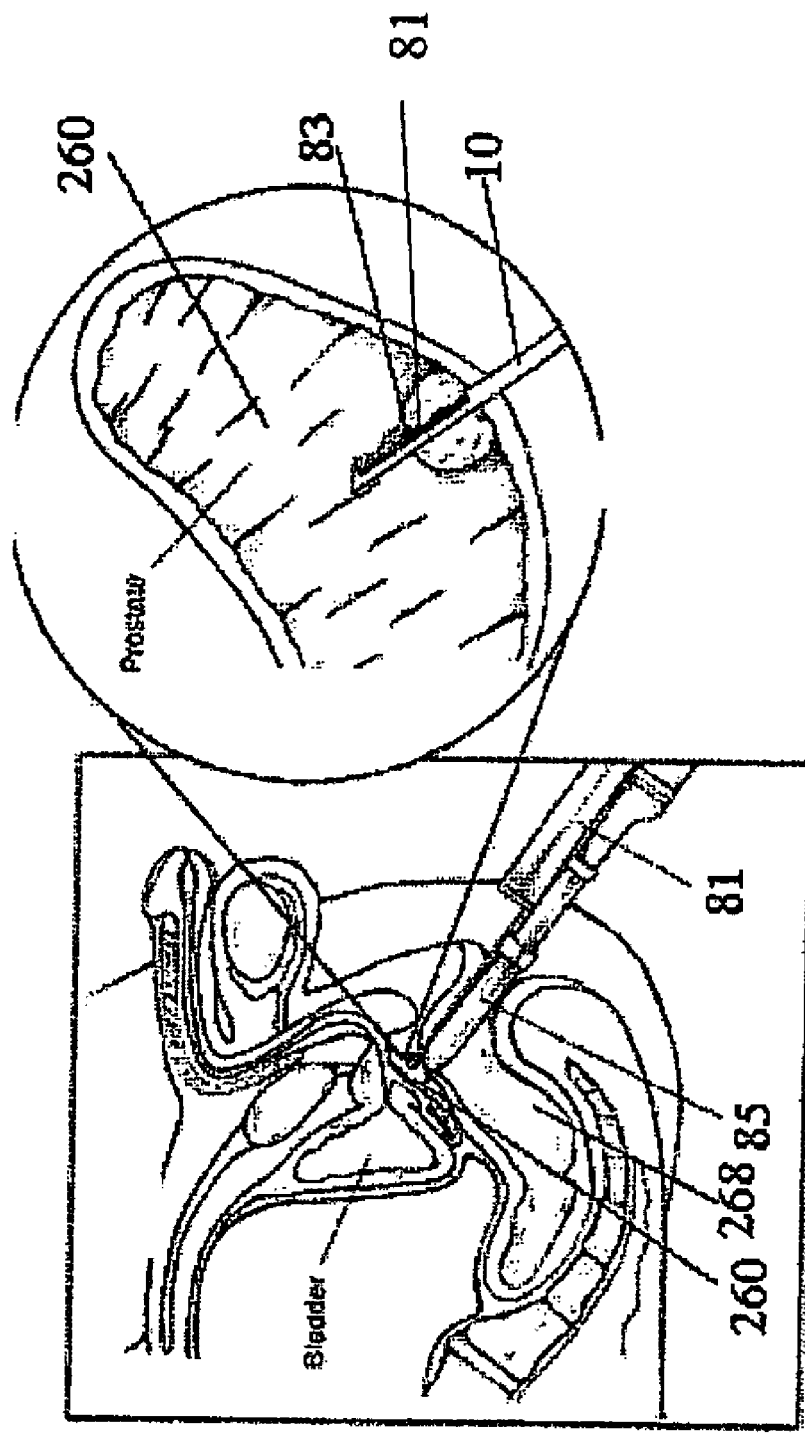
FIG. 30 schematically illustrates the radioactive-emission-measuring probe for the prostate, integrated with a surgical needle, in accordance with another embodiment of the present invention.
Figure 31:
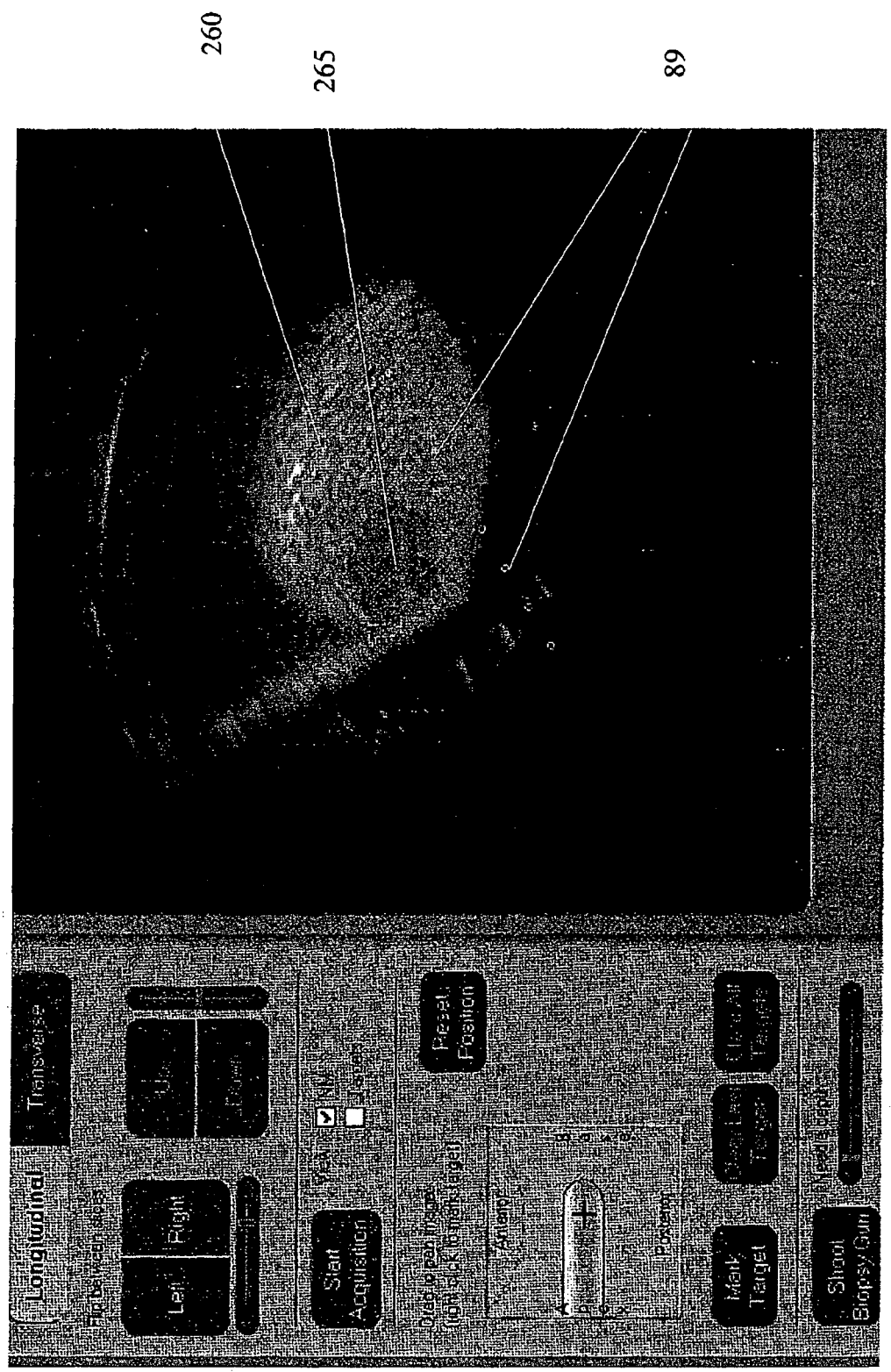
FIGS. 31 and 32 schematically illustrate the operation of the surgical needle of FIG. 30.
Figure 32:
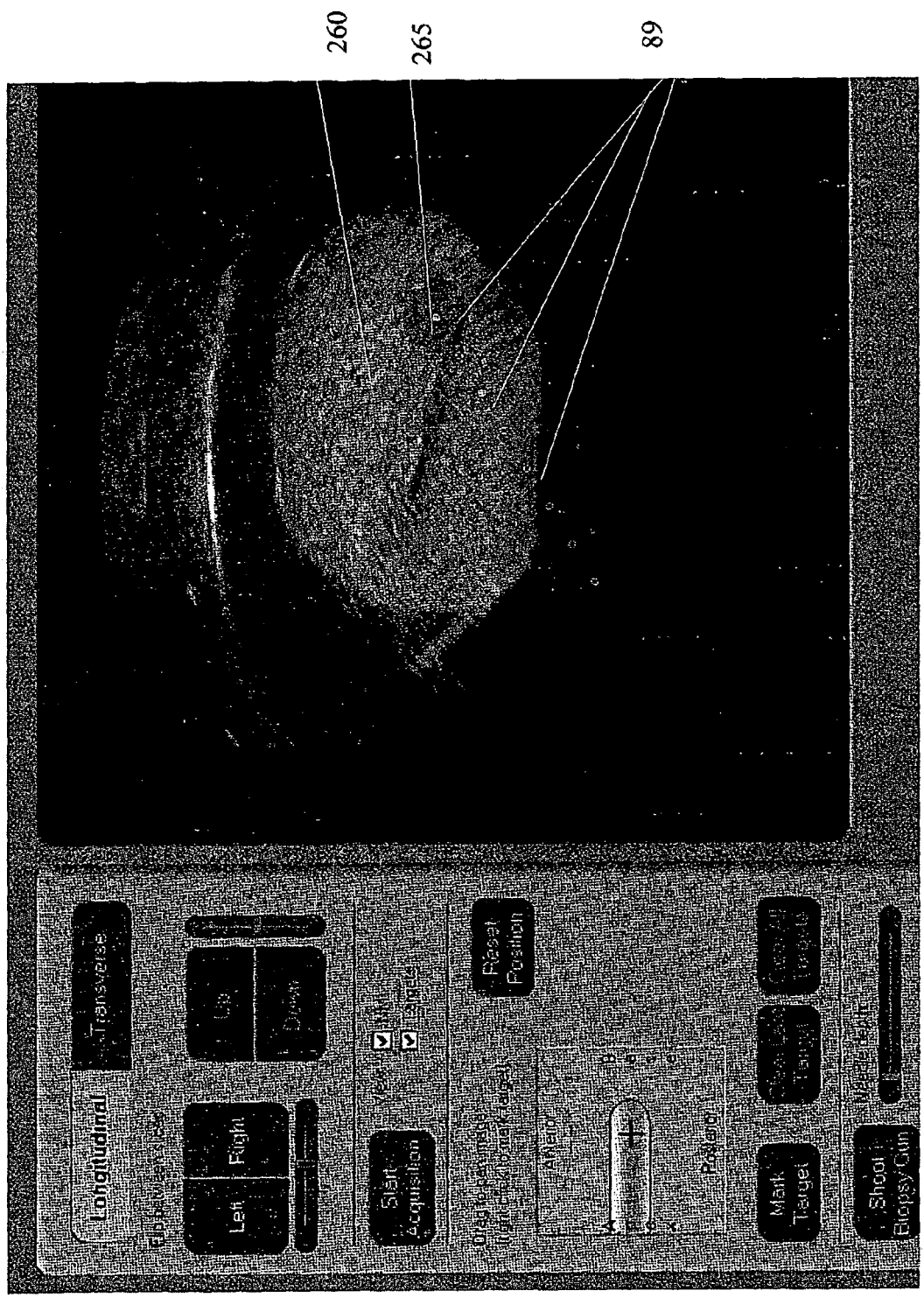

FIGS. 30-32 schematically illustrate the radioactive-emission-measuring probe 10, for the prostate, in accordance with another embodiment of the present invention. In accordance with the present embodiment, the probe 10 further includes an ultrasound transducer 85, and a surgical needle 83, in a needle guide 31, arranged alongside the probe 10, for obtaining a biopsy or for other minimally invasive procedures.

FIG. 30 schematically illustrates the surgical needle 81 as it penetrates the prostate 260 from the rectum 268.

FIGS. 31 and 32 schematically illustrate the manner of guiding the needle 31. A track 89 shows the surgeon the direction of the needle, while the probe 10 produces the functional image of the pathology 265 in the prostate 260. By moving the probe 10, manually, the surgeon can align the track 89 with the pathology 265, as shown in FIG. 32. Once aligned, he can eject the needle 83, as shown in FIG. 30.

Example 10

Figure 33:
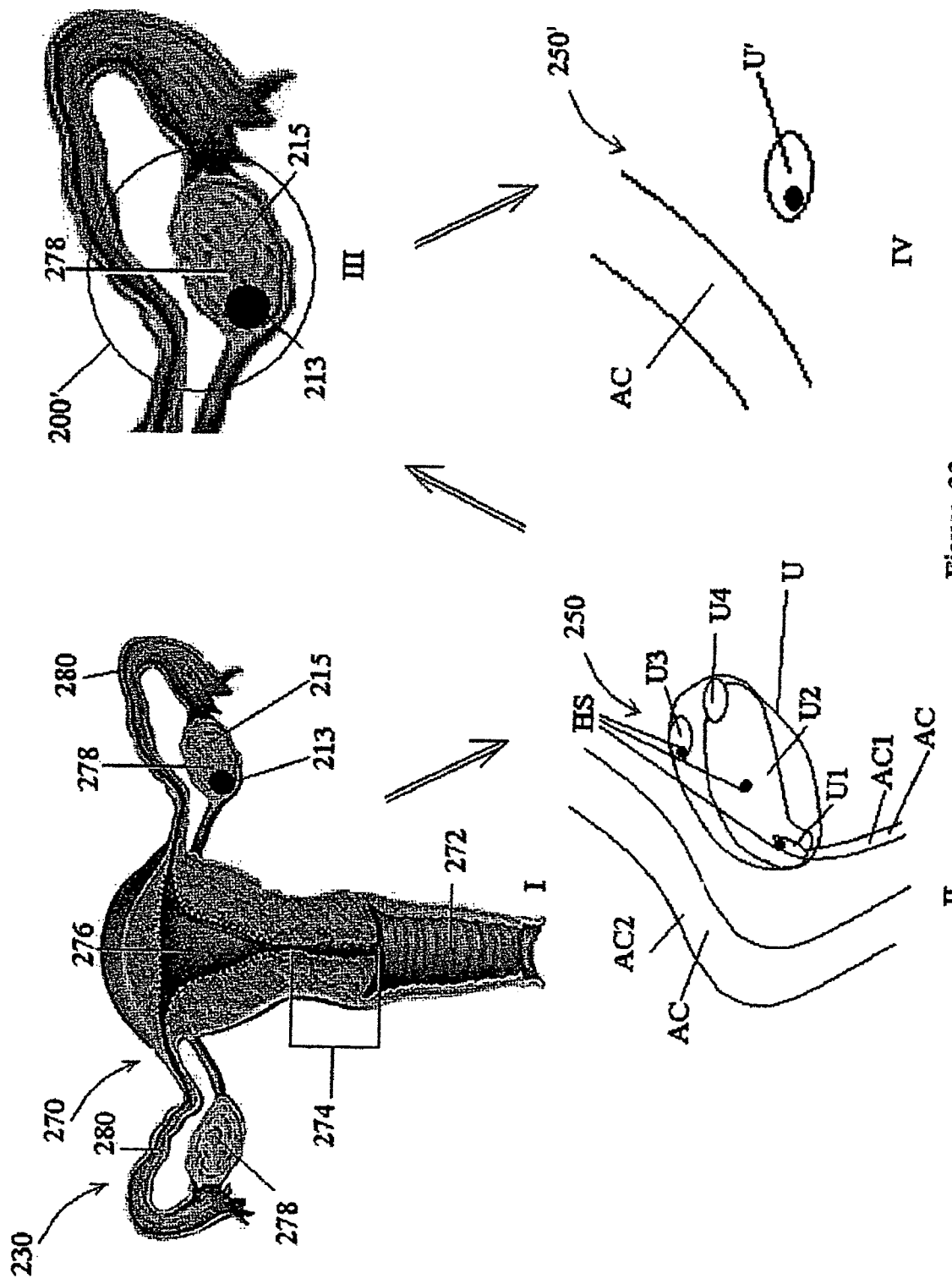
FIG. 33 schematically illustrates the modeling of the female reproductive system as a process of two iterations, for zooming in on a pathology, in accordance with embodiments of the present invention.

Referring further to the drawings, FIG. 33 pictorially illustrates the method 340 for zooming in on a suspected pathological feature in a woman's reproductive system, as a process of two or more iterations, in accordance with embodiments of the present invention, as follows:

As seen in FIG. 33, the method 340 may be described, pictorially, as follows:

In I: The region of interest 200, associated with the woman's reproductive system 215, is defined for the body section 230.

In II: The model 250 of the volume U, is provided for the region of interest 200, possibly with one or several of the modeled organ targets HS, and within the anatomical constraints AC, for obtaining the optimal set of views for the region of interest 200. The optimal set of views is then applied to the body section 230.

In III: When a suspected organ target 213 is identified, in vivo, by radioactive-emission measurements at the optimal set of views, a second, inner region of interest 200' is defined, encircling the suspected pathological feature.

In IV: A model 250' of a volume U' is provided for the second, inner region of interest 200', preferably, with at least one modeled organ target HS, simulating the suspected organ target 213, for obtaining an optimal pathology set of views for the region of interest 200'. The second, pathology set of views is then applied to the body section 230.

Figure 34A:
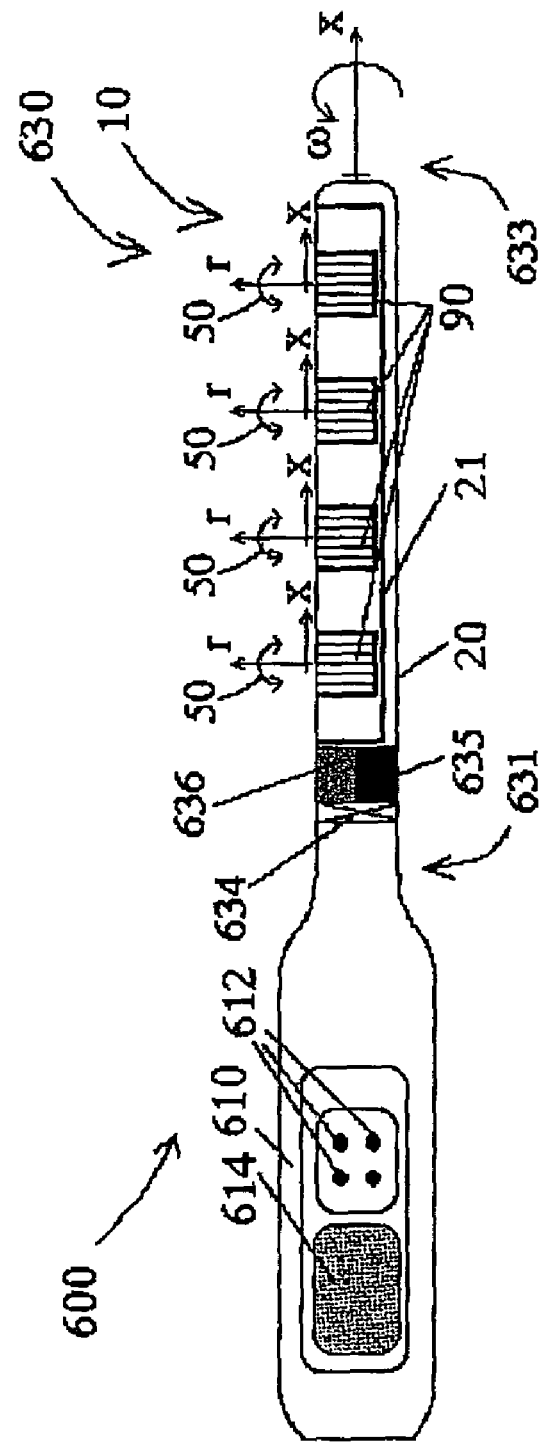
FIGS. 34A-34R schematically illustrate radioactive-emission measuring probes 600, tailored for imaging the woman's reproductive system and optimized with respect to the functional information gained, regarding the body structures of the woman's reproductive system, in accordance with embodiments of the present invention.
Figure 34K:
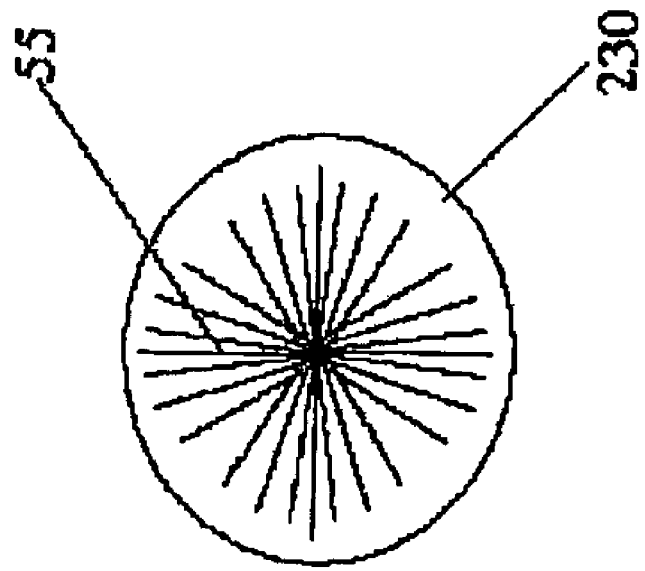
Figure 34J:
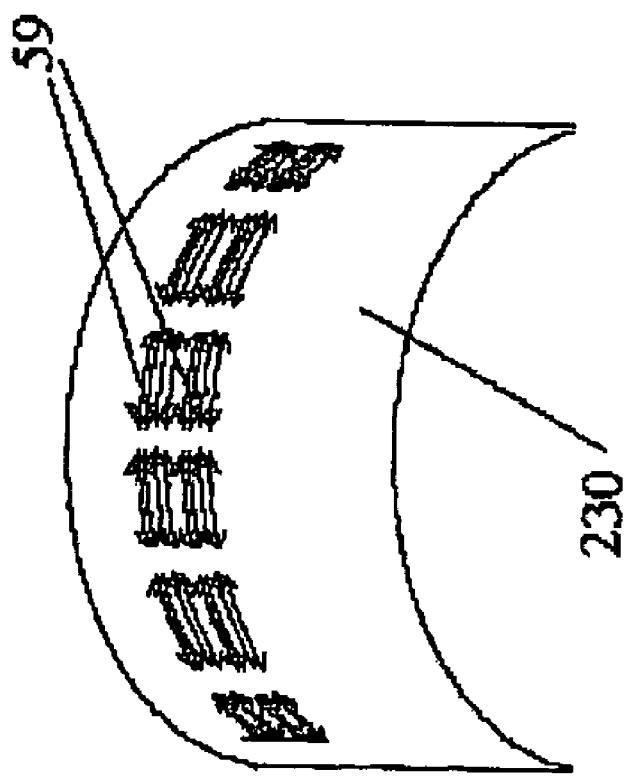
Figure 34R:
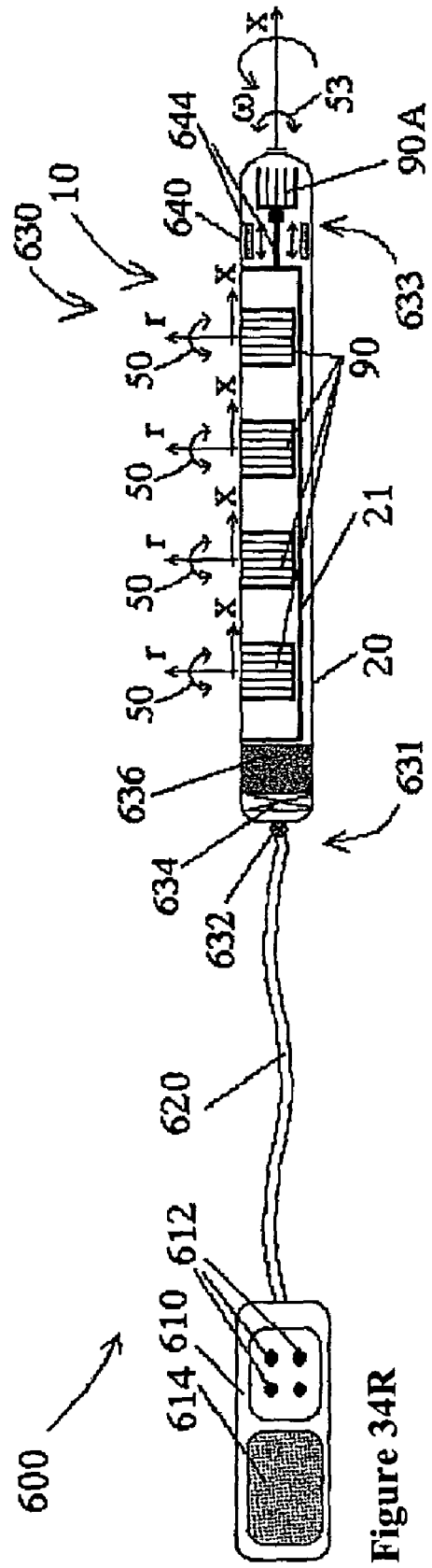

Referring further to the drawings, FIGS. 34A-34R schematically illustrate radioactive-emission measuring probes 600, tailored for imaging the woman's reproductive system and optimized with respect to the functional information gained, regarding the body structures of the woman's reproductive system, such as the cervix 274, the uterus 276, the ovaries 278, and the fallopian tubes 280, in accordance with preferred embodiments of the present invention.

FIG. 34A schematically illustrates the basic radioactive-emission measuring probe 600, for a body lumen, for example, the vagina 272, the cervix 274, the uterus 276, the rectum 292, or the sigmoid colon 294. The probe 600 includes an extracorporeal portion 610, which preferably comprises a control unit, and an intracorporeal portion 630, having proximal and distal ends 631 and 633, with respect to an operator (not shown).

The control unit of the extracorporeal portion 610 may include control buttons 612 and possibly a display screen 614, and may provide connections with a computer station. It may receive power from a grid or be battery operated. The control unit of the extracorporeal portion 610 may further include a computer or a microcomputer. It will be appreciated that the control unit may be incorporated with the intracorporeal section 630, and operated remotely.

The intracorporeal portion 630 defines a cylindrical coordinate system of x;r, wherein x is the longitudinal axis. The plurality of blocks 90 along the length of the intracorporeal portion 630 is housed in an inner housing 21 (FIG. 20H).

Each of the blocks 90 is adapted for the windshield-wiper like oscillatory motion, around the radius r, as denoted by the arrows 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Additionally, the inner housing 21 is adapted for rotational motion around the x-axis, in the direction of ω, wherein after each step of oscillatory motion at a certain orientation of ω, the inner housing rotates by a step to a new orientation of ω, and the oscillatory motion is repeated.

As a consequence, a plurality of broken line traces 59 are formed, in the body section 230, as seen in FIG. 34J.

Preferably, the controller or the computer registers the locations and orientations of each detecting unit or block and correlates the measurements with the corresponding positions and orientations.

A position-tracking device 635 may also be used, for providing information regarding the position of the probe 600 relative to a known reference. For example, if a structural scan, or another scan by another imager has been made, the position-tracking device 635 may be used to register the previous scan with the measurements of the probe 600.

It will be appreciated that the probe 600 may include detecting units 12 rather then blocks 90.

Preferably, the housing 20 remains stationary and is substantially transparent to nuclear radiation, formed, for example, of a hydrocarbon material.

The intracorporeal portion 630 may further include dedicated electronics 634 and motion providers 636, such as miniature motors and motion transfer systems, as known.

FIGS. 34B and 34C schematically illustrate side and distal views, respectively, of the radioactive-emission measuring probe 600, having an ultrasound imager 640 at its distal tip 633. The ultrasound imager 640 may provide a structural image which may be correlated with the functional image. Additionally, it may be used for providing the size and location of the body structure for modeling. Furthermore, it may be used for providing attenuation correction to the radioactive emission measurements.

FIGS. 34D and 34E schematically illustrate side and distal views, respectively, of the radioactive-emission measuring probe 600, having an MRI imager 642 at its distal tip 633. The MRI imager 642 may provide a structural image which may be correlated with the functional image. Additionally, it may be used for providing the size and location of the body structure for modeling. Furthermore, it may be used for providing attenuation correction to the radioactive emission measurements.

FIGS. 34F-34I schematically illustrate the radioactive-emission measuring probe 600, having a distal block 90A at its distal tip 633. The distal block 90A at the distal tip is also adapted for oscillatory motion, but about the x-axis, as seen by an arrow 53. When combined with the rotational motion around the x-axis, it produces traces 55 in the shape of a star, in the body section 230, as seen in FIG. 34K.

It will be appreciated that a single distal detecting unit may be employed in place of the distal block 90A.

FIGS. 34L-34Q schematically illustrates the radioactive-emission measuring probe 600, for a body lumen, having the distal block 90A at its distal tip 633, adapted for a deployed and a retracted position, and for oscillatory motion about the x-axis, when deployed. The probe 600 further has the ultrasound imager 640 at its distal tip 633, as a ring, similarly having a deployed and a retracted position.

FIGS. 34N-34P illustrate the distal block 90A deployed, and the ultrasound imager 640 retracted. In this manner, the ultrasound imager 640 does not obstruct the oscillatory motion of the distal block 90A at the distal tip 633.

FIG. 34Q illustrates the distal block 90A retracted and the ultrasound imager deployed so the distal block 90A does not obstruct the view of the ultrasound imager. It will be appreciated that the ultrasound image is to be taken once, from the distal tip 633, while the radioactive-emission measurements are to be taken at a plurality of orientations, from the distal tip 633.

FIG. 34R illustrates the probe 600 with a cable 620 connecting the intracorporeal portion 630 and the extracorporeal portion 610, for example, for imaging the ovaries and the fallopian tubes from the sigmoid colon.

It will be appreciated that the probes 600 of the present invention may also be moved manually, both linearly, into the body lumen and rotationally, around its longitudinal axis, preferably while the position-tracking device 635 (FIG. 34A) registers its position.

It will be appreciated that a probe with a single block or a single detecting unit may also be used.

Example 11

Figure 35A:
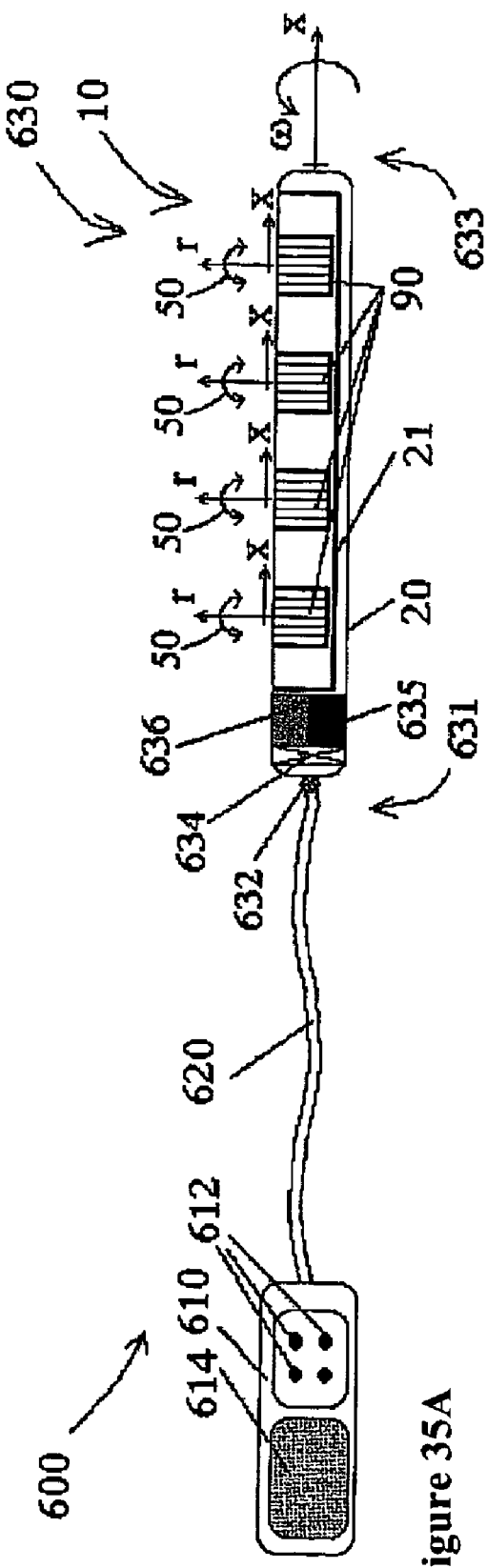
FIGS. 35A-35Q schematically illustrate radioactive-emission measuring probes 600, adapted for the esophagus, in accordance with embodiments of the present invention.
Figure 35F:
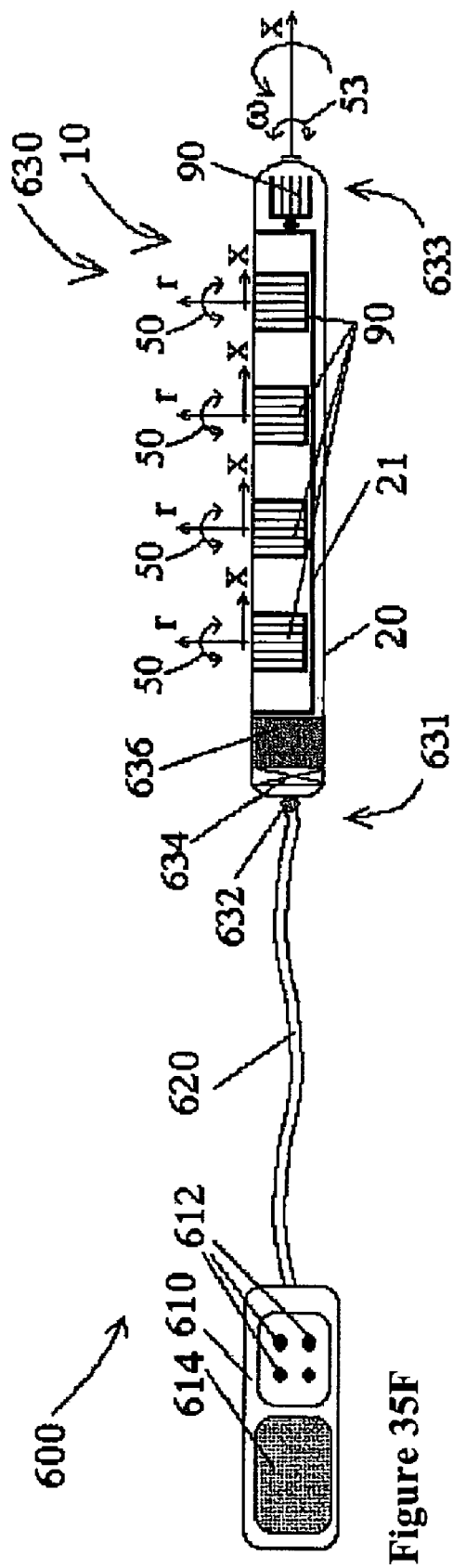
FIG. 35R schematically illustrates an esophagus nearby organs.
FIG. 35S schematically illustrates a stomach and nearby organs.
Figure 35G:
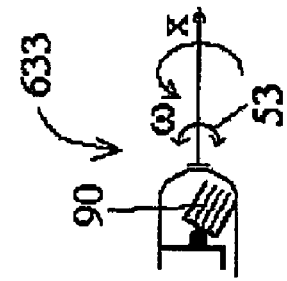
Figure 35H:
Figure 35I:
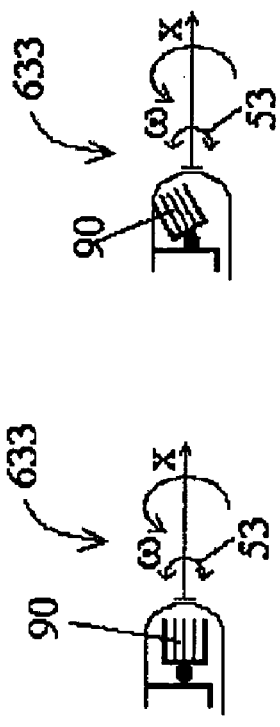

Referring further to the drawings, FIGS. 35A-35Q schematically illustrate radioactive-emission measuring probes 600, adapted for the esophagus, in accordance with preferred embodiments of the present invention.

FIG. 35A schematically illustrates the basic radioactive-emission measuring probe 600, for the esophagus. The probe 600 includes an extracorporeal portion 610, which comprises a control unit, and an intracorporeal portion 630, having proximal and distal ends 631 and 633, with respect to an operator (not shown). A flexible cable 620 connects between them.

The control unit 610 may include control buttons 612 and possibly a display screen 614, and may provide connections with a computer station. It may receive power from a grid or be battery operated. The control unit 610 may further include a computer or a microcomputer.

The intracorporeal portion 630 is constructed essentially as the probe 10 of FIG. 23C and FIGS. 20A-20H, and specifically, FIG. 20H.

Thus, the intracorporeal section 630 defines a cylindrical coordinate system of x;r, wherein x is the longitudinal axis. The plurality of blocks 90 along the intracorporeal portion 630 is housed in an inner housing 21.

Each of the blocks 90 is adapted for the windshield-wiper like oscillatory motion, around the radius r, as denoted by the arrows 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Additionally, the inner housing 21 is adapted for rotational motion around the x-axis, in the direction of ω, wherein after each step of oscillatory motion at a certain orientation of ω, the inner housing rotates by a step to a new orientation of ω, and the oscillatory motion is repeated.

Figure 35K:
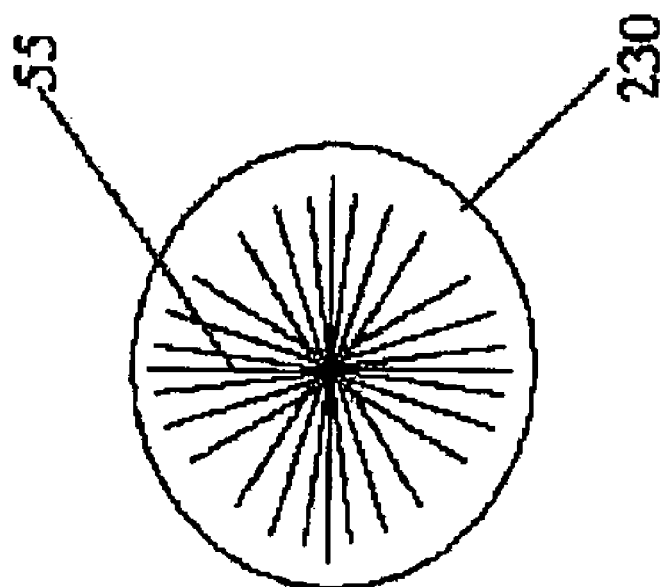
Figure 35J:
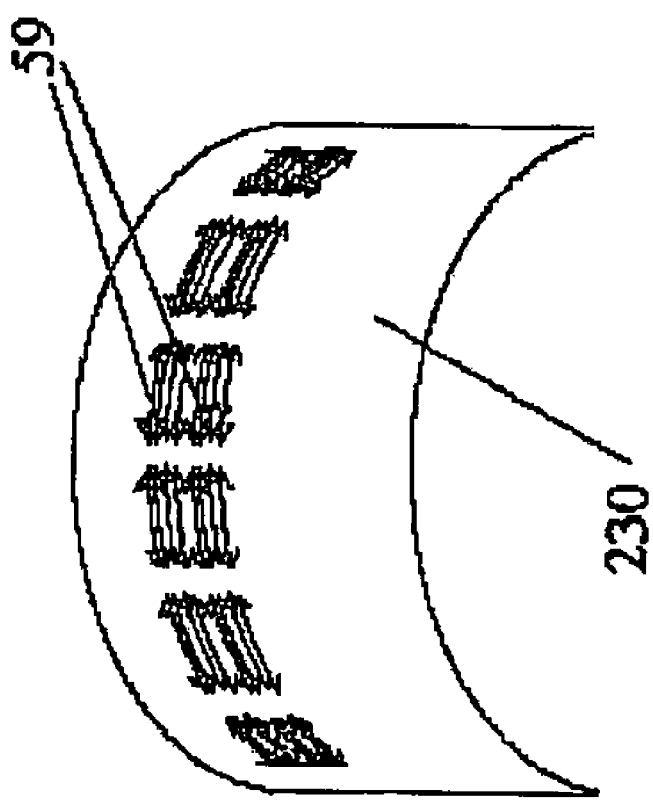

As a consequence, a plurality of broken line traces 59 are formed, in the body section 230, as seen in FIG. 35J.

Preferably, the controller or the computer registers the locations and orientations of each detecting unit or block and correlates the measurements with the corresponding positions and orientations.

A position-tracking device 635 may also be used, for providing information regarding the position of the probe relative to a known reference.

It will be appreciated that the probe 600 may include detecting units 12 rather then blocks 90, for example, as taught in conjunction with FIGS. 20A-20G.

Preferably, the housing 20 remains stationary, and has an external surface, which is substantially transparent to nuclear radiation.

A ball bearing 632 may be used at the connecting point with the cable 620, to enable the rotational motion.

The intracorporeal section 630 may further include dedicated electronics 634 and motion providers 636, such as miniature motors and motion transfer systems, as known. Alternatively, the motion may be transferred via the cable 620.

FIGS. 35B and 35C schematically illustrate side and distal views, respectively, of the radioactive-emission measuring probe 600, for the esophagus, having an ultrasound imager 640 at its distal tip 633. The ultrasound imager 640 may provide a structural image which may be correlated with the functional image. Additionally, it may be used for providing the size and location of the relevant organ for modeling. Furthermore, it may be used for providing attenuation correction to the radioactive emission measurements.

FIGS. 35D and 35E schematically illustrate side and distal views, respectively, of the radioactive-emission measuring probe 600, for the esophagus, having an MRI imager 642 at its distal tip 633. The MRI imager 642 may provide a structural image which may be correlated with the functional image. Additionally, it may be used for providing the size and location of the relevant organ for modeling. Furthermore, it may be used for providing attenuation correction to the radioactive emission measurements.

FIGS. 35F-35I schematically illustrate the radioactive-emission measuring probe 600, for the esophagus, having a block 90 at its distal tip 633. The block 90 at the distal tip is also adapted for oscillatory motion, but about the x-axis, as seen by an arrow 53. When combined with the rotational motion around the x-axis, it produces traces 55 in the shape of a star, in the body section 230, as seen in FIG. 35K.

FIGS. 35L-35Q schematically illustrates the radioactive-emission measuring probe 600, for the esophagus, having a block 90 at its distal tip 633, adapted for a deployed and a retracted position, and for oscillatory motion about the x-axis, when deployed. The probe 600 further has the ultrasound imager 640 at its distal tip 633, as a ring, similarly having a deployed and a retracted position.

FIGS. 35N-35P illustrate the block 90 deployed, and the ultrasound imager 640 retracted. In this manner, the ultrasound imager 640 does not obstruct the oscillatory motion of the block 90 at the distal tip 633.

FIG. 35Q illustrates the block 90 retracted and the ultrasound imager deployed so the block 90 does not obstruct the view of the ultrasound imager. It will be appreciated that the ultrasound image is to be taken once, from the distal tip 633, while the radioactive-emission measurements are to be taken at a plurality of orientations, from the distal tip 633.

Figure 35R:
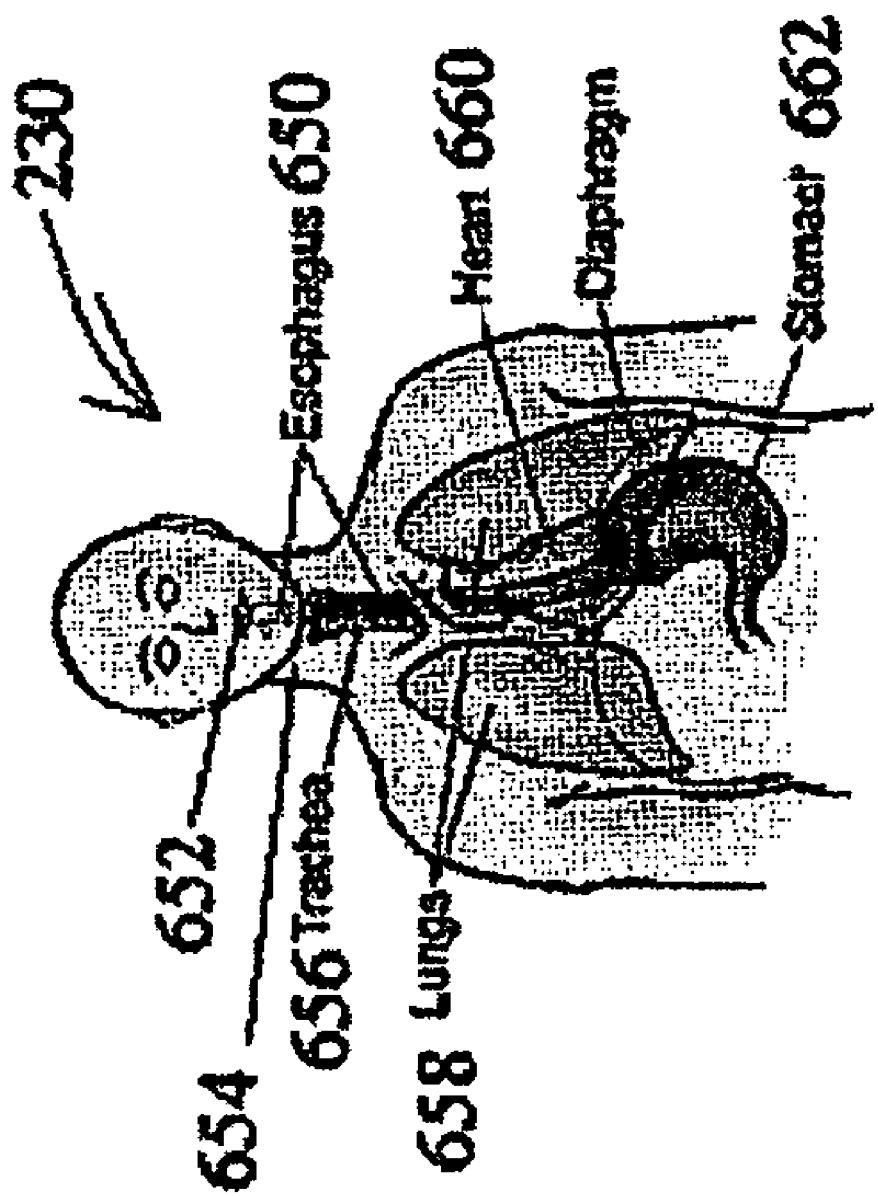

FIG. 35R schematically illustrates the body section 230, showing an esophagus 650 and nearby organs, such as the heart 660 and the lungs 658.

Figure 35S:
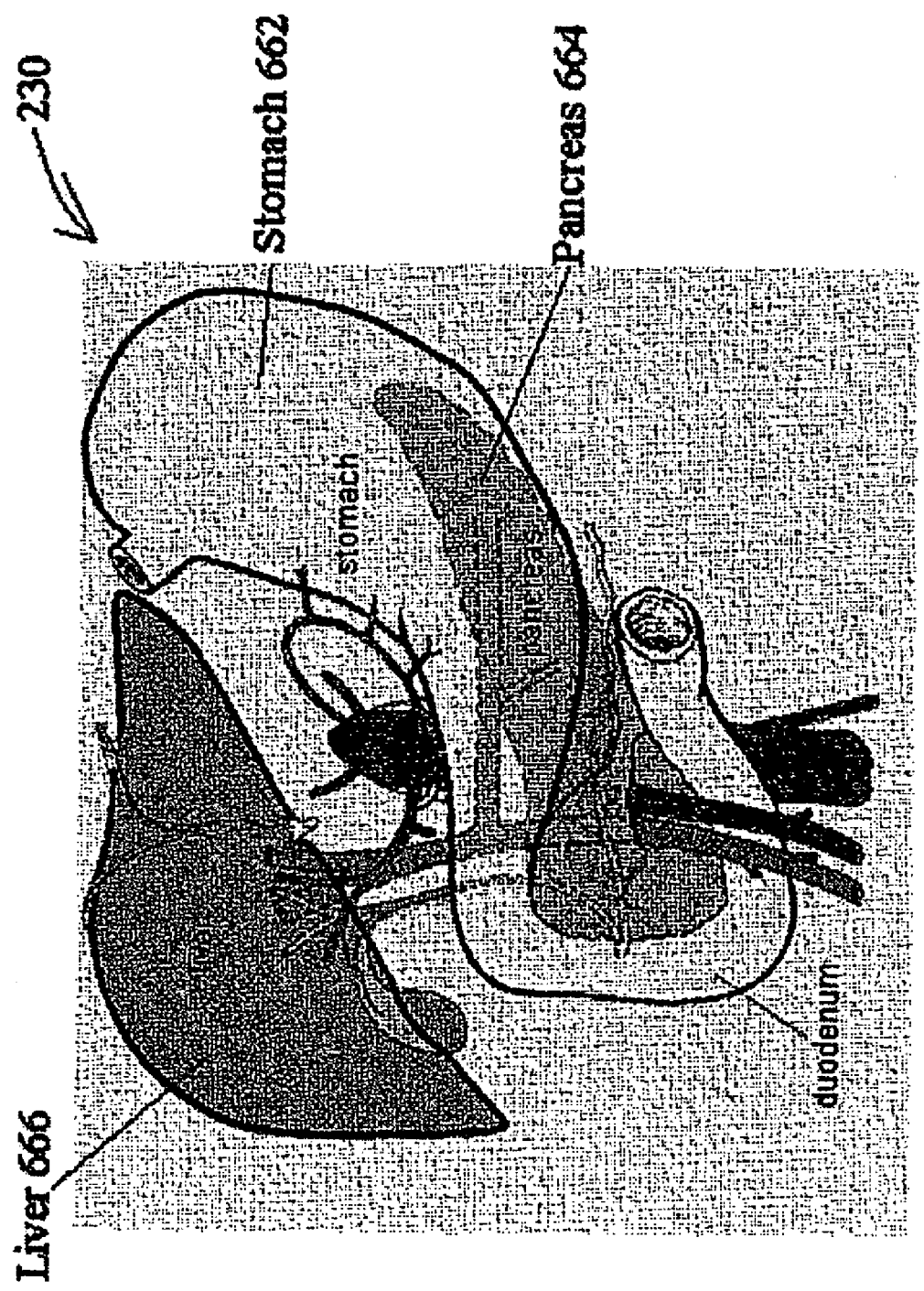

FIG. 35S schematically illustrates the body section 230, showing the stomach 662, and nearby organs, such as the pancreas 664, and the liver 666.

The radioactive-emission measuring probe 600 for the esophagus (FIGS. 35A-35Q), is adapted for oral insertion, through a mouth 652, and is further designed for identifying pathological features in a neck area 654, for example, as relating to the vocal cords, the thyroid glands, the submandibular glands. Additionally, it is designed for identifying pathological features in the trachea 656, the lungs 658, the heart 660, the breasts, the stomach 662, the pancreas 664, and the liver 666, as well as other relevant organs and glands, for example, the lymph glands.

The probe system of the present invention allows imaging of internal organs from a close proximity. Additionally, it is particularly advantageous for overweight people and for women with large breasts, for whom extracorporeal imaging, for example, extracorporeal cardiac imaging by nuclear emission measurements, is ineffective, because of losses in the tissue.

For cardiac imaging, the radiopharmaceuticals associated with the probe of FIGS. 35A-35Q may be Myoview™ (technetium Tc-99m tetrofosmin), a cardiac imaging agent, of GE Healthcare, GE Medical Systems, http://www.gehealthcare.com/contact/contact_details.html#diothers. Alternatively, it may be Cardiolite (Sestamibi radilabeled with TC99), of DuPont, http://www1.dupont.com/NASApp/dupontglobal/corp/index.jsp?page=/content/US/en_US/contactus.html. It will be appreciated that other agents may be used, as known, for other relevant organs, for example, for the detection of cancerous tissue or other pathologies.

Example 12

Figures 36A, 36B, 36C:
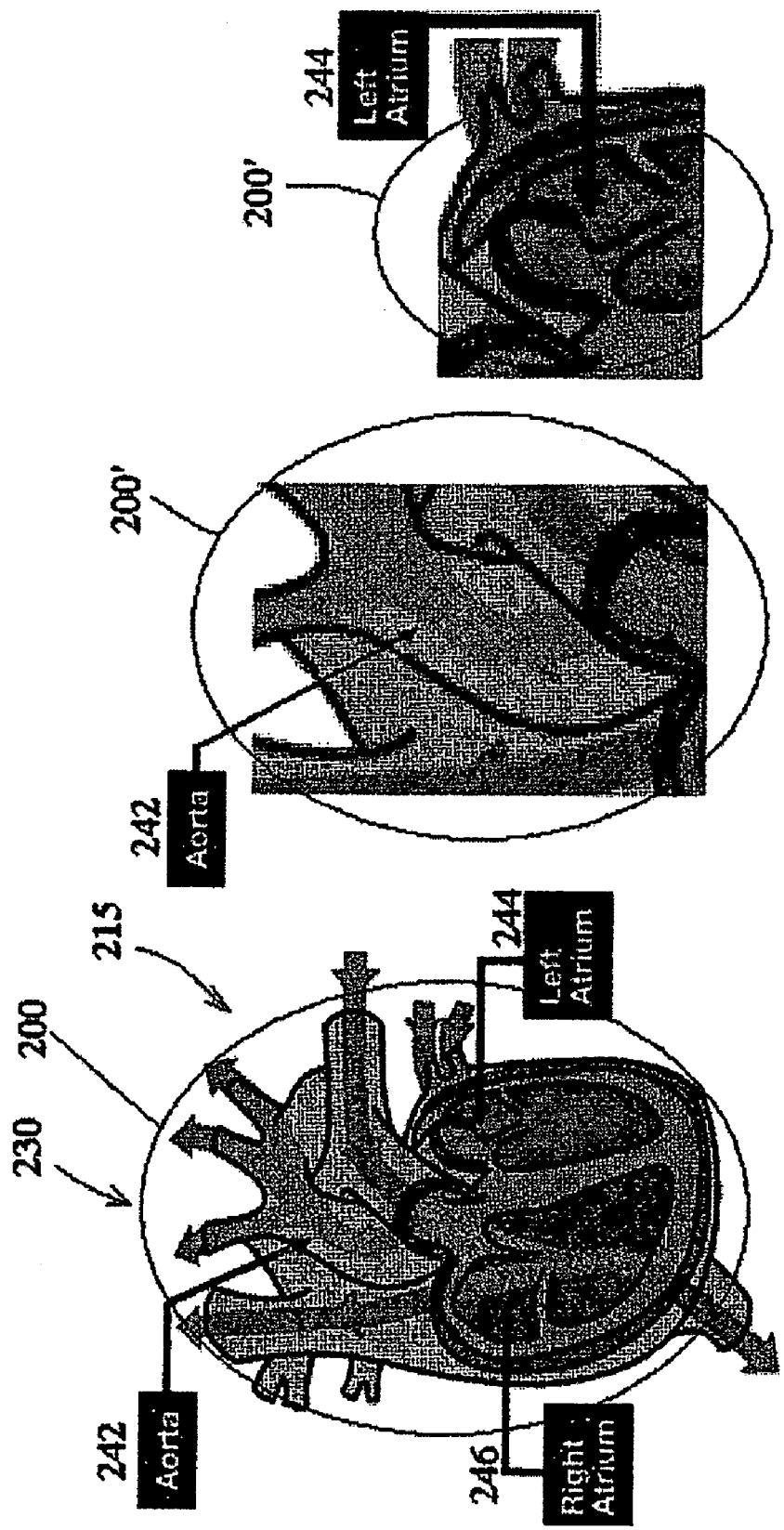
FIGS. 36A-36C schematically illustrate a heart.

Referring further to the drawings, FIGS. 36A-36C schematically illustrate the body section 230, as a heart, which includes the region of interest 200, associated with the organ 215, being the heart 215. The heart 215 includes an aorta 242, a left atrium 244 and a right atrium 246.

FIG. 36B schematically illustrates a second, inner region of interest 200', associated with the aorta 242.

Similarly, FIG. 36C schematically illustrates a second, inner region of interest 200', associated with the left atrium 244.

Referring further to the drawings, FIGS. 37A-43E schematically illustrate a cardiac probe system 500, in accordance with a preferred embodiment of the present invention.

FIGS. 37A-37D schematically illustrate the basic components of the cardiac probe system 500, in accordance with embodiments of the present invention. These include an operator computer station 510, a chair 520, and a radioactive-emission-measuring probe assembly 530.

Figures 37A, 37B, 37C:
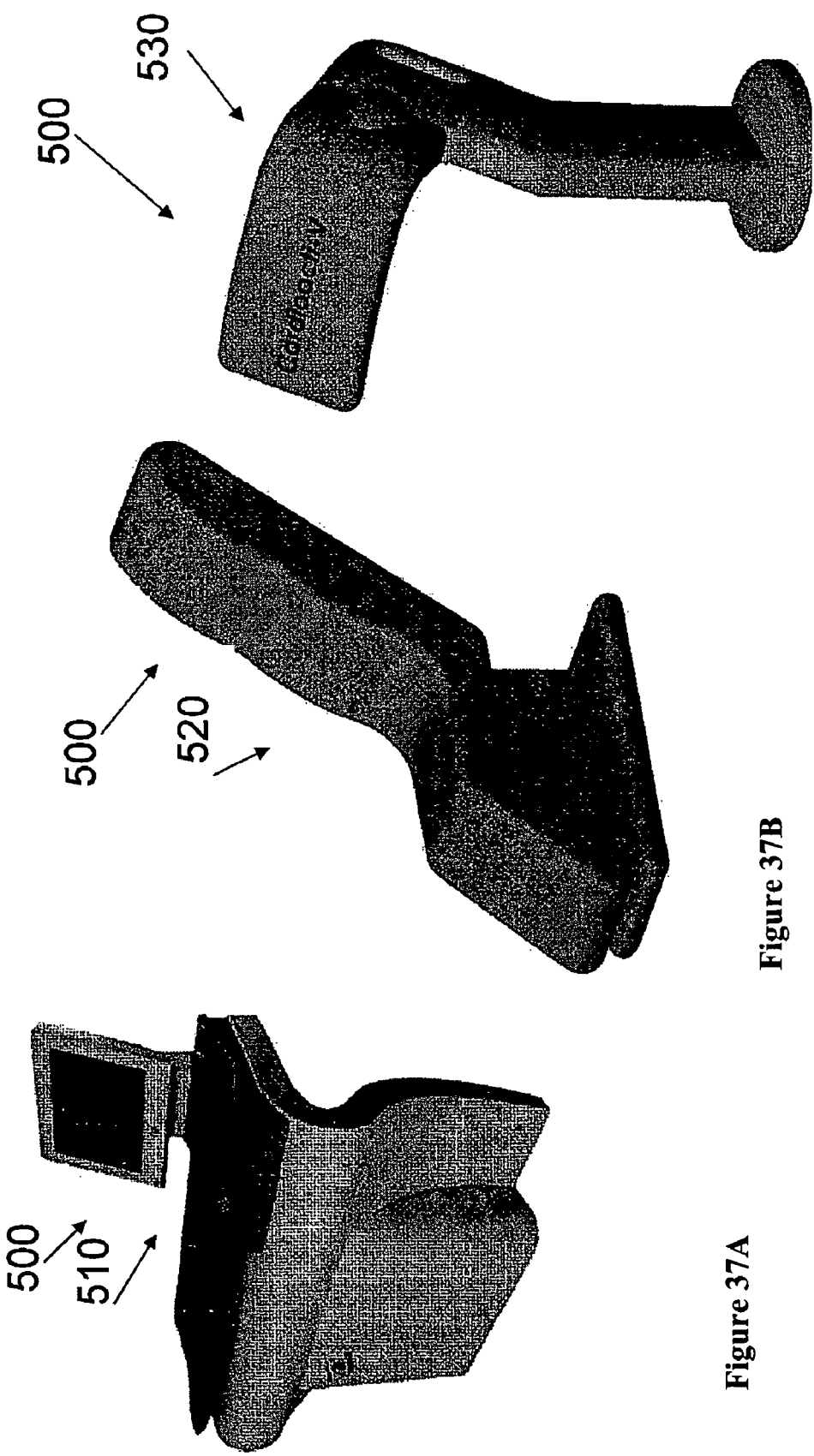
FIGS. 37A-37D schematically illustrate the basic components of the cardiac probe system, in accordance with embodiments of the present invention.
Figure 37D:
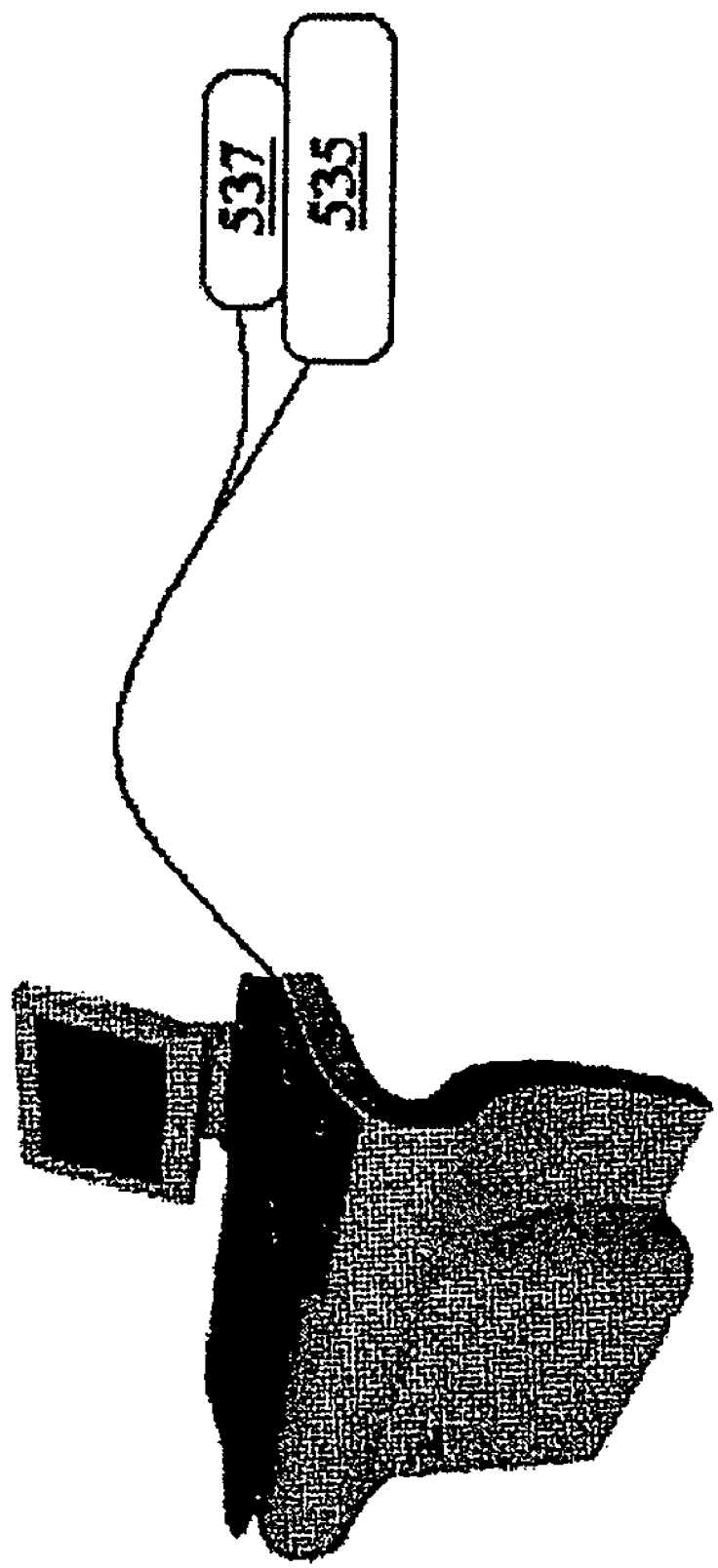

As seen in FIG. 37D, computer station 510 may be further adapted for input of an ultrasound imager 535, for example, a handheld ultrasound imager 535, possibly with a position-tracking device 537, or a 3-D ultrasound imager. The data provided by the ultrasound imager 535 may be used in the modeling of the heart. Preferably, the data of the ultrasound imager may be co-registered with the radioactive emission measurements, on the same frame of reference, for providing co-registration of structural and functional imaging. It will be appreciated that the imager 535 may be an MRI imager.

Figure 38:
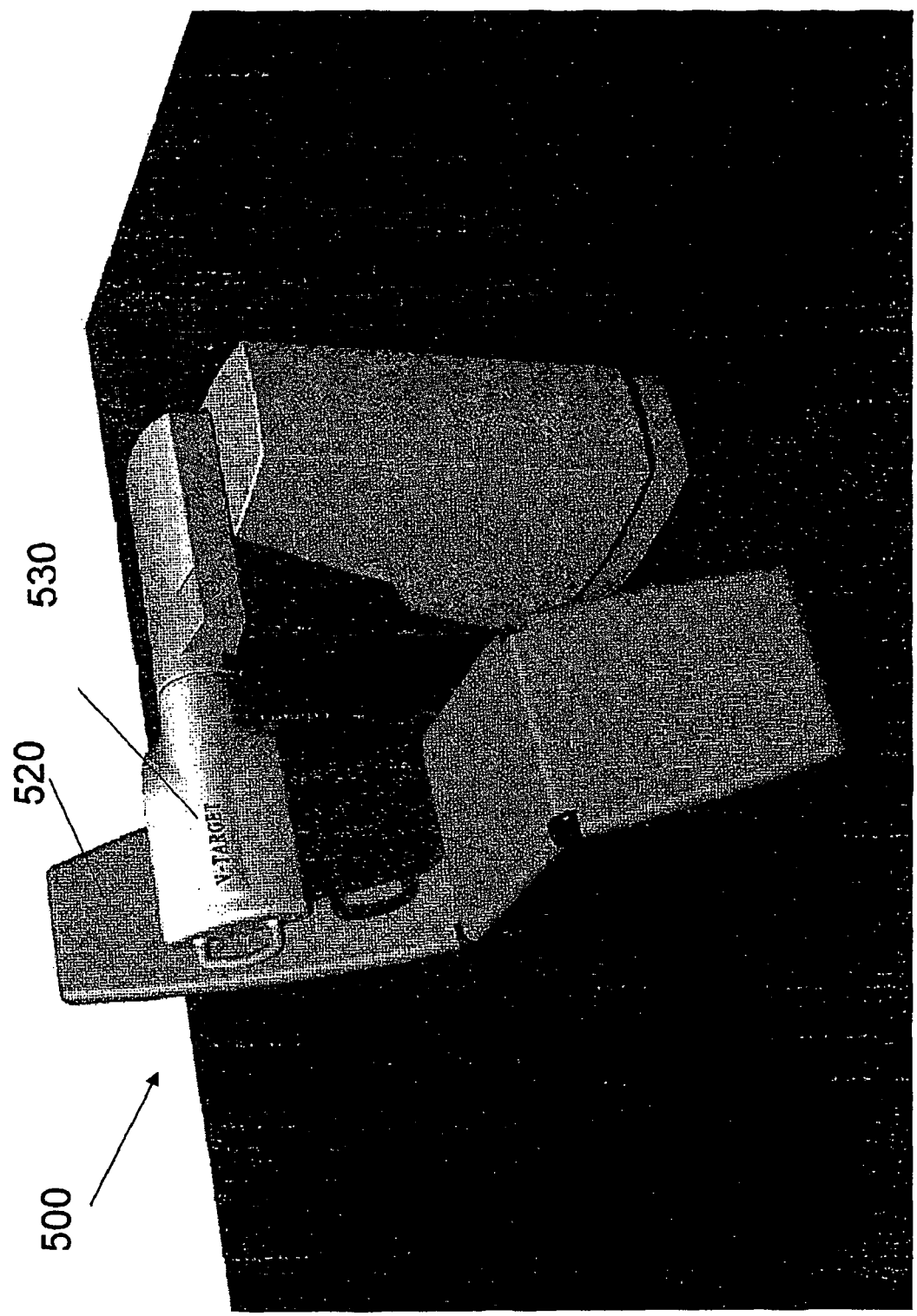
FIG. 38 schematically illustrates the chair and the probe assembly, arranged for operation, in accordance with an embodiment of the present invention.

FIG. 38 schematically illustrates the chair 520 and the probe assembly 530, arranged for operation, in accordance with a preferred embodiment of the present invention. Preferably, the chair 520 is in a partial reclining position, and the probe assembly 530 is designed to come against it, opposite the chest of a person, when sitting on the chair 520. Preferably, the probe assembly 530 includes a housing, which is substantially transparent to radioactive emission. Alternatively, no housing, or a housing which is open on the side facing a patient may be used.

It will be appreciated that another chair or a bed may be used rather than the chair 520. Alternatively, the patient may be standing.

Figure 39A:
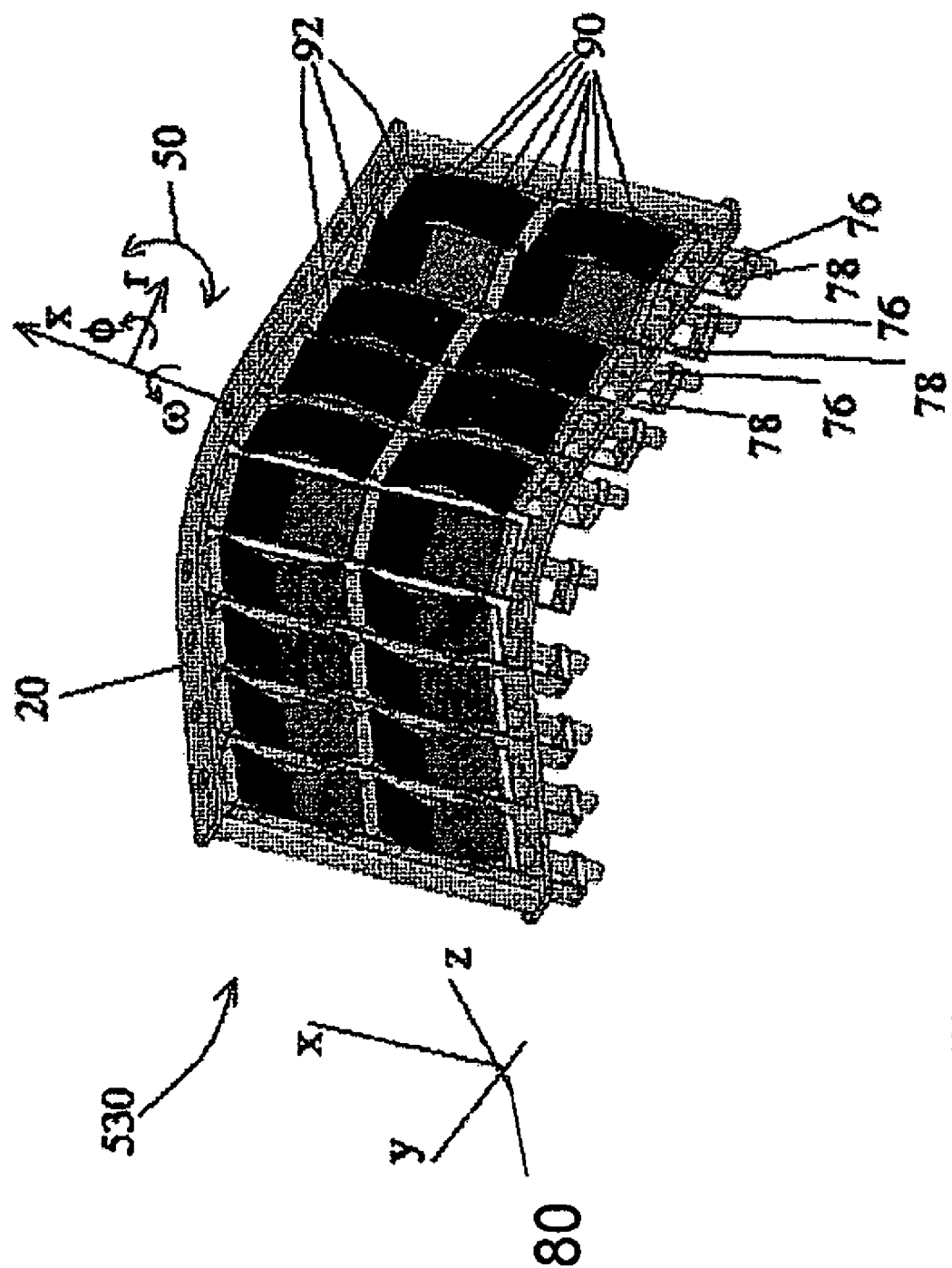
FIGS. 39A-39B schematically illustrate possible inner structures of the probe assembly, in accordance with preferred embodiments of the present invention.
Figure 39B:
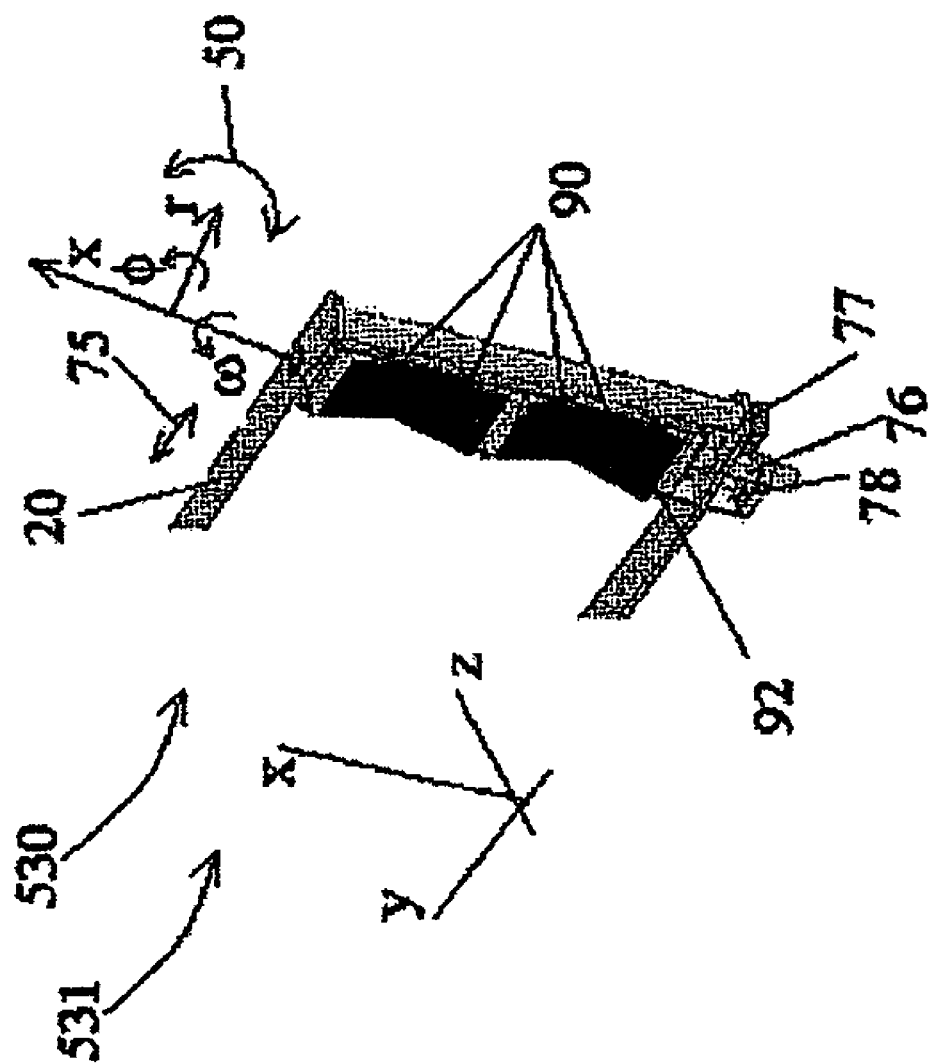

FIGS. 39A-39B schematically illustrate possible inner structures of the probe assembly, in accordance with preferred embodiments of the present invention.

FIG. 39A schematically illustrates the inner structure of the probe assembly 530, showing the housing 20, the parallel lines of assemblies 92, possibly of an even number, each with a dedicated motion provider 76 and a dedicated secondary motion provider 78, and the rows of blocks 90, possibly arranged in pairs, along the assemblies 92.

The probe assembly 530 defines an internal frame of reference 80, while each assembly 92 has a reference cylindrical coordinate system of x;r, with rotation around x denoted by ω and rotation around r denoted by φ, wherein the oscillatory motion about r is denoted by the arrow 50.

Preferably, the motion of the probe assembly 530 corresponds to that described hereinabove, in conjunction with FIGS. 20A-20H and 22A-22H, as follows:

The plurality of blocks 90 is adapted for the windshield-wiper like oscillatory motion, around the radius r, as denoted by the arrow 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Furthermore, the plurality of assemblies 92 are preferably arranged in parallel, and their rotational motions, around the x-axis, in the direction of ω, may also be synchronized in an antipodal manner, so as to be diametrically opposed to each other, as shown hereinabove, in FIG. 22C, by arrows 62, and as shown hereinabove in FIG. 22G, by arrows 64. However, other motions are also possible. For example, the assemblies 92 may move together, or independently. It will be appreciated that an odd number of assemblies 92 is also possible.

Thus, the resultant traces are a large plurality of the broken line traces 59, as seen hereinabove, in conjunction with FIGS. 22D and 22H, on the chest of the patient.

In accordance with the present example, i. The different blocks 90 provide views from different orientations;
ii. The different blocks 90 may change their view orientations;
iii. The different assemblies 92 provide views from different orientations; and
iv. The different assemblies 92 may change their view orientations.

The operational manner of the probe 530 is described hereinbelow in conjunction with FIG. 23D, for the at least two assemblies 92.

Preferably, the motions of the blocks 90 and of the assemblies 92 are contained within the housing 20, so that the external surface of the probe assembly 530 remains stationary, wherein the external surface of the probe assembly 530 is substantially transparent to nuclear radiation. Alternatively, the housing may be open on the side facing the patient.

It will be appreciated that the oscillatory motions need not be synchronized in an antipodal manner. Rather, the blocks 90 may move together, or independently. It will be appreciated that an odd number of blocks 90 is also possible.

It will be appreciated that probe 530 may include a plurality of assemblies 92, which are not parallel to each other. For example, the assemblies 92 may be at right angles to each other, or at some other angle. It will be appreciated that the assemblies 92 may include detecting units 12 rather then blocks 90, for example, as in the probe 10 of FIGS. 20A-20G.

FIG. 39B schematically illustrates a section 531 of the probe assembly 530, showing the inner structure thereof, in accordance with another embodiment of the present invention. Accordingly, the probe assembly 530 may include the housing 20, and a single one of the assemblies 92, within the housing 20, having the dedicated motion provider 76, the dedicated secondary motion provider 78, and the rows of blocks 90. Additionally, in accordance with the present embodiment, the probe assembly 530 includes a tertiary motion provider 77, for sliding the assembly 90 laterally, in the directions of the arrow 75, along the chest of the patient (not shown). In this manner, imaging of the chest may be performed with the single assembly 92.

FIGS. 40A and 40B schematically illustrate the assembly 92 and the block 90, in accordance with a preferred embodiment of the present invention. In essence, the assembly 92 is constructed in a manner similar to the probe 10 of FIGS. 20A-20H, and specifically FIG. 20H, and according to FIG. 23D, hereinabove.

Thus the assembly 92 includes a row of at least two blocks 90, each adapted of oscillatory motion about r. The blocks 90 are arranged within the inner housing 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

Figure 41:
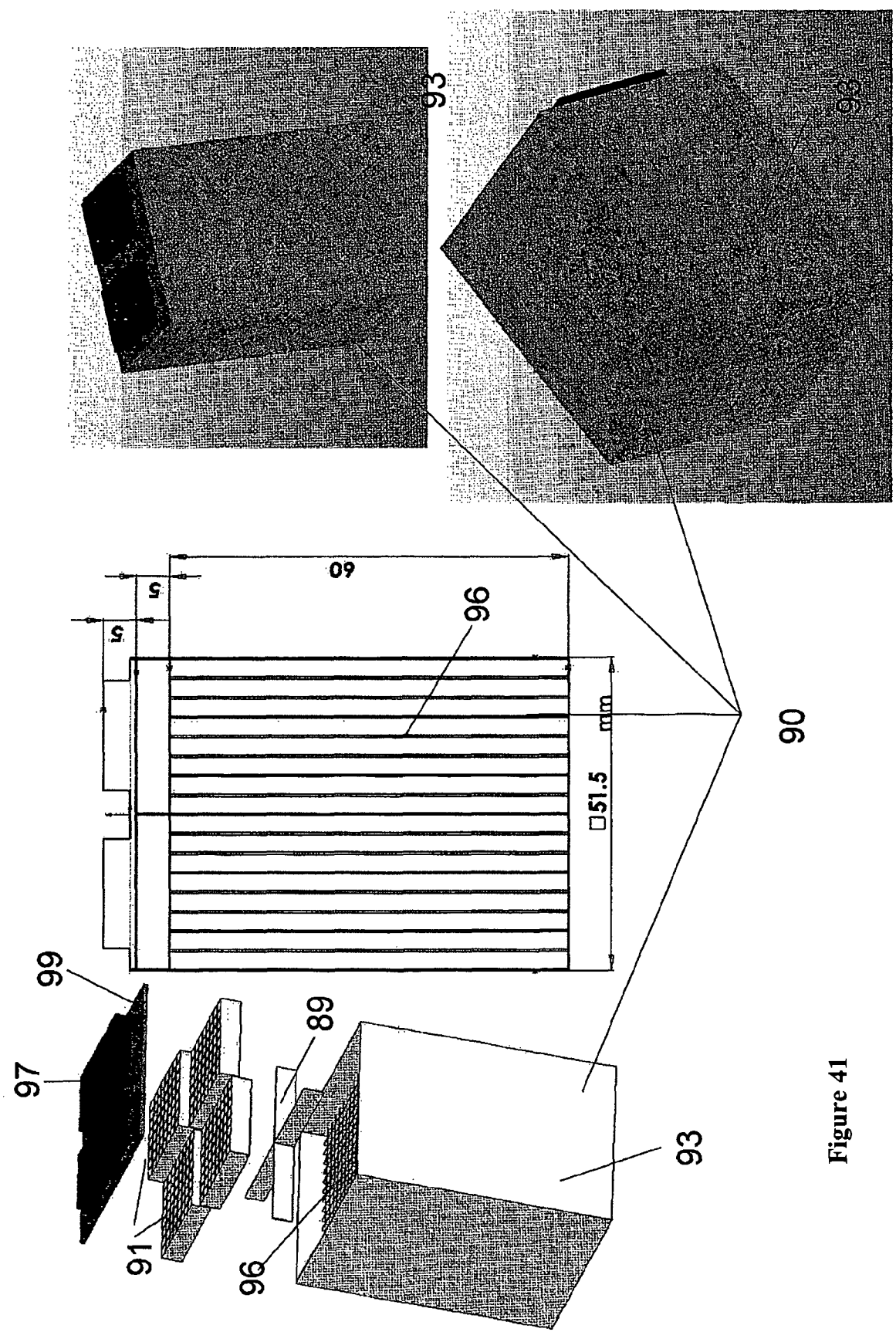

FIG. 41 schematically illustrates the block 90, in accordance with a preferred embodiment of the present invention. The block 90 includes a frame 93, which houses the detector material 91, which is preferably pixilated, and the collimators 96. Additionally, the frame 93 houses dedicated electronics 97, preferably on a PCB board 99. Furthermore, where several modules of the detector material 91 need to be used, a structural element 89 may be provided to hold the different modules of the detector material 91 together. It will be appreciated that a single pixel detector may be used. Alternatively, a single module of a pixilated detector may be used. Alternatively, the block 90 may be constructed as any of the examples taught in conjunction with FIGS. 17A-17L, or as another block, as known.

The dimensions, which are provided in FIG. 41, are in mm. It will be appreciated that other dimensions, which may be larger or smaller, may similarly be used.

Figure 42:
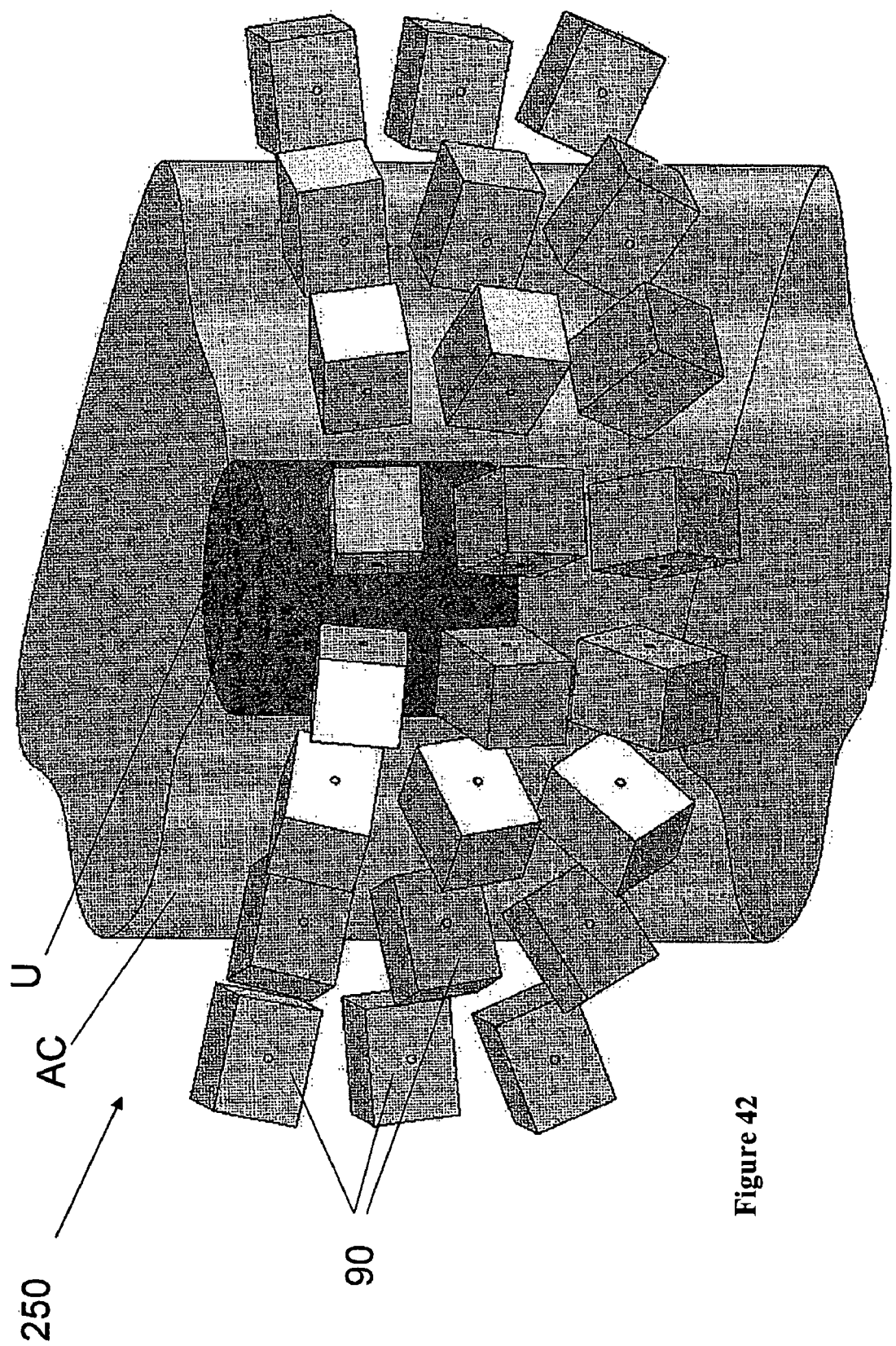
FIG. 42 schematically illustrates the cardiac model, in accordance with a preferred embodiment of the present invention.

FIG. 42 schematically illustrates the cardiac model 250, in accordance with a preferred embodiment of the present invention. The cardiac model 250 includes the volume U, for example, as a cylinder, and the anatomical constraints AC. The rows of blocks 90 are arranged around the volume U, as permissible by the anatomical constraints AC.

FIGS. 43A-43E schematically illustrate the blocks 90, arranged for viewing the cardiac model 250, in accordance with a preferred embodiment of the present invention.

In FIG. 43A, the block 90 is shown with the frame 93, which houses the detector material 91, which is preferably pixilated, and the collimators 96. Additionally, the frame 93 houses the dedicated electronics 97, on the PCB board 99.

In FIG. 43A, fields of view 98 of the blocks 90 are seen for a situation wherein adjacent blocks 90A and 90B move in an antipodal manner, while adjacent blocks 90B and 90C move in a nearly parallel manner. The figure illustrates that when moving in an antipodal manner, the blocks 90 do not obstruct each other's field of view 98. Yet, when moving in a parallel manner, or a near parallel manner, obstruction may occur.

A similar observation is made by FIG. 43C, wherein the adjacent blocks 90B and 90C move in an antipodal manner, while the adjacent blocks 90A and 90B move in a near parallel manner.

Again, it will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

FIG. 43D illustrates possible dimensions for the cardiac model 250. The dimensions are in mm. It will be appreciated that other dimensions are similarly possible. Furthermore, It will be appreciated that the model 250 may be based on general medical information of the organ 215 and common pathological features associated with it. Additionally, the model may be based on information related to a specific patient, such as age, sex, weight, and body type. Furthermore, a structural image, such as by ultrasound or MRI, may be used for providing information about the size and location of the heart 215 in relation to the body section 230 (FIG. 5A), for generating the model 250.

FIG. 43E schematically illustrates a possible arrangement of the blocks 90 for viewing the volume U of the model 250, within the anatomical constrains AC. The significance of the present invention, as illustrated by FIG. 43E is that all the blocks maintain a close proximity to the modeled volume U, and to the region of interest, in vivo, even as they move. This is in sharp contrast to the prior art, for example, as taught by U.S. Pat. No. 6,597,940, to Bishop, et al, and U.S. Pat. No. 6,671,541, to Bishop, in which the blocks are fixed within a rigid housing, so that as some of the blocks are placed in close proximity to the body, others are forced away from the body, and their counting efficiency deteriorates.

Preferably, the radiopharmaceuticals associated with the probe of FIGS. 37A-52E may be Myoview™ (technetium Tc-99m tetrofosmin), a cardiac imaging agent, of GE Healthcare, GE Medical Systems, http://www.gehealthcare.com/contact/contact_details.html#diothers. Alternatively, it may be Cardiolite (Sestamibi radilabeled with TC99), of DuPont, http://www1.dupont.com/NASApp/dupontglobal/corp/index.jsp?page=/content/US/en_US/contactus.html. It will be appreciated that other agents may be used.

It will be appreciated that cardiac imaging, in accordance with embodiments of the present invention relates to the imaging of the whole heart, or to a portion of the heart, or to blood vessels near the heart, for example, the coronary artery.

Example 13

Figure 44:
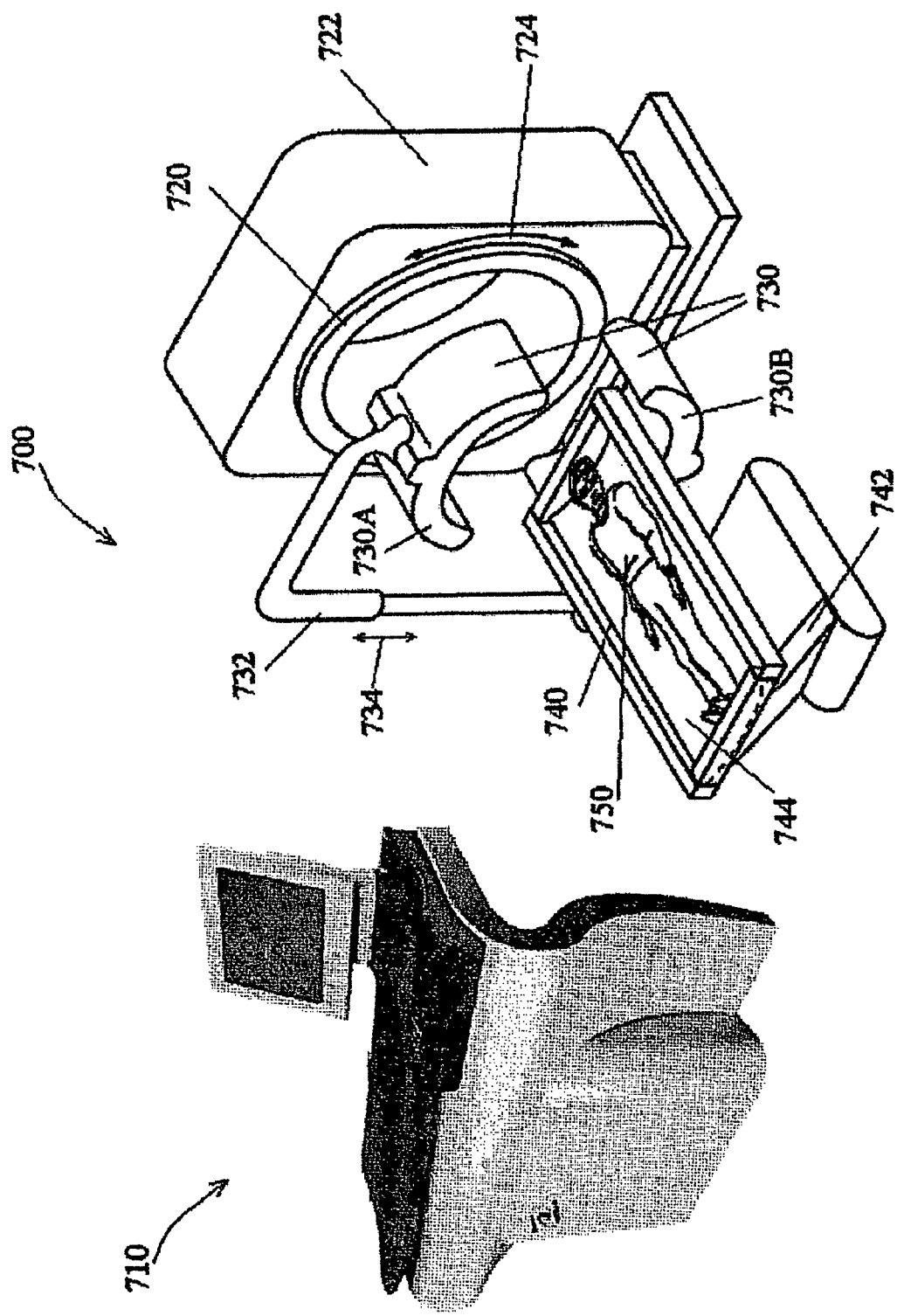
FIG. 44 schematically illustrates a dual imaging system for radioactive-emission-measurements in tandem with a three-dimensional structural imager, in accordance with a preferred embodiment of the present invention.

Referring further to the drawings, FIG. 44 schematically illustrates a dual imaging system 700 for radioactive-emission-measurements in tandem with a three-dimensional structural imager, in accordance with a preferred embodiment of the present invention.

The dual imaging system 700 includes a three-dimensional structural imager 720, preferably, on a structural-imager gantry 722, and a radioactive-emission measuring probe 730, preferably, on a probe gantry 732. A patient 750 may lie on a bed 740, which is adapted for motion into the radioactive-emission measuring probe 730 and the three-dimensional structural imager 720, on a bed gantry 742.

A control unit 710 controls the operation of the dual system 700, including the three-dimensional structural imager 720, the radioactive-emission measuring probe 730, and the bed 740. The control unit 710 may also analyze the data.

Alternatively, two control units may be used, one for controlling the three-dimensional structural imager 720 and another for controlling the radioactive-emission measuring probe 730. It will be appreciated that the control system of the radioactive-emission measuring probe 730 generally controls the order of the operation of the dual system 700, wherein the radioactive-emission measuring may be performed before or after the structural imaging.

It will be further appreciated that the radioactive-emission measuring probe 730 may be configured as an add-on system, adapted for operating with an existing structural imager. It may be supplied with a dedicated software, for example, in a CD format, or with its own control unit, which is preferably adapted for communication with the structural imager control unit.

The three-dimensional structural imager 720 may be, for example, a CT or an MRI, which defines a frame of reference, wherein the radioactive-emission measuring probe 730 is co-registered to the frame of reference.

In this manner, co-registration of functional and structural images is possible. Additionally, the structural image may be used for providing tissue information for attenuation correction of the functional image, resulting in a more accurate functional image.

The radioactive-emission measuring probe 730 may be constructed as one arc 730A, preferably adapted for viewing a full width of a body from a single position of the probe 730. Alternatively, the radioactive-emission measuring probe 730 may be constructed as two arcs 730A and 730B, which are adapted for viewing a full circumference of a body, from a single position of the probe 730. It will be appreciated that the probe 730 may have other geometries, for example, a circle, an ellipse, a polygon, a plurality of arcs forming a circle, or a plurality of sections, forming a polygon, or other shapes.

Preferably, where the probe 730 is adapted for viewing a full circumference of a patient, from a single position, the bed 740 is formed as a stretcher, with a sheet 744, which is substantially transparent to radioactive emission, for example, of a hydrocarbon material.

Figure 45:
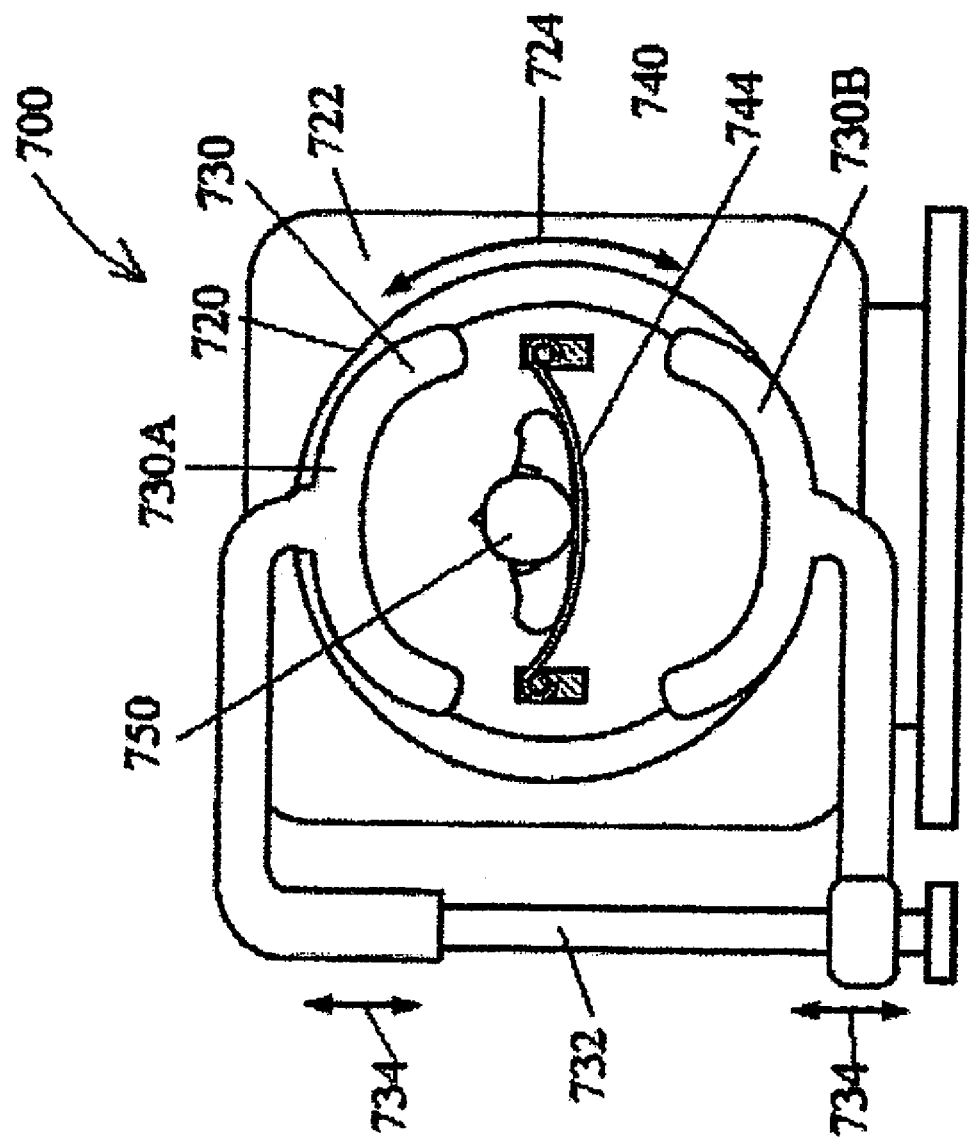
FIG. 45 schematically illustrates a cross-sectional view of dual imaging system for radioactive-emission-measurements in tandem with a three-dimensional structural imager, in accordance with a preferred embodiment of the present invention.

FIG. 45 schematically illustrates a cross-sectional view of dual imaging system 700 for radioactive-emission-measurements in tandem with a three-dimensional structural imager, in accordance with a preferred embodiment of the present invention.

Preferably, the gantry 732 of the probe 730 is adapted for vertical motion, as described by the arrows 734, so as to bring the probe 730 closer to the patient 750.

Additionally, the gantry 722 of the three-dimensional structural imager 720 may be adapted for rotation, as described by an arrow 724.

The bed 740 is preferably adapted for motion into and out of the probe 730 and the three-dimensional structural imager 720.

Preferably, the rate of imaging by the three-dimensional structural imager 720 and by the radioactive-emission measuring probe is substantially the same, to the bed moves into the two imagers at a constant speed.

It will be appreciated that the body structure that may be imaged may be an organ, such as a heart or a pancreas, a gland, such as a thyroid gland or a lymph gland, blood vessels, for example, the coronary artery or the pulmonary artery, a portion of an organ, such as an aorta or a left atrium of a heart, a bone, a ligament, a joint, a section of the body, such as a chest or an abdomen, or a whole body.

Preferably, the radiopharmaceuticals associated with the probe of the present invention be any one of the following:

1. anti-CEA, a monoclonal antibody fragment, which targets CEA—produced and shed by colorectal carcinoma cells—and may be labeled by $Tc^{99m}$ or by other radioisotopes, for example, iodine isotopes (Jessup J M, 1998, Tumor markers—prognostic and therapeutic implications for colorectal carcinoma, Surgical Oncology; 7: 139-151);

2. $In^{111}$-Satumomab Pendetide (Oncoscint®), designed to target TAG-72, a mucin-like glycoprotein, expressed in human colorectal, gastric, ovarian, breast and lung cancers, but rarely in healthy human adult tissues (Molinolo A; Simpson J F; et al., 1990, Enhanced tumor binding using immunohistochemical analyses by second generation anti-tumor-associated glycoprotein 72 monoclonal antibodies versus monoclonal antibody B72.3 in human tissue, Cancer Res., 50(4): 1291-8);

3. Lipid-Associated Sialic Acid (LASA), a tumor antigen, used for colorectal carcinoma, with a similar sensitivity as anti-CEA monoclonal antibody fragment but a greater specificity for differentiating between benign and malignant lesions (Ebril K M, Jones J D, Klee G G, 1985, Use and limitations of serum total and lipid-bound sialic acid concentrations as markers for colorectal cancer, Cancer; 55:404-409);

4. Matrix Metaloproteinase-7 (MMP-7), a proteins enzyme, believed to be involved in tumor invasion and metastasis (Mori M, Barnard G F et al., 1995, Overexpression of matrix metalloproteinase-7 mRNA in human colon carcinoma, Cancer; 75: 1516-1519);

5. $Ga^{67}$ citrate, used for detection of chronic inflammation (Mettler F A, and Guiberteau M J, Eds., 1998, Inflammation and infection imaging, Essentials of nuclear medicine, Fourth edition, Pgs: 387-403);

6. Nonspecific-polyclonal immunoglobulin G (IgG), which may be labeled with both $In^{111}$ or $Tc^{99m}$, and which has a potential to localize nonbacterial infections (Mettler F A, and Guiberteau M J, ibid);

7. Radio-labeled leukocytes, such as such as $In^{111}$ oxine leukocytes and $Tc^{99m}$ HMPAO leukocytes, which are attracted to sites of inflammation, where they are activated by local chemotactic factors and pass through the endothelium into the soft tissue (Mettler F A, and Guiberteau M J, ibid; Corstens F H; van der Meer J W, 1999, Nuclear medicine's role in infection and inflammation, Lancet; 354 (9180): 765-70); and 8. $Tc^{99m}$ bound to Sodium Pertechnetate, which is picked up by red blood cells, and may be used for identifying blood vessels and vital organs, such as the liver and the kidneys, in order to guide a surgical instrument without their penetration.

It will be appreciated that other agents may be used.

Figure 46A:
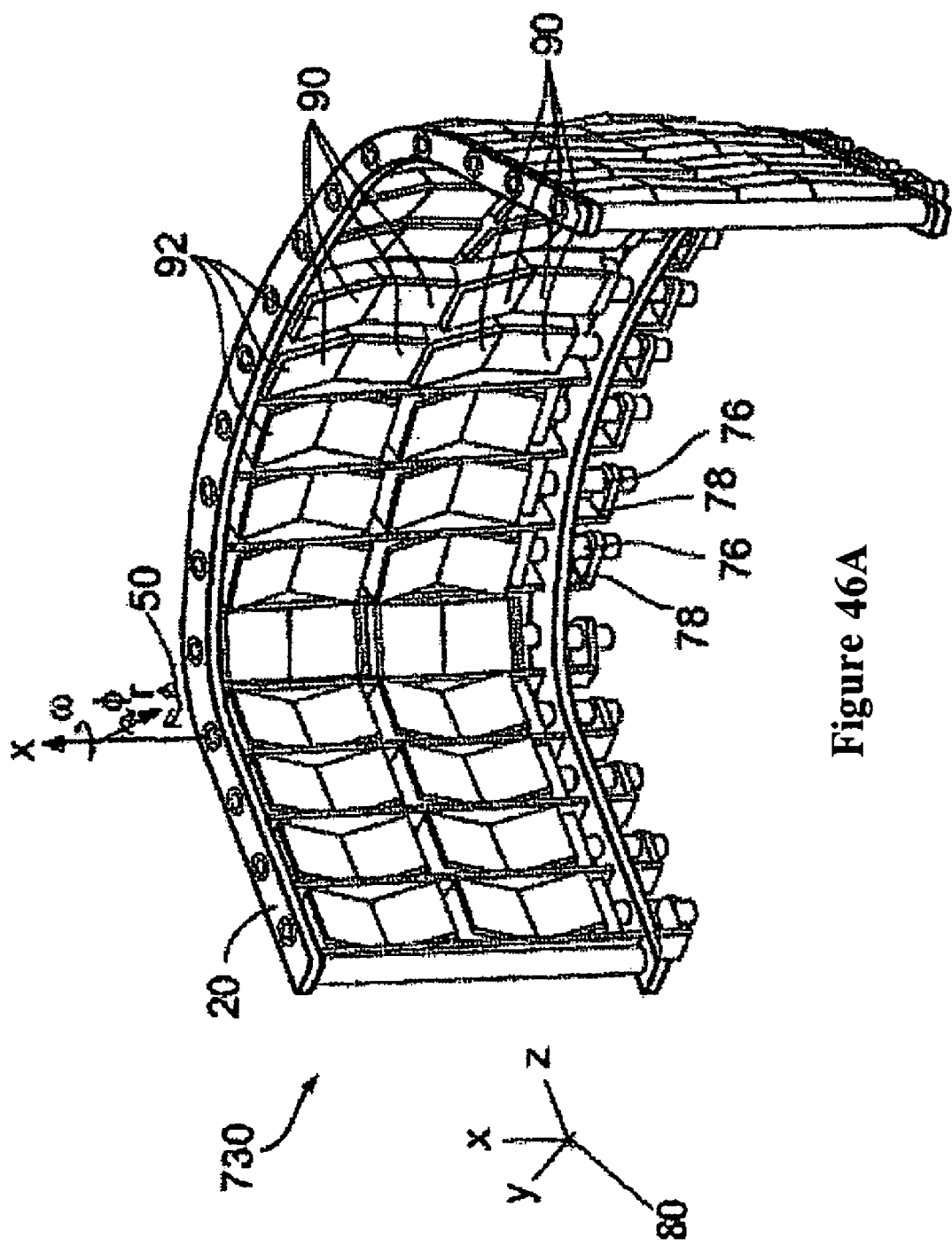
FIGS. 46A-46C schematically illustrate possible inner structures and arrangement of the probe of the dual imaging system, in accordance with preferred embodiments of the present invention.
Figure 46B:
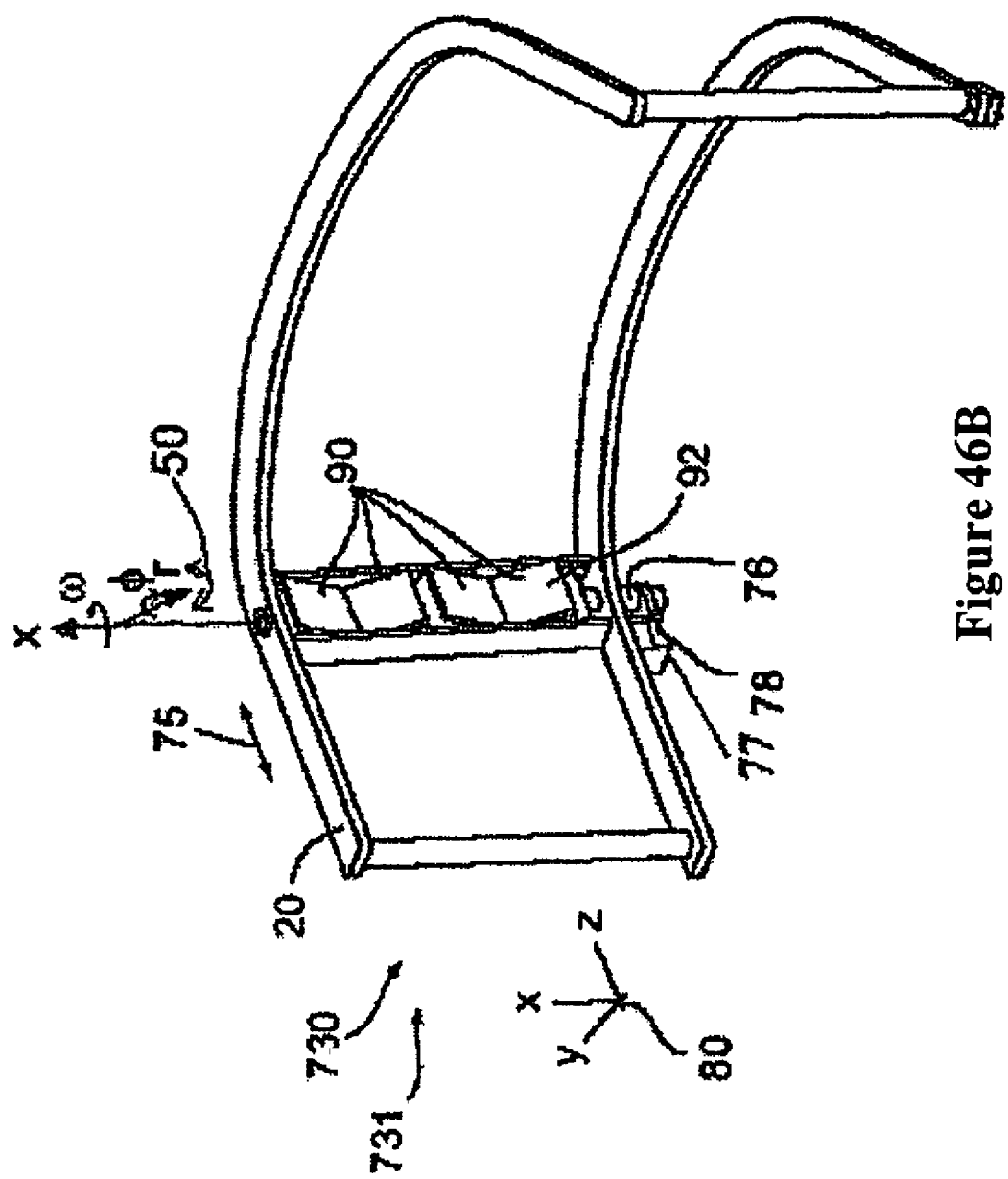
Figure 46C:
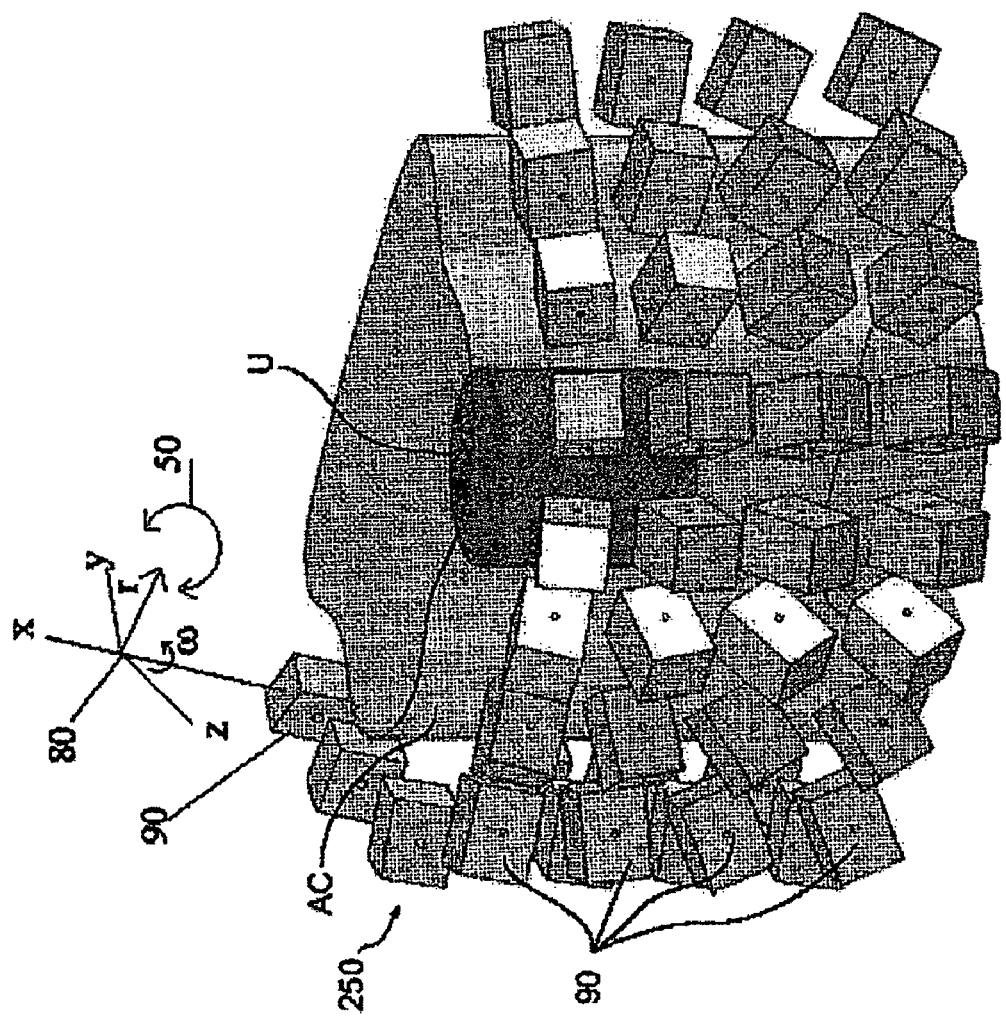

FIGS. 46A-46C schematically illustrate possible inner structures and arrangement of the probe 730, of the dual imaging system, in accordance with preferred embodiments of the present invention.

FIG. 46A schematically illustrates the inner structure of the probe 730, showing the housing 20 and the parallel lines of the assemblies 92, possibly of an even number, each with the row of blocks 90, possibly arranged in pairs. Each of the assemblies 92 preferably includes the dedicated motion provider 76, for providing the rotational motion around x, and the dedicated secondary motion provider 78, for providing the oscillatory motion about r in the direction of the arrow 50.

The probe 730 defines an internal frame of reference 80, while each assembly 92 has a reference cylindrical coordinate system of x;r, with rotation around x denoted by ω and rotation around r denoted by φ, wherein the oscillatory motion about r is denoted by the arrow 50.

Preferably, the motions of the assemblies 92 and the blocks 90 correspond to those described hereinabove, in conjunction with FIGS. 20A-20H and 22A-22H, as follows:

The plurality of blocks 90 is adapted for the windshield-wiper like oscillatory motion, around the radius r, as denoted by the arrow 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Furthermore, the plurality of assemblies 92 are preferably arranged in parallel, and their rotational motions, around the x-axis, in the direction of ω, may also be synchronized in an antipodal manner, so as to be diametrically opposed to each other, as shown hereinabove, in FIG. 22C, by arrows 62, and as shown hereinabove in FIG. 22G, by arrows 64. However, other motions are also possible. For example, the assemblies 92 may move together, or independently. It will be appreciated that an odd number of assemblies 92 is also possible.

Thus, the resultant traces are a large plurality of the broken line traces 59, as seen hereinabove, in conjunction with FIGS. 22D and 22H, on the skin of the patient.

In accordance with the present example,
i. The different blocks 90 provide views from different orientations;
ii. The different blocks 90 change their view orientations;
iii. The different assemblies 92 provide views from different orientations; and
iv. The different assemblies 92 change their view orientations.

The operational manner of the probe 730 is described hereinbelow in conjunction with FIG. 23D, for the at least two assemblies 92.

Preferably, the motions of the blocks 90 and of the assemblies 92 are contained within the housing 20, so that the housing 20 of the probe 730 remains stationary, wherein the external surface of the probe 730 is substantially transparent to nuclear radiation. Alternatively, the housing may be open on the side facing the patient.

It will be appreciated that the oscillatory motions need not be synchronized in an antipodal manner. Rather, the blocks 90 may move together, or independently. It will be appreciated that an odd number of blocks 90 is also possible.

It will be appreciated that the probe 730 may include a plurality of assemblies 92, which are not parallel to each other. For example, the assemblies 92 may be at right angles to each other, or at some other angle. It will be appreciated that the assemblies 92 may include detecting units 12 rather then blocks 90, for example, as in the probe 10 of FIGS. 20A-20G.

FIG. 46B schematically illustrates a section 731 of the probe 730, showing the inner structure thereof, in accordance with another embodiment of the present invention. Accordingly, the probe 730 may include the housing 20, and a single one of the assemblies 92, within the housing 20, having the dedicated motion provider 76, the dedicated secondary motion provider 78, and the rows of blocks 90. Additionally, in accordance with the present embodiment, the probe 730 includes a tertiary motion provider 77, for sliding the assembly 90 laterally, in the directions of an arrow 75.

FIG. 46C schematically illustrates an alternative arrangement of the blocks 90 around the volume U of the model 250, wherein each of the blocks 90 is provided with motion around the x axis, in the direction of Φ, and with the oscillatory motion about r, preferably in the y-z plane, as illustrated by the arrow 50. Accordingly, the assemblies 92 need not be used. Rather, each of the blocks 90 may communicate with two motion providers which provide it with the two types of motion.

Figures 47A, 47B:
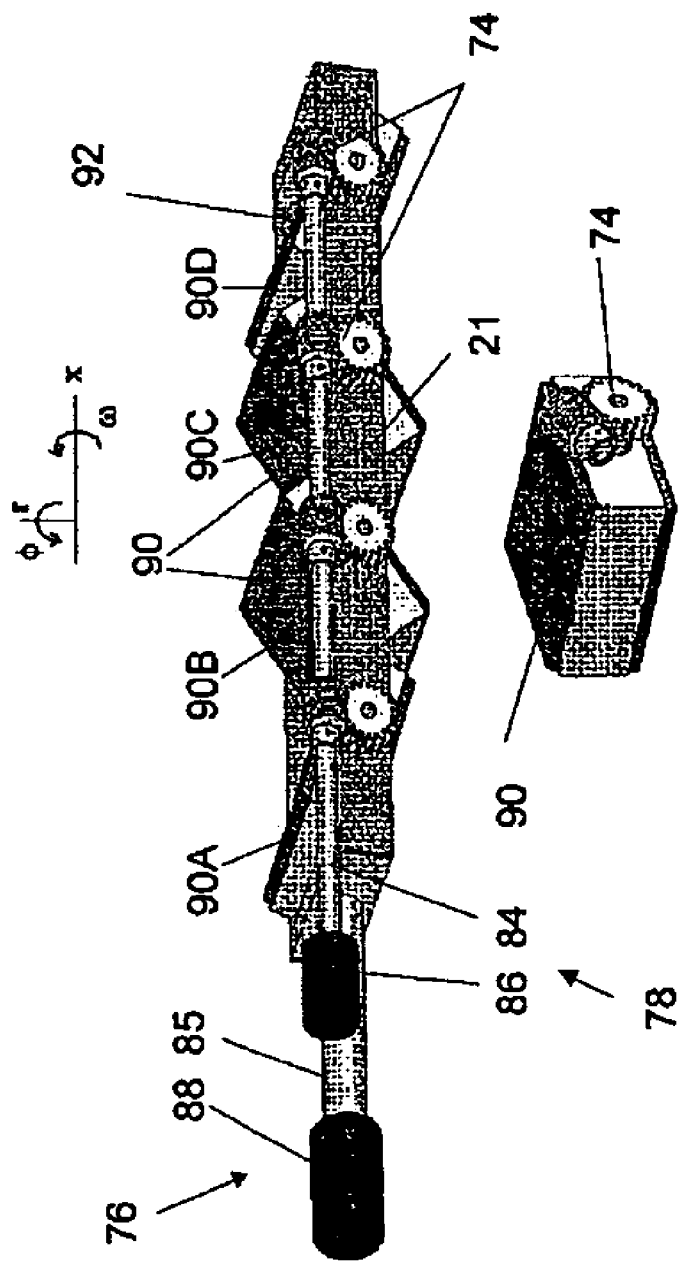
FIGS. 47A and 47B schematically illustrate the assembly 92 and the block 90, in accordance with a preferred embodiment of the present invention.

FIGS. 47A and 47B schematically illustrate the assembly 92 and the block 90, in accordance with a preferred embodiment of the present invention. In essence, the assembly 92 is constructed in a manner similar to the probe 10 of FIGS. 20A-20H, and specifically FIG. 20H, and according to FIG. 23D, hereinabove.

Thus the assembly 92 includes a row of at least two blocks 90, each adapted of oscillatory motion about r. The blocks 90 are arranged within the inner housing 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

It will be appreciated that many other probes and probe systems may be considered and the examples here are provided merely to illustrate the many types of combinations that may be examined, in choosing and scoring a probe design, both in terms of information and in terms of secondary considerations, such as rate of data collection, cost, and complexity of the design.

Example 14

Brain cancer is the leading cause of cancer-related death in patients younger than age 35, and in the United States, the annual incidence of brain cancer generally is 15-20 cases per 100,000 people.

There are two types of brain tumors: primary brain tumors that originate in the brain and metastatic (secondary) brain tumors that originate from cancer cells that have migrated from other parts of the body.

Approximately 17,000 people in the United States are diagnosed with primary cancer each year; nearly 13,000 die of the disease. Amongst children, the annual incidence of primary brain cancer is about 3 per 100,000.

Primary Brain Tumors are generally named according to the type of cells or the part of the brain in which they begin. The most common are gliomas, which begin in glial cells, and of which there are several types, as follows:

Astrocytoma, a tumor which arises from star-shaped glial cells called astrocytes, and which in adults, most often arises in the cerebrum, whereas in children, it occurs in the brain stem, the cerebrum, and the cerebellum.

Brain stem glioma, a tumor that occurs in the lowest part of the brain, and is diagnosed in young children as well as in middle-aged adults.

Ependymoma, a tumor, most common in middle-aged adults, which arises from cells that line the ventricles or the central canal of the spinal cord and which occurs in children and young adults.

Oligodendroglioma, a rare tumor, which arises from cells that make the fatty substance that covers and protects nerves and usually occurs in the cerebrum, grows slowly and generally does not spread into surrounding brain tissue.

Some types of brain tumors do not begin in glial cells. The most common of these are:

Medulloblastoma, also called a primitive neuroectodermal tumor, a tumor which usually arises in the cerebellum and is the most common brain tumor in children.

Meningioma, which arises in the meninges and usually grows slowly.

Schwannoma, also called an acoustic neuroma, and occurring most often in adults, it is a tumor that arises from a Schwann cell, of the cells that line the nerve that controls balance and hearing, in the inner ear.

Craniopharyngioma, a tumor which grows at the base of the brain, near the pituitary gland, and most often occurs in children.

Germ cell tumor of the brain, a tumor which arises from a germ cell, generally, in people younger than 30, the most common type of which is a germinoma.

Pineal region tumor, a rare brain tumor, which arises in or near the pineal gland, located between the cerebrum and the cerebellum.

Certain inherited diseases are associated with brain tumors, for example, Multiple endocrine neoplasia type 1 (pituitary adenoma), Neurofibromatosis type 2 (brain and spinal cord tumors), Retinoblastoma (malignant retinal glioma), Tuberous sclerosis (primary brain tumors), and Von Hippel-Lindau disease (retinal tumor, CNS tumors). Furthermore, genetic mutations and deletions of tumor suppressor genes (i.e., genes that suppress the development of malignant cells) increase the risk for some types of brain cancer.

Additionally, exposure to vinyl chloride is an environmental risk factor for brain cancer. Vinyl chloride is a carcinogen, used in the manufacturing of plastic products such as pipes, wire coatings, furniture, car parts, and house wares, and is present in tobacco smoke. Manufacturing and chemical plants may release vinyl chloride into the air or water, and it may leak into the environment as a result of improper disposal. People who work in these plants or live in close proximity to them have an increased risk for brain cancer.

Secondary brain cancer occurs in 20-30% of patients with metastatic disease and its incidence increases with age. In the United States, about 100,000 cases of secondary brain cancer are diagnosed each year. Patients with a history of melanoma, lung, breast, colon, or kidney cancer are at risk for secondary brain cancer.

Brain tumors can obstruct the flow of cerebrospinal fluid (CSF), which results in the accumulation of CSF (hydrocephalus) and increased intracranial pressure (IICP). Nausea, vomiting, and headaches are common symptoms. They can damage vital neurological pathways and invade and compress brain tissue. Symptoms usually develop over time and their characteristics depend on the location and size of the tumor.

The first step in diagnosing brain cancer involves evaluating symptoms and taking a medical history. If there is any indication that there may be a brain tumor, various tests are done to confirm the diagnosis, including a complete neurological examination, imaging tests, and biopsy.

Figure 48B:
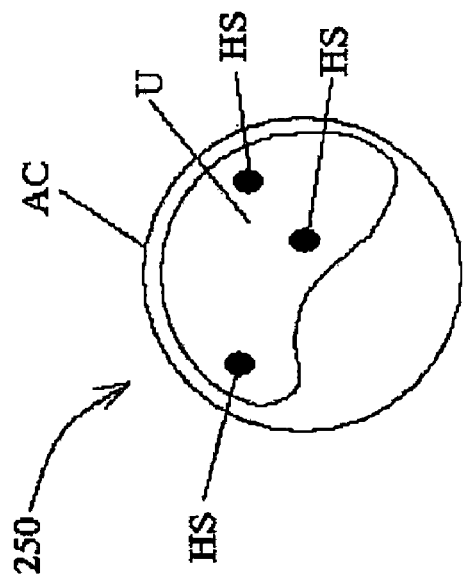
FIGS. 48A-48B present the principles of modeling, for obtaining an optimal set of views, for a brain, in accordance with embodiments of the present invention.
Figure 48A:
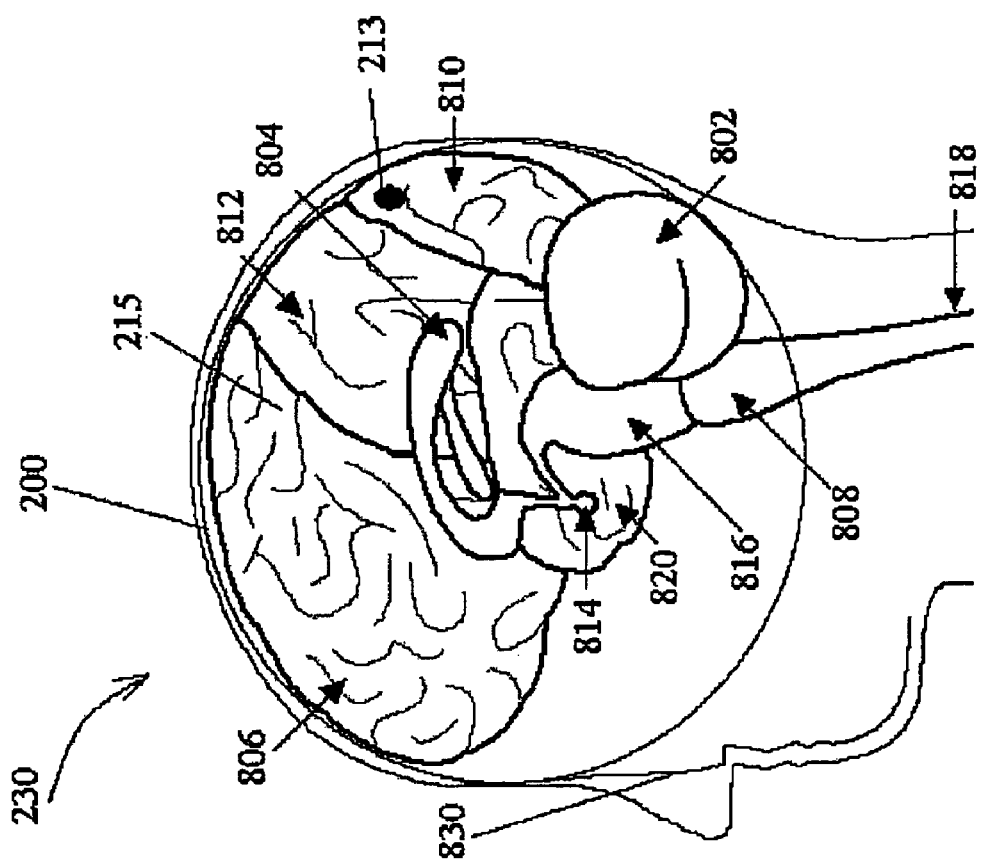

Referring now to the drawings, FIGS. 48A-48B present the principles of modeling, for obtaining an optimal set of views, for a brain 215, in accordance with embodiments of the present invention.

FIG. 48A schematically illustrates a body section 230, illustrating the organ 215, being the brain 215. The brain 215 is enclosed within a skull 830 and includes:

a cerebellum 802, which is the part of the brain below the back of the cerebrum. it regulates balance, posture, movement, and muscle coordination;

a corpus callosum 804, which is a large bundle of nerve fibers that connect the left and right cerebral hemispheres;

a frontal lobe of the cerebrum 806, which is the top, front regions of each of the cerebral hemispheres, and is used for reasoning, emotions, judgment, and voluntary movement;

a medulla oblongata 808, which is the lowest section of the brainstem (at the top end of the spinal cord) and controls automatic functions including heartbeat, breathing, and the like;

a occipital lobe of the cerebrum 810, which is the region at the back of each cerebral hemisphere, at the back of the head, and contains the centers of vision and reading ability;

a parietal lobe of the cerebrum 812, which is the middle lobe of each cerebral hemisphere between the frontal and occipital lobes, located at the upper rear of the head, and which contains important sensory centers;

a pituitary gland 814, which is a gland attached to the base of the brain that secretes hormones, and is located between the pons and the corpus callosum;

pons 816, which is the part of the brainstem that joins the hemispheres of the cerebellum and connects the cerebrum with the cerebellum, located just above the medulla oblongata;

a spinal cord 818, which is a thick bundle of nerve fibers that runs from the base of the brain to the hip area, through the spine (vertebrae);

a temporal lobe of the cerebrum 820, which is the region at the lower side of each cerebral hemisphere, located at the sides of the head and containing centers of hearing and memory.

The brain 215 may include a pathological feature 213, termed herein an organ target 213. A region of interest (ROI) 200 may be defined so as to encompass the brain 215 and the pathological feature 213.

As seen in FIG. 48B, the region of interest 200 of FIG. 48A is modeled as a model 250 of a volume U, and the organ target 213 is modeled as a modeled organ targets HS. Additionally, there are certain physical viewing constraints, associated with the region of interest 200, which are modeled as anatomical constraints AC. In the present case, the skull 830 creates viewing constraints, and generally, imaging the brain is performed extracorporeally.

Figure 49:
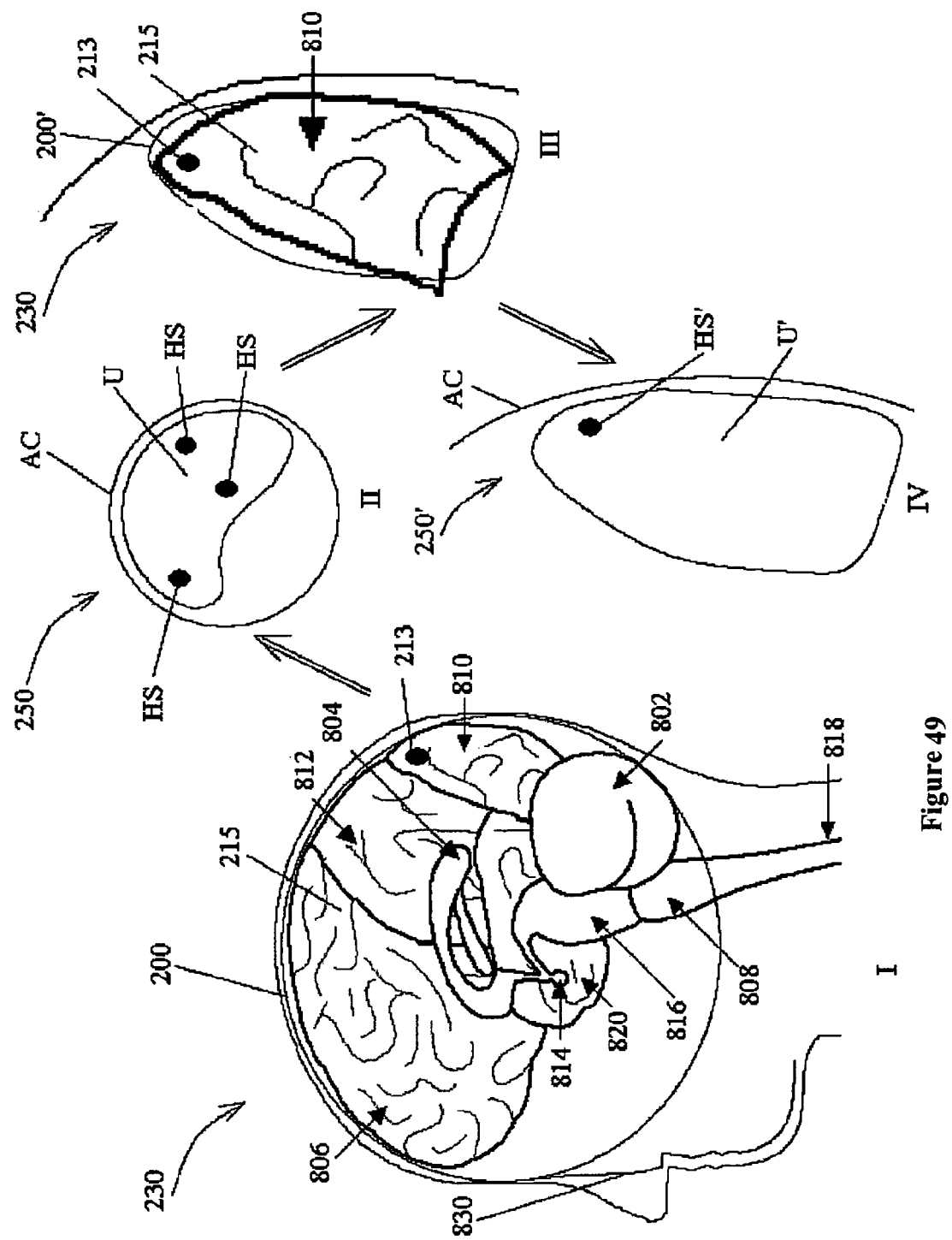
FIG. 49 pictorially illustrates a method for zooming in on a suspected pathological feature in a brain, as a process of two or more iterations, in accordance with embodiments of the present invention.

Referring further to the drawings, FIG. 49 pictorially illustrates a method 340 for zooming in on a suspected pathological feature, as a process of two or more iterations, in accordance with embodiments of the present invention, as follows:

As seen in FIG. 49, the method 340 may be described, pictorially, as follows:

In I: The region of interest 200, associated with the organ 215, such as the brain 215, is defined for the body section 230.

In II: The model 250 of the volume U is provided for the region of interest 200, possibly with one or several of the modeled organ targets HS, and within the anatomical constraints AC, for obtaining the optimal set of views for the region of interest 200. The optimal set of views is then applied to the region of interest 200, encompassing the brain 215 of the body section 230.

In III: When the suspected organ target 213 is identified, in vivo, in the brain 215, by radioactive-emission measurements at the optimal set of views, a second, inner region of interest 200' is defined, encircling the suspected pathological feature. For example, if a suspected pathology 213 is identified in the occipital lobe 810 of the cerebrum, that is, the region at the back of each cerebral hemisphere at the back of the head, the second region of interest 200' is defined so as to encircle the occipital lobe 810 of the cerebrum.

In IV: A model 250' of a volume U' is provided for the second, inner region of interest 200', preferably, with at least one modeled organ target HS, simulating the suspected organ target 213, for obtaining an optimal pathology set of views for the region of interest 200'. The second, pathology set of views is then applied to the second, inner region of interest 200' of the body section 230. In the present example, the second, pathology set of views is then applied to the occipital lobe 810 of the cerebrum, in vivo.

Referring further to the drawings, FIGS. 50A-51H schematically illustrate a probe system 850 for the brain, in accordance with a preferred embodiment of the present invention.

FIGS. 50A-50C schematically illustrate the radioactive-emission-measuring probe for the brain, in accordance with embodiments of the present invention;

Preferably, radioactive-emission-measuring probe 850 for the brain is shaped as a helmet 860, adapted for wearing on a head 862. The helmet 860 is preferably mounted on a gantry 870, which may be adjustable in the directions of arrows 872, 874 and 876, for adapting to individual heights and comfort.

Alternatively, no gantry is used, and the helmet 860 may be worn directly on the head 862, for example, like a motorcycle helmet.

A chair 880 may be provided for the comfort of the patient.

Preferably, the radioactive-emission-measuring probe 850 for the brain is operable with a control unit 890, which may be a desktop computer, a laptop, or the like. The control unit 890 is preferably used both for controlling the motions of the detecting units 12, blocks 90 and assemblies 92 of the radioactive-emission-measuring probe 850 for the brain and for analyzing the data.

It will be appreciated that the radioactive-emission-measuring probe 850 for the brain may be supplied merely as the probe helmet 860 and a data storage device, such as a CD 892, a disk 892, or the like, containing the appropriate software, for operation with an existing computer, at the site.

It will be appreciated that the radioactive-emission-measuring probe 850 for the brain may be operable with a structural imager, as taught by commonly owned PCT publication WO2004/042546, whose disclosure is incorporated herein by reference. The structural imager may be a handheld ultrasound imager, possibly with a position-tracking device, a 3-D imager such as an ultrasound imager, a CT imager, or an MRI imager, as known. The data provided by the structural imager may be used for any one or a combination of the following:

i. obtaining accurate dimensional data for modeling the brain 215, as taught in conjunction with FIGS. 48A-49 and 11-12;

ii. providing attenuation correction for the radioactive-emission-measurements, based on the structural data, as taught by commonly owned PCT publication WO2004/042546; and iii. co-registering the functional and structural images, as taught, for example, by commonly owned PCT publication WO2004/042546.

Referring further to the drawings FIGS. 51A-51K schematically illustrate inner structures of the probe 850, for the brain, in accordance with several embodiments of the present invention.

Figures 51A, 51B, 51C:
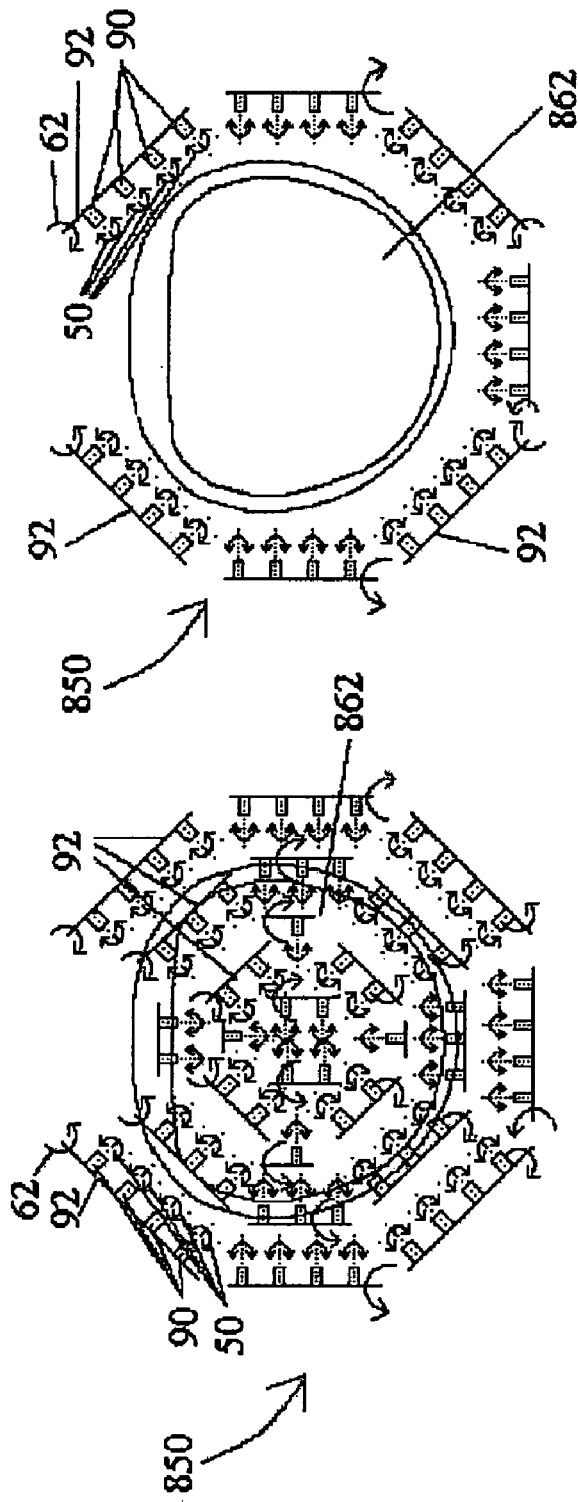

FIG. 51A schematically illustrates the assembly 92, comprising, for example four of the blocks 90, adapted for oscillatory motion about the r-axis, as illustrated by the arrows 50, and adapted for rotational motion about the x-axis, as illustrated by the arrow 62, as taught, for example, in conjunction with FIGS. 22A-22H. It will be appreciated that detecting units 12 may be used in place of blocks 90.

FIG. 51B schematically illustrates a possible cross sectional view of the probe 850 (FIG. 50C), showing an arrangement of the assemblies 92, laterally around the head 862.

FIG. 51C schematically illustrates a top view of the probe 850, showing an arrangement of the assemblies 92, laterally around the head 862. It will be appreciated that the number of the blocks 90 may vary around the head 862.

Figure 51F:
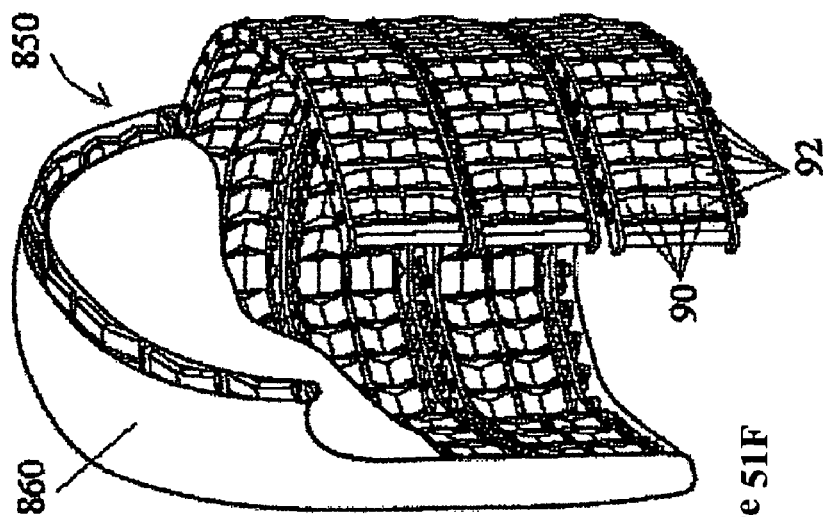
Figure 51E:
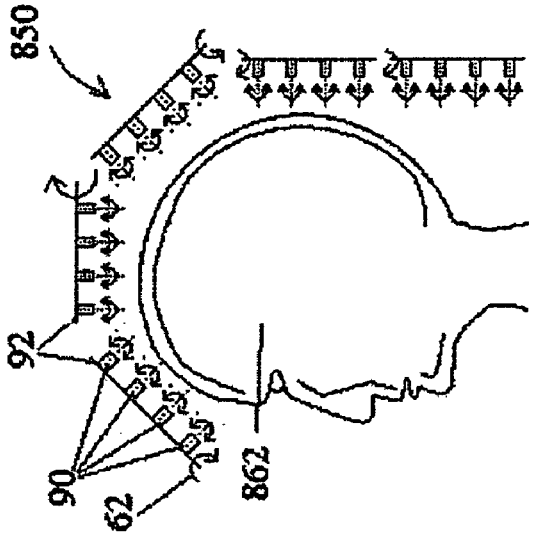
Figure 51D:
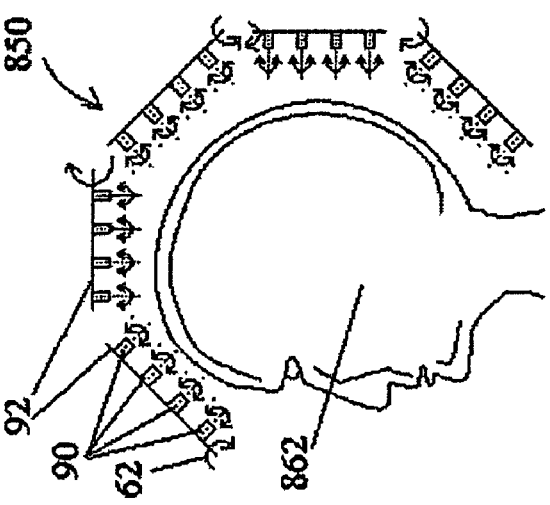

FIGS. 51D and 51E schematically illustrate other possible cross sectional views of the probe 850, showing arrangements of the assemblies 92, vertically around the head 862.

FIG. 51F schematically illustrates the probe 850 formed as the helmet 860, with the assemblies 92, arranged as illustrated by the cross sectional view of FIG. 51E. It will be appreciated that other arrangements are similarly possible. Preferably, the probe helmet 860 includes a housing 864. Preferably, the motions of the blocks 90 and of the assemblies 92 are contained within the housing 864.

Preferably, the proximal side of the housing 864 with respect to the head 862 (FIG. 50C) is transparent to nuclear radiation. Alternatively, the proximal side with respect to the head 862 is open.

FIG. 51G schematically illustrates another arrangement of the blocks 90 around the head 862, wherein the blocks 90 are not arranged in assemblies 92; rather each block 90 moves as an individual body. It will be appreciated that the detecting units 12 may be used in place of the blocks 90.

FIGS. 51H-51K schematically illustrate possible rotational motions of the blocks 90, each of the blocks 90 moving as an individual body for obtaining views of different orientations. As seen in FIG. 51H, the block 90 rotates around x as seen by an arrow 852 and at each position around x, oscillates about x, as seen by an arrow 851. The resultant traces are seen in FIG. 51I as a star of line traces 854.

Alternatively, as seen in FIG. 51J, the block 90 rotates around y as seen by an arrow 853 and at each position around y, oscillates about x, as seen by the arrow 851. The resultant traces are seen in FIG. 51K, as line traces 855.

The assembly 92 and the block 90, in accordance with a preferred embodiment of the present invention are described in FIGS. 40A and 40B, hereinabove.

Thus the assembly 92 includes a row of at least two blocks 90, each adapted of oscillatory motion about r. The blocks 90 are arranged within the inner housing 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

It will be appreciated that imaging, in accordance with embodiments of the present invention relates to the imaging of the whole brain, or to a portion of the brain, or to blood vessels near the brain, for example, the coronary artery.

Preferably, the radiopharmaceuticals associated with the probe of the present invention may be Tc99m-d, 1-hexamethyl propylene amine oxime (1-HMPAO) commercially known as Ceretec by GE-Amersham, or $^{99m}$Tc-ECD, commercially known as Neurolite, and made by Bristol Myers Squibb.

The present invention applies to the two types of brain tumors: primary brain tumors, which originate in the brain and metastatic (secondary) brain tumors that originate from cancer cells that have migrated from other parts of the body.

Additionally, the primary brain tumors may be gliomas, which begin in glial cells, and of which there are several types, as follows:

Astrocytoma, a tumor which arises from star-shaped glial cells called astrocytes, and which in adults, most often arises in the cerebrum, whereas in children, it occurs in the brain stem, the cerebrum, and the cerebellum.

Brain stem glioma, a tumor that occurs in the lowest part of the brain, and is diagnosed in young children as well as in middle-aged adults.

Ependymoma, a tumor, most common in middle-aged adults, which arises from cells that line the ventricles or the central canal of the spinal cord and which occurs in children and young adults.

Oligodendroglioma, a rare tumor, which arises from cells that make the fatty substance that covers and protects nerves and usually occurs in the cerebrum, grows slowly and generally does not spread into surrounding brain tissue.

Additionally or alternatively, the present invention applies to other types of brain tumors, which do not begin in glial cells. The most common of these are:

Medulloblastoma, also called a primitive neuroectodermal tumor, a tumor which usually arises in the cerebellum and is the most common brain tumor in children.

Meningioma, which arises in the meninges and usually grows slowly.

Schwannoma, also called an acoustic neuroma, and occurring most often in adults, it is a tumor that arises from a Schwann cell, of the cells that line the nerve that controls balance and hearing, in the inner ear.

Craniopharyngioma, a tumor which grows at the base of the brain, near the pituitary gland, and most often occurs in children.

Germ cell tumor of the brain, a tumor which arises from a germ cell, generally, in people younger than 30, the most common type of which is a germinoma.

Pineal region tumor, a rare brain tumor, which arises in or near the pineal gland, located between the cerebrum and the cerebellum.

Additionally or alternatively, the present invention applies to tumors associated with certain inherited diseases; for example, Multiple endocrine neoplasia type 1 (pituitary adenoma), Neurofibromatosis type 2 (brain and spinal cord tumors), Retinoblastoma (malignant retinal glioma), Tuberous sclerosis (primary brain tumors), and Von Hippel-Lindau disease (retinal tumor, CNS tumors), and genetic mutations and deletions of tumor suppressor genes (i.e., genes that suppress the development of malignant cells), which increase the risk for some types of brain cancer.

Additionally or alternatively, the present invention applies to tumors associated with exposure to vinyl chloride.

Additionally or alternatively, the present invention applies to secondary brain cancer, for example, originating from the lungs, the breasts, or other parts of the body.

It will be appreciated that the present invention further applies to other types brain tumors, which may be malignant or benign, blood clots in the brain, and other brain pathologies. It will be appreciated that many other probes and probe systems may be considered and the examples here are provided merely to illustrate the many types of combinations that may be examined, in choosing and scoring a probe design, both in terms of information and in terms of secondary considerations, such as rate of data collection, cost, and complexity of the design.

Example 15

Figure 52A:
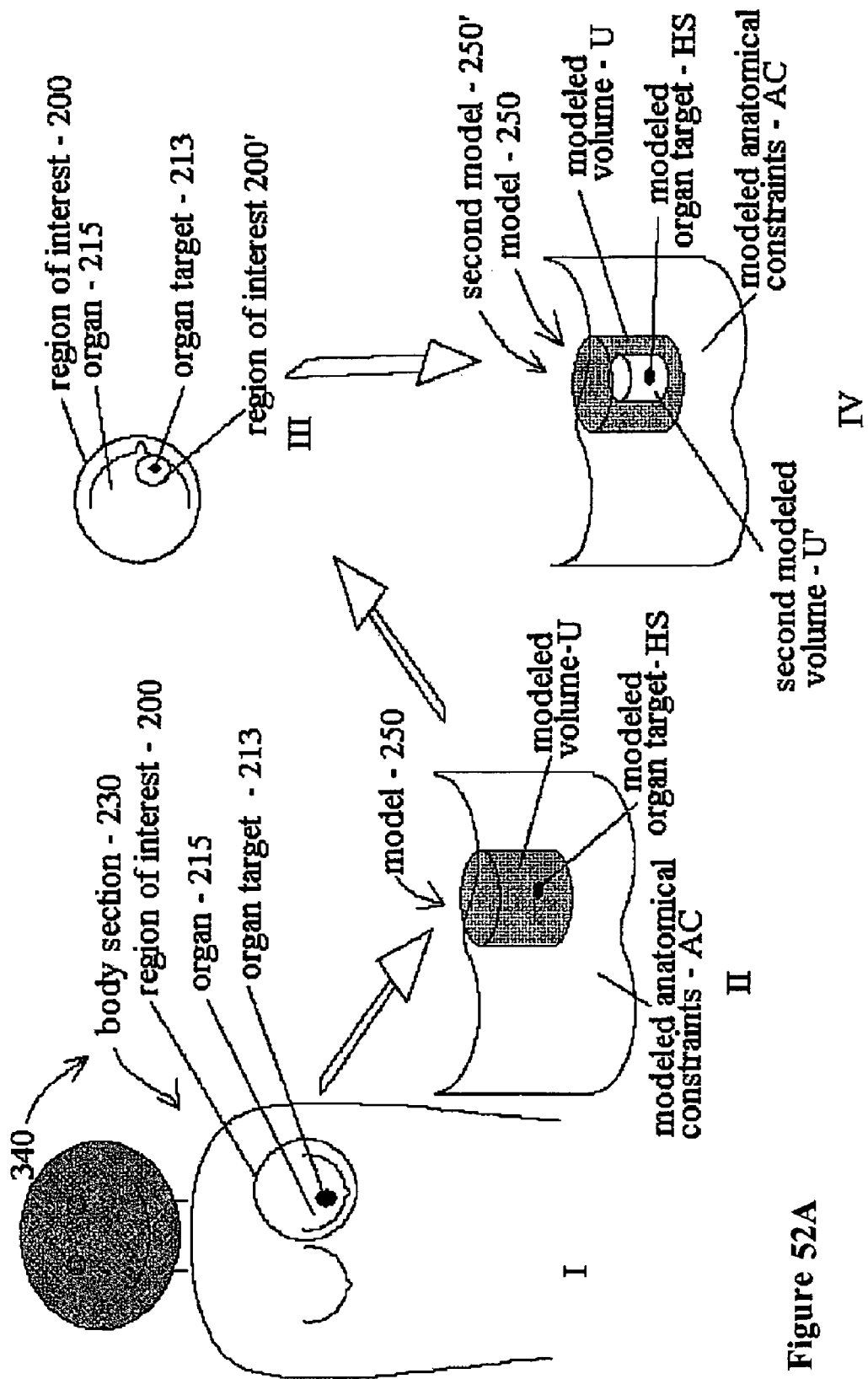
FIG. 52A pictorially illustrates a method for zooming in on a suspected pathological feature in a breast, as a process of two or more iterations, in accordance with an embodiment of the present invention.

FIG. 52A pictorially illustrates a method for zooming in on a suspected pathological feature in a breast, as a process of two or more iterations, in accordance with an embodiment of the present invention.

As seen in FIG. 52A, the method 340 may be described, pictorially, as follows:

In I: The region of interest 200, associated with the organ 215, such as the breast 215, is defined for the body section 230.

In II: The model 250 of the volume U is provided for the region of interest 200, possibly with one or several of the modeled organ targets HS, and within the anatomical constraints AC, for obtaining the optimal set of views for the region of interest 200. The optimal set of views is then applied to the region of interest 200, encompassing the breast 215 of the body section 230.

In III: When the suspected organ target 213 is identified, in vivo, in the breast 215, by radioactive-emission measurements at the optimal set of views, a second, inner region of interest 200' is defined, encircling the suspected pathological feature.

In IV: A second model 250' of a second volume U' is provided for the second, inner region of interest 200', preferably, with at least one modeled organ target HS, simulating the suspected organ target 213, for obtaining an optimal pathology set of views for the second region of interest 200'. The second, pathology set of views is then applied to the second, inner region of interest 200' of the body section 230.

Figure 52B:
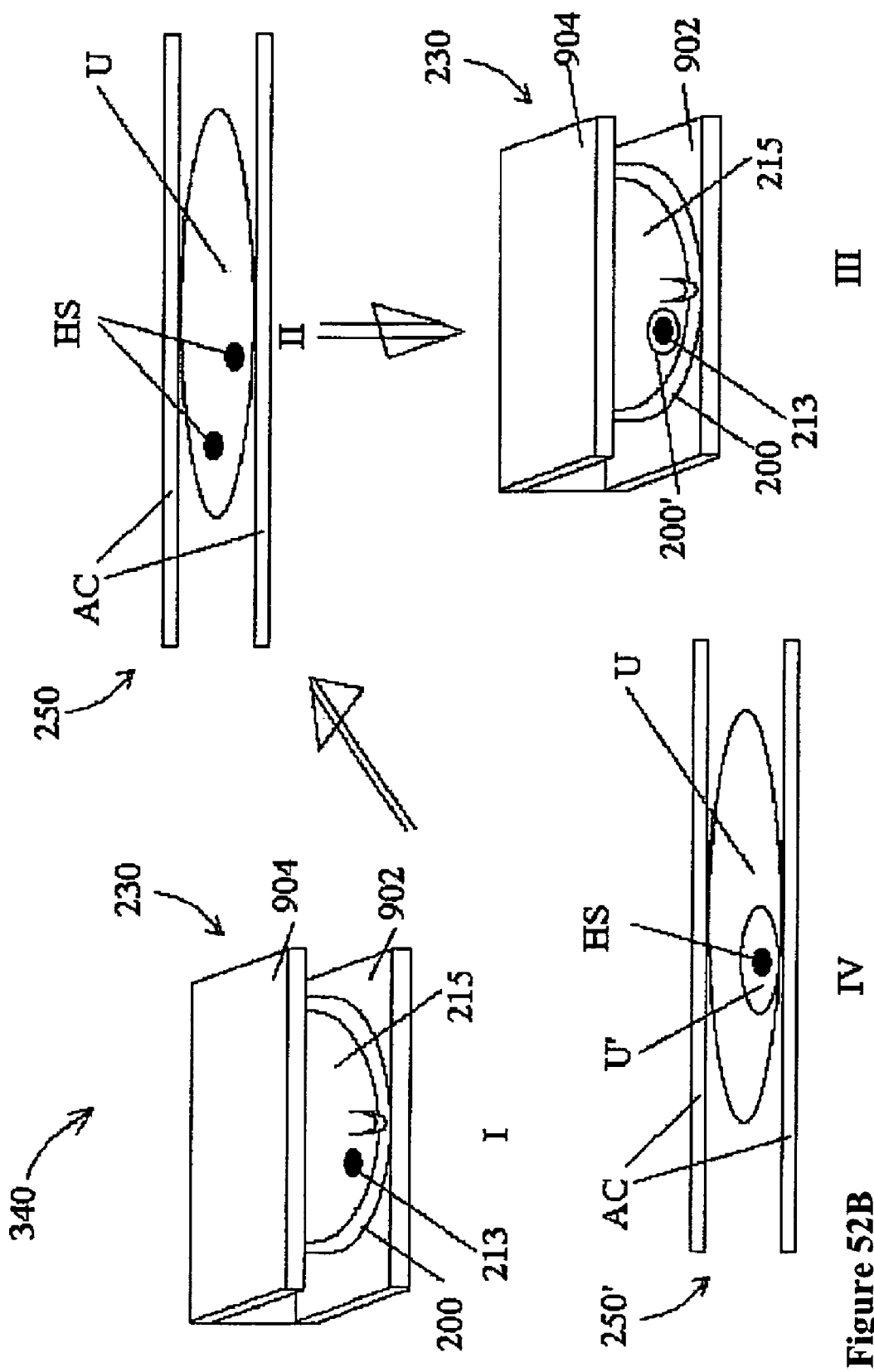
FIG. 52B pictorially illustrates a method for zooming in on a suspected pathological feature in a breast, when held between support and compression plates, as a process of two or more iterations, in accordance with another embodiment of the present invention.

Alternatively, FIG. 52B pictorially illustrates a method for zooming in on a suspected pathological feature in a breast, when the breast is held between support and compression plates, as a process of two or more iterations, in accordance with another embodiment of the present invention.

Thus, as seen in FIG. 52B, the method 340 may be described, pictorially, as follows:

In I: The region of interest 200, associated with the organ 215, such as the breast 215, is defined for the body section 230, when compressed between two plates 902 and 904, for example, mammograph plates.

In II: The model 250 of the volume U is provided for the region of interest 200, possibly with one or several of the modeled organ targets HS, and within the anatomical constraints AC, representing the mammograph plates, for obtaining the optimal set of views for the region of interest 200. The optimal set of views is then applied to the region of interest 200, encompassing the breast 215 of the body section 230.

In III: When the suspected organ target 213 is identified, in vivo, in the breast 215, by radioactive-emission measurements at the optimal set of views, a second, inner region of interest 200' is defined, encircling the suspected organ target 213.

In IV: A second model 250' of a second volume U' is provided for the second, inner region of interest 200', preferably, with at least one modeled organ target HS, simulating the suspected organ target 213, for obtaining an optimal pathology set of views for the second region of interest 200'. The second, pathology set of views is then applied to the second, inner region of interest 200' of the body section 230.

Mammography is currently the most effective method of screening for breast cancer, for the detection of early non-palpable tumors. In essence, it involves compressing the breast between two plates, a support plate and a compression plate, and passing x-rays through the compressed breast. The compression is desirous both in order to spread the breast fatty tissue thin, to reduce its attenuation, and in order to fix the breast tissue, with respect to a frame of reference, so that the x-ray image may be correlated with a surgical tool frame of reference, such as a biopsy needle frame of reference, for guiding the surgical tool to a suspected location on the x-ray image, without the breast tissue moving between the taking of the x-ray image and the guiding of the surgical tool.

Often stereotactic mammography is applied, meaning that the x-ray head is rotated with respect to the plates, so as to provide at least two views of the fixed breast, compressed between the plates, from at least two angles, for stereo imaging.

In general, each breast is imaged separately, generally, both in a vertical direction and from the side (laterally), preferably, stereotactically. In other words, generally, at least four views of each breast are taken, two vertically and two laterally.

A surgical instrument, for example, a biopsy needle, or an ablation device, such as a cryosurgery device, an ultrasound ablation device, a knife, or a laser ablation device, may be built onto the mammograph, its frame of reference correlated with that of the x-ray image.

FIG. 53A schematically illustrates the basic mammograph 900, showing a structural support 929, which defines a frame of reference 80, and which includes a support plate 902 and a compression plate 904, the compression plate 904 being adapted for motion along an arrow 906, so as to compress a breast 909 on the support plate 902.

An x-ray tube 905 is preferably arranged so as to move within a track 907, for obtaining x-ray images of the compressed breast 909 from at least two views, so as to obtain stereotactic viewing, for depth evaluation. A film 901 is preferably arranged under the breast 909, for example, under the support plate 902, for registering the x-ray image.

Additionally, the mammograph 900 is preferably adapted for rotation, as illustrated by an arrow 908, for compressing a breast from at least two orientations, for example vertically and laterally.

A surgical tool 903, for example, a biopsy needle 903 or an ablation device 903, such as by cryosurgery or laser, or a knife 903, may be built onto the mammograph 900, its frame of reference correlated with the frame of reference 80, using position tracking devices or a linkage system, as known.

FIG. 53B schematically illustrates a system 925 of an ultrasound imager 915, operative with the two plates 902 and 904, in accordance with embodiments of the present invention. The importance of performing ultrasound between two plates, as in the case of x-rays, is that the two plates fix the breast with respect to the frame of reference 80, and in fact, convert the breast to a rigid-like tissue, so that any suspicious findings can be located by the surgical tool 903.

In FIG. 53B, the ultrasound imager 915 is arranged to slide along tracks 917, for example, on the compression plate 904, while a layer of gel 913 or hydrogel 913, between the compression plate 904 and the breast 909 ensures good contact for ultrasound imaging. In this manner, an ultrasound image, correlated to the frame of reference 80, when the breast is under compression, may be obtained.

FIG. 53C schematically illustrates a system 925 of an ultrasound imager 915, operative with the two plates 902 and 904, and a surgical instrument, co-registered to the ultrasound imager, in accordance with embodiments of the present invention.

As seen in FIG. 53C the ultrasound imager 915 may be built onto the structural support 929, its frame of reference correlated with the frame of reference 80, using position tracking devices or a linkage system, as known.

Figure 54A:
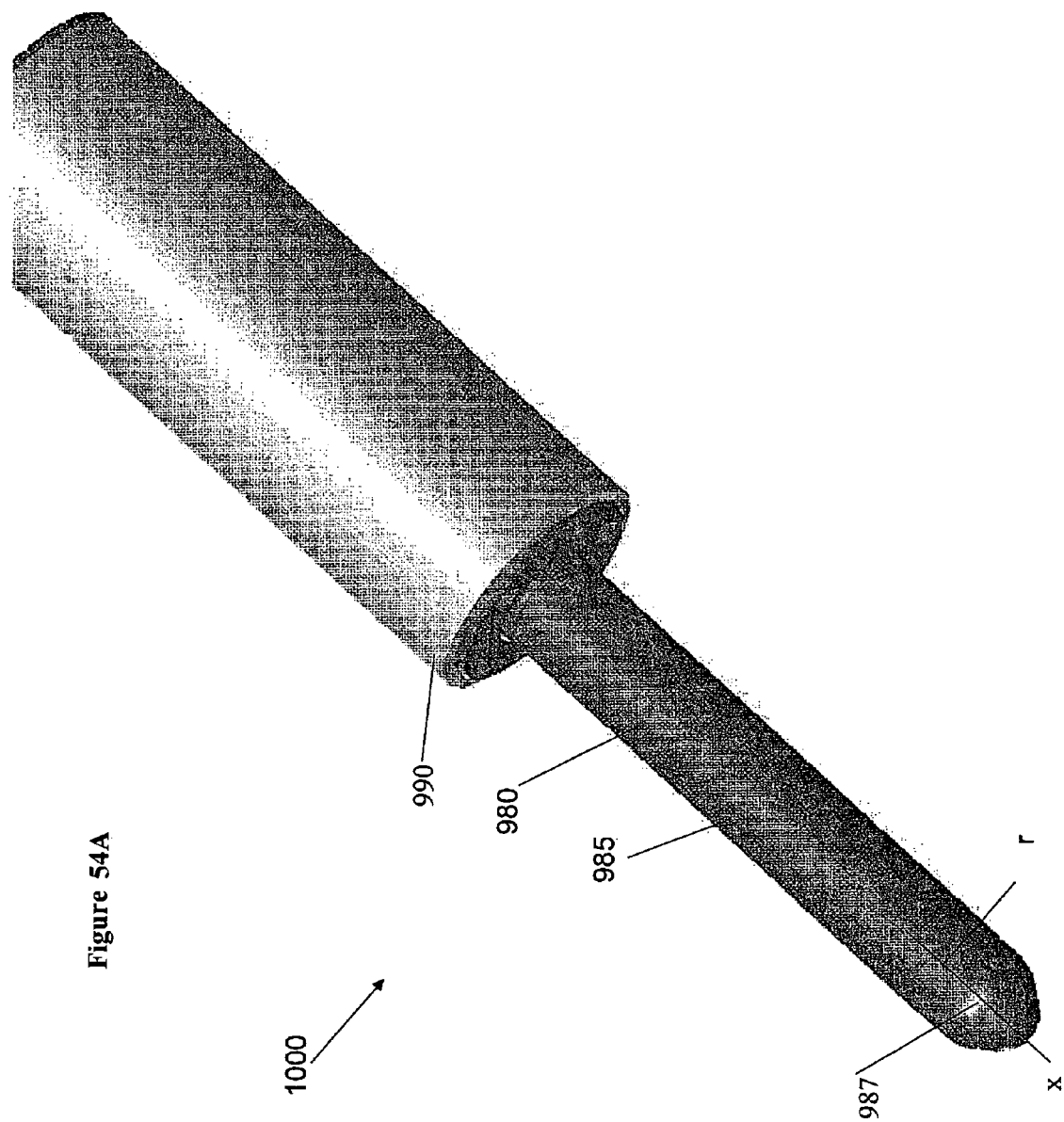

Referring further to the drawings, FIGS. 54A-54E schematically illustrate an assembly, configured for operation with a mammograph-like radioactive-emission-measuring probe for the breast, in accordance with embodiments of the present invention Specifically, FIG. 54A schematically illustrates an external appearance of the radioactive-emission-measuring probe 1000, for the breast. The probe 1000 has a driving portion 990 and an imaging portion 980, enclosed in a sheath 985. The imaging portion 980 defines cylindrical coordinates 987 of a longitudinal axis along the x-axis, and an r-axis, perpendicular to the longitudinal axis.

Figure 54B:
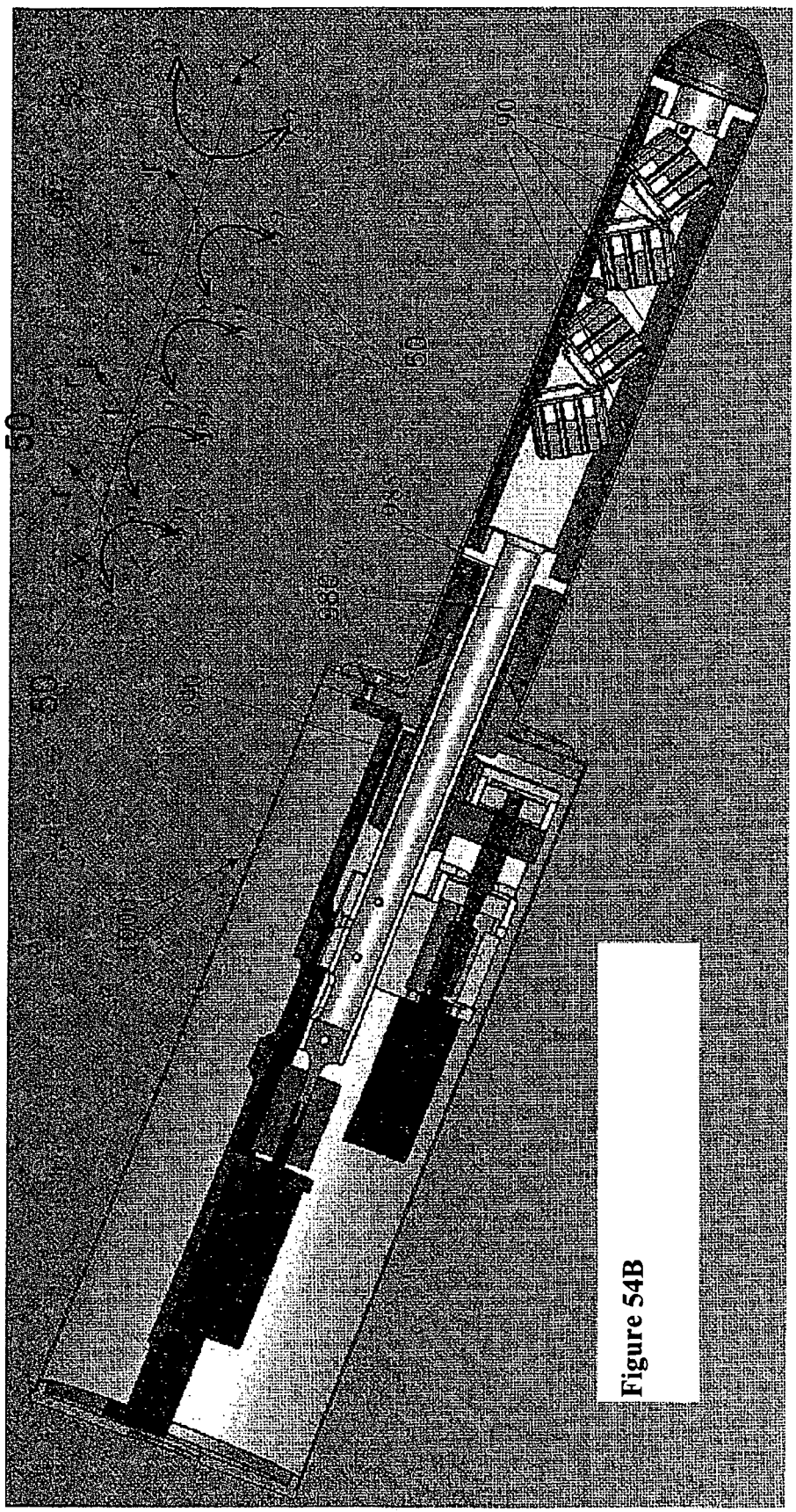
Figure 54C:
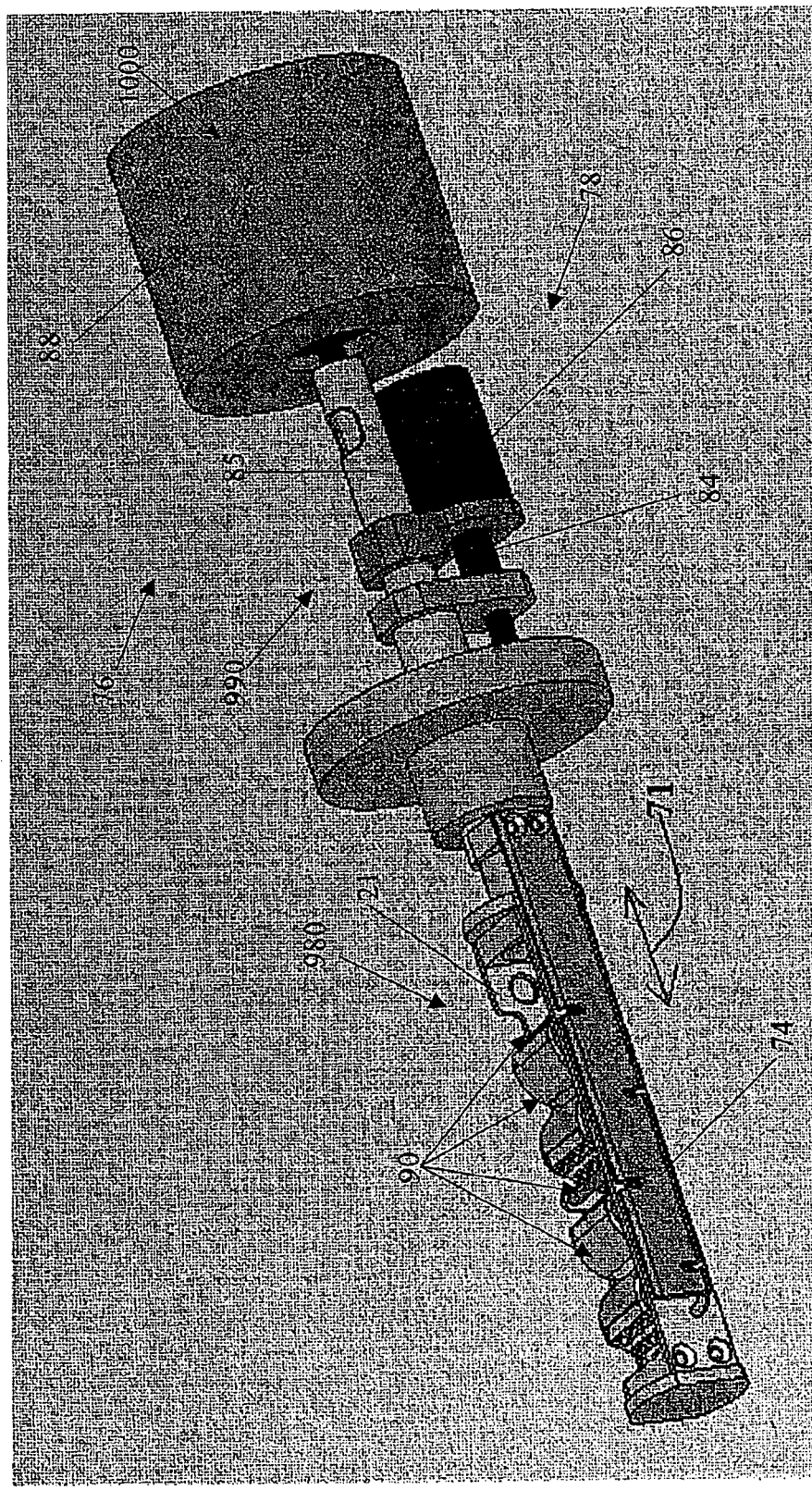

FIGS. 54B-54C schematically illustrate an internal structure of the radioactive-emission-measuring probe 1000, for the breast. The imaging portion 980 includes several of the blocks 90, for example, between two and six of the blocks 90, arranged within the sheath 985. It will be appreciated that another number, which may be larger or smaller, and which may be odd or even, may be employed.

In FIG. 54C, the motions experienced by the blocks 90 are illustrated with respect to the cylindrical coordinates 987 of x;r.

A first motion is a rotational motion of all the blocks 90, moving as a single body, with the shaft 85 and the internal housing 21, around the x-axis, in the direction between +ω and −ω, as illustrated by the arrow 52. The first motion is powered by the motor 88.

A second motion is an oscillatory motion of the individual blocks 90, powered by the secondary motor 86, the secondary shaft 84, and the motion transfer link 74, the motion transfer link 74 moving in a linear, sliding motion, as shown by the arrow 71.

At each orientation of the internal housing 21 with respect to ω, around x, the second, oscillatory motion about r takes place, individually by each of the block 90, the oscillatory motion about r being between −φ and +φ, as illustrated by the arrow 50, and as taught hereinabove, in conjunction with FIG. 21A-21H.

Thus, the overall motion is as illustrated hereinabove, in conjunction with FIG. 16D and FIGS. 21A-21H.

Further as seen in FIG. 54C, the rotational motion in the direction of the arrow 52 is provided by a motor 88 and the shaft 85, which together form the motion provider 76. The motor 88 may be an electric motor, for example, a servo motor. The oscillatory motion in the direction of the arrow 50 is provided by a secondary motor 86, a secondary shaft 84 and a motion transfer link 74. The secondary motor 86 may also be an electric motor, for example, a servo motor. The secondary motor 86, secondary shaft 84 and the motion transfer link 74, together, form the secondary motion provider 78, for the oscillatory motion, in the direction of the arrow 50.

Thus, for the radioactive-emission-measuring probe 1000, for the breast:
i. The different blocks 90 provide views from different orientations; and
ii. The different blocks 90 may change their view orientations independent of each other.

It is important to point out that during the operation of the probe 1000, the sheath 985 of the imaging portion 980 (FIGS. 54A and 54B) remains stationary, while the internal housing 21 (FIG. 54C) rotates around the x axis. The sheath 985 may be formed of a carbon fiber, a plastic, or another material, which is substantially transparent to nuclear radiation.

FIGS. 54D and 54E illustrate further the oscillatory motion of the blocks 90, within the sheath 985, as described by the arrows 50, by showing the blocks 90 at different positions, along their oscillatory travel. FIGS. 54D and 54E further illustrate a viewing side 986 and a back side 988 for the probe 1000.

Referring further to the drawings, FIGS. 55A-55K schematically illustrate systems 910, which include the radioactive-emission-measuring probes 1000 for the breast, operating with systems, in which a breast is compressed between two plates, for example, as in the mammograph 900, in accordance with embodiments of the present invention.

Figures 55A, 55B:
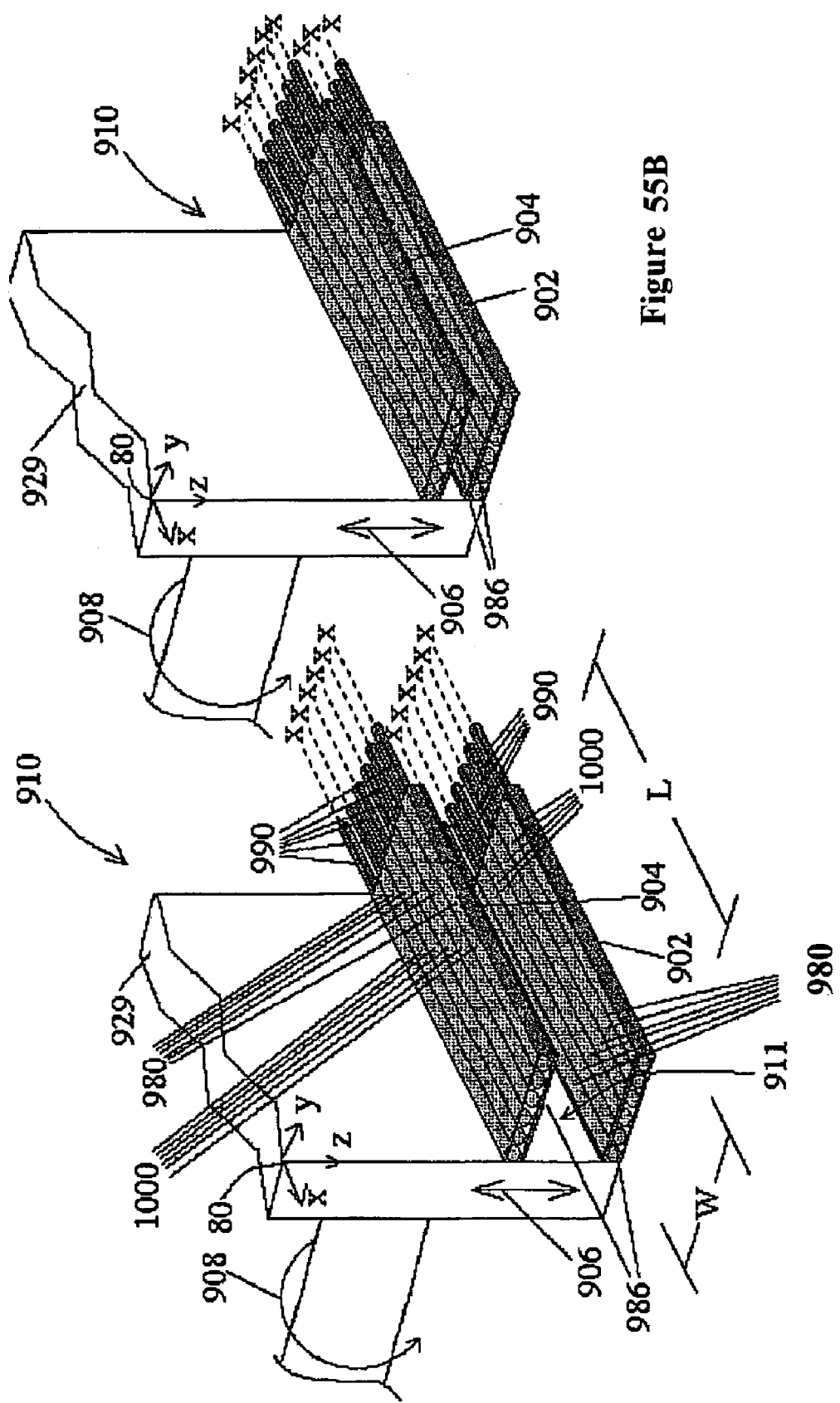
FIGS. 55A-55K schematically illustrate radioactive-emission-measuring probes for the breast, wherein the breast is compressed between two plates, in accordance with embodiments of the present invention.

Preferably, as seen in FIGS. 55A and 55B, the probes 1000 are mounted onto the two plates, the compression plate 904, and the support plate 902, such that their viewing sides 986 face each other. Preferably, the probes 1000 are aligned with the x axis, as seen. Alternatively, the probes 1000 may be aligned with the y axis. It will be appreciated that the probes 1000 may be mounted only on one plate, the compression plate 904 or the support plate 902.

Figure 55C:
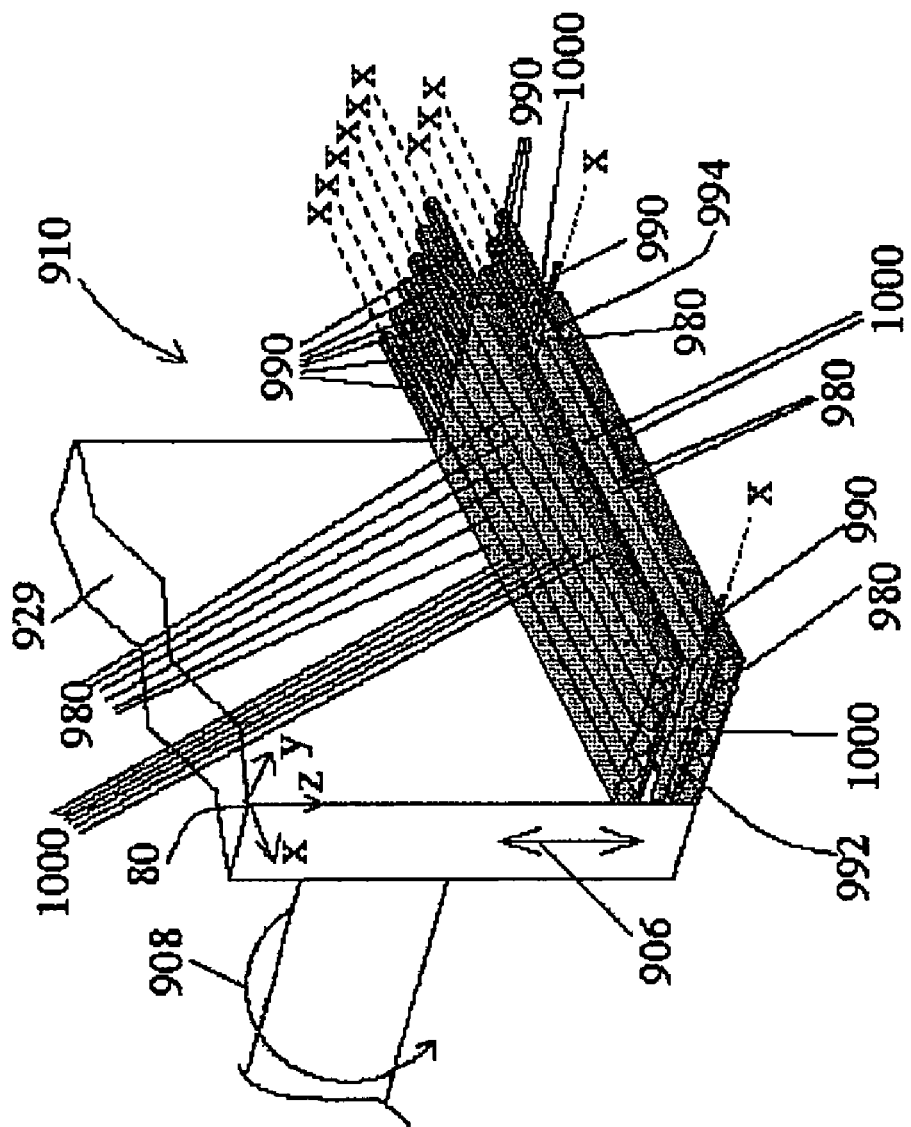

Additionally, as seen in FIG. 55C, one or several of the probes 1000 may be mounted as edge probes, for positioning at edges 992 and 994, supplementing the probes 1000 mounted on the plates, for obtaining views from the sides of the compressed breast.

Figure 55E:
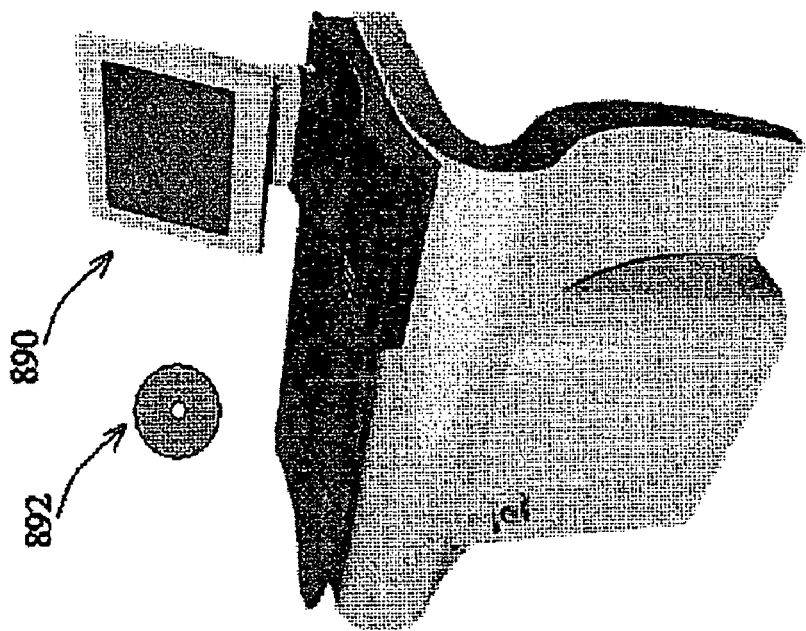
Figure 55D:
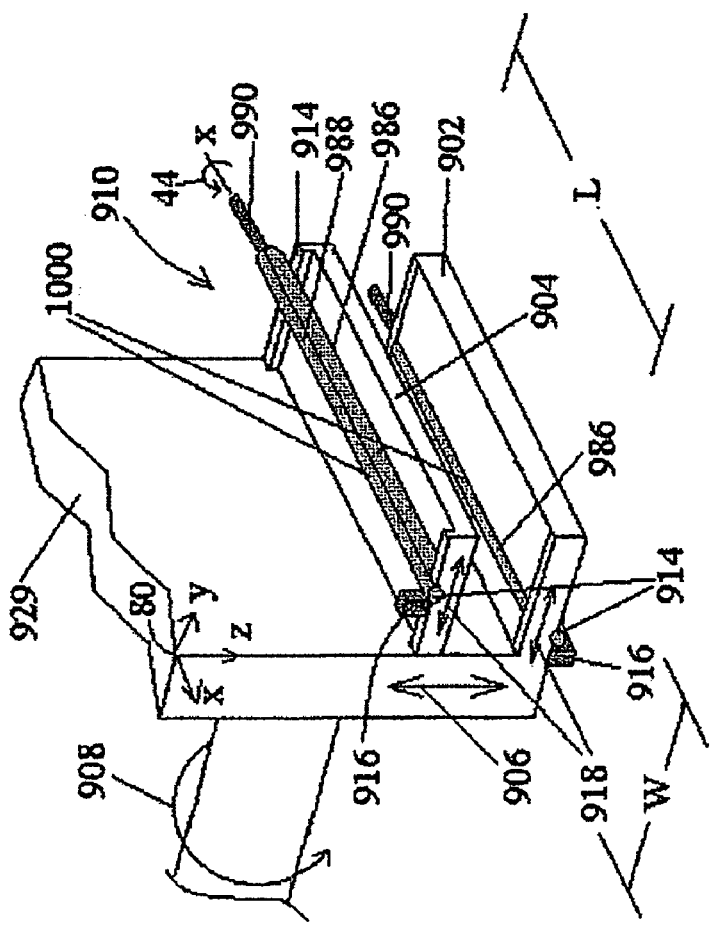

An alternative embodiment is illustrated in FIG. 55D, wherein a single one of the probes 1000 may be mounted on each of the plates 902 and 904, the probe 1000 being adapted for travel along a track 914, in a direction of an arrow 918, by a dedicated motion provider 916, thus providing the views that a plurality of the probes 1000 would have provided, as illustrated in FIGS. 55A-55B.

It will be appreciated that edge probes 1000, may be added to the embodiment of FIG. 55D, in a manner similar to that of FIG. 55C.

FIG. 55E schematically illustrates a control unit 890, for controlling the motions of the blocks 90 or the detecting units 12 (FIGS. 20A-22D) of the probes 1000 and for analyzing the measurements and constructing the images. Preferably, a single control unit is used both for the x-ray imager, or the ultrasound imager 915, on the one hand, and the radioactive-emission-measuring probes 1000, on the other. Alternatively, individual control units may be used, one for each modality. Alternatively, the system 910 for the breast is provided with a storage device 892, such as a CD or a disk, which contains the software for operating the system 910 for the breast with an existing computer on the site. It will be appreciated that the control unit 890 may be a PC, a laptop, a palmtop, a computer station operating with a network, or any other computer as known.

In accordance with embodiments of the present invention, frames may be provided for mounting the radioactive-emission-measuring probes 1000 on the plates 902 and 904.

Figure 55F:
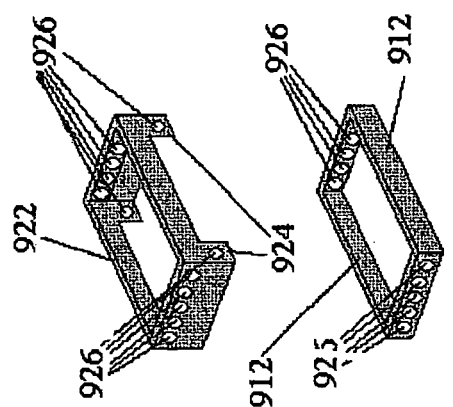

As seen in FIG. 55F, a frame 912 may be provided for either the support plate 902 or the compression plate 904, designed for accepting the probes 1000 lengthwise, by inserting the probes 1000 in holes 926.

Figure 55G:
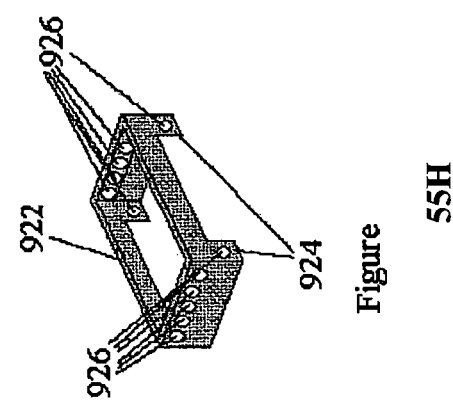

Alternatively, as seen in FIG. 55G, the frame 912 may be designed for accepting the probes 1000 widthwise.

Figure 55H:
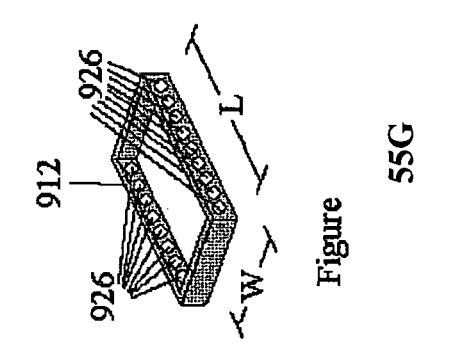

Additionally, as seen in FIG. 55H, a frame 922 is designed for accepting the probes 1000 widthwise or lengthwise, wherein the frame 922 further includes an edge section 924, for supporting the edge probes of FIG. 55C.

Figure 55I:
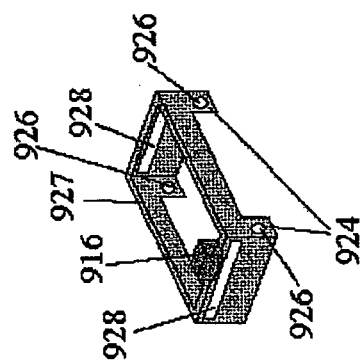

Furthermore, as seen in FIG. 55I, two complementary frames may be provided, one designed as the frame 922, for accepting the probes 1000 lengthwise (or widthwise) along the plate and for accepting the edge probes, as illustrated in FIG. 55H, and the other, designed as the frame 912, for accepting the probes 1000 lengthwise (or widthwise) along the plate.

Figure 55J:
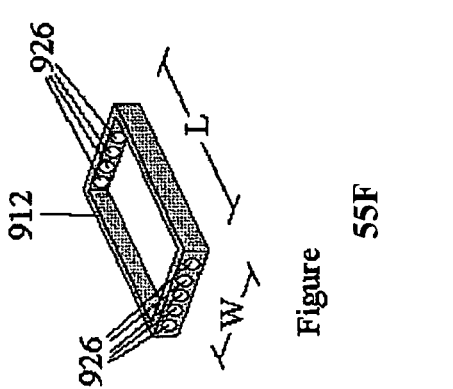

As seen in FIG. 55J, a frame 923 may be designed for accepting a single one of the probes 1000, lengthwise, adapted for sliding widthwise along the plate, in a channel 928, by the dedicated motion provider 916. Alternatively, the frame 923 may be designed for accepting the probe 1000 widthwise, adapted for sliding lengthwise.

Figure 55K:
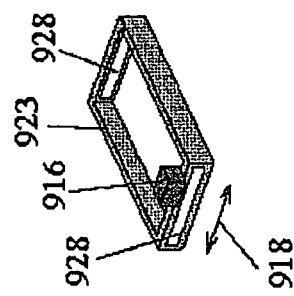

As seen in FIG. 55K, a frame 927 may be designed for accepting a single one of the probes 1000, for example, lengthwise, adapted for sliding widthwise along the plate, in a channel 928, by the dedicated motion provider 916, wherein the frame 927 further includes the edge section 924, for supporting the edge probe 1000 of FIG. 55C.

In accordance with embodiments of the present invention, nuclear imaging by radioactive-emission-measurements, co-registered with x-ray mammography, may be obtained as follows:
step 1: the breast is compressed between the plates;
step 2: an x-ray mammography is performed, as seen in FIG. 53A, preferably from at least two orientations of the x-ray tube 905;
step 3: the probes 1000 are mounted on the plates, and radioactive-emission measurements are performed;
step 4: where necessary, the surgical tool 903 may be employed, while the breast is still compressed between the two plates.

It will be appreciated that steps 2 and 3 may be performed in any order.

Preferably, the images of the x-ray mammography and the nuclear imaging are co-registered and analyzed together.

However, it will be appreciated that only nuclear imaging by radioactive-emission measurements may be performed, without x-ray imaging.

Where ultrasound imaging co-registered with nuclear imaging by radioactive-emission-measurements is desired, a method applies, as follows:
step 1: a hydrogel layer is placed between one of the plates, for example, the compression plate 904 and the breast, or a gel is spread over the breast, so as to serve as an ultrasound interface between the plate and the breast;
step 2: the breast is compressed between the plates;
step 3: the probes 1000 are mounted on the plates, and radioactive-emission measurements are performed;

step 4: the probes 1000 are replaced by an ultrasound imager, for example as illustrated in FIG. 53B or 53C, and ultrasound imaging is performed;

step 5: where necessary, the surgical tool 903 may be employed, while the breast is still compressed between the two plates.

It will be appreciated that the steps 3 and 4 may be performed in any order.

Preferably, the images of the x-ray mammography and the nuclear imaging are co-registered and analyzed together.

Figure 56A:
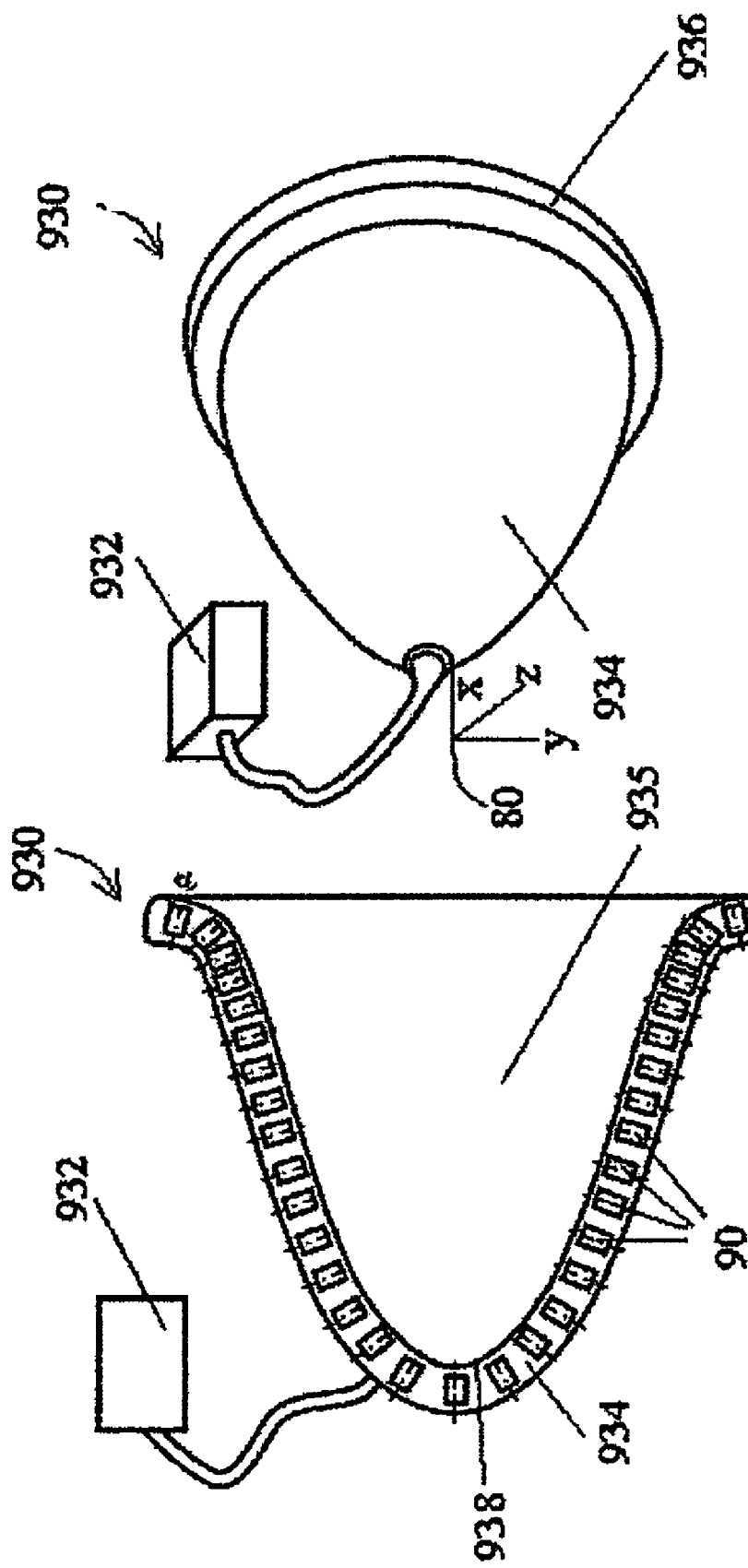

Referring further to the drawings, FIGS. 56A-56C schematically illustrate a radioactive-emission-measuring probe 930, for imaging a breast under vacuum, in accordance with another preferred embodiment of the present invention.

As seen in FIG. 56A, the probe 930 includes a vacuum cup 934, shaped as a cone and connected to a vacuum system 932, for creating a vacuum in a cavity 935 within. The vacuum in the cavity is used both to stretch the breast so as to spread the fatty tissue thin and to fix the breast tissue with respect to a frame of reference, so a surgical device may be employed, where needed, while the breast tissue remains fixed in place.

A vacuum ring 936, for example of natural or synthetic rubber, helps maintain the vacuum in the cup 934.

The vacuum cup 934 defines the frame of reference 80 and a plurality of the blocks 90 are arranged along the walls 938 of the suction cup 934, each adapted for at least one, and preferably two rotational motions, for example, as illustrated in conjunction with FIGS. 25A-25E and FIGS. 25I-25J, or FIGS. 25F-25H, for imaging a breast in the cavity 935. Alternatively, the blocks 90 may be arranged in the assemblies 92, as illustrated in conjunction with FIGS. 24A-24H.

A surgical tool may be attached to the probe 930, and correlated to its frame of reference, for example as taught in conjunction with FIG. 53B.

The motions of the blocks 90 are preferably automatic, controlled by the control unit 890 (FIG. 55C).

Preferably, the inner walls 938 of the cup 934 are substantially transparent to radioactive emission.

FIG. 56B schematically illustrates an embodiment wherein a vacuum cylinder 934 is used in place of a conical cup, and the blocks 90 are arranged in assemblies 92, for example, as illustrated in conjunction with FIGS. 16E and 24A-24H.

FIG. 56C schematically illustrates an embodiment wherein the vacuum cylinder 934 is used, and a single one of the assemblies 92 is arranged for traveling around the cylinder 934, in the direction of an arrow 940, by a motion provider 942.

Referring further to the drawings, FIGS. 57A-57F schematically illustrate a radioactive-emission-measuring probe 950, for imaging the breasts in the natural state, in accordance with another preferred embodiment of the present invention.

As seen in FIG. 57A, the radioactive-emission-measuring probe 950, for imaging the breasts in a natural state, is designed as an extracorporeal unit which may be positioned against the breasts, operating as taught in conjunction with any one of FIGS. 20A-25J. Preferably, the radioactive-emission-measuring probe 950, for imaging the breasts is attached to a gantry 952, which may provide adjustments as seen by arrows 954 and 956.

Additionally, the patient may be positioned on a chair 960, as seen in FIG. 57B.

The control unit 890 is illustrated in FIG. 57C.

The control unit 890 may be used for controlling the motions of the blocks 90 (FIGS. 24A-24H or 25A-25J) or the detecting units 12 (FIGS. 20A-20G, or FIGS. 22A-22D) and for analyzing the measurements and constructing the images. Alternatively, the radioactive-emission-measuring probe 910 for the breast is supplied with a storage device 892, which contains the software for operating the radioactive-emission-measuring probe 910 for the breast with an existing computer on the site. It will be appreciated that the control unit 890 may be a PC, a laptop, a palmtop, a computer station operating with a network, or any other computer as known.

FIG. 57D schematically illustrates a woman 970 being examined by the radioactive-emission-measuring probe 950, when seated on the chair 960. It will be appreciated that the examination may also be conducted when the woman 970 is standing or lying on a bed.

FIG. 57E schematically illustrates the inner structure radioactive-emission-measuring probe 950 in accordance with a preferred embodiment of the present invention. FIG. 57E shows the housing 20, the parallel lines of assemblies 92, possibly of an even number, each with a dedicated motion provider 76 and a dedicated secondary motion provider 78, and the rows of blocks 90, possibly arranged in pairs, along the assemblies 92.

The probe 950 defines the frame of reference 80, while each assembly 92 has a reference cylindrical coordinate system of x;r, with rotation around x denoted by the arrow 62 and oscillatory motion about r, denoted by the arrow 50.

Figure 57F:
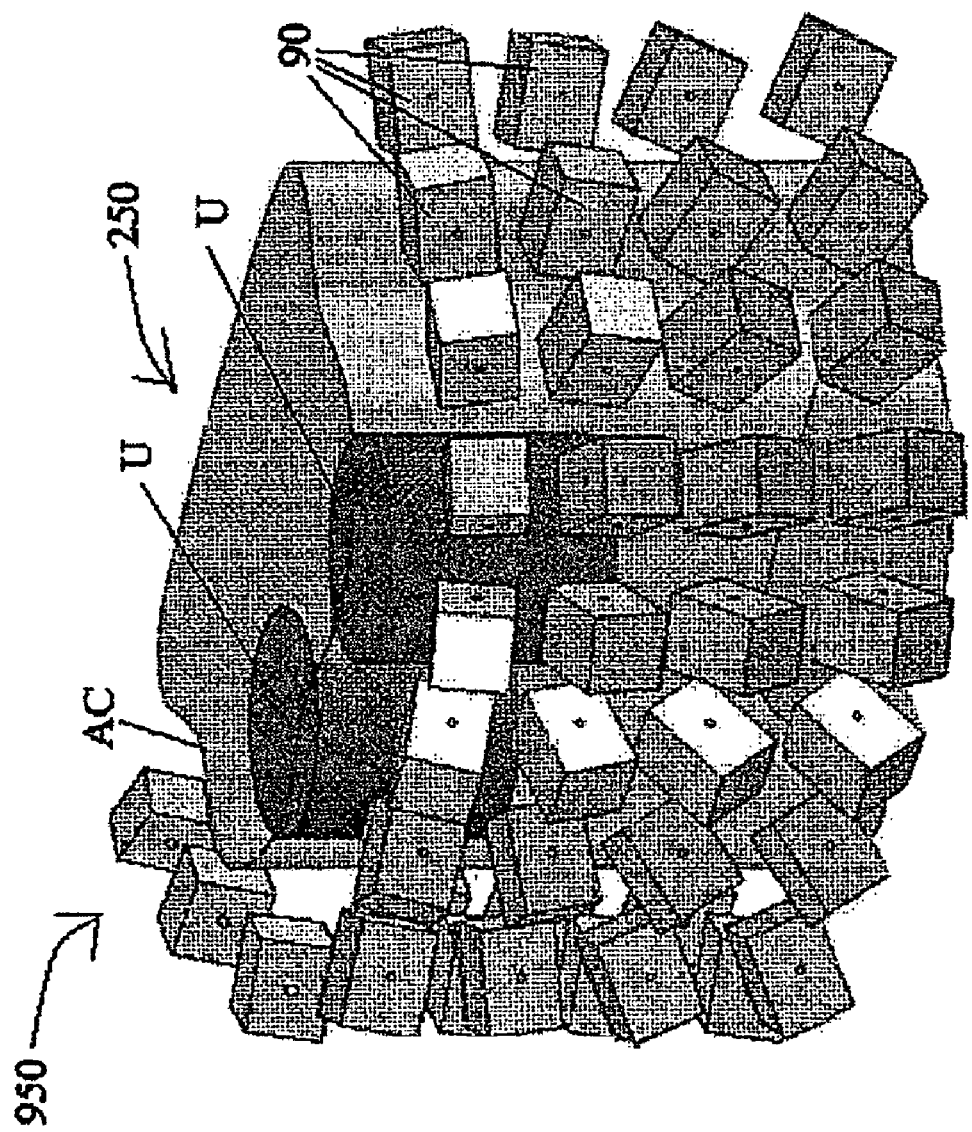

FIG. 57F schematically illustrates the model 250 of the two breasts, modeled as the volumes U, and the anatomical constraints associated with them, for determining an optimal set of views for radioactive-emission measurements.

It will be appreciated that imaging, in accordance with embodiments of the present invention relates to the imaging of the whole breast, or to a portion of the breast, the armpits near the breasts, (and) or the two breasts.

Preferably, the radiopharmaceuticals associated with the radioactive-emission-measuring probe for the breast may be $Tc^{99m}$ bound to Sestamibi, a small protein molecule, made for example, by Bristol Myers Squibb, and marketed as Miraluma, used widely for breast cancer detection.

The present invention applies to detecting and differentiating between various types of breast disorders, for example as illustrated in FIG. 1A, hereinabove, as follows.

i. fibroadenomas 8, which are fibrous, benign growths in breast tissue.

ii. cysts 9, which are fluid-filled sacs and may disappear sometimes by themselves, or a doctor may draw out the fluid with a needle.

iii. a breast abscess 11, which is a collection of pus, resulting from an infection.

iv. fibrocystic breast disease 13, which is a common condition characterized by an increase in the fibrous and glandular tissues in the breasts, resulting in small, nodular cysts, noncancerous lumpiness, and tenderness, wherein treatment of the cysts may be all that is needed.

v. a tumor 15, which may be precancerous or cancerous, and which usually shows up as a white area on a mammogram even before it can be felt. In cases where the tumor 15 is cancerous, it may appear as a white area with radiating arms. A cancerous tumor 15 may have no symptoms or may cause swelling, tenderness, discharge from the nipple 4, indentation of the nipple 4, or a dimpled appearance 17 in the skin over the tumor.

Additionally, the present invention applies to detecting various types of breast cancers, such as:

i. ductal cancer, which affects the cells of the ducts;

ii. lobular cancer, which begins in the lobes or lobules of the breast; and iii. inflammatory breast cancer, which is an uncommon type of breast cancer and causes the breast to be warm, red, and swollen.

It will be appreciated that the present invention further applies to other types breast disorders, which may be cancerous, precancerous, or benign.

Additionally or alternatively, the present invention applies to secondary breast cancer, for example, originating from the lungs, or other parts of the body.

Furthermore, the radioactive-emission-measuring probe for the breast may be designed for and used on a single breast or designed for and used simultaneously on the two breasts.

It will be appreciated that although breast cancer in men and children is rare, the present invention may be used for the detection of breast cancer in men and children as well.

\*\*

It will be appreciated that many other probes and probe systems may be considered and the examples here are provided merely to illustrate the many types of combinations that may be examined, in choosing and scoring a probe design, both in terms of information and in terms of secondary considerations, such as rate of data collection, cost, and complexity of the design.

It will be appreciated that the methods of the present invention apply to pathological features that may be modeled as regions of concentrated radiations, or hot regions, regions of low-level radiation, which is nonetheless above background level, and regions of little radiation, or cold regions, below the background level. However, in general, for identifying a pathological feature of the heart, they relate to cold regions.

It will be appreciated that the methods of the present inventions may be operable by computer systems and stored as computer programs on computer-readable storage media.

It will be appreciated that the body may be an animal body or a human body.

It will be appreciated that the radioactive-emission-measuring systems, probes and methods of the present invention may be used with commonly owned US Applications 20040015075 and 20040054248 and commonly owned PCT publication WO2004/042546, all of whose disclosures are incorporated herein by reference. These describe systems and methods for scanning a radioactive-emission source with a radioactive-emission-measuring probe of a wide-aperture collimator, and at the same time, monitoring the position of the radioactive-emission-measuring probe, at very fine time intervals, to obtain the equivalence of fine-aperture collimation. In consequence, high-efficiency, high-resolution, images of a radioactive-emission source are obtained.

Commonly owned US application 20040054248 and commonly owned PCT publication WO2004/042546 further disclose various extracorporeal and intracorporeal systems, of radioactive-emission-measuring probes, of relatively wide apertures, associated with position-tracking devices.

It will be appreciated that the radioactive-emission-measuring systems, probes and methods of the present invention may be used with commonly owned U.S. Pat. No. 6,173,201 to Front, whose disclosure is incorporated herein by reference, as well as by M. W. Vannier and D. E. Gayou, "Automated registration of multimodality images", Radiology, vol. 169 pp. 860-861 (1988); J. A. Correia, "Registration of nuclear medicine images, J. Nucl. Med., vol. 31 pp. 1227-1229 (1990); J-C Liehn, A. Loboguerrero, C. Perault and L. Demange, "superposition of computed tomography and single photon emission tomography immunoscinigraphic images in the pelvis: validation in patients with colorectal or ovarian carcinoma recurrence", Eur. J. Nucl. Med., vol. 19 pp. 186-194 (1992); F. Thomas et al., "Description of a prototype emission transmission computed tomography imaging system", J. Nucl. Med., vol. 33 pp. 1881-1887 (1992); D. A. Weber and M. Ivanovic, "Correlative image registration", Sem. Nucl. Med., vol. 24 pp. 311-323 (1994); and Hasegawa et al., U.S. Pat. No. 5,376,795.

These relate to the acquisition of both a functional image of the body, such as a radioactive-emission image, and a structural image, such as an ultrasound, an x-ray, or an MRI image, and their co-registration on a single frame of reference.

In essence, several images may be acquired and co-registered to the same frame of reference, as follows:

i. a first functional image scan, based for example, on anti-CEA monoclonal antibody fragment, labeled by iodine isotopes, may be acquired for targeting CEA-produced and shed by colorectal carcinoma cells for detecting a pathological feature, such as colorectal carcinoma;

ii. a second functional image, based for example, on nonspecific-polyclonal immunoglobulin G (IgG), which may be labeled with $Tc^{99m}$, may be acquired for locating blood vessels and vital structures, such as the heart, or the stomach, co-registered with the first functional image and the pathological feature detected on it, in order to locate the pathological feature in reference to blood vessels and vital organs; and iii. a structural image, such as an ultrasound image, may be used for general structural anatomy, co-registered with the first and second functional images, in order to locate the pathological feature in reference to bones and the general anatomic structure.

Thus, a physician may locate the pathological feature in reference to the blood vessels, vital organs, and the bones, and guide a minimally invasive surgical instrument to the pathological feature, while avoiding the blood vessels, vital organs, and bones. The minimally invasive surgical instrument may be a biopsy needle, a wire, for hot resection, a knife for cold resection, an instrument of focused energy, to produce ablation, for example, by ultrasound, or by laser, an instrument for cryosurgery, an instrument for croyetherapy, or an instrument for bractherapy, wherein seeds of a radioactive metal are planted close to a tumor, for operating as a radioactive source near the tumor.

Commonly owned PCT publication WO2004/042546 further discloses that the surgical instrument may be visible on at least one of the images, for example, on the structural image, to enable the physician to see the instrument, the pathological feature, and the surrounding anatomy on the display 129 (FIG. 3A). Additionally, the surgical instrument may be radioactively labeled, to be visible also on the functional image. PCT publication WO2004/042546 further disclose various extracorporeal and intracorporeal systems, of radioactive-emission-measuring probes, and structural imagers such as an ultrasound probe or an MRI probe.

Commonly owned U.S. Pat. No. 6,173,201, to Front further discloses a method of stereotactic therapy, wherein a frame, which includes at least three markers, visible on a structural image, is rigidly secured to a patient. The structural image of a region inside the patient's body, which includes a pathological feature and the markers, is acquired. A functional image of the pathological feature is then acquired and co-registered with the structural image, to correlate the images to the same frame of reference. A stereotactic guide is rigidly attached to the frame and is used to guide a surgical instrument, such as a biopsy needle or a brachytherapy needle, to the pathological feature, with reference to the co-registered images.

Thus the radioactive-emission-measuring systems, probes and methods of the present invention may be used together with position tracking devices, for enhanced image acquisition, they may be used together with structural imager and structural imaging for correlating functional and structural images, and they may be used for guiding minimally invasive surgical instruments, such as a biopsy needle, a wire, for hot resection, a knife for cold resection, an instrument of focused energy, to produce ablation, for example, by ultrasound, or by laser, an instrument for cryosurgery, an instrument for croyetherapy, or an instrument for bractherapy.

It will be appreciated that a structural image, such as by ultrasound may further be used and in order to provide information about the size and location of the body structure 215 for the purpose of creating the model 250 (FIG. 5A).

It will be appreciated that a structural image, such as by ultrasound may further be used and in order to provide information about tissue attenuation, for example, as taught in conjunction by commonly owned PCT publication WO2004/042546, whose disclosure is incorporated herein by reference. The information may then be used to correct the radioactive-emission measurements.

It is expected that during the life of this patent many relevant radioactive-emission-measuring systems, probes and methods will be developed and the scope of these terms is intended to include all such new technologies a priori.

As used herein the term "about" refers to ±20%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, any citation or identification of any reference in this application shall not be construed as an admission that such reference is available as prior art to the present invention.

What is claimed:

1. A radioactive-emission-measuring-probe system, for tomographic imaging of a body structure of the patient, after an administration of a radiopharmaceutical, the radioactive-emission-measuring-probe system comprising:
    a housing for tomographic imaging of the body structure, the housing remaining stationary during data acquisition for a tomographic image;
    at least one detector assembly system, mounted within the housing, the detector assembly system comprising:
        a plurality of internal housings each comprises:
            a plurality of collimated solid-state detecting units, arranged within the internal housing, each of the detecting units defining a solid-state detector pixel- and a solid collection angle, and
            at least one internal housing motion provider having a motion transfer link configured for providing a rotational motion to one of the plurality of internal housings around a respective rotation axis, during said data acquisition for the tomographic image; and
    a controller, configured for controlling said detector motion provider;
    wherein said housing is contoured so as to bring said plurality of collimated solid-state detecting units to a close proximity with the body structure.

2. The radioactive-emission-measuring-probe system of claim 1, wherein the internal housing rotational motion is an oscillatory rotational motion, so as to result it a sweeping motion.

3. The radioactive-emission-measuring-probe system of claim 1, and further including a plurality of detector assembly systems, arranged along the housing contour, each of the detector assembly systems being configured for an assembly rotational motion around a different assembly axis of rotation.

4. The radioactive-emission-measuring-probe system of claim 1, wherein the plurality of detecting units are configured for detecting-unit sweeping motions in an additional direction, during data acquisition for the tomographic image.

5. The radioactive-emission-measuring-probe system of claim 1, wherein the plurality of detecting units are arranged in arrays, to form rigid blocks, and the blocks are configured for block sweeping motions in an additional direction, during data acquisition for the tomographic image, the blocks' axes of rotation being orthogonal to the assembly's axis of rotation.

6. The radioactive-emission-measuring-probe system of claim 1, and further including an assembly motion provider, in mechanical communicating with the internal housing, for providing assembly lateral motion, during data acquisition for the tomographic image.

7. The radioactive-emission-measuring-probe system of claim 6, wherein the assembly lateral motion is an oscillatory lateral motion.

8. The radioactive-emission-measuring-probe system of claim 1, wherein
    said plurality of collimated solid-state detecting units are mounted and directed within the internal housing so as to obtain an optimal set of views of a region of interest associated with the heart for reconstructing a three-dimensional image thereof;
    wherein said housing is contoured so as to bring said plurality of collimated solid-state detecting units to a close proximity with the thorax.

9. The radioactive-emission-measuring-probe system of claim 1, wherein said
    plurality of collimated solid-state detecting units are arranged and directed within the internal housing so as to capture a set of optimal views of a region of interest associated with the brain for reconstructing a three-dimensional image thereof;
    wherein said housing is contoured so as to bring said plurality of collimated solid-state detecting units to a close proximity with the head.

10. The radioactive-emission-measuring-probe system of claim 1, further comprises
    a three-dimensional structural imager.

11. The dual imaging system of claim 10, wherein the three-dimensional structural imager is selected from the group consisting of an x-ray CT, an MRI, a three-dimensional ultrasound, and a combination thereof.

12. The radioactive-emission-measuring-probe system of claim 1, wherein said housing is shaped for insertion to a body lumen, for tomographic imaging the body structure from the body lumen,
    said housing being contoured so as to bring said plurality of collimated solid-state detecting units to a close proximity with the body structure from the body lumen.

13. The breast radioactive-emission-measuring-probe system of claim 1,
wherein said plurality of collimated solid-state detecting units are arranged and directed within the internal housing to capture a set of optimal views of a region of interest associated with a breast for reconstructing a three-dimensional image thereof;
wherein said housing is contoured so as to bring said plurality of collimated solid-state detecting units to a close proximity with the breast.

14. The radioactive-emission-measuring-probe system of claim 13, and further including a plurality of detector assembly systems, arranged on at least one of a support plate and a compression plate, each of the detector assembly systems being configured for an assembly rotational motion around a different assembly axis of rotation.

15. The radioactive-emission-measuring-probe system of claim 13, and further including a plurality of detector assembly systems, arranged on both a support plate and a compression plate, each of the detector assembly systems being configured for an assembly rotational motion around a different assembly axis of rotation.

16. The radioactive-emission-measuring-probe system of claim 13, wherein the plurality of detecting units are arranged in arrays, to form rigid blocks, and the blocks are configured for block sweeping motions in an additional direction, during data acquisition for the tomographic image, the blocks' axes of rotation being orthogonal to the assembly's axis of rotation,
and further including an assembly motion provider, in mechanical communication with each of the blocks within the internal housing, for providing the blocks with the block sweeping motion in the additional direction.

17. The radioactive-emission-measuring-probe system of claim 13, and further including an ultrasound imager, co-registered to the breast radioactive-emission-measuring-probe system.

18. The radioactive-emission-measuring-probe system of claim 13, and further including an x-ray imager, co-registered to the breast radioactive-emission-measuring-probe system.

19. The radioactive-emission-measuring-probe system of claim 13, and further including a surgical instrument, co-registered to the breast radioactive-emission-measuring-probe.

20. The radioactive-emission-measuring-probe system of claim 1, comprising circuitry configured to drive said system to perform diagnostic radioactive-emission measurements of an in-vivo body structure, selectively at a predefined set of views,
wherein said circuitry controller is further configured to:
(a) model suspected pathology and anatomical constraints, which limit accessibility to the suspected pathology within the body-structure;
(b) obtain a collection of views of the modeled suspected pathology and the modeled anatomical constraints;
(c) form sets of views from the collection of views and scoring them, with a scoring function;
(d) select one of the sets of views from a second collection of views, based on its score, as a predefined pathology set of views; and
(e) drive said system to perform diagnostic radioactive-emission measurements of the in-vivo pathology, selectively at the predefined pathology set of views.

21. The radioactive-emission-measuring-probe system of claim 1, wherein said at least one detector assembly is configured for translation motion relative to said housing during said data acquisition.

22. The radioactive-emission-measuring-probe system of claim 1, wherein said controller is configured for controlling said assembly rotational motion according to a model modeling the anatomical constraints, which limit accessibility to the body.

23. The radioactive-emission-measuring-probe system of claim 1, wherein at least a portion of said housing is which is substantially transparent to nuclear radiation.

24. The radioactive-emission-measuring-probe system of claim 1, wherein said housing having an open counter.

* * * * *